US010351611B2

(12) United States Patent
Lai et al.

(10) Patent No.: US 10,351,611 B2
(45) **Date of Patent: *Jul. 16, 2019**

(54) MICRODYSTROPHIN PEPTIDES AND METHODS FOR TREATING MUSCULAR DYSTROPHY USING THE SAME

(71) Applicant: THE CURATORS OF THE UNIVERSITY OF MISSOURI, Columbia, MO (US)

(72) Inventors: Yi Lai, Columbia, MO (US); Junling Zhao, Columbia, MO (US); Yongping Yue, Columbia, MO (US); Dongsheng Duan, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 34 days.

This patent is subject to a terminal disclaimer.

(21) Appl. No.: 15/487,919

(22) Filed: Apr. 14, 2017

(65) Prior Publication Data

US 2017/0349640 A1 Dec. 7, 2017

Related U.S. Application Data

(63) Continuation of application No. 14/091,326, filed on Nov. 26, 2013, now Pat. No. 9,624,282.

(60) Provisional application No. 61/797,012, filed on Nov. 26, 2012.

(51) Int. Cl.

*C07K 14/17* (2006.01)
*C07K 14/47* (2006.01)
*A61K 38/17* (2006.01)
*A61K 47/64* (2017.01)

(52) U.S. Cl.

CPC ...... *C07K 14/4708* (2013.01); *A61K 38/1719* (2013.01); *A61K 47/645* (2017.08); *C07K 14/4716* (2013.01); *A01K 2207/05* (2013.01)

(58) Field of Classification Search

CPC .... A61K 38/00; A61K 38/1719; A61K 35/34; C12N 15/86; C07K 14/4708; C07K 14/4707; G01N 2800/2878; G01N 2800/2885; G01N 2800/2892

See application file for complete search history.

(56) References Cited

U.S. PATENT DOCUMENTS 7,892,824 B2* 2/2011 Duan .................. A61K 48/005 435/320.1
9,624,282 B2* 4/2017 Lai ..................... C07K 14/4708
2008/0249052 A1* 10/2008 Duan .................. A61K 48/005 514/44 R

FOREIGN PATENT DOCUMENTS

WO 2008088895 A9 7/2008

OTHER PUBLICATIONS

Sonnemann et al. Functional substitution by TAT-utrophin in dystrophin-deficient mice. PLoS Med. 2009; 6(5): e1000083. (Year: 2009).*
Adams, ME et al., “Absence of alpha-syntrophin leads to structurally aberrant neuromuscular synapses deficient in utrophin”, J Cell Biol, 150(6), 2000, 1385-1398.
Betts, C. A. et al., “Optimizing tissue-specific antisense oligonucleotide-Peptide conjugates”, Methods Mol Biol 867, 2012, 415-435.
Bhagavati, S., “Exon-skipping therapy for Duchenne muscular dystrophy”, Lancet 379, e10; author reply e10-11, 2012.
Bostick, B. et al., “Systemic AAV-9 transduction in mice is influenced by animal age but not by the route of administration”, Gene Ther 14, 2007, 1605-1609.
Brenman, J. E. et al., “Interaction of nitric oxide synthase with the postsynaptic density protein PSD-95 and alpha1-syntrophin mediated by PDZ domains”, Cell 84, 1996, 757-767.
Brenman, JE et al., “Nitric oxide synthase complexed with dystrophin and absent from skeletal muscle sarcolemma in Duchenne muscular dystrophy”, Cell 82(5), 1995, 743-752.
Chao, DS et al., “Selective loss of sarcolemmal nitric oxide synthase in Becker muscular dystrophy”, J Exp Med 184 (2), 1996, 609-618.
Choy, E. et al., “Endomembrane trafficking of ras: the CAAX motif targets proteins to the ER and Goigi”, Cell 98, 1999, 69-80.
Cirak, S. et al., “Exon skipping and dystrophin restoration in patients with Duchenne muscular dystrophy after systemic phosphorodiamidate morpholino oligomer treatment: an open-label, phase 2, doseescalation study”, Lancet 378, 2011, 595-605.
Djinovic-Carugo, K. et al., “The spectrin repeat: A structural platform for cytoskeletal protein assemblies”, FEBS Lett 513(1), 119-123.
England, S. B. et al., “Very mild muscular dystrophy associated with the deletion of 46% of dystrophin”, Nature 343, 1990, 180-182.
Foster, H. et al., “Codon and mRNA sequence optimization of microdystrophin transgenes improves expression and physiological outcome in dystrophic mdx mice following AAV2/8 gene transfer”, Mol Ther 16, 2008, 1825-1832.
Goemans, N. M. et al., “Systemic administration of PRO051 in Duchenne's muscular dystrophy”, N Engl J med 364, 2011, 1513-1522.
Grady, RM et al., “Skeletal and cardiac myopathies in mice lacking utrophin and dystrophin: A model for Duchenne muscular dystrophy”, Cell 90(4), 1997, 729-738.

(Continued)

*Primary Examiner* — Marcela M Cordero Garcia
*Assistant Examiner* — Jia-Hai Lee
(74) *Attorney, Agent, or Firm* — Yang Tang; Perkins Coie LLP

(57) ABSTRACT

According to the embodiments described herein, a series of biological materials for treatment/therapy of DMD and/or BMD through the recovery of sarcolemmal nNOS is provided. The biological material comprises the complete dystrophin repeats R16 and R17 or certain domains, sections, or fragments of the dystrophin repeats R16 and R17. In some aspects, such domains, sections, or fragments may be selected from sequence motifs including dystrophin R17 α1 helix, α2 and α3 helices of both R16 and R17, or a combination thereof.

8 Claims, 44 Drawing Sheets

Specification includes a Sequence Listing.

(56) References Cited

OTHER PUBLICATIONS

Gregorevic, P. et al., "rAAV6-microdystrophin preserves muscle function and extends lifespan in severely dystrophic mice", Nat Med 12, 2006, 787-789.
Gregorevic, P. et al., "Systemic delivery of genes to striated muscles using adenoassociated viral vectors", Nat Med 10, 2004, 828-834.
Hancock, JF et al., "A polybasic domain or palmitoylation is required in addition to the CAAX motif to localize p21ras to the plasma membrane", Cell 631(1), 1990, 133-139.
Harper, SQ et al., "Modular flexibility of dystrophin: Implications for gene therapy of Duchenne muscular dystrophy", Nat Med 8(3), 2002, 253-261.
Hillier, BJ et al., "Unexpected modes of PDZ domain scaffolding revealed by structure of nNOS-syntrophin complex", Science 284(5415), 1999, 812-815.
Ho, A. et al., "Synthetic protein transduction domains: enhanced transduction potential in vitro and in vivo", Cancer Res 61, 2001, 474-477.
Hsieh, C. H. et al., "MicroRNA profiling in ischemic injury of the gracillis muscle in rats", BMC Musculoskelet Disord 11, 2010, 123.
Inagaki, K. et al., "Robust systemic transduction with AAV9 vectors in mice: efficient global cardic gene transfer superior to that of AAV8", Mol Ther 14, 2006, 45-53.
Ipsaro, JJ et al., "Structural basis for spectrin recognition by ankyrin", Blood 115(20), 2010, 4093-4101.
Ivanova, G. D. et al., "Improved cell-penetrating peptide-PNA conjugates for splicing redirection in HeLa cells and exon skipping in mdx mouse muscle", Nucleic Acids Res 36, 2008, 6418-6428.
Jearawiriyapaisarn, N. et al., "Sustained dystrophin expression induced by peptideconjugated morpholino oligomers in the muscles of mdx mice", Mol Ther 16, 2008, 1624-1629.
Judge, LM et al., "Dissecting the signaling and mechanical functions of the dystrophin-glycoprotein complex", J Cell Sci 119 (Pt 8), 2006, 1537-1546.
Kamneya, S. et al., "Alpha1-syntrophin gene distruption results in the absence of neuronal-type nitric-oxide synthase at the sarcolemma but does not induce muscle degeneration", J Biol Chem 274(4), 1999, 2193-2200.
Kaplan, et al., "Cationic TAT peptide transduction domain enters cells by macropinocytosis", J Control Release, 102(1), Jan. 20, 2005, 247-253.
Karnoub, A. E. et al., "Ras oncogenes: split personalities", Nat Rev Mol Cell Biol 9, 2008, 517-531.
Kobayashi, YM et al., "Sarcolemma-localized nNOS is required to maintain activity after mild exercise", Nature 456(7221), 2008, 511-515.
Kunkel, LM, "William Allan Award Address. Cloning of the DMD gene", Am J Hum Genet 76(2), 2005, 205-214.
Lai, et al., "a2 and a3 helices of dystrophin R16 and R17 frame a microdomain in the a1 helix of dystrophin R17 for neuronal NOS binding", PNAS, 110 (2), 2013, 525-530.
Lai, et al., "Dystrophins carrying spectrin-like repeats 16 and 17 anchor nNOS to the sarcolemma and enhance exercise performance in a mouse model of muscular dystrophy", The Journal of Clinical Investigation, 119(3), 2009, 624-635.
Lai, Y et al., "Dystrophins carrying spectrin-like repeats 16 and 17 anchor nNOS to the sarcolemma and enhance exercise performance in a mouse model of muscular dystrophy", J Clin Invest 119(3), 2009, 624-635.
Lai, Y et al., "Efficient in vivo gene expression by trans-splicing adeno-associated viral vectors", Nat Biotechnol 23(11), 2005, 1435-1439.
Le Rumeur, E. et al., "A new twist to coiled coil", FEBS Lett 586 (17), 2012, 2717-2722.
Le Rumeur, E. et al., "Dystrophin: More than just the sum of its parts", Biochim Biophys Acta 1804(9), 2010, 1713-1722.
Legrand, B. et al., "Computational study of the human dystrophin repeats: interaction properties and molecular dynamics", PLoS ONE 6(8): e23819, 2011.
Li, D. et al., "iNOS ablation does not improve specific force of the extensor digitorum longus muscle in dystrophin-deficient mdx4cv mice", PLoS ONE 6(6):e2618, 2011b.
Li, D. et al., "Nitrosative stress elicted by nNOSu delocalization inhibits muscle force in dystrophin-null mice", J Pathol 223(1), 2011a, 88-98.
Li, D. et al., "Sarcolemmal nNOS anchoring reveals a qualitative difference between dystrophin and utrophin", J Cell Sci 123 (Pt 12), 2010, 2008-2013.
Li, D. et al., "Sub-physiological sarcoglycan expression contributes to compensatory muscle protection in mdx mice", Hum Mol Genet 18(7), 2009, 1209-1220.
Li, X. et al., "Synthetic muscle promoters: activities exceeding naturally occurring regulatory sequences.", Nat Biotechnol 17, 1999, 241-245.
Morris, G. et al., "Monitoring duchenne muscular dystrophy gene therapy with epitope-specific monoclonal antibodies", Methods Mol Biol 709, 2011, 39-61.
Morris, M. C. et al., "A peptide carrier for the delivery of biologically active proteins into mammalian cells", Nat Biotechnol 19, 2001, 1173-1176.
Moulton, H. M., "Cell-penetrating peptides enhance systemic delivery of antisense morpholino oligomers", Methods Mol Biol 867, 2012, 407-414.
Nakamura, A. et al., "Exon-skipping therapy for Duchenne muscular dystrophy", Lancet 378, 2011, 546-547.
Navarro-Lerida, I. et al., "N-terminal palmitoylation within the appropriate amino acid environment conveys on NOS2 the ability to progress along the intracellular sorting pathways", J Cell Sci 119, 2006, 1558-1569.
Neri, M. et al., "Dystrophin levels as low as 30% are sufficient to avoid muscular dystrophy in the human", Neuromuscul Disord 17, 2007, 913-918.
Nishida, C. R. et al., "Electron transfer and catalytic activity of nitric oxide synthases. Chimeric constructs of the neuronal, inducible, and endothelial isoforms", J Biol Chem 273, 1998, 5566-5571.
Qiao, C. et al., "AAV6 capsid tyrosine to phenylalanine mutations improve gene transfer to skeletal muscle", Hum Gene Ther 21(10), 2010, 1343-1348.
Remington, , "The Science and Practice of Pharmacy 21st Edition", Univ. of Sciences in Philadelphia (USIP), Lippincott Williams & Wilkins, Philadelphia, PA, 2005.
Roseguini, B. T. et al., "Intermittent pneumatic leg compressions acutely upregulate VEGF and MCP-1 expression in skeletal muscle", Am J Physiol Heart Circ Physiol 298, 2010, H1991-2000.
Rybakova, IN et al., "Utrophin binds laterally along actin filamens and can couple costameric actin with sarcolemma when overexpressed in dystrophin-deficient muscle", Mol Biol Cell 13(5), 2002, 1512-1521.
Sander, M. et al., "Functional muscle ischemia in neuronal nitric oxide synthase deficient skeletal muscle of children with Duchenne muscular dystrophy", Proc Natl Acad Sci USA 97(25), 2000, 13818-13823.
Schwarze, S. R. et al., "In vivo protein transduction: delivery of a biologically active protein into the mouse", Science 285, 1999, 1569-1572.
Shin, JH et al., "Recombinant adeno-associated viral vector production and purification", Methods Mol Biol 798, 2012, 267-284.
Sirsi, S. R. et al., "Functionalized PEG-PEI copolymers complexed to exon-skipping oligonucleotides improve dystrophin expression in mdx mice", Hum Gene Ther 19, 2008, 795-806.
Sonnemann, et al., "Functional substitution by TAT-utrophin in dystrophin-deficient mice.", PLoS Med., 6(5):e1000083, May 26, 2009.
Sonnemann, K. J. et al., "Functional Substitution by TAT-Utrophin in Dystrophin-Deficient Mice", PLoS Med; 6(5): e1000083, May 26, 2009.
Stabach, PR et al., "The structure of the ankyrin-binding site of beta-spectrin reveals how tandem spectrin-repeats generate unique ligand-binding properties", Blood 113(22), 2009, 5377-5384.

(56) References Cited

OTHER PUBLICATIONS

Thomas, G. D. et al., "Vasomodulation by skeletal muscle-derived nitric oxide requires alphasyntrophin alphasyntrophinmediated sarcolemmal localization of neuronal Nitric oxide synthase", Circ Res 92, 2003, 554-560.
Thomas, GD et al., "Impaired metabolic modulation of alpha-adrenergic vasoconstriction in dystrophin-deficient skeletal muscle", Proc Natl Acad Sci USA 95(25), 1998, 15090-15095.
Tochio, H. et al., "Solution structure of the extended neuronal nitric oxide synthase PDZ domain complexed with an associated peptide", Nat Struct Biol 6(5), 1999, 417-421.
Torelli, S. et al., "Absence of neuronal nitric oxide synthase (nNOS) as a pathological marker for the diagnosis of Becker muscular dystrophy with rod domain deletions", Neuropathol Appl Neurobiol 30(5), 2004, 540-545.
Van Deutekom, J. C. et al., "Local dystrophin restoration with antisense obligonucleotide PRO051", N Engl J Med 357, 2007, 2677-2686.
Wang, B. et al., "Adeno-associated virus vector carrying human minidystrophin genes effectively ameliorates muscular dystrophy in mdx mouse model", Proc Natl Acad Sci U S A 97, 2000, 13714-13719.
Wang, Q. et al., "TAT-mediated protein transduction of Nogo extracellular peptide 1-40 and its biological activity", Cell Mol Neurobiol 29, 2009, 97-108.
Wells, KE et al., "Relocalization of neuronal nitric oxide synthase (nNOS) as a marker for complete restoration of the dystrophin associated protein complex in skeletal muscle", Neuromuscul Disord 13(1), 2003, 21-31.
White, S. J. et al., "Copy number variation in the genome; the human DMD gene as an example", Cytogenet Genome Res 115, 2006, 240-246.
Wu, B. et al., "Effective rescue of dystrophin improves cardiac function in dystrophin-deficient mice by a modified morpholino oligomer", Proc Natl Acad Sci U S A 105, 2008, 14814-14819.
Yin, H et al., "Cell-penetrating peptide-conjugated antisense oligonucleotides restore systemic muscle and cardiac dystrophin expression and function", Hum Mol Genet 17, 2008, 3909-3918.
Yin, H. et al., "A fusion peptide directs enhanced systemic dystrophin exon skipping and functional restoration in dystrophin-deficient mdx mice", Hum Mol Genet 18, 2009, 4405-4414.
Yin, H. et al., "Optimization of peptide nucleic acid antisense oligonucleotides for local and systemic dystrophin splice correction in the mdx mouse", Mol Ther 18, 2010, 819-827.
Yokota, T. et al., "Efficacy of systemic morpholino exon-skipping in Duchenne dystrophy dogs", Ann Neurol 65, 2009, 667-676.
Yue, Y et al., "C-terminal-truncated microdystrophin recruits dystrobrevin and syntrophin to the dystrophin-associated glycoprotein complex and reduces muscular dystrophy in symptomatic ultrophin/dystrophin double-knockout mice", Mol Ther 14 (1), 2006, 79-87.
Zhong, L. et al., "Next generation of adeno-associated virus 2 vectors: Point mutations in tyrosines lead to high-efficiency tranduction at lower doses.", Proc Natl Acad Sci USA 105(22), 2008, 7827-7832.

* cited by examiner

FIG. 4(A)
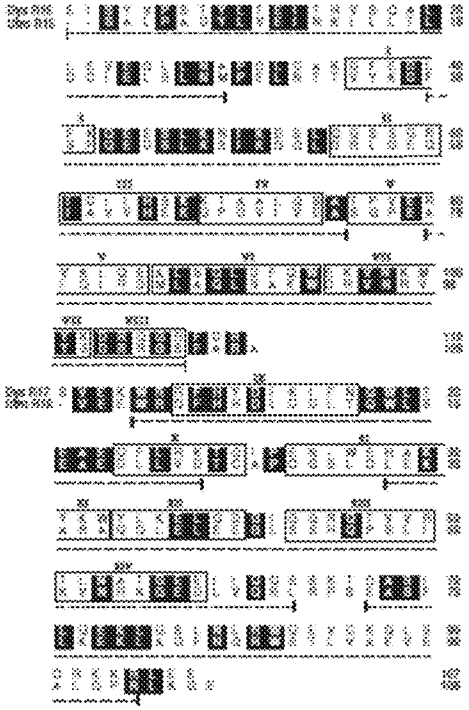
FIG. 4(B)
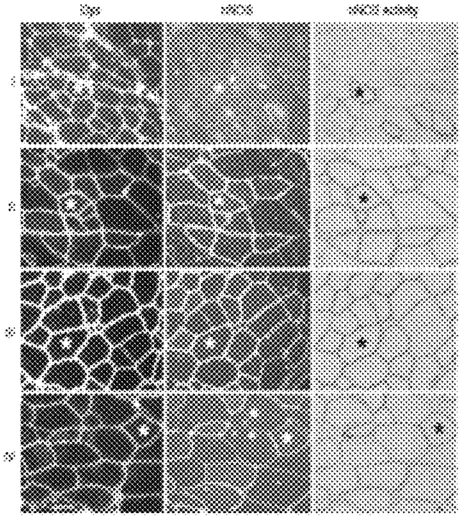
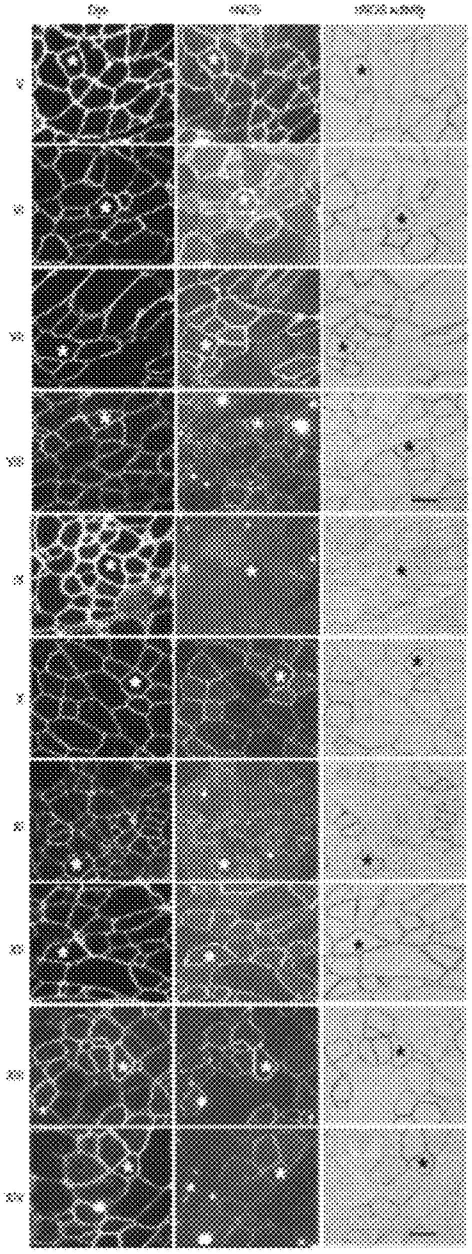

FIG. 9

| Construct name | Configuration | Lab log no | Source |
|---|---|---|---|
| Microdystrophin | | | |
| ΔR2-R15/ΔR18-R23/ΔC | NT, H1, R1, R16, R17, R24, H4, CR | YL90 | Fig. S1 |
| NT.R16/17.CR.GFP | NT, H1, R16, R17, H4, CR, GFP | YL228 | Fig. S1 |
| R16/17.CR.GFP | R16, R17, H4, CR, GFP | YL230 | Fig. S1 |
| NT.R16/17.GFP | NT, H1, R16, R17, GFP | YL229 | Fig. S1 |
| R16/17.GFP | R16, R17, GFP | YL231 | Fig. 1 |
| R16/17.GFP.Pal | R16, R17, GFP, Pal | YL299 | Fig. 1 |
| Microutrophin and repeat-modified microutrophin | | | |
| μ-Utro (ΔR2-R14/ΔR17-R21/ΔC) | Flag, Utro(NT, H1, R1, R15, R16, R22, H4, CR) | YL239 | Fig. S2 |
| μ-Utro+Dys R16/17 (ΔR2-R21/ΔC+Dys R16/17) | Flag, Utro(NT, H1, R1), Dys R16, Dys R17, Utro(R22, H4, CR) | YL223 | Fig. S2 |
| Microdomain-modified microdystrophin | | | |
| Construct I | NT, H1, R1, R16(Utro microdomain VYKDFSF), R17, R24, H4, CR | YL278 | Fig. 2 |
| Construct II | NT, H1, R1, R16(Utro microdomain DRLGEQ), R17, R24, H4, CR | YL279 | Fig. 2 |
| Construct III | NT, H1, R1, R16(Utro microdomain AVVHEK), R17, R24, H4, CR | YL280 | Fig. 2 |
| Construct IV | NT, H1, R1, R16(Utro microdomain QPDVIVE), R17, R24, H4, CR | YL281 | Fig. 2 |
| Construct V | NT, H1, R1, R16(Utro microdomain SGPEAIQIRD), R17, R24, H4, CR | YL282 | Fig. 2 |
| Construct VI | NT, H1, R1, R16(Utro microdomain MLAQLNAKW), R17, R24, H4, CR | YL283 | Fig. 2 |
| Construct VII | NT, H1, R1, R16(Utro microdomain DRVNRVYS), R17, R24, H4, CR | YL284 | Fig. 2 |
| Construct VIII | NT, H1, R1, R16(Utro microdomain DRRGS), R17, R24, H4, CR | YL285 | Fig. 2 |
| Construct IX | NT, H1, R1, R16, R17(Utro microdomain QPHHDIDQLT), R24, H4, CR | YL286 | Fig. 2 |
| Construct X | NT, H1, R1, R16, R17(Utro microdomain DLLVDTC), R24, H4, CR | YL287 | Fig. 2 |
| Construct XI | NT, H1, R1, R16, R17(Utro microdomain DGSLDLEKARA), R24, H4, CR | YL288 | Fig. 2 |
| Construct XII | NT, H1, R1, R16, R17(Utro microdomain QQLFLEE), R24, H4, CR | YL289 | Fig. 2 |
| Construct XIII | NT, H1, R1, R16, R17(Utro microdomain SSHQPSLI), R24, H4, CR | YL290 | Fig. 2 |
| Construct XIV | NT, H1, R1, R16, R17(Utro microdomain KVNRKGED), R24, H4, CR | YL291 | Fig. 2 |
| Microdomain-modified microutrophin | | | |
| μ-Utro+Dys R17 microdomain IX | Flag, Utro (NT, H1, R1, R15, R16(Dys R17 microdomain IX), R22, H4, CR) | YL325 | Fig. 3 |
| Linker region-modified microdystrophin | | | |
| Mutant-1 | NT, H1, R1, R16(Utro R15 3'-linker sequence), R17, R24, H4, CR | YL312 | Table S2 |
| Mutant-2 | NT, H1, R1, R16(Dys R15 3'-linker sequence), R17, R24, H4, CR | YL313 | Table S2 |
| Mutant-3 | NT, H1, R1, R16(Dys repeat 3'- linker consensus sequence), R17, R24, H4, CR | YL314 | Table S2 |
| Mutant-4 | NT, H1, R1, R16, R17(Utro R16 3'-linker sequence), R24, H4, CR | YL315 | Table S2 |
| Repeat-modified microdystrophin | | | |
| μ-Dys+Utro R15 | NT, H1, R1, Utro(R15), R17, R24, H4, CR | YL310 | Fig. S3 |
| μ-Dys+Utro R16 | NT, H1, R1, R16, Utro(R16), R24, H4, CR | YL311 | Fig. S3 |
| Helix deleted microdystrophin | | | |
| ΔR16-α1 | NT, H1, R1, R16(α2, α3), R17, R24, H4, CR | YL180 | Fig. 5A |
| ΔR16-α2 | NT, H1, R1, R16(α1, α3), R17, R24, H4, CR | YL181 | Fig. 5A |
| ΔR16-α3 | NT, H1, R1, R16(α1, α2), R17, R24, H4, CR | YL182 | Fig. 5A |
| ΔR17-α1 | NT, H1, R1, R16, R17(α2, α3), R24, H4, CR | YL183 | Fig. 5A |
| ΔR17-α2 | NT, H1, R1, R16, R17(α1, α3), R24, H4, CR | YL184 | Fig. 5A |
| Helix substituted microdystrophin | | | |
| R16 α1* | NT, H1, R1, R18(α1)+R16(α2, α3), R17, R24, H4, CR | YL232 | Fig. 5B |
| R16 α2* | NT, H1, R1, R16(α1)+R18(α2)+R16(α3), R17, R24, H4, CR | YL233 | Fig. 5B |
| R16 α3* | NT, H1, R1, R16(α1, α2)+R18(α3), R17, R24, H4, CR | YL234 | Fig. 5B |
| R17 α2* | NT, H1, R1, R16, R17(α1)+R18(α2)+R17(α3), R24, H4, CR | YL236 | Fig. 5B |
| R17 α3* | NT, H1, R1, R16, R17(α1, α2)+R18(α3), R24, H4, CR | YL273 | Fig. 5B |
| R16 α1*+R17* | NT, H1, R1, R2(α1)+R16(α2, α3), R3, H2, R24, H4, CR | YL270 | Table S2 |
| R16*+R17α3* | NT, H1, R1, R2, R17(α1, α2)+R3(α3), H2, R24, H4, CR | YL271 | Table S2 |
| R16 α1*+R17 α3* | NT, H1, R1, R2(α1)+R16(α2, α3), R17(α1, α2)+R3(α3), H2, R24, H4, CR | YL272 | Table S2 |
| R17 α1* | NT, H1, R1, R16, R18(α1)+R17(α2, α3), R24, H4, CR | YL235 | Table S2 |
| R16 α2 with R4 α2 | NT, H1, R1, R16(α1)+R4(α2)+R16(α3), R17, R24, H4, CR | YL382 | Table S2 |
| R16 α3 with R4 α3 | NT, H1, R1, R16(α1, α2)+R4(α3), R17, R24, H4, CR | YL383 | Table S2 |
| R17 α2 with R5 α2 | NT, H1, R1, R16, R17(α1)+R5(α2)+R17(α3), R24, H4, CR | YL384 | Table S2 |
| R17 α3 with R5 α3 | NT, H1, R1, R16, R17(α1, α2)+R5(α3), R24, H4, CR | YL385 | Table S2 |

Constructs are listed in the order as they appear in the manuscript. CR, cystein-rich domain; H, hinge; NT, N-terminal domain; Pal, palmitoylation membrane targeting sequence, R, spectrin-like repeat; Utro, utrophin.

FIG. 10

| Construct name | Configuration* | Lab log no. | nNOS binding |
| --- | --- | --- | --- |
| Linker region-modified microdystrophin | | | |
| Original linker sequence (R16/R17) | FDR/SVEK | | |
| Mutant-1 | FAR/SVEK | YL312 | Yes |
| Mutant-2 | FAQ/SVEK | YL313 | Yes |
| Mutant-3 | LEE/SVEK | YL314 | Yes |
| Mutant-4 | FDR/AVEE | YL315 | Yes |
| Helix-substituted microdystrophin | | | |
| Original configuration (R16/R17) | R16(α1),R16(α2),R16(α3)/R17(α1),R17(α2),R17(α3) | | |
| R16 α1#+R17# | R2(α1),R16(α2),R16(α3)/R3(α1),R3(α2),R3(α3) | YL270 | No |
| R16#+R17α3# | R2(α1),R2(α2),R2(α3)/R17(α1),R17(α2),R3(α3) | YL271 | No |
| R16 α1#+R17 α3# | R2(α1),R16(α2),R16(α3)/R17(α1),R17(α2),R3(α3) | YL272 | No |
| R17 α1# | R16(α1),R16(α2),R16(α3)/R18(α1),R17(α2),R17(α3) | YL235 | No |
| R16 α2 with R4 α2 | R16(α1),R4(α2),R16(α3)/R17(α1),R17(α2),R17(α3) | YL382 | No |
| R16 α3 with R4 α3 | R16(α1),R16(α2),R4(α3)/R17(α1),R17(α2),R17(α3) | YL383 | No |
| R17 α2 with R5 α2 | R16(α1),R16(α2),R16(α3)/R17(α1),R5(α2),R17(α3) | YL384 | No |
| R17 α3 with R5 α3 | R16(α1),R16(α2),R16(α3)/R17(α1),R17(α2),R5(α3) | YL385 | No |

*Mutation is highlighted in boldface letters.

Dystrophin

Utrophin

FIG. 13

| | Normal | DMD | BMD | DMD receiving exon skipping or gene therapy |
|---|---|---|---|---|
| Dystrophin | Full-length Dystrophin | No | Truncated Dystrophins | Truncated Dystrophins |
| Sarcolemmal nNOS | Yes | No | Mostly No | Mostly No |

FIG. 14

| | Muscle Force | Dystrophic Phenotype | Sarcolemmal nNOS | Blood Perfusion | Running Performance | Ischemic Injury |
|---|---|---|---|---|---|---|
| ΔH2-R19 | Improved | Improved | No | No | No | No |
| ΔH2-R15 | Improved | Improved | Recovered | Improved | Improved | Prevented |

FIG. 19

| Experimental Group | Negative Control | Therapeutic Control | Positive Control |
| --- | --- | --- | --- |
| ΔH2-R19 injected with recombinant R16/17 protein | ΔH2-R19 injected with saline | ΔH2-R19 injected with AAV.R16/17.Pal | ΔH2-R15 |

FIG. 21

SEQ ID NO: 1: Nucleotide sequence of ΔH2-R19 (mini-dystrophin with 8 repeats and 3 hinges) (This minigene does not carry R16 or R17. It cannot restore nNOS)

ATGCTTGGTGGGAAGAAGTAGAGGACTGTTATGAAAGAGAAGATGTTCAAAAGAAAACATTCACAAAATGGGTAAAT
GCACAATTTTCTAAGTTTGGGAAGCAGCATATTGAGAACCTCTTCAGTGACCTACAGGATGGGAGGCGCCTCCTAGA
CCTCCTCGAAGGCCTGACAGGGCAAAAACTGCCAAAAGAAAAAGGATCCACAAGAGTTCATGCCCTGAACAATGTCA
ACAAGGCACTGCGGGTTTTGCAGAACAATAATGTTGATTTAGTGAATATTGGAAGTACTGACATCGTAGATGGAAAT
CATAAACTGACTCTTGGTTTGATTTGGAATATAATCCTCCACTGGCAGGTCAAAAATGTAATGAAAAATATCATGGC
TGGATTGCAACAAACCAACAGTGAAAAGATTCTCCTGAGCTGGGTGCGACAATCAACTCGTAATTATCCACAGGTTA
ATGTAATCAACTTCACCACCAGCTGGTCTGATGGCCTGGCTTTGAATGCTCTCATCCATAGTCATAGGCCAGACCTA
TTTGACTGGAATAGTGTGGTTTGCCAGCAGTCAGCCACACAACGACTGGAACATGCATTCAACATCGCCAGATATCA
ATTAGGCATAGAGAAACTACTCGATCCTGAAGATGTTGATACCACCTATCCAGATAAGAAGTCCATCTTTAATGTAC
ATCACATCACTCTTCCAAGTTTTGCCTCAACAAGTGAGCATTGAAGCCATCCAGGAAGTGGAAATGTTGCCAAGGCC
ACCTAAAGTGACTAAAGAAGAACATTTTCAGTTACATCATCAAATGCACTATTCTCAACAGATCACGGTCAGTCTAG
CACAGGGATATGAGAGAACTTCTTCCCCTAAGCCTCGATTCAAGAGCTATGCCTACACACAGGCTGCTTATGTCACC
ACCTCTGACCCTACACGGAGCCCATTTCCTTCACAGCATTTGGAAGCTCCTGAAGACAAGTCATTTGGCAGTTCATT
GATGGAGAGTGAAGTAAACCTGGACCGTTATCAAACAGCTTTAGAAGAAGTATTATCGTGGCTTCTTTCTGCTGAGG
ACACATTGCAAGCACAAGGAGAGATTTCTAATGATGTGGAAGTGGTGAAAGACCAGTTTCATACTCATGAGGGGTAC
ATGATGGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAGGGTAG
CTAGCATGGAAAAACAAAGCAATTTACATAGAGTTTTAATGGATCTCCAGAATCAGAAACTGAAAGAGTTGAATGAC
TGGCTAACAAAAACAGAAGAAAGAACAAGGAAAATGGAGGAAGAGCCTCTTGGACCTGATCTTGAAGACCTAAAACG
CCAAGTACAACAACATAAGGTGCTTCAAGAAGATCTAGAACAAGAACAAGTCAGGGTCAATTCTCTCACTCACATGG
TGGTGGTAGTTGATGAATCTAGTGGAGATCACGCAACTGCTGCTTTGGAAGAACAACTTAAGGTATTGGGAGATCGA
TGGGCAAACATCTGTAGATGGACAGAAGACCGCTGGGTTCTTTTACAAGACATCCTTCTCAAATGGGAACGTCTTAC
TGAAGAACAGTGCCTTTTTAGTGCATGGCTTTCAGAAAAAGAAGATGCAGTGAACAAGATTCACACAACTGGCTTTA
AAGATCAAAATGAAATGTTATCAAGTCTTCAAAAACTGGCCGTTTTAAAAGCGGATCTAGAAAAGAAAAAGCAATCC
ATGGGCAAACTGTATTCACTCAAACAAGATCTTCTTTCAACACTGAAGAATAAGTCAGTGACCCAGAAGACGGAAGC
ATGGCTGGATAACTTTGCCCGGTGTTGGGATAATTTAGTCCAAAAACTTGAAAAGAGTACAGCACAGATTTCACAGC
AGCCTGACCTAGCTCCTGGACTGACCACTATTGGAGCCTCTCCTACTCAGACTGTTACTCTGGTGACACAACCTGTG
GTTACTAAGGAAACTGCCATCTCCAAACTAGAAATGCCATCTTCCTTGATGTTGGAGGTACCTGCTCTGGCAGATTT
CAACCGGGCTTGGACAGAACTTACCGACTGGCTTTCTCTGCTTGATCAAGTTATAAAATCACAGAGGGTGATGGTGG
GTGACCTTGAGGATATCAACGAGATGATCATCAAGCAGAAGGCAACAATGCAGGATTTGGAACAGAGGCGTCCCCAG
TTGGAAGAACTCATTACCGCTGCCCAAAATTTGAAAAACAAGACCAGCAATCAAGAGGCTAGAACAATCATTACGGA
TCGAATTGAAAGAATTCAGAATCAGTGGGATGAAGTACAAGAACACCTTCAGAACCGGAGGCAACAGTTGAATGAAA
TGTTAAAGGATTCAACACAATGGCTGGAAGCTAAGGAAGAAGCTGAGCAGGTCTTAGGACAGGCCAGAGCCAAGCTT
GAGTCATGGAAGGAGGGTCCCTATACAGTAGATGCAATCCAAAAGAAAATCACAGAAACCAAGCAGTTGGCCAAAGA
CCTCCGCGAGTGGCAGACAAATGTAGATGTGGCAAATGACTTGGCCCTGAAACTTCTGCGGGATTATTCTGCAGATG
ATACCAGAAAAGTCCACATGATAACAGAGAATATCAATGCCTCTTGGAGAAGCATTCATAAAAGGGTGAGTGAGCGA
GAGGCTGCTTTGGAAGAAACTCATAGATTACTGCAACAGTTCCCCCTGGACCTGGAAAAGTTTCTTGCCTGGCTTAC
AGAAGCTGAAACAACTGCCAATGTCCTACAGGATGCTACCCGTAAGGAAAGGCTCCTAGAAGACTCCAAGGGAGTAA
AAGAGCTGATGAAACAATGGCAAGACCTCCAAGGTGAAATTGAAGCTCACACAGATGTTTATGACAACCTGGATGAA
AACAGCCAAAAAATCCTGAGATCCCTGGAAGGTTCCGATGATGCAGTCCTGTTACAAAGACGTTTGGATAACATGAA
CTTCAAGTGGAGTGAACTTCGGAAAAAGTCTCTCAACATTAGGTCCCATTTGGAAGCCAGTTCTGACCAGTGGAAGC
GTCTGCACCTTTCTCTGCAGGAACTTCTGGTGTGGCTACAGCTGAAAGATGATGAATTAAGCCGGCAGGCACCTATT
GGAGGCGACTTTCCAGCAGTTCAGAAGCAGAACGATGTACATAGGGCCTTCAAGAGGGAATTGAAAACTAAAGAACC
TGTAATCATGAGTACTCTTGAGACTGTACGAATATTTCTGACAGAGCAGCCTTTGGAAGGACTAGAGAAACTCTACC
AGGAGCCCAGAGAGCTGCCTCCTGAGGAGAGAGCCCAGAATGTCACTCGGCTTCTACGAAAGCAGGCTGAGGAGGTC
AATACTGAGTGGGAAAAATTGAACCTGCACTCCGCTGACTGGCAGAGAAAAATAGATGAGACCCTTGAAAGACTCCA
GGAACTTCAAGAGGCCACGGATGAGCTGGACCTCAAGCTGCGCCAAGCTGAGGTGATCAAGGGATCCTGGCAGCCCG
TGGGCGATCTCCTGATTGACTCTCTCCAAGATCACCTCGAGAAAGTCAAGGCACTTCGAGGAGAAATTGCGCCTCTG
AAAGAGAACGTGAGCGACGTCAATGACCTTGCTCGCCAGCTTACCACTTTGGGCATTCAGCTCTCACCGTATAACCT

FIG. 21 (con't)

CAGCACTCTGGAAGACCTGAACACCAGATGGAAGCTTCTGCAGGTGGCCGTCGAGGACCGAGTCAGGCAGCTGCATG
AAGCCCACAGGGACTTTGGTCCAGCATCTCAGCACTTTCTTTCCACGTCTGTCCAGGGTCCCTGGGAGAGAGCCATC
TCGCCAAACAAAGTGCCCTACTATATCAACCACGAGACTCAAACAACTTGCTGGGACCATCCCAAAATGACAGAGCT
CTACCAGTCTTTAGCTGACCTGAATAATGTCAGATTCTCAGCTTATAGGACTGCCATGAAACTCCGAAGACTGCAGA
AGGCCCTTTGCTTGGATCTCTTGAGCCTGTCAGCTGCATGTGATGCCTTGGACCAGCACAACCTCAAGCAAAATGAC
CAGCCCATGGATATCCTGCAGATTATTAATTGTTTGACCACTATTTATGACCGCCTGGAGCAAGAGCACAACAATTT
GGTCAACGTCCCTCTCTGCGTGGATATGTGTCTGAACTGGCTGCTGAATGTTTATGATACGGGACGAACAGGGAGGA
TCCGTGTCCTGTCTTTAAAAGTGGCATCATTTCCCTGTGTAAAGCACATTTGGAAGACAAGTACAGATACCTTTTCA
AGCAAGTGGCAAGTTCAACAGGATTTTGTGACCAGCGCAGGCTGGGCCTCCTTCTGCATGATTCTATCCAAATCCAA
GACAGTTGGGTGAAGTTGCATCCTTTGGGGGCAGTAACATTGAGCCAAGTGTCCGGAGCTGCTTCCAATTTGCTAAT
AATAAGCCAGAGATCGAAGCGGCCCTCTTCCTAGACTGGATGAGACTGGAACCCCAGTCCATGGTGTGGCTGCCCGT
CCTGCACAGAGTGGCTGCTGGAGAAACTGCCAAGCATCAGGCCAAATGTAACATCTGCAAAGAGTGTCCAATCATTG
GATTCAGGTACAGGAGTCTAAAGCACTTTAATTATGACATCTGCCAAAGCTGCTTTTTTTCTGGTCGAGTTGCAAAA
GGCCATAAAATGCACTATCCCATGGTGGAATATTGCACTCCGACTACATCAGGAGAAGATGTTCGAGACTTTGCCAA
GGTACTAAAAAACAAATTTCGAACCAAAAGGTATTTTGCGAAGCATCCCCGAATGGGCTACCTGCCAGTGCAGACTG
TCTTAGAGGGGGACAACATGGAAACGCCTGCCTCGTCCCCTCAGCTTTCACACGATGATACTCATTCACGCATTGAA
CATTATGCTAGCAGGCTAGCAGAAATGGAAAACAGCAATGGATCTTATCTAAATGATAGCATCTCTCCTAATGAGAG
CATAGATGATGAACATTTGTTAATCCAGCATTACTGCCAAAGTTTGAACCAGGACTCCCCCCTGAGCCAGCCTCGTA
GTCCTGCCCAGATCTTGATTTCCTTAGAGAGTGAGGAAAGAGGGGAGCTAGAGAGAATCCTAGCAGATCTTGAGGAA
GAAAACAGGAATCTGCAAGCAGAATATGACCGTCTAAAGCAGCAGCACGAACATAAAGGCCTGTCCCCACTGCCGTC
CCCTCCTGAAATGATGCCCACCTCTCCCCAGAGTCCCCGGGATGCTGAGCTCATTGCTGAGGCCAAGCTACTGCGTC
AACACAAAGGCCGCCTGGAAGCCAGGATGCAAATCCTGGAAGACCACAATAAACAGCTGGAGTCACAGTTACACAGG
CTAAGGCAGCTGCTGGAGCAACCCCAGGCAGAGGCCAAAGTGAATGGCACAACGGTGTCCTCTCCTTCTACCTCTCT
ACAGAGGTCCGACAGCAGTCAGCCTATGCTGCTCCGAGTGGTTGGCAGTCAAACTTCGGACTCCATGGGTGAGGAAG
ATCTTCTCAGTCCTCCCCAGGACACAAGCACAGGGTTAGAGGAGGTGATGGAGCAACTCAACAACTCCTTCCCTAGT
TGAAGAGGAAGAAATACCCCTGGAAAGCCAATGAGAGAGGACACAATGTAG

FIG. 22

SEQ ID NO: 2: Nucleotide sequence of ΔH2-R15 (mini-dystrophin with 12 repeats and 3 hinges) (This minigene carries both R16 and R17. It can restore nNOS)

ATGCTTTGGTGGGAAGAAGTAGAGGACTGTTATGAAAGAGAAGATGTTCAAAAGAAAACATTCACAAAATGGGTAAA
TGCACAATTTTCTAAGTTTGGGAAGCAGCATATTGAGAACCTCTTCAGTGACCTACAGGATGGGAGGCGCCTCCTAG
ACCTCCTCGAAGGCCTGACAGGGCAAAAACTGCCAAAAGAAAAAGGATCCACAAGAGTTCATGCCCTGAACAATGTC
AACAAGGCACTGCGGGTTTTGCAGAACAATAATGTTGATTTAGTGAATATTGGAAGTACTGACATCGTAGATGGAAA
TCATAAACTGACTCTTGGTTTGATTTGGAATATAATCCTCCACTGGCAGGTCAAAAATGTAATGAAAAATATCATGG
CTGGATTGCAACAAACCAACAGTGAAAAGATTCTCCTGAGCTGGGTCCGACAATCAACTCGTAATTATCCACAGGTT
AATGTAATCAACTTCACCACCAGCTGGTCTGATGGCCTGGCTTTGAATGCTCTCATCCATAGTCATAGGCCAGACCT
ATTTGACTGGAATAGTGTGGTTTGCCAGCAGTCAGCCACACAACGACTGGAACATGCATTCAACATCGCCAGATATC
AATTAGGCATAGAGAAACTACTCGATCCTGAAGATGTTGATACCACCTATCCAGATAAGAAGTCCATCTTAATGTAC
ATCACATCACTCTTCCAAGTTTTGCCTCAACAAGTGAGCATTGAAGCCATCCAGGAAGTGGAAATGTTGCCAAGGCC
ACCTAAAGTGACTAAAGAAGAACATTTTCAGTTACATCATCAAATGCACTATTCTCAACAGATCACGGTCAGTCTAG
CACAGGGATATGAGAGAACTTCTTCCCCTAAGCCTCGATTCAAGAGCTATGCCTACACACAGGCTGCTTATGTCACC
ACCTCTGACCCTACACGGAGCCCATTTCCTTCACAGCATTTGGAAGCTCCTGAAGACAAGTCATTTGGCAGTTCATT
GATGGAGAGTGAAGTAAACCTGGACCGTTATCAAACAGCTTTAGAAGAAGTATTATCGTGGCTTCTTTCTGCTGAGG
ACACATTGCAAGCACAAGGAGAGATTTCTAATGATGTGGAAGTGGTGAAAGACCAGTTTCATACTCATGAGGGGTAC
ATGATGGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAGGGTAG
CTAGCATGGAAAAACAAAGCAATTTACATAGAGTTTTAATGGATCTCCAGAATCAGAAACTGAAAGAGTTGAATGAC
TGGCTAACAAAAACAGAAGAAAGAACAAGGAAAATGGAGGAAGAGCCTCTTGGACCTGATCTTGAAGACCTAAAACG
CCAAGTACAACAACATAAGGTGCTTCAAGAAGATCTAGAACAAGAACAAGTCAGGGTCAATTCTCTCACTCACATGG
TGGTGGTAGTTGATGAATCTAGTGGAGATCACGCAACTGCTGCTTTGGAAGAACAACTTAAGGTATTTGGAGATCG
ATGGGCAAACATCTGTAGATGGACAGAAGACCGCTGGGTTCTTTTACAAGACATCCTTCTCAAATGGCAACGTCTTA
CTGAAGAACAGTGCCTTTTTAGTGCATGGCTTTCAGAAAAAGAAGATGCAGTGAACAAGATTCACACAACTGGCTTT
AAAGATCAAAATGKAATGTTATCAAGTCTTCAAAAAGTGGCCGTTTTAAAAGCGGATCTAGAAAAGAAAAAGCAATC
CATGGGCAAACTGTATTCACTCAAACAAGATCTTCTTTCAACACTGAAGAATAAGTCAGTGACCCAGAAGACGGAAG
CATGGCTGGATAACTTTGCCCGGTGTTGGGATAATTTAGTCCAAAAACTTGAAAAGAGTACAGCACAGATTTCACAG
GAAATTTCTTATGTGCCTTCTACTTATTTGACTGAAATCACTCATGTCTCACAAGCCCTATTAGAAGTGGAACAACT
TCTCAATGCTCCTGACCTCTGTGCTAAGGACTTTGAAGATCTCTTTAAGCAAGAGGAGTCTCTGAAGAATATAAAAG
ATAGTCTACAACAAAGCTCAGGTCGGATTGACATTATTCATAGCAAGAAGACAGCAGCATTGCAAAGTGCAACGCCT
GTGGAAAGGGTGAAGCTACAGGAAGCTCTCTCCCAGCTTGATTTCCAATGGGAAAAAGTTAACAAAATGTACAAGGA
CCGACAAGGGCGATTTGACAGATCTGTTGAGAAATGGCGGCGTTTTCATTATGATATAAAGATATTTAATCAGTGGC
TAACAGAAGCTGAACAGTTTCTCAGAAAGACACAAATTCCTGAGAATTGGGAACATGCTAAATACAAATGGTATCTT
AAGGAACTCCAGGATGGCATTGGGCAGCGGCAAACTGTTGTCAGAACATTGAATGCAACTGGGGAAGAAATAATTCA
GCAATCCTCAAAAACAGATGCCAGTATTCTACAGGAAAAATTGGGAAGCCTGAATCTGCGGTGGCAGGAGGTCTGCA
AACAGCTGTCAGACAGAAAAAAGAGGCTAGAAGAACAAAAGAATATCTTGTCAGAATTTCAAAGAGATTTAAATGAA
TTTGTTTTATGGTTGGAGGAAGCAGATAACATTGCTAGTATCCCACTTGAACCTGGAAAAGAGCAGCAACTAAAAGA
AAAGCTTGAGCAAGTCAAGTTACTGGTGGAAGAGTTGCCCCTGCGCCAGGGAATTCTCAAACAATTAAATGAAACTG
GAGGACCCGTGCTTGTAAGTGCTCCCATAAGCCCAGAAGAGCAAGATAAACTTGAAAATAAGCTCAAGCAGACAAAT
CTCCAGTGGATAAAGGTTTCCAGAGCTTTACCTGAGAAACAAGGAGAAATTGAAGCTCAAATAAAAGACCTTGGGCA
GCTTGAAAAAAAGCTTGAAGACCTTGAAGAGCAGTTAAATCATCTGCTGCTGTGGTTATCTCCTATTAGGAATCAGT
TGGAAATTTATAACCAACCAAACCAAGAAGGACCATTTGACGTTCAGGAAACTGAAATAGCAGTTCAAGCTAAACAA
CCGGATGTGGAAGAGATTTTGTCTAAAGGGCAGCATTTGTACAAGGAAAAACCAGCCACTCAGCCAGTGAAGAGGAA
GTTAGAAGATCTGAGCTCTGAGTGGAAGGCGGTAAACCGTTTACTTCAAGAGCTGAGGGCAAAGCAGCCTGACCTAG
CTCCTGGACTGACCACTATTGGAGCCTCTCCTACTCAGACTGTTACTCTGGTGACACAACCTGTGGTTACTAAGGAA
ACTGCCATCTCCAAACTAGAAATGCCATCTTCCTTGATGTTGGAGGTACCTGCTCTGGCAGATTTCAACCGGGCTTG
GACAGAACTTACCGACTGGCTTTCTCTGCTTGATCAAGTTATAAAATCACAGAGGGTGATGGTGGGTGACCTTGAGG
ATATCAACGAGATGATCATCAAGCAGAAGGCAACAATGCAGGATTTGGAACAGAGGCGTCCCCAGTTGGAAGAACTC
ATTACCGCTGGCCAAAATTTGAAAAACAAGACCAGCAATCAAGAGGCTAGAACAATCATTACGGATCGAATTGAAAG
AATTCAGAATCAGTGGGATGAAGTACAAGAACACCTTCAGAACCGGAGGCAACAGTTGAATGAAATGTTAAAGGATT
CAACACAATGGCTGGAAGCTAAGGAAGAAGCTGAGCAGGTCTTAGGACAGGCCAGAGCCAAGCTTGAGTCATGGAAG

FIG. 22 (con't)

GAGGGTCCCTATACAGTAGATGCAATCCAAAAGAAAATCACAGAAACCAAGCAGTTGGCCAAAGACCTCCGCCAGTG
GCAGACAAATGTAGATGTGGCAAATGACTTGGCCCTGAAACTTCTCCGGGATTATTCTGCAGATGATACCAGAAAAG
TCCACATGATAACAGAGAATATCAATGCCTCTTGGAGAAGCATTCATAAAAGGGTGAGTGAGCGAGAGGCTGCTTTG
GAAGAAACTCATAGATTACTGCAACAGTTCCCCCTGGACCTGGAAAAGTTTCTTGCCTGGCTTACAGAAGCTGAAAC
AACTGCCAATGTCCTACAGGATGCTACCCGTAAGGAAAGGCTCCTAGAAGACTCCAAGGGAGTAAAAGAGCTGATGA
AACAATGGCAAGACCTCCAAGGTGAAATTGAAGCTCACACAGATGTTTATCACAACCTGGATGAAAACAGCCAAAAA
ATCCTGAGATCCCTGGAAGGTTCCGATGATGCAGTCCTGTTACAAAGACGTTTGGATAACATGAACTTCAAGTGGAG
TGAACTTCGGAAAAAGTCTCTCAACATTAGGTCCCATTTGGAAGCCAGTTCTGACCAGTGGAAGCGTCTGCACCTTT
CTCTGCAGGAACTTCTGGTGTGGCTACAGCTGAAAGATGATGAATTAAGCCGGCAGGCACCTATTGGAGGCGACTTT
CCAGCAGTTCAGAAGCAGAACGATGTACATAGGGCCTTCAAGAGGGAATTGAAAACTAAAGAACCTGTAATCATGAG
TACTCTTGAGACTGTACGAATATTTCTGACAGAGCAGCCTTTGGAAGGACTAGAGAAACTCTACCAGGAGCCCAGAG
AGCTGCCTCCTGAGGAGAGAGCCCAGAATGTCACTCGGCTTCTACGAAAGCAGGCTGAGGAGGTCAATACTGAGTGG
GAAAAATTGAACCTGCACTCCGCTGACTGGCAGAGAAAAATAGATGAGACCCTTGAAAGACTCCAGGAACTTCAAGA
GGCCACGGATGAGCTGGACCTCAAGCTGCGCGAAGCTGAGGTGATCAAGGGATCCTGGCAGCCCGTGGGCGATCTCC
TCATTGACTCTCTCCAAGATCACCTCGAGAAAGTCAAGGCACTTCGAGGAGAAATTGCGCCTCTGAAAGAGAACGTG
AGCCACGTCAATGACCTTGCTCGCCAGCTTACCACTTTGGGCATTCAGCTCTCACCGTATAACCTCAGCACTCTGGA
AGACCTGAACACCAGATGGAAGCTTCTGCAGGTGGCCGTCGAGGACCGAGTCAGGCAGCTGCATGAAGCCCACAGGG
ACTTTGGTCCAGCATCTCAGCACTTTCTTTCCACGTCTGTCCAGGGTCCCTGGGAGAGAGCCATCTCGCCAAACAAA
GTGCCCTACTATATCAACCACGAGACTCAAACAACTTGCTGGGACCATCCCAAAATGACAGAGCTCTACCAGTCTTT
AGCTGACCTGAATAATGTCAGATTCTCAGCTTATAGGACTGCCATGAAACTCCGAAGACTGCAGAAGGCCCTTTGCT
TGGATCTCTTGAGCCTGTCAGCTGCATGTGATGCCTTGGACCAGCACAACCTCAAGCAAAATGACCAGCCCATGGAT
ATCCTGCAGATTATTAATTGTTTGACCACTATTTATGACCGCCTGGAGCAAGAGCACAACAATTTGGTGAACGTGCC
TCTCTGCGTGGATATGTGTCTGAACTGGCTGGTGAATGTTTATGATACGGGACGAACAGGGAGGATCCGTGTCCTGT
CTTTTAAAACTGGCATCATTTCCCTGTGTAAAGCACATTTGGAAGACAAGTACAGATACCTTTTCAAGCAAGTGGGA
AGTTCAACAGGATTTTGTGACCAGCGCAGGCTGGGCCTCCTTCTGCATGATTCTATCCAAATTCCAAGACAGTTGGG
TGAAGTTGCATCCTTTGGGGGCAGTAACATTGAGCCAAGTGTCCGGAGCTGCTTCCAATTTGCTAATAATAAGCCAG
AGATCGAAGCGGCCCTCTTCCTAGACTGGATGAGACTGGAACCCCAGTCCATGGTGTGGCTGCCCGTCCTGCACAGA
GTGGCTGCTGCAGAAACTGCCAAGCATCAGGCCAAATGTAACATCTGCAAAGAGTGTCCAATCATTGGATTCAGGTA
CAGGAGTCTAAAGCACTTTAATTATGACATCTGCCAAAGCTGCTTTTTTTCTGGTCGAGTTGCAAAAGGCCATAAAA
TGCACTATCCCATGGTGGAATATTGCACTCCGACTACATCAGGAGAAGATGTTCGAGACTTTGCCAAGGTACTAAAA
AACAAATTTCGAACCAAAAGGTATTTTGCGAAGCATCCCCGAATGGGCTACCTGCCAGTGCAGACTGTCTTAGAGGG
GGACAACATGGAAACGCCTGCCTCGTCCCCTCAGCTTTCACAGGATGATACTCATTCACGCATTGAACATTATGCTA
GCAGGCTAGCAGAAATGGAAAACAGCAATGGATCTTTATCTAAATGATAGCATCTCTCCTAATGAGAGCATAGATGA
TGAACATTTGTTAATCCAGCATTACTGCCAAAGTTTGAACCAGGACTCCCCCCTGAGCCAGCCTCGTAGTCCTGCCC
AGATCTTGATTTCCTTAGAGAGTGAGGAAAGAGGGGAGCTAGAGAGAATCCTAGCAGATCTTGAGGAAGAAAACAGG
AATCTGCAAGCAGAATATGACCGTCTAAAGCAGCAGCACGAACATAAAGGCCTGTCCCCACTGCCGTCCCCTCCTGA
AATGATGCCCACCTCTCCCCAGAGTCCCCGGGATGCTGAGCTCATTGCTGAGGCCAAGCTACTGCGTCAACACAAAG
GCCGCCTGGAAGCCAGGATGCAAATCCTGGAAGACCACAATAAACAGCTGGAGTCACAGTTACACAGGCTAAGGCAG
CTGGTGGAGCAACCCCAGGCAGAGGCCAAAGTGAATGGCACAACGGTGTCCTCTCCTTCTACCTCTCTACAGAGGTC
CGACAGCAGTCAGCCTATGCTGCTCCGAGTGGTTGGCAGTCAAACTTCGGACTCCATGGGTGAGGAAGATCTTCTCA
GTCCTCCCCAGGACACAAGCACAGGGTTAGAGGAGGTGATGGAGCAACTCAACAACTCCTTCCCTAGTTCAAGAGGA
AGAAATACCCCTGGAAAGCCAATGAGAGAGGACACAATGTAG

FIG. 23

SEQ ID NO: 3: Nucleotide sequence of ΔR2-R15/ΔR18-23/ΔC (micro-dystrophin with 4 repeats and 2 hinges, no C-terminal domain)(This microgene carries both R16 and R17. It can restore nNOS)

ATGCTTTGGTGGGAAGAAGTAGAGGACTGTTATGAAAGAGAAGATGTTCAAAAGAAAACATTCACAAAATGGGTAAA
TGCACAATTTTCTAAGTTTGGGAAGCAGCATATTGAGAACCTCTTCAGTGACCTACAGGATGGGAGGCGCCTCCTAG
ACCTCCTCGAAGGCCTGACAGGGCAAAAACTGCCAAAAGAAAAAGGATCCACAAGAGTTCATGCCCTGAACAATGTC
AACAAGGCACTGCGGGTTTTGCAGAACAATAATGTTGATTTAGTGAATATTGGAAGTACTGACATCGTAGATGGAAA
TCATAAACTGACTCTTGGTTTGATTTGGAATATAATCCTCCACTGGCAGGTCAAAAATGTAATGAAAAATATCATGG
CTGGATTGCAACAAACCAACAGTGAAAAGATTCTCCTGAGCTGGGTCCGACAATCAACTCGTAATTATCCACAGGTT
AATGTAATCAACTTCACCACCAGCTGGTCTGATGGCCTGGCTTTGAATGCTCTCATCCATAGTCATAGGCCAGACCT
ATTTGACTGGAATAGTGTGGTTTGCCAGCAGTCAGCCACACAACGACTGGAACATGCATTCAACATCGCCAGATATC
AATTAGGCATAGAGAAACTACTCGATCCTGAAGATGTTGATACCACCTATCCAGATAAGAAGTCCATCTTAATGTAC
ATCACATCACTCTTCCAAGTTTTGCCTCAACAAGTGAGCATTGAAGCCATCCAGGAAGTGGAAATGTTGCCAAGGCC
ACCTAAAGTGACTAAAGAAGAACATTTTCAGTTACATCATCAAATGCACTATTCTCAACAGATCACGGTCAGTCTAG
CACAGGGATATGAGAGAACTTCTTCCCCTAAGCCTCGATTCAAGAGCTATGCCTACACACAGGCTGCTTATGTCACC
ACCTCTGACCCTACACGGAGCCCATTTCCTTCACAGCATTTGGAAGCTCCTGAAGACAAGTCATTTGGCAGTTCATT
GATGGAGAGTGAAGTAAACCTGGACCGTTATCAAACAGCTTTAGAAGAAGTATTATCGTGGCTTCTTTCTGCTGAGG
ACACATTGCAAGCACAAGGAGAGATTTCTAATGATGTGGAAGTGGTGAAAGACCAGTTTCATACTCATGAGGGGTAC
ATGATGGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAGGGTAG
CTAGCATGGAAAAACAAAGCAATTACATAGAGAAATTTCTTATGTGCCTTCTACTTATTTGACTGAAATCACTCATG
TCTCACAAGCCCTATTAGAAGTGGAACAACTTCTCAATGCTCCTGACCTCTGTGCTAAGGACTTTGAAGATCTCTTT
AAGCAAGAGGAGTCTCTGAAGAATATAAAAGATAGTCTACAACAAAGCTCAGGTCGGATTGACATTATTCATAGCAA
GAAGACAGCAGCATTGCAAAGTGCAACGCCTGTGGAAAGGGTGAAGCTACAGGAAGCTCTCTCCCAGCTTGATTTCC
AATGGGAAAAAGTTAACAAAATGTACAAGGACCGACAAGGGCGATTTGACAGATCTGTTGAGAAATGGCGGCGTTTT
CATTATGATATAAAGATATTTAATCAGTGGCTAACAGAAGCTGAACAGTTTCTCAGAAAGACACAAATTCCTGAGAA
TTGGGAACATGCTAAATACAAATGGTATCTTAAGGAACTCCAGGATGGCATTGGGCAGCGGCAAACTGTTGTCAGAA
CATTGAATGCAACTGGGGAAGAAATAATTCAGCAATCCTCAAAAACAGATGCCAGTATTCTACAGGAAAAATTGGGA
AGCCTGAATCTGCGGTGGCAGGAGGTCTGCAAACAGCTGTCAGACAGAAAAAAGAGGCTAGAAGAAACCCTTGAAAG
ACTCCAGGAACTTCAAGAGGCCACGGATGAGCTGGACCTCAAGCTGCGCCAAGCTGAGGTGATCAAGGGATCCTGGC
AGCCCGTGGGCGATCTCCTCATTGACTCTCTCCAAGATCACCTCGAGAAAGTCAAGGCACTTCGAGGAGAAATTGCG
CCTCTGAAAGAGAACGTGAGCCACGTCAATGACCTTGCTCGCCAGCTTACCACTTTGGGCATTCAGCTCTCACCGTA
TAACCTCAGCACTCTGGAAGACCTGAACACCAGATGGAAGCTTCTGCAGGTGGCCGTCGAGGACCGAGTCAGGCAGC
TGCATGAAGCCCACAGGGACTTTGGTCCAGCATCTCAGCACTTTCTTTCCACGTCTGTCCAGGGTCCCTGGGAGAGA
GCCATCTCGCCAAACAAAGTGCCCTACTATATCAACCACGAGACTCAAACAACTTGCTGGGACGATCCCAAAATGAC
AGAGCTCTACCAGTCTTTAGCTGACCTGAATAATGTCAGATTCTCAGCTTATAGGACTGCCATGAAACTCCGAAGAC
TGCAGAAGGCCCTTTGCTTGGATCTCTTGAGCCTGTCAGCTGCATGTGATGCCTTGGACCAGCACAACCTCAAGCAA
AATGACCAGCCCATGGATATCCTGCAGATTATTAATTGTTTGACCACTATTTATGACCGCCTGGAGCAAGAGCACAA
CAATTTGGTCAACGTCCCTCTCTGCGTGGATATGTGTCTGAACTGGCTGCTGAATGTTTATGATACGGGACGAACAG
GGAGGATCCGTGTCCTGTCTTTTAAAACTGGCATCATTTCCCTGTGTAAAGCACATTTGGAAGACAAGTACAGATAC
CTTTTCAAGCAAGTGGCAAGTTCAACAGGATTTTGTGACCAGCGCAGGCTGGGCCTCCTTCTGCATGATTCTATCCA
AATTCCAAGACAGTTGGGTGAAGTTGCATCCTTTGGGGGCAGTAACATTGAGCCAAGTGTCCGGAGCTGCTTCCAAT
TTGCTAATAATAAGCCAGAGATCGAAGCGGCCCTCTTCCTAGACTGGATGAGACTGGAACCCCAGTCCATGGTGTGG
CTGCCCGTCCTGCACAGAGTGGCTGCTGCAGAAACTGCCAAGCATCAGGCCAAATGTAACATCTGCAAAGAGTGTCC
AATCATTGGATTCAGGTACAGGAGTCTAAAGCACTTTAATTATGACATCTGCCAAAGCTGCTTTTTTTCTGGTCGAG
TTGCAAAAGGCCATAAAATGCACTATCCCATGGTGGAATATTGCACTCCGACTACATCAGGAGAAGATGTTCGAGAC
TTTGCCAAGGTACTAAAAAACAAATTTCGAACCAAAAGGTATTTTGCGAAGCATCCCCGAATGGGCTACCTGCCAGT
GCAGACTGTCTTAGAGGGGGACAACATGGAAACTGACACAATGTAG

FIG. 24

SEQ ID NO: 4: nucleotide sequence of ΔR4-R23/ΔC (micro-dystrophin with 4 repeats and 3 hinges, no C-terminal domain)(This microgene does not include R16 or R17. It cannot restore nNOS)

ATGCTTTGGTGGGAAGAAGTAGAGGACTGTTATGAAAGAGAAGATGTTCAAAAGAAAACATTCACAAAATGGGTAAA
TGCACAATTTTCTAAGTTTGGGAAGCAGCATATTGAGAACCTCTTCAGTGACCTACAGGATGGGAGGCGCCTCCTAG
ACCTCCTCGAAGGCCTGACAGGGCAAAAACTGCCAAAAGAAAAAGGATCCACAAGAGTTCATGCCCTGAACAATGTC
AACAAGGCACTGCGGGTTTTGCAGAACAATAATGTTGATTTAGTGAATATTGGAAGTACTGACATCGTAGATGGAAA
TCATAAACTGACTCTTGGTTTGATTTGGAATATAATCCTCCACTGGCAGGTCAAAAATGTAATGAAAAATATCATGG
CTGGATTGCAACAAACCAACAGTGAAAAGATTCTCCTGAGCTGGGTCCGACAATCAACTCGTAATTATCCACAGGTT
AATGTAATCAACTTCACCACCAGCTGGTCTGATGGCCTGGCTTTGAATGCTCTCATCCATAGTCATAGGCCAGACCT
ATTTGACTGGAATAGTGTGGTTTGCCAGCAGTCAGCCACACAACGACTGGAACATGCATTCAACATCGCCAGATATC
AATTAGGCATAGAGAAACTACTCGATCCTGAAGATGTTGATACCACCTATCCAGATAAGAAGTCCATCTTAATGTAC
ATCACATCACTCTTCCAAGTTTTGCCTCAACAAGTGAGCATTGAAGCCATCCAGGAAGTGGAAATGTTGCCAAGGCC
ACCTAAAGTGACTAAAGAAGAACATTTTCAGTTACATCATCAAATGCACTATTCTCAACAGATCACGGTCAGTCTAG
CACAGGGATATGAGAGAACTTCTTCCCCTAAGCCTCGATTCAAGAGCTATGCCTACACACAGGCTGCTTATGTCACC
ACCTCTGACCCTACACGGAGCCCATTTCCTTCACAGCATTTGGAAGCTCCTGAAGACAAGTCATTTGGCAGTTCATT
GATGGAGAGTGAAGTAAACCTGGACCGTTATCAAACAGCTTTAGAAGAAGTATTATCGTGGCTTCTTTCTGCTGAGG
ACACATTGCAAGCACAAGGAGAGATTTCTAATGATGTGGAAGTGGTGAAAGACCAGTTTCATACTCATGAGGGGTAC
ATGATGGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAGGGTAG
CTAGCATGGAAAAACAAAGCAATTTACATAGAGTTTTAATGGATCTCCAGAATCAGAAACTGAAAGAGTTGAATGAC
TGGCTAACAAAAACAGAAGAAAGAACAAGGAAAATGGAGGAAGAGCCTCTTGGACCTGATCTTGAAGACCTAAAACG
CCAAGTACAACAACATAAGGTGCTTCAAGAAGATCTAGAACAAGAACAAGTCAGGGTCAATTCTCTCACTCACATGG
TGGTGGTAGTTGATGAATCTAGTGGAGATCACGCAACTGCTGCTTTGGAAGAACAACTTAAGGTATTGGGAGATCGA
TGGGCAAACATCTGTAGATGGACAGAAGACCGCTGGGTTCTTTTACAAGACATCCTTCTCAAATGGCAACGTCTTAC
TGAAGAACAGTGCCTTTTTAGTGCATGGCTTTCAGAAAAAGAAGATGCAGTGAACAAGATTCACACAACTGGCTTTA
AAGATCAAAATGAAATGTTATCAAGTCTTCAAAAACTGGCCGTTTTAAAAGCGGATCTAGAAAAGAAAAAGCAATCC
ATGGGCAAACTGTATTCACTCAAACAAGATCTTCTTTCAACACTGAAGAATAAGTCAGTGACCCAGAAGACGGAAGC
ATGGCTGGATAACTTTGCCCGGTGTTGGGATAATTTAGTCCAAAAACTTGAAAAGAGTACAGCACAGATTTCACAGG
CTGTCACCACCACTCAGCCATCACTAACACAGACAACTGTAATGGAAACAGTAACTACGGTGACCACAAGGGAACAG
ATCCTGGTAAAGCATGCTCAAGAGGAACTTCCACCACCACCTCCCCAAAAGAAGAGGCAGATTACTGTGGATACCCT
TGAAAGACTCCAGGAACTTCAAGAGGCCACGGATGAGCTGGACCTCAAGCTGCGCCAAGCTGAGGTGATCAAGGGAT
CCTGGCAGCCCGTGGGCGATCTCCTCATTGACTCTCTCCAAGATCACCTCGAGAAAGTCAAGGCACTTCGAGGAGAA
ATTGCGCCTCTGAAAGAGAACGTGAGCCACGTCAATGACCTTGCTCGCCAGCTTACCACTTTGGGCATTCAGCTCTC
ACCGTATAACCTCAGCACTCTGGAAGACCTGAACACCAGATGGAAGCTTCTGCAGGTGGCCGTCGAGGACCGAGTCA
GGCAGCTGCATGAAGCCCACAGGGACTTTGGTCCAGCATCTCAGCACTTTCTTTCCACGTCTGTCCAGGGTCCCTGG
GAGAGAGCCATCTCGCCAAACAAAGTGCCCTACTATATCAACCACGAGACTCAAACAACTTGCTGGGACGATCCCAA
AATGACAGAGCTCTACCAGTCTTTAGCTGACCTGAATAATGTCAGATTCTCAGCTTATAGGACTGCCATGAAACTCC
GAAGACTGCAGAAGGCCCTTTGCTTGGATCTCTTGAGCCTGTCAGCTGCATGTGATGCCTTGGACCAGCACAACCTC
AAGCAAAATGACCAGCCCATGGATATCCTGCAGATTATTAATTGTTTGACCACTATTTATGACCGCCTGGAGCAAGA
GCACAACAATTTGGTCAACGTCCCTCTCTGCGTGGATATGTGTCTGAACTGGCTGCTGAATGTTTATGATACGGGAC
GAACAGGGAGGATCCGTGTCCTGTCTTTTAAAACTGGCATCATTTCCCTGTGTAAAGCACATTTGGAAGACAAGTAC
AGATACCTTTTCAAGCAAGTGGCAAGTTCAACAGGATTTTGTGACCAGCGCAGGCTGGGCCTCCTTCTGCATGATTC
TATCCAAATTCCAAGACAGTTGGGTGAAGTTGCATCCTTTGGGGGCAGTAACATTGAGCCAAGTGTCCGGAGCTGCT
TCCAATTTGCTAATAATAAGCCAGAGATCGAAGCGGCCCTCTTCCTAGACTGGATGAGACTGGAACCCCAGTCCATG
GTGTGGCTGCCCGTCCTGCACAGAGTGGCTGCTGCAGAAACTGCCAAGCATCAGGCCAAATGTAACATCTGCAAAGA
GTGTCCAATCATTGGATTCAGGTACAGGAGTCTAAAGCACTTTAATTATGACATCTGCCAAAGCTGCTTTTTTTCTG
GTCGAGTTGCAAAAGGCCATAAAATGCACTATCCCATGGTGGAATATTGCACTCCGACTACATCAGGAGAAGATGTT
CGAGACTTTGCCAAGGTACTAAAAAACAAATTTCGAACCAAAAGGTATTTTGCGAAGCATCCCCGAATGGGCTACCT
GCCAGTGCAGACTGTCTTAGAGGGGGACAACATGGAAACTGACACAATGTAG

FIG. 25

SEQ ID NO: 5: AV.CMV..ΔR2-15/ΔR18-23/ΔC (This AAV vector contains four repeats and two hinges. It carries both R16 and R17 and it can restore nNOS)

CATTAATGAATCGGCCAACGCGCGGGGAGAGGCGGTTTGCGTATTGGGCGCTCTTCCGCTTCCTCGCTCACTGACTC
GCTGCGCTCGGTCGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACCGTAAAAAGGCCGCGTTGCTGGCG
TTTTTCCATAGGCTCCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCTGACAGTTACCAATGC
TTAATCAGTGAGGCACCTATCTCAGCGATCTGTCTATTTCGTTCATCCATAGTTGCCTGACTCCCCGTCGTGTAGAT
AACTACGATACGGGAGGGCTTACCATCTGGCCCCAGTGCTGCAATGATACCGCGAGACCCACGCTGACCGGCTCCAG
ATTTATCAGCAATAAACCAGCCAGCCGGAAGGGCCGAGCGCAGAAGTGGTCCTGCAAGTTTATCCGCCTCCATCCAG
TGTATTAATTGTTGCCGGGAAGCTAGAGTAAGTAGTTCGCCAGTTAATAGTTTGCGCAACGTTGTTGCCATTGCTAC
AGGCATCGTGGTGTCAGGCTCGTCGTTTGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATCGTTGTCAGAAGTAAGTTGGCCGCAGTG
TTATCACTCATGGTTATGGCAGCACTGCATAATTCTCTTACTGTCATGCCATCCGTAAGATGCTTTTCTGTGACTGG
TGAGTACTCAACCAAGTCATTCTGAGAATAGTGTATGCGGCGACCGAGTTGCTCTTGCCCGGCGTCAATACGGGATA
ATACCGCGCCACATAGCAGAACTTTAAAAGTGCTCATCATTGGAAAACGTTCTTCGGGGCGAAAACTCTCAAGGATC
TTACCGCTGTTGAGATCCAGTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGCGACACGGAAATGTTGATACTC
ATACTCTTCCTTTTTCAATATTATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCACCTGACGTCTAAGAAACCATTATTA
TCATGACATTAACCTATAAAAATAGGCGTATCACGAGGCCCTTTCGTCTCGCGCGTTTCGGTGATGACGGTGAAAAG
CTCTGACACATGCAGCTCCCGGAGACGGTCACAGCTTGTCTGTAAGCGGATGCCGGGAGCAGACAAGCCCGTCAGGG
CGCGTCAGCGGGTGTTGGCGGGTGTCGGGGCTGGCTTAACTATGCGGCATCAGAGCAGATTGTACTGAGAGTGCACC
ATATGCGGTGTGAAATACCGCACAGATGCGTAAGGAGAAAATACCGCATCAGGAATTCCAACATCCAATAAATCATA
CAGGCAAGGCAAAGAATTAGCAAAATTAAGCAATAAAGCCTCAGAGCATAAAGCTAAATCGGTTGTACCAAAAACAT
TATGACCCTGTAATACTTTTGCGGGAGAAGCCTTTATTTCAACGCAAGGATAAAAATTTTTAGAACCCTCATATATT
TTAAATGCAATGCCTGAGTAATGTGTAGGTAAAGATTCAAACGGGTGAGAAAGGCCGGAGACAGTCAAATCACCATC
AATATGATATTCAACCGTTCTAGCTGATAAATTCATGCCGGAGAGGGTAGCTATTTTTGAGAGGTCTCTACAAAGGC
TATCAGGTCATTGCCTGAGAGTCTGGAGCAAACAAGAGAATCGATGAACGGTAATCGTAAAACTAGCATGTCAATCA
TATGTACCCCGGTTGATAATCAGAAAAGCCCCAAAAACAGGAAGATTGTATAAGCAAATATTTAAATTGTAAACGTT
AATATTTTGTTAAAATTCGCGTTAAATTTTTGTAAATCAGCTCATTTTTTAACCAATAGGCCGAAATCGGCAAAATC
CCTTATAAATCAAAAGAATAGACCGAGATAGGGTTGAGTGTTGTTCCAGTTTGGAACAAGAGTCCACTATTAAAGAA
CGTGGACTCCAACGTCAAAGGGCGAAAAACCGTCTATCAGGGCGATGGCCCACTACGTGAACCATCACCCTAATCAA
GTTTTTTGGGGTCGAGGTGCCGTAAAGCACTAAATCGGAACCCTAAAGGGAGCCCCCGATTTAGAGCTTGACGGGGA
AAGCCGGCGAACGTGGCGAGAAAGGAAGGGAAGAAAGCGAAAGGAGCGGGCGCTAGGGCGCTGGCAAGTGTAGCGGT
CACGCTGCGCGTAACCACCACACCCGCCGCGCTTAATGCGCCGCTACAGGGCGCGTACTATGGTTGCTTTGACGAGC
AGGTATAACGTGCTTTCCTCGTTAGAATCAGAGCGGGAGCTAAACAGGAGGCCGATTAAAGGGATTTTAGACAGGAA
CGGTACGCCAGAATCCTGAGAAGTGTTTTTATAATCAGTGAGGCCACCGAGTAAAAGAGTCTGTCGATCACGCAAAT
TAACCGTTGTCGCAATACTTCTTTGATTAGTAATAACATCACTTGCCTGAGTAGAAGAACTCAAACTATCGGCCTTG
CTGGTAATATCCAGAACAATATTACCGCCAGCCATTGCAAGAGGAAAAACGCTCATGGAAATACCTACATTTTGACG
CTCAATCGTCTGGAATTCCATTCGCCATTCAGGCTGCGCAACTGTTGGGAAGGGCGATCGGTGCGGGCCTCTTCGCT
ATTACGCCAGCTGGCGCGCTCGCTCGCTCACTGAGGCCGCCCGGGCAAAGCCCGGGCGTCGGGCGACCTTTGGTCGC
CCGGCCTCAGTGAGCGAGCGAGCGCGCAGAGAGGGAGTGGCCAACTCCATCACTAGGGGTTCCTTGTAGTTAATGAT
TAACCCGCCATGCTACTTATCTACGGCCGCGGTACCGCGTTACATAACTTACGGTAAATGGCCCGCCTGGCTGACCG
CCCAACGACCCCCGCCCATTGACGTCAATAATGACGTATGTTCGCATAGTAACGCCAATAGGGACTTTCCATTGACG

FIG. 25 (cont'd)

TCAATGGGTGGAGTATTTACGGTAAACTGCCCACTTGGCAGTACATCAAGTGTATCATATGCCAAGTACGCCCCCTA
TTGACGTCAATGACGGTAAATGGCCCGCCTGGCATTATGCCCAGTACATGACCTTATGGGACTTTCCTACTTGGCAG
TACATCTACGTATTAGTCATCGCTATTACCATGGTGATGCGGTTTTGGCAGTACATCAATGGGCGTGGATAGCGGTT
TGACTCACGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTATATAAGC
AGAGCTCGTTTAGTGAACCGTCTAGACGGCCGCGGTTTTTTTATCGCTGCCTTGATATACACTTTCCACCATGCTT
TGGTGGGAAGAAGTAGAGGACTGTTATGAAAGAGAAGATGTTCAAAAGAAAACATTCACAAAATGGGTAAATGCACA
ATTTTCTAAGTTTGGGAAGCAGCATATTGAGAACCTCTTCAGTGACCTACAGGATGGGAGGGGCCTCCTAGACCTCC
TCGAAGGCCTGACAGGGCAAAAACTGCCAAAAGAAAAAGGATCCACAAGAGTTCATGCCCTGAACAATGTCAACAAG
GCACTGCGGGTTTTGCAGAACAATAATGTTGATTTAGTGAATATTGGAAGTACTGACATCGTAGATGGAAATCATAA
ACTGACTCTTGGTTTGATTTGGAATATAATCCTCCACTGGCAGGTCAAAAATGTAATGAAAAATATCATGGCTGGAT
TGCAACAAACCAACAGTGAAAAGATTCTCCTGAGCTGGGTCCGACAATCAACTCGTAATTATCCACAGGTTAATGTA
ATCAACTTCACCACCAGCTGGTCTGATGGCCTGGCTTTGAATGCTCTCATCCATAGTCATAGGCCAGACCTATTTGA
CTGGAATAGTGTGGTTTGCCAGCAGTCAGCCACACAACGACTGGAACATGCATTCAACATCGCCAGATATCAATTAG
GCATAGAGAAACTACTCGATCCTGAAGATGTTGATACCACCTATCCAGATAAGAAGTCCATCTTAATGTACATCACA
TCACTCTTCCAAGTTTTGCCTCAACAAGTGAGCATTGAAGCCATCCAGGAAGTGGAAATGTTGCCAAGGCCACCTAA
AGTGACTAAAGAAGAACATTTTCAGTTACATCATCAAATGCACTATTCTCAACAGATCACGGTCAGTCTAGCACAGG
GATATGAGAGAACTTCTTCCCCTAAGCCTCGATTCAAGAGCTATGCCTACACACAGGCTGCTTATGTCACCACCTCT
GACCCTACACGGAGCCCATTTCCTTCACAGCATTTGGAAGCTCCTGAAGACAAGTCATTTGGCAGTTCATTGATGGA
GAGTGAAGTAAACCTGGACCGTTATCAAACAGCTTTAGAAGAAGTATTATCGTGGCTTCTTTCTGCTGAGGACACAT
TGCAAGCACAAGGAGAGATTTCTAATGATGTGGAAGTGGTGAAAGACCAGTTTCATACTCATGAGGGGTACATGATG
GATTTGACAGCGCATCAGGGCCGGGTTGGTAATATTCTACAATTGGGAAGTAAGCTGATTGGAACAGGAAAATTATC
AGAAGATGAAGAAACTGAAGTACAAGAGCAGATGAATCTCCTAAATTCAAGATGGGAATGCCTCAGGGTAGCTAGCA
TGGAAAAACAAAGCAATTTACATAGAGAAATTTCTTATGTGCCTTCTACTTATTTGACTGAAATCACTCATGTCTCA
CAAGCCCTATTAGAAGTGGAACAACTTCTCAATGCTCCTGACCTCTGTGCTAAGGACTTTGAAGATCTCTTTAAGCA
AGAGGAGTCTCTGAAGAATATAAAAGATAGTCTACAACAAAGCTCAGGTCGGATTGACATTATTCATAGCAAGAAGA
CAGCAGCATTGCAAAGTGCAACGCCTGTGGAAAGGGTGAAGCTACAGGAAGCTCTCTCCGAGCTTGATTTCCAATGG
GAAAAAGTTAACAAAATGTACAAGGACCGACAAGGGCGATTTGACAGATCTGTTGAGAAATGGCGGCGTTTTCATTA
TGATATAAAGATATTTAATCAGTGGCTAACAGAAGCTGAACAGTTTCTCAGAAAGAGACAAATTCCTGAGAATTGGG
AACATGCTAAATACAAATGGTATCTTAAGGAACTCCAGGATGGCATTGGGCAGCGGCAAACTGTTGTCAGAACATTG
AATGCAACTGGGGAAGAAATAATTCAGCAATCCTCAAAAACAGATGCCAGTATTCTACAGGAAAAATTGGGAAGCCT
GAATCTGCGGTGGCAGGAGGTCTGCAAACAGCTGTCAGACAGAAAAAAGAGGCTAGAAGAAACCCTTGAAAGACTCC
AGGAACTTCAAGAGGCCACGGATGAGGTGGACCTCAAGCTGCGCCAAGCTGAGGTGATCAAGGGATCCTGGCAGCCC
GTGGGCGATCTCCTCATTGACTCTCTCCAAGATCACCTCGAGAAAGTCAAGGCACTTCGAGGAGAAATTGCGCCTCT
GAAAGAGAACGTGAGCCACGTCAATGACCTTGCTCGCCAGCTTACCACTTTGGGCATTCAGCTCTCACCGTATAACC
TCAGCACTCTGGAAGACCTGAACACCAGATGGAAGCTTCTGCAGGTGGCCGTCGAGGACCGAGTCAGGCAGCTGCAT
GAAGCCCACAGGGACTTTGGTCCAGCATCTCAGCACTTTCTTTCCACGTCTGTCCAGGGTCCCTGGGAGAGAGCCAT
CTCGCCAAACAAAGTGCCCTACTATATCAACCACGAGACTCAAACAACTTGCTGGGACCATCCCAAAATGACAGAGC
TCTACCAGTCTTTAGCTGACCTGAATAATGTCAGATTCTCAGCTTATAGGACTGCCATGAAACTCCGAAGACTGCAG
AAGGCCCTTTGCTTGGATCTCTTGAGCCTGTCAGCTGCATGTGATGCCTTGGACCAGCACAACCTCAAGCAAAATGA
CCAGCCCATGGATATCCTGCAGATTATTAATTGTTTGACCACTATTTATGACCGCCTGGAGCAAGAGCACAACAATT
TGGTCAACGTCCCTCTCTGCGTGGATATGTGTCTGAACTGGCTGCTGAATGTTTATGATACGGGACGAACAGGGAGG
ATCCGTGTCCTGTCTTTTAAAACTGGCATCATTTCCCTGTGTAAAGCACATTTGGAAGACAAGTACAGATACCTTTT
CAAGCAAGTGGCAAGTTCAACAGGATTTTGTGACCAGCGCAGGCTGGGCCTCCTTCTGCATGATTCTATCCAAATTC
CAAGACAGTTGGGTGAAGTTGCATCCTTTGGGGGCAGTAACATTGAGCCAAGTGTCCGGAGCTGCTTCCAATTTGCT
AATAATAAGCCAGAGATCGAAGCGGCCCTCTTCCTAGACTGGATGAGACTGGAACCCCAGTCCATGGTGTGGCTGCC
CGTCCTGCACAGAGTGGCTGCTGCAGAAACTGCCAAGCATCAGGCCAAATGTAACATCTGCAAAGAGTGTCCAATCA
TTGGATTCAGGTACAGGAGTCTAAAGCACTTTAATTATGACATCTGCCAAAGCTGCTTTTTTTCTGGTCGAGTTGCA
AAAGGCCATAAAATGCACTATCCCATGGTGGAATATTGCACTCCGACTACATCAGGAGAAGATGTTCGAGACTTTGC
CAAGGTACTAAAAAACAAATTTCGAACCAAAAGGTATTTTGCGAAGCATCCCCGAATGGGCTACCTGCCAGTGCAGA
CTGTCTTAGAGGGGGACAACATGGAAACTGACACAATGTAGGAAGTCTTTTCCACATGGCAGATGATTTGGGCAGAG
CGATGGAGTCCTTAGTATCAGTCATGACAGATGAAGAAGGAGCAGAATAAATGTTTTACAACTCCTGATTCCCGCAT
GCGGCCGATCCAGACATGATAAGATACATTGATGAGTTTGGACAAACCACAACTAGAATGCAGTGAAAAAAATGCTT
TATTTGTGAAATTTGTGATGCTATTGCTTTATTTGTAACCATTATAAGCTGCAATAAACAAGTTAACAACAACATT

FIG. 25 (cont'd)

GCATTCATTTTATGTTTCAGGTTCAGGGGGAGGTGTGGGAGGTTTTTTGCGGCCGTAGATAAGTAGCATGGCGGGTT
AATCATTAACTACAAGGAACCCCTAGTGATGGAGTTGGCCACTCCCTCTCTGCGCGCTCGCTCGCTCACTGAGGCCG
GGCGACCAAAGGTCGCCCGACGCCCGGGCTTTGCCCGGGCGGCCTCAGTGAGCGAGCGAGCGCGCAGCTGCTG

FIG. 26

SEQ ID NO: 6: Nucleotide sequence of human dystrophin spectrin-like repeats 16 and 17 (R16/R17)

ATTCACACTGTCCGTGAAGAAACGATGATGGTGATGACTGAAGACATGCCTTTGGAAATTTCTTATGTGCCTTCTAC
TTATTTGACTGAAATCACTCATGTCTCACAAGCCCTATTAGAAGTGGAACAACTTCTCAATGCTCCTGACCTCTGTG
CTAAGGACTTTGAAGATCTCTTTAAGCAAGAGGAGTCTCTGAAGAATATAAAAGATAGTCTACAACAAAGCTCAGGT
CGGATTGACATTATTCATAGCAAGAAGACAGCAGCATTGCAAAGTGCAACGCCTGTGGAAAGGGTGAAGCTACAGGA
AGCTCTCTCCCAGCTTGATTTCCAATGGGAAAAAGTTAACAAAATGTACAAGGACCGACAAGGGCGATTTGACAGAT
CTGTTGAGAAATGGCGGCGTTTTCATTATGATATAAAGATATTTAATCAGTGGCTAACAGAAGCTGAACAGTTTCTC
AGAAAGACACAAATTCCTGAGAATTGGGAACATGCTAAATACAAATGGTATCTTAAGGAACTCCAGGATGGCATTGG
GCAGCGGCAAACTGTTGTCAGAACATTGAATGCAACTGGGGAAGAAATAATTCAGCAATCCTCAAAAACAGATGCCA
GTATTCTACAGGAAAAATTGGGAAGCCTGAATCTGCGGTGGCAGGAGGTCTGCAAACAGCTGTCAGACAGAAAAAAG
AGGCTAGAAGAA

SEQ ID NO: 7: Amino acid sequence of human dystrophin spectrin-like repeats 16 and 17 (R16/R17)

EISYVPSTYLTEITHVSQALLEVEQLLNAPDLCAKDFEDLFKQEESLKNIKDSLQQSSGRIDIIHSKKTAALQSATP
VERVKLQEALSQLDFQWEKVNKMYKDRQGRFDRSVEKWRRFHYDIKIFNQWLTEAEQFLRKTQIPENWEHAKYKWYL
KELQDGIGQRQTVVRTLNATGEEIIQQSSKTDASILQEKLGSLNLRWQEVCKQLSDRKKRLEE

FIG. 27

SEQ ID NO: 8: Full-length dystrophin nucleotide sequence (The full-length gene carries R16 and R17. It can restore nNOS)

ATGCTTTGGTGGGAAGAAGTAGAGGACTGTTATGAAAGAGAAGATGTTCAAAAGAAAACATTCACAAAATGGGTAAA
TGCACAATTTTCTAAGTTTGGGAAGCAGCATATTGAGAACCTCTTCAGTGACCTACAGGATGGGAGGCGCCTCCTAG
ACCTCCTCGAAGGCCTGACAGGGCAAAAACTGCCAAAAGAAAAAGGATCCACAAGAGTTCATGCCCTGAACAATGTC
AACAAGGCACTGCGGGTTTTGCAGAACAATAATGTTGATTTAGTGAATATTGGAAGTACTGACATCGTAGATGGAAA
TCATAAACTGACTCTTGGTTTGATTTGGAATATAATCCTCCACTGGCAGGTCAAAAATGTAATGAAAAATATCATGG
CTGGATTGCAACAAACCAACAGTGAAAAGATTCTCCTGAGCTGGGTCCGACAATCAACTCGTAATTATCCACAGGTT
AATGTAATCAACTTCACCACCAGCTGGTCTGATGGCCTGGCTTTGAATGCTCTCATCCATAGTCATAGGCCAGACCT
ATTTGACTGGAATAGTGTGGTTTGCCAGCAGTCAGCCACACAACGACTGGAACATGCATTCAACATCGCCAGATATC
AATTAGGCATAGAGAAACTACTCGATCCTGAAGATGTTGATACCACCTATCCAGATAAGAAGTCCATCTTAATGTAC
ATCACATCACTCTTCCAAGTTTTGCCTCAACAAGTGAGCATTGAAGCCATCCAGGAAGTGGAAATGTTGCCAAGGCC
ACCTAAAGTGACTAAAGAAGAACATTTTCAGTTACATCATCAAATGCACTATTCTCAACAGATCACGGTCAGTCTAG
CACAGGGATATGAGAGAACTTCTTCCCCTAAGCCTCGATTCAAGAGCTATGCCTACACACAGGCTGCTTATGTCACC
ACCTCTGACCCTACACGGAGCCCATTTCCTTCACAGCATTTGGAAGCTCCTGAAGACAAGTCATTTGGCAGTTCATT
GATGGAGAGTGAAGTAAACCTGGACCGTTATCAAACAGCTTTAGAAGAAGTATTATCGTGGCTTCTTTCTGCTGAGG
ACACATTTGCAAGCACAAGGAGAGATTCTAATGATGTGGAAGTGGTGAAAGACCAGTTTCATACTCATGAGGGGTAC
ATGATGGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAGGGTAG
CTAGCATGGAAAAACAAAGCAATTTACATAGAGTTTTAATGGATCTCCAGAATCAGAAACTGAAAGAGTTGAATGAC
TGGCTAACAAAAACAGAAGAAAGAACAAGGAAAATGGAGGAAGAGCCTCTTGGACCTGATCTTGAAGACCTAAAACG
CCAAGTACAACAACATAAGGTGCTTCAAGAAGATCTAGAACAAGAACAAGTCAGGGTCAATTTCTCTCACTCACATG
GTGGTGGTAGTTGATGAATGTAGTGGAGATCACGCAACTGCTGCTTTGGAAGAACAACTTAAGGTATTGGGAGATCG
ATGGGCAAACATCTGTAGATGGACAGAAGACCGCTGGGTTCTTTTACAAGACATCCTTCTCAAATGGCAACGTCTTA
CTGAAGAACAGTGCCTTTTTAGTGCATGGCTTTCAGAAAAAGAAGATGCAGTGAACAAGATTCACACAACTGGCTTT
AAAGATCAAAATGAAATGTTATCAAGTCTTCAAAAACTGGCCGTTTTAAAAGCGGATCTAGAAAAGAAAAAGCAATC
CATGGGCAAACTGTATTCACTCAAACAAGATCTTCTTTCAACACTGAAGAATAAGTCAGTGACCCAGAAGACGGAAG
CATGGCTGGATAACTTTGCCCGGTGTTGGGATAATTTAGTCCAAAAACTTGAAAAGAGTACAGCACAGATTTCACAG
GCTGTCACCACCACTCAGCCATCACTAACACAGACAACTGTAATGGAAACAGTAACTACGGTGACCACAAGGGAACA
GATCCTGGTAAAGCATGCTCAAGAGGAACTTCCACCACCACCTCCCCAAAAGAAGAGGCAGATTACTGTGGATTCTG
AAATTTAGGAAAAGGTTGGATGTTGATATAACTGAACTTCACAGCTGGATTACTCGCTCAGAAGCTGTGTTGCAGAG
TCCTGAATTTGCAATCTTTCGGAAGGAAGGCAACTTCTCAGACTTAAAAGAAAAAGTCAATGCCATAGAGCGAGAAA
AAGCTGAGAAGTTCAGAAAACTGCAAGATGCCAGCAGATCAGCTCAGGCCCTGGTGGAACAGATGGTGAATGAGGGT
GTTAATGCAGATAGCATCAAACAAGCCTCAGAACAACTGAACAGCCGGTGGATCGAATTCTGCCAGTTGCTAAGTGA
GAGACTTAACTGGCTGGAGTATCAGAACAACATCATCGCTTTCTATAATCAGCTACAACAATTGGAGCAGATGACAA
CTACTGCTGAAAACTGGTTGAAAATCCAACCCACCACCCCATCAGAGCCAACAGCAATTAAAAGTCAGTTAAAAATT
TGTAAGGATGAAGTCAACCGGCTATCAGGTCTTCAACCTCAAATTGAACGATTAAAAATTCAAAGCATAGCCCTGAA
AGAGAAAGGACAAGGACCCATGTTCCTGGATGCAGACTTTGTGGCCTTTACAAATCATTTTAAGCAAGTCTTTTCTG
ATGTGCAGGCCAGAGAGAAAGAGCTACAGACAATTTTTGACACTTTGCCACCAATGCGCTATCAGGAGACCATGAGT
GCCATCAGGACATGGGTCCAGCAGTCAGAAACCAAACTCTCCATAGCTCAACTTAGTGTCACCGACTATGAAATCAT
GGAGCAGAGACTCGGGGAATTGCAGGCTTTACAAAGTTCTCTGCAAGAGCAACAAAGTGGCCTATACTATCTCAGCA
CCACTGTGAAAGAGATGTCGAAGAAAGCGCCCTCTGAAATTAGCCGGAAATATCAATCAGAATTTGAAGAAATTGAG
GGACGCTGGAAGAAGCTCTCCTCCCAGCTGGTTGAGCATTTGTCAAAAGCTAGAGGAGCAAATGAATAAACTCCGAA
AAATTCAGAATCACATACAAACCCTGAAGAAATGGATGGCTGAAGTTGATGTTTTTCTGAAGGAGGAATGGCCTGCC
CTTGGGGATTCAGAAATTCTAAAAAAGCAGCTGAAACAGTGCAGACTTTTAGTCAGTGATATTCAGACAATTCAGCC
CAGTCTAAACAGTGTCAATGAAGGTGGGCAGAAGATAAAGAATGAAGCAGAGCCAGAGTTTGCTTCGAGACTTGAGA
CAGAACTCAAAGAACTTAACACTCAGTGGGATCACATGTGCCAACAGGTCTATGCCAGAAAGGAGGCCTTGAAGGGA
GGTTTGGAGAAAACTGTAAGCCTCCAGAAAGATCTATCAGAGATGCACGAATGGATGACACAAGCTGAAGAAGAGTA
TCTTGAGAGAGATTTTGAATATAAAACTCCAGATGAATTACAGAAAGCAGTTGAAGAGATGAAGAGAGCTAAAGAAG
AGGCCCAACAAAAAGAAGCGAAAGTGAAACTCCTTACTGAGTCTGTAAATAGTGTCATAGCTCAAGCTCCACCTGTA
GCACAAGAGGCCTTAAAAAAGGAACTTGAAACTCTAACCACCAACTACCAGTGGCTCTGCACTAGGCTGAATGGGAA
ATGCAAGACTTTGGAAGAAGTTTGGGCATGTTGGCATGAGTTATTGTCATACTTGGAGAAAGCAAACAAGTGGCTAA

FIG. 27 (cont'd)

ATGAAGTAGAATTTAAACTTAAAACCACTGAAAACATTCCTGGCGGAGCTGAGGAAATCTCTGAGGTGCTAGATTCA
CTTGAAAATTTGATGCGACATTCAGAGGATAACCCAAATCAGATTCGCATATTGGCACAGACCCTAACAGATGGCGG
AGTCATGGATGAGCTAATCAATGAGGAACTTGAGACATTTAATTCTCGTTGGAGGGAACTACATGAAGAGGCTGTAA
GGAGGCAAAAGTTGCTTGAACAGAGCATCCAGTCTGCCCAGGAGACTGAAAAATCCTTACACTTAATCCAGGAGTCC
CTCACATTCATTGACAAGCAGTTGGCAGCTTATATTGCAGACAAGGTGGACGCAGCTCAAATGCCTCAGGAAGCCCA
GAAAATCCAATCTGATTTGACAAGTCATGAGATCAGTTTAGAAGAAATGAAGAAACATAATCAGGGGAAGGAGGCTG
CCCAAAGAGTCCTGTCTCAGATTGATGTTGCACAGAAAAAATTACAAGATGTCTCCATGAAGTTTCGATTATTCCAG
AAACCAGCCAATTTGAGCTGCGTCTAGAAGAAAGTAAGATGATTTTAGATGAAGTGAAGATGCACTTGCCTGCATTG
GAAACAAAGAGTGTGGAACAGGAAGTAGTACAGTCACAGCTAAATCATTGTGTGAACTTGTATAAAAGTCTGAGTGA
AGTGAAGTCTGAAGTGGAAATGGTGATAAAGACTGGACGTCAGATTGTACAGAAAAAGCAGACGGAAAATCCCAAAG
AACTTGATGAAAGAGTAACAGCTTTGAAATTGCATTATAATGAGCTGGGAGCAAAGGTAACAGAAAGAAAGCAACAG
TTGGAGAAATGCTTGAAATTGTCCCGTAAGATGCGAAAGGAAATGAATGTCTTGACAGAATGGCTGGCAGCTACAGA
TATGGAATTGACAAAGAGATCAGCAGTTGAAGGAATGCCTAGTAATTTGGATTCTGAAGTTGCCTGGGGAAAGGCTA
CTCAAAAAGAGATTGAGAAACAGAAGGTGCACCTGAAGAGTATCACAGAGGTAGGAGAGGCCTTGAAAACAGTTTTG
GGCAAGAAGGAGACGTTGGTGGAAGATAAACTCAGTCTTCTGAATAGTAACTGGATAGCTGTCACCTCCCGAGCAGA
AGAGTGGTTAAATCTTTTGTTGGAATACCAGAAACACATGGAAACTTTTGACCAGAATGTGGACCACATCACAAAGT
GGATCATTCAGGCTGACACACTTTTGGATGAATCAGAGAAAAAGAAACCCCAGCAAAAAGAAGACGTGCTTAAGCGT
TTAAAGGCAGAACTGAATGACATACGCCCAAAGGTGGACTCTACACGTGACCAAGCAGCAAACTTGATGGCAAACCG
CGGTGACCACTGCAGGAAATTAGTAGAGCCCCAAATCTCAGAGCTCAACCATCGATTTGCAGCCATTTCACACAGAA
TTAAGACTGGAAAGGCCTCCATTCCTTTGAAGGAATGGAGCAGTTTAACTCAGATATACAAAAATTGCTTGAACCAC
TGGAGGCTGAAATTCAGCAGGGGGTGAATCTGAAAGAGGAAGAGTTCAATAAAGATATGAATGAAGACAATGAGGGT
ACTGTAAAAGAATTGTGCAAAGAGGAGACAACTTACAACAAAGAATCACAGATGAGAGAAAGAGAGAGGAAATAAAG
ATAAAACAGCAGCTGTTACAGACAAAACATAATGCTCTCAAGGATTTGAGGTCTCAAAGAAGAAAAAAGGCTCTAGA
AATTTCTCATCAGTGGTATCAGTACAAGAGGCAGGCTGATGATCTCCTGAAATGCTTGGATGACATTGAAAAAAAAT
TAGCCAGCCTACCTGAGCCCAGAGATGAAAGGAAAATAAAGGAAATTGATCGGGAATTGCAGAAGAAGAAAGAGGAG
CTGAATGCAGTGCGTAGGCAAGCTGAGGGCTTGTCTGAGGATGGGGCCGCAATGGCAGTGGAGCCAACTCAGATCCA
GCTCAGCAAGCGCTGGCGGGAAATTGAGAGCAAATTTGCTCAGTTTCGAAGACTCAACTTTGCACAAATTCACACTG
TCCGTGAAGAAACGATGATGGTGATGACTGAAGACATGCCTTTGGAAATTTCTTATGTGCCTTCTACTTATTTGACT
GAAATCACTCATGTCTCACAAGCCCTATTAGAAGTGGAACAACTTCTCAATGCTCCTGACCTCTGTGCTAAGGACTT
TGAAGATCTCTTTAAGCAAGAGGAGTCTCTGAAGAATATAAAAGATAGTCTACAACAAAGCTCAGGTCGGATTGACA
TTATTCATAGCAAGAAGACAGCAGCATTGCAAAGTGCAACGCCTGTGGAAAGGGTGAAGCTACAGGAAGCTCTCTCC
CAGCTTGATTTCCAATGGGAAAAAGTTAACAAAATGTACAAGGACCGACAAGGGCGATTTGACAGATCTGTTGAGAA
ATGGCGGCGTTTTCATTATGATATAAAGATATTTAATCAGTGGCTAACAGAAGCTGAACAGTTTCTCAGAAAGACAC
AAATTCCTGAGAATTGGGAACATGCTAAATACAAATGGTATCTTAAGGAACTCCAGGATGGGATGGGCAGCGGCAAA
CTGTTGTCAGAACATTGAATGCAACTGGGGAAGAAATAATTCAGCAATCCTCAAAAACAGATGGCAGTATTCTACAG
GAAAAATTGGGAAGCCTGAATCTGCGGTGGCAGGAGGTCTGCAAACAGCTGTCAGACAGAAAAAAGAGGCTAGAAGA
ACAAAAGAATATCTTGTCAGAATTTCAAAGAGATTTAAATGAATTTGTTTTATGGTTGGAGGAAGCAGATAACATTG
CTAGTATCCCACTTGAACCTGGAAAAGAGCAGCAACTAAAAGAAAAGCTTGAGCAAGTCAAGTTACTGGTGGAAGAG
TTGCCCCTGCGCCAGGGAATTCTCAAACAATTAAATGAAACTGGAGGACCCGTGCTTGTAAGTGCTCCCATAAGCCC
AGAAGAGCAAGATAAACTTGAAAATAAGCTCAAGCAGACAAATCTCCAGTGGATAAAGGTTTCCAGAGCTTTACCTG
AGAAACAAGGAGAAATTTGAAGCTCAAATAAAAGACCTTGGGCAGCTTGAAAAAAAGCTTGAAGACCTTGAAGAGCA
GTTAAATCATCTGCTGCTGTGGTATCTCCTATTAGGAATCAGTTGGAAATTTATAACCAACCAAACCAAGAAGGACC
ATTTGACGTTCAGGAAACTGAAATAGCAGTTCAAGCTAAACAACCGGATGTGGAAGAGATTTTGTCTAAAGGGCAGC
ATTTGTACAAGGAAAAACCAGCCACTCAGCCAGTGAAGAGGAAGTTAGAAGATCTGAGCTCTGAGTGGAAGGCGGTA
AACCGTTTACTTCAAGAGCTGAGGGCAAAGCAGCCTGACCTAGCTCCTGGACTGACCACTATTGGAGCCTCTCCTAC
TCAGACTGTTACTCTGGTGACACAACCTGTGGTTACTAAGGAAACTGCCATCTCCAAACTAGAAATGCCATCTTCCT
TGATGTTGGAGGTACCTGCTCTGGCAGATTTCAACCGGGCTTGGACAGAACTTACCGACTGGCTTTCTCTGCTTGAT
CAAGTTATAAAATCACAGAGGGTGATGGTGGGTGACCTTGAGGATATCAACGAGATGATCATCAAGCAGAAGGCAAC
AATGCAGGATTTGGAACAGAGGCGTCCCCAGTTGGAAGAACTCATTACCGCTGCCCAAAATTTGAAAAACAAGACCA
GCAATCAAGAGGCTAGAACAATCATTACGGATCGAATTGAAAGAATTCAGAATCAGTGGGATGAAGTACAAGAACAC
CTTCAGAACCGGAGGCAACAGTTGAATGAAATGTTAAAGGATTCAACACAATGGCTGGAAGCTAAGGAAGAAGCTGA
GCAGGTCTTAGGACAGGCCAGAGCCAAGCTTGAGTCATGGAAGGAGGGTCCCTATACAGTAGATGCAATCCAAAAGA
AAATCACAGAAACCAAGCAGTTGGCCAAAGACCTCCGCCAGTGGCAGACAAATGTAGATGTGGCAAATGACTTGGCC
CTGAAACTTCTCCGGGATTATTCTGCAGATGATACCAGAAAAGTCCACATGATAACAGAGAATATCAATGCCTCTTG

FIG. 27 (cont'd)

GAGAAGCATTCATAAAAGGGTGAGTGAGCGAGAGGCTGCTTTGGAAGAAACTCATAGATTACTGCAACAGTTCCCCC
TGGACCTGGAAAAGTTTCTGCCTGGCTTACAGAAGCTGAAACAACTGCCAATGTCCTACAGGATGCTACCCGTAAGG
AAAGGCTCCTAGAAGACTCCAAGGGAGTAAAAGAGCTGATGAAACAATGGCAAGACCTCCAAGGTGAAATTGAAGCT
CACACAGATGTTTATCACAACCTGGATGAAAACAGCCAAAAAATCCTGAGATCCCTGGAAGGTTCCGATGATGCAGT
CCTGTTACAAAGACGTTTGGATAACATGAACTTCAAGTGGAGTGAACTTCGGAAAAAGTCTCTCAACATTAGGTCCC
ATTTGGAAGCCAGTTCTGACCAGTGGAAGCGTCTGCACCTTTCTCTGCAGGAACTTCTGGTGTGGCTACAGCTGAAA
GATGATGAATTAAGCCGGCAGGCACCTATTTGGAGGCGACTTTCCAGCAGTTCAGAAGCAGAACGATGTACATAGGG
CCTTCAAGAGGGAATTGAAAACTAAAGAACCTGTAATCATGAGTACTCTTGAGACTGTACGAATATTTCTGACAGAG
CAGCCTTTGGAAGGACTAGAGAAACTCTACCAGGAGCCCAGAGAGCTGCCTCCTGAGGAGAGAGCCCAGAATGTCAC
TCGGCTTCTACGAAAGCAGGCTGAGGAGGTCAATACTGAGTGGGAAAAATTGAACCTGCACTCCGCTGACTGGCAGA
GAAAAATAGATGAGACCCTTGAAAGACTCCAGGAACTTCAAGAGGCCACGGATGAGCTGGACCTCAAGCTGCGCCAA
GCTGAGGTGATCAAGGGATCCTGGCAGCCCGTGGGCGATCTCCTCATTGACTCTCTCCAAGATCACCTCGAGAAAGT
CAAGGCACTTCGAGGAGAAATTGCGCCTCTGAAAGAGAACGTGAGCCACGTCAATGACCTTGCTCGCCAGCTTACCA
CTTTGGGCATTCAGCTCTCACCGTATAACCTCAGCACTCTGGAAGACCTGAACACCAGATGGAAGCTTCTGCAGGTG
GCCGTCGAGGACCGAGTCAGGCAGCTGCATGAAGCCCACAGGGACTTTGGTCCAGCATCTCAGCACTTTCTTTCCAC
GTCTGTCCAGGGTCCCTGGGAGAGAGCCATCTCGCCAAACAAAGTGCCCTACTATATCAACCACGAGACTGAAACAA
CTTGCTGGGACCATCCCAAAATGACAGAGCTCTACCAGTCTTTAGCTGACCTGAATAATGTCAGATTCTCAGCTTAT
AGGACTGCCATGAAACTCCGAAGACTGCAGAAGGCCCTTTGCTTGGATCTCTTGAGCCTGTCAGCTGCATGTGATGC
CTTGGACGAGCACAACCTCAAGCAAAATGACCAGCCCATGGATATCCTGCAGATTATTAATTGTTTGACCACTATTT
ATGACCGCCTGGAGCAAGAGCACAACAATTTGGTCAACGTCCCTCTCTGCGTGGATATGTGTCTGAACTGGCTGCTG
AATGTTTATGATACGGGACGAACAGGGAGGATCCGTGTCCTGTCTTTTAAAACTGGCATCATTTCCCTGTGTAAAGC
ACATTTGGAAGACAAGTACAGATACCTTTTCAAGCAAGTGGCAAGTTCAACAGGATTTTGTGACCAGCGCAGGCTGG
GCCTCCTTCTGCATGATTCTATCCAAATTCCAAGACAGTTGGGTGAAGTTGCATCCTTTGGGGGCAGTAACATTGAG
CCAAGTGTCCGGAGCTGCTTCCAATTTGCTAATAATAAGCCAGAGATCGAAGCGGCCCTCTTCCTAGACTGGATGAG
ACTGGAACCCCAGTCCATGGTGTGGCTGCCCGTCCTGCACAGAGTGGCTGCTGCAGAAACTGCCAAGCATCAGGCCA
AATGTAACATCTGCAAAGAGTGTCCAATCATTTGGATTCAGGTACAGGAGTCTAAAGCACTTTAATTATGACATCTG
CCAAAGCTGCTTTTTTTCTGGTCGAGTTGCAAAAGGCCATAAAATGCACTATCCCATGGTGGAATATTGCACTCCGA
CTACATCAGGAGAAGATGTTCGAGACTTTGCCAAGGTACTAAAAAACAAATTTCGAACCAAAAGGTATTTTGCGAAG
CATCCCCGAATGGGCTACCTGCCAGTGCAGACTGTCTTAGAGGGGGACAACATGGAAACTCCCGTTACTCTGATCAA
CTTCTGGCCAGTAGATTCTGCGCCTGCCTCGTCCCCTCAGCTTTCACACGATGATACTCATTCACGCATTGAACATT
ATGCTAGCAGGCTAGCAGAAATGGAAAACAGCAATGGATCTTATCTAAATGATAGCATCTCTCCTAATGAGAGCATA
GATGATGAACATTTGTTAATCCAGCATTACTGCCAAAGTTTGAACCAGGACTCCCCCCTGAGCCAGCCTCGTAGTCC
TGCCCAGATCTTGATTCCTTAGAGAGTGAGGAAAGAGGGGAGCTAGAGAGAATCCTAGCAGATCTTGAGGAAGAAAA
CAGGAATCTGCAAGGAGAATATGACCGTCTAAAGCAGCAGCACGAACATAAAGGCCTGTCCCCACTGCCGTCCCCTC
CTGAAATGATGCCCACCTGTCCCCAGAGTCCCCGGGATGCTGAGCTCATTGCTGAGGCCAAGCTACTGCGTCAACAC
AAAGGCCGCCTGGAAGCCAGGATGCAAATCCTGGAAGACCACAATAAACAGCTGGAGTCACAGTTACACAGGCTAAG
GCAGCTGCTGGAGCAACCCCAGGCAGAGGCCAAAGTGAATGGCACAACGGTGTCCTCTCCTTCTACCTCTCTACAGA
GGTCCGACAGCAGTCAGCCTATGCTGCTCCGAGTGGTTGGCAGTCAAACTTCGGACTCCATGGGTGAGGAAGATCTT
CTCAGTCCTCCCCAGGACACAAGCACAGGGTTAGAGGAGGTGATGGAGCAACTCAACAACTCCTTCCCTAGTTCAAG
AGGAAGAAATACCCCTGGAAAGCCAATGAGAGAGGACACAATGTAG

FIG. 28

SEQ ID NO: 9: Full-length human dystrophin amino acid sequence

MLWWEEVEDCYEREDVQKKTFTKWVNAQFSKFGKQHIENLFSDLQDGRRLLDLLEGLTGQKLPKEKGSTRVHALNNV
NKALRVLQNNNVDLVNIGSTDIVDGNHKLTLGLIWNIILHWQVKNVMKNIMAGLQQTNSEKILLSWVRQSTRNYPQV
NVINFTTSWSDGLALNALIHSHRPDLFDWNSVVCQQSATQRLEHAFNIARYQLGIEKLLDPEDVDTTYPDKKSILMY
ITSLFQVLPQQVSIEAIQEVEMLPRPPKVTKEEHFQLHHQMHYSQQITVSLAQGYERTSSPKPRFKSYAYTQAAYVT
TSDPTRSPFPSQHLEAPEDKSFGSSLMESEVNLDRYQTALEEVLSWLLSAEDTLQAQGEISNDVEVVKDQFHTHEGY
MMDLTAHQGRVGNILQLGSKLIGTGKLSEDEETEVQEQMNLLNSRWECLRVASMEKQSNLHRVLMDLQNQKLKELND
WLTKTEERTRKMEEEPLGPDLEDLKRQVQQHKVLQEDLEQEQVRVNSLTHMVVVVDESSGDHATAALEEQLKVLGDR
WANICRWTEDRWVLLQDILLKWQRLTEEQCLFSAWLSEKEDAVNKIHTTGFKDQNEMLSSLQKLAVLKADLEKKKQS
MGKLYSLKQDLLSTLKNKSVTQKTEAWLDNFARCWDNLVQKLEKSTAQISQAVTTTQPSLTQTTVMETVTTVTTREQ
ILVKHAQEELPPPPPQKKRQITVDSEIRKRLDVDITELHSWITRSEAVLQSPEFAIFRKEGNFSDLKEKVNAIERER
AEKFRKLQDASRSAQALVEQMVNEGVNADSIKQASEQLNSRWIEFCQLLSERLNWLEYQNNIIAFYNQLQQLEQMTT
TAENWLKIQPTTPSEPTAIKSQLKICKDEVNRLSGLQPQIERLKIQSIALKEKGQGPMFLDADFVAFTNHFKQVFSD
VQAREKELQTIFDTLPPMRYQETMSAIRTWVQQSETKLSIPQLSVTDYEIMEQRLGELQALQSSLQEQQSGLYYLST
TVKEMSKKAPSEISRKYQSEFEEIEGRWKKLSSQLVEHCQKLEEQMNKLRKIQNHIQTLKKWMAEVDVFLKEEWPAL
GDSEILKKQLKQCRLLVSDIQTIQPSLNSVNEGGQKIKNEAEPEFASRLETELKELNTQWDHMCQQVYARKEALKGG
LEKTVSLQKDLSEMHEWMTQAEEEYLERDFEYKTPDELQKAVEEMKRAKEEAQQKEAKVKLLTESVNSVIAQAPPVA
QEALKKELETLTTNYQWLCTRLNGKCKTLEEVWACWHELLSYLEKANKWLNEVEFKLKTTENIPGGAEEISEVLDSL
ENLMRHSEDNPNQIRILAQTLTDGGVMDELINEELETFNSRWRELHEEAVRRQKLLEQSIQSAQETEKSLHLIQESL
TFIDKQLAAYIADKVDAAQMPQEAQKIQSDLTSHEISLEEMKKHNQGKEAAQRVLSQIDVAQKKLQDVSMKFRLFQK
PANFELRLQESKMILDEVKMHLPALETKSVEQEVVQSQLNHCVNLYKSLSEVKSEVEMVIKTGRQIVQKKQTENPKE
LDERVTALKLHYNELGAKVTERKQQLEKCLKLSRKMRKEMNVLTEWLAATDMELTKRSAVEGMPSNLDSEVAWGKAT
QKEIEKQKVHLKSITEVGEALKTVLGKKETLVEDKLSLLNSNWIAVTSRAEEWLNLLLEYQKHMETFDQNVDHITKW
IIQADTLLDESEKKKPQQKEDVLKRLKAELNDIRPKVDSTRDQAANLMANRGDHCRKLVEPQISELNHRFAAISHRI
KTGKASIPLKELEQFNSDIQKLLEPLEAEIQQGVNLKEEDFNKDMNEDNEGTVKELLQRGDNLQQRITDERKREEIK
IKQQLLQTKHNALKDLRSQRRKKALEISHQWYQYKRQADDLLKCLDDIEKKLASLPEPRDERKIKEIDRELQKKKEE
LNAVRRQAEGLSEDGAAMAVEPTQIQLSKRWREIESKFAQFRRLNFAQIHTVREETMMVMTEDMPLEISYVPSTYLT
EITHVSQALLEVEQLLNAPDLCAKDFEDLFKQEESLKNIKDSLQQSSGRIDIIHSKKTAALQSATPVERVKLQEALS
QLDFQWEKVNKMYKDRQGRFDRSVEKWRRFHYDIKIFNQWLTEAEQFLRKTQIPENWEHAKYKWYLKELQDGIGQRQ
TVVRTLNATGEEIIQQSSKTDASILQEKLGSLNLRWQEVCKQLSDRKKRLEEQKNILSEFQRDLNEFVLWLEEADNI
ASIPLEPGKEQQLKEKLEQVKLLVEELPLRQGILKQLNETGGPVLVSAPISPEEQDKLENKLKQTNLQWIKVSRALP
EKQGEIEAQIKDLGQLEKKLEDLEEQLNHLLLWLSPIRNQLEIYNQPNQEGPFDVQETEIAVQAKQPDVEEILSKGQ
HLYKEKPATQPVKRKLEDLSSEWKAVNRLLQELRAKQPDLAPGLTTIGASPTQTVTLVTQPVVTKETAISKLEMPSS
LNLEVPALADFNRAJTELTDWLSLLDQVIKSQRVMVGDLEDINEMIIKQKATMQDLEQRRPQLEELITAAQNLKNKT
SNQEARTIITDRIERIQNQWDEVQEHLQNRRQQLNEMLKDSTQWLEAKEEAEQVLGQARAKLESWKEGPYTVDAIQK
KITETKQLAKDLRQWQTNVDVANDLALKLLRDYSADDTRKVHMITENINASWRSIHKRVSEREAALEETHRLLQQFP
LDLEKFLAWLTEAETTANVLQDATRKERLLEDSKGVKELMKQWQDLQGEIEAHTDVYHNLDENSQKILRSLEGSDDA
VLLQRRLDNMNFKWSELRKKSLNIRSHLEASSDQWKRLHLSLQELLVWLQLKDDELSRQAPIGGDFPAVQKQNDVHR
AFKRELKTKEPVIMSTLETVRIFLTEQPLEGLEKLYQEPRELPPEERAQNVTRLLRKQAEEVNTEWEKLNLHSADWQ
RKIDETLERLQELQEATDELDLKLRQAEVIKGSWQPVGDLLIDSLQDHLEKVKALRGEIAPLKENVSHVNDLARQLT
TLGIQLSPYNLSTLEDLNTRWKLLQVAVEDRVRQLHEAHRDFGPASQHFLSTSVQGPWERAISPNKVPYYINHETQT
TCWDHPKMTELYQSLADLNNVRFSAYRTAMKLRRLQKALCLDLLSLSAACDALDQHNLKQNDQPMDILQIINCLTTI
YDRLEQEHNNLVNVPLCVDMCLNWLLNVYDTGRTGRIRVLSFKTGIISLCKAHLEDKYRYLFKQVASSTGFCDQRRL
GLLLHDSIQIPRQLGEVASFGGSNIEPSVRSCFQFANNKPEIEAALFLDWMRLEPQSMVWLPVLHRVAAAETAKHQA
KCNICKECPIIGFRYRSLKHFNYDICQSCFFSGRVAKGHKMHYPMVEYCTPTTSGEDVRDFAKVLKNKFRTKRYFAK
HPRMGYLPVQTVLEGDNMETPVTLINFWPVDSAPASSPQLSHDDTHSRIEHYASRLAEMENSNGSYLNDSISPNESI
DDEHLLIQHYCQSLNQDSPLSQPRSPAQILISLESEERGELERILADLEEENRNLQAEYDRLKQQHEHKGLSPLPSP
PEMMPTSPQSPRDAELIAEAKLLRQHKGRLEARMQILEDHNKQLESQLHRLRQLLEQPQAEAKVNGTTVSSPSTSLQ
RSDSSQPMLLRVVGSQTSDSMGEEDLLSPPQDTSTGLEEVMEQLNNSFPSSRGRNTPGKPMREDTM

FIG. 29

Human dystrophin - domain nucleotide sequences

SEQ ID NO: 10: N-terminal domain
ATGCTTTGGTGGGAAGAAGTAGAGGACTGTTATGAAAGAGAAGATGTTCAAAAGAAAACATTCACAAAATGGGTAAA
TGCACAATTTTCTAAGTTTGGGAAGCAGCATATTGAGAACCTCTTCAGTGACCTACAGGATGGGAGGCGCCTCCTAG
ACCTCCTCGAAGGCCTGACAGGGCAAAAACTGCCAAAAGAAAAAGGATCCACAAGAGTTCATGGCCTGAACAATGTC
AACAAGGCACTGCGGGTTTTGCAGAACAATAATGTTGATTTAGTGAATATTGGAAGTACTGACATCGTAGATGGAAA
TCATAAACTGACTCTTGGTTTGATTTGGAATATAATCCTCCACTGGCAGGTCAAAAATGTAATGAAAAATATCATGG
CTGGATTGCAACAAACCAACAGTGAAAAGATTCTCCTGAGCTGGGTCCGACAATCAACTCGTAATTATCCACAGGTT
AATGTAATCAACTTCACCACCAGCTGGTCTGATGGCCTGGCTTTGAATGCTCTCATCCATAGTCATAGGCCAGACCT
ATTTGACTGGAATAGTGTGGTTTGCCAGCAGTCAGCCACACAACGACTGGAACATGCATTCAACATCGCCAGATATC
AATTAGGCATAGAGAAACTACTCGATCCTGAAGATGTTGATACCACCTATCCAGATAAGAAGTCCATCTTAATGTAC
ATCACATCACTCTTCCAAGTTTTGCCTCAACAAGTGAGCATTGAAGCCATCCAGGAAGTGGAA SEQ ID NO: 11: Hinge 1
ATGTTGCCAAGGCCACCTAAAGTGACTAAAGAAGAACATTTTCAGTTACATCATCAAATGCACTATTCTCAACAGAT
CACGGTCAGTCTAGCACAGGGATATGAGAGAACTTCTTCCCCTAAGCCTCGATTCAAGAGCTATGCCTACACACAGG
CTGCTTATGTCACCACCTCTGACCCTACACGGAGCCCATTTCCTTCACAGCATTTGGAAGCTCCTGAAGACAAGTCA
TTTGGCAGTTCATTGATGGAG SEQ ID NO: 12: Repeat 1
AGTGAAGTAAACCTGGACCGTTATCAAACAGCTTTAGAAGAAGTATTATCGTGGCTTCTTTCTGCTGAGGACACATT
GCAAGCACAAGGAGAGATTTCTAATGATGTGGAAGTGGTGAAAGACCAGTTTCATACTCATGAGGGGTACATGATGG
ATTTGACAGCCCATCAGGGCCGGGTTGGTAATATTCTACAATTGGGAAGTAAGCTGATTGGAACAGGAAAATTATCA
GAAGATGAAGAAACTGAAGTACAAGAGCAGATGAATCTCCTAAATTCAAGATGGGAATGCCTCAGGGTAGCTAGCAT
GGAAAAACAAAGCAATTTACATAGA SEQ ID NO: 13: Repeat 2
GTTTTAATGGATCTCCAGAATCAGAAACTGAAAGAGTTGAATGACTGGCTAACAAAAACAGAAGAAAGAACAAGGAA
AATGGAGGAAGAGCCTCTTGGACCTGATCTTGAAGACCTAAAACGCCAAGTACAACAACATAAGGTGCTTCAAGAAG
ATCTAGAACAAGAACAAGTCAGGGTCAATTCTCTCACTCACATGGTGGTGGTAGTTGATGAATCTAGTGGAGATCAC
GCAACTGCTGCTTTGGAAGAACAACTTAAGGTATTGGGAGATCGATGGGCAAACATCTGTAGATGGACAGAAGACCG
CTGGGTTCTTTTACAAGAC SEQ ID NO: 14: Repeat 3
ATCCTTCTCAAATGGCAACGTCTTACTGAAGAACAGTGCCTTTTTAGTGCATGGCTTTCAGAAAAAGAAGATGCAGT
GAACAAGATTCACACAACTGGCTTTAAAGATCAAAATGAAATGTTATCAAGTCTTCAAAAACTGGCCGTTTTAAAAG
CGGATCTAGAAAAGAAAAAGCAATCCATGGGCAAACTGTATTCACTCAAACAAGATCTTCTTTCAACACTGAAGAAT
AAGTCAGTGACCCAGAAGACGGAAGCATGGCTGGATAACTTTGCCCGGTGTTGGGATAATTTAGTCCAAAAACTTGA
AAAGAGTACAGCACAGATTTCACAG SEQ ID NO: 15: Hinge 1
GCTGTCACCACCACTCAGCCATCACTAACACAGACAACTGTAATGGAAACAGTAACTACGGTGACCACAAGGGAACA
GATCCTGGTAAAGCATGCTCAAGAGGAACTTCCACCACCACCTCCCCAAAAGAAGAGGCAGATTACTGTGGAT SEQ ID NO: 16: Repeat 4
TCTGAAATTAGGAAAAGGTTGGATGTTGATATAACTGAACTTCACAGCTGGATTACTCGCTCAGAAGCTGTGTTGCA
GAGTCCTGAATTTGCAATCTTTCGGAAGGAAGGCAACTTCTCAGACTTAAAAGAAAAAGTCAATGCCATAGAGCGAG
AAAAAGCTGAGAAGTTCAGAAAACTGCAAGATGCCAGCAGATCAGCTCAGGCCCTGGTGGAACAGATGGTGAATGAG
GGTGTTAATGCAGATAGCATCAAACAAGCCT

FIG. 29 (cont'd)

SEQ ID NO: 17: Repeat 5
CAGAACAACTGAACAGCCGGTGGATCGAATTCTGCCAGTTGCTAAGTGAGAGACTTAACTGGCTGGAGTATCAGAAC
AACATCATCGCTTTCTATAATCAGCTACAACAATTGGAGCAGATGACAACTACTGCTGAAAACTGGTTGAAAATCCA
ACCCACCACCCCATCAGAGCCAACAGCAATTAAAAGTCAGTTAAAAATTTGTAAGGATGAAGTCAACCGGCTATCAG
GTCTTCAACCTCAAATTGAACGATTAAAAATTCAAAGCATAGCCCTGAAAGAGAAAGGACAAGGACCCATGTTCCTG
GATGCAGACTTTGTGGCCTTTACAAATCATTTTAAGCAAGTCTTTTCTGATGTGCAGGCCAGAGAGAAAGAGCTACA
GACA SEQ ID NO: 18: Repeat 6
ATTTTTGACACTTTGCCACCAATGCGCTATCAGGAGACCATGAGTGCCATCAGGACATGGGTCCAGCAGTCAGAAAC
CAAACTCTCCATACCTCAACTTAGTGTCACCGACTATGAAATCATGGAGCAGAGACTCGGGGAATTGCAGGCTTTAC
AAAGTTCTCTGCAAGAGCAACAAAGTGGCCTATACTATCTCAGCACCACTGTGAAAGAGATGTCGAAGAAAGCGCCC
TCTGAAATTAGCCGGAAATATCAATCAGAATTTGAAGAAATTGAGGGACGCTGGAAGAAGCTCTCCTCCCAGCTGGT
TGAGCATTGTCAAAAGCTAGAGGAG SEQ ID NO: 19: Repeat 7
CAAATGAATAAACTCCGAAAAATTCAGAATCACATACAAACCCTGAAGAAATGGATGGCTGAAGTTGATGTTTTTCT
GAAGGAGGAATGGCCTGCCCTTGGGGATTCAGAAATTCTAAAAAAGCAGCTGAAACAGTGCAGACTTTTAGTCAGTG
ATATTCAGACAATTCAGCCCAGTCTAAACAGTGTCAATGAAGGTGGGCAGAAGATAAAGAATGAAGCAGAGCCAGAG
TTTGCTTCGAGACTTGAGACAGAACTCAAAGAACTTAACACTCAGTGGGATCACATGTGCCAACAGGTCTATGCCAG
AAAGGAGGCCTTGAAGGGA SEQ ID NO: 20: Repeat 8
GGTTTGGAGAAAACTGTAAGCCTCCAGAAAGATCTATCAGAGATGCACGAATGGATGACACAAGCTGAAGAAGAGTA
TCTTGAGAGAGATTTTGAATATAAAACTCCAGATGAATTACAGAAAGCAGTTGAAGAGATGAAGAGAGCTAAAGAAG
AGGCCCAACAAAAAGAAGCGAAAGTGAAACTCCTTACTGAGTCTGTAAATAGTGTCATAGCTCAAGCTCCACCTGTA
GCACAAGAGGCCTTAAAAAAGGAACTTGAAACTCTAACCACCAACTACCAGTGGCTCTGCACTAGGCTGAATGGGAA
ATGCAAGACTTTGGAAGAA SEQ ID NO: 21: Repeat 9
GTTTGGGCATGTTGGCATGAGTTATTGTCATACTTGGAGAAAGCAAACAAGTGGCTAAATGAAGTAGAATTTAAACT
TAAAACCACTGAAAACATTCCTGGCGGAGCTGAGGAAATCTCTGAGGTGCTAGATTCACTTGAAAATTTGATGCGAC
ATTCAGAGGATAACCCAAATCAGATTCGCATATTGGCACAGACCCTAACAGATGGCGGAGTCATGGATGAGCTAATC
AATGAGGAACTTGAGACATTTAATTCTCGTTGGAGGGAACTACATGAAGAGGCTGTAAGGAGGCAAAAGTTGCTTGA
ACAG SEQ ID NO: 22: Repeat 10
AGCATCCAGTCTGCCCAGGAGACTGAAAAATCCTTACACTTAATCCAGGAGTCCCTCACATTCATTGACAAGCAGTT
GGCAGCTTATATTGCAGACAAGGTGGACGCAGCTCAAATGCCTCAGGAAGCCCAGAAAATCCAATCTGATTTGACAA
GTCATGAGATCAGTTTAGAAGAAATGAAGAAACATAATCAGGGGAAGGAGGCTGCCCAAAGAGTCCTGTCTCAGATT
GATGTTGCACAGAAAAAATTACAAGATGTCTCCATGAAGTTTCGATTATTCCAGAAA SEQ ID NO: 23: Repeat 11
CCAGCCAATTTTGAGCTGCGTCTACAAGAAAGTAAGATGATTTTAGATGAAGTGAAGATGCACTTGCCTGCATTGGA
AACAAAGAGTGTGGAACAGGAAGTAGTACAGTCACAGCTAAATCATTGTGTGAACTTGTATAAAAGTCTGAGTGAAG
TGAAGTCTGAAGTGGAAATGGTGATAAAGACTGGACGTCAGATTGTACAGAAAAAGCAGACGGAAAATCCCAAAGAA
CTTGATGAAAGAGTAACAGCTTTGAAATTGCATTATAATGAGCTGGGAGCAAAGGTAACAGAAAGAAAGCAACAGTT
GGAGAAA

FIG. 29 (cont'd)

SEQ ID NO: 24: Repeat 12
TGCTTGAAATTGTCCCGTAAGATGCGAAAGGAAATGAATGTCTTGACAGAATGGCTGGCAGCTACAGATATGGAATT
GACAAAGAGATCAGCAGTTGAAGGAATGCCTAGTAATTTGGATTCTGAAGTTGCCTGGGGAAAGGCTACTCAAAAAG
AGATTGAGAAACAGAAGGTGCACCTGAAGAGTATCACAGAGGTAGGAGAGGCCTTGAAAACAGTTTTGGGCAAGAAG
GAGACGTTGGTGGAAGATAAACTCAGTCTTCTGAATAGTAACTGGATAGCTGTCACCTCCCGAGCAGAAGAGTGGTT
AAATCTTTTGTTGGAA SEQ ID NO: 25: Repeat 13
TACCAGAAACACATGGAAACTTTTGACCAGAATGTGGACCACATCACAAAGTGGATCATTCAGGCTGACACACTTTT
GGATGAATCAGAGAAAAAGAAACCCCAGCAAAAAGAAGACGTGCTTAAGCGTTTAAAGGCAGAACTGAATGACATAC
GCCCAAAGGTGGACTCTACACGTGACCAAGCAGCAAACTTGATGGCAAACCGCGGTGACCACTGCAGGAAATTAGTA
GAGCCCCAAATCTCAGAGCTCAACCATCGATTTGCAGCCATTTCACACAGAATTAAGACTGGAAAGGCCTCCATT SEQ ID NO: 26: Repeat 14
CCTTTGAAGGAATTGGAGCAGTTTAACTCAGATATACAAAAATTGCTTGAACCACTGGAGGCTGAAATTCAGCAGGG
GGTGAATCTGAAAGAGGAAGACTTCAATAAAGATATGAATGAAGACAATGAGGGTACTGTAAAAGAATTGTTGCAAA
GAGGAGACAACTTACAACAAAGAATCACAGATGAGAGAAAGAGAGAGGAAATAAAGATAAAACAGCAGCTGTTACAG
ACAAAACATAATGCTCTCAAGGATTTGAGGTCTCAAAGAAGAAAAAAGGCTCTAGAA SEQ ID NO: 27: Repeat 15
ATTTCTCATCAGTGGTATCAGTACAAGAGGCAGGCTGATGATCTCCTGAAATGCTTGGATGACATTGAAAAAAAATT
AGCCAGCCTACCTGAGCCCAGAGATGAAAGGAAAATAAAGGAAATTGATCGGGAATTGCAGAAGAAGAAAGAGGAGC
TGAATGCAGTGCGTAGGCAAGCTGAGGGCTTGTCTGAGGATGGGGCCGCAATGGCAGTGGAGCCAACTCAGATCCAG
CTCAGCAAGCGCTGGCGGGAAATTGAGAGCAAATTTGCTCAGTTTCGAAGACTCAACTTTGCACAA SEQ ID NO: 28: Repeat 16
ATTCACACTGTCCGTGAAGAAACGATGATGGTGATGACTGAAGACATGCCTTTGGAAATTTCTTATGTGCCTTCTAC
TTATTTGACTGAAATCACTCATGTCTCACAAGCCCTATTAGAAGTGGAACAACTTCTCAATGCTCCTGACCTCTGTG
CTAAGGACTTTGAAGATCTCTTTAAGCAAGAGGAGTCTCTGAAGAATATAAAAGATAGTCTACAACAAAGCTCAGGT
CGGATTGACATTATTCATAGCAAGAAGACAGCAGCATTGCAAAGTGCAACGCCTGTGGAAAGGGTGAAGCTACAGGA
AGCTCTCTCCCAGCTTGATTTCCAATGGGAAAAAGTTAACAAAATGTACAAGGACCGACAAGGGCGATTTGACAGA SEQ ID NO: 29: Repeat 17
TCTGTTGAGAAATGGCGGCGTTTTCATTATGATATAAAGATATTTAATCAGTGGCTAACAGAAGCTGAACAGTTTCT
CAGAAAGACACAAATTCCTGAGAATTGGGAACATGCTAAATACAAATGGTATCTTAAGGAACTCCAGGATGGCATTG
GGCAGCGGCAAACTGTTGTCAGAACATTGAATGCAACTGGGGAAGAAATAATTCAGCAATCCTCAAAAACAGATGCC
AGTATTCTACAGGAAAAATTGGGAAGCCTGAATCTGCGGTGGCAGGAGGTCTGCAAACAGCTGTCAGACAGAAAAA
GAGGCTAGAAGAA SEQ ID NO: 30: Repeat 18
CAAAAGAATATCTTGTCAGAATTTCAAAGAGATTTAAATGAATTTGTTTTATGGTTGGAGGAAGCAGATAACATTGC
TAGTATCCCACTTGAACCTGGAAAAGAGCAGCAACTAAAAGAAAAGCTTGAGCAAGTCAAGTTACTGGTGGAAGAGT
TGCCCCTGCGCCAGGGAATTCTCAAACAATTAAATGAAACTGGAGGACCCGTGCTTGTAAGTGCTCCCATAAGCCCA
GAAGAGCAAGATAAACTTGAAAATAAGCTCAAGCAGACAAATCTCCAGTGGATAAAGGTTTCCAGAGCTTTACCTGA
GAAACAAGGAGAAATTGAAGCT SEQ ID NO: 31: Repeat 19
CAAATAAAAGACCTTGGGCAGCTTGAAAAAAAGCTTGAAGACCTTGAAGAGCAGTTAAATCATCTGCTGCTGTGGTT
ATCTCCTATTAGGAATCAGTTGGAAATTTATAACCAACCAAACCAAGAAGGACCATTTGACGTTCAGGAAACTGAAA
TAGCAGTTCAAGCTAAACAACCGGATGTGGAAGAGATTTTGTCTAAAGGGCAGCATTTGTACAAGGAAAAACCAGCC
ACTCAGCCAGTGAAGAGGAAGTTAGAAGATCTGAGCTCTGAGTGGAAGGCGGTAAACCGTTTACTTCAAGAGCTGAG
GGCAAAG

FIG. 29 (cont'd)

SEQ ID NO: 32: Hinge 3
CAGCCTGACCTAGCTCCTGGACTGACCACTATTGGAGCCTCTCCTACTCAGACTGTTACTCTGGTGACACAACCTGT
GGTTACTAAGGAAACTGCCATCTCCAAACTAGAAATGCCATCTTCCTTGATGTTGGAGGTACCT SEQ ID NO: 33: Repeat 20
GCTCTGGCAGATTTCAACCGGGCTTGGACAGAACTTACCGACTGGCTTTCTCTGCTTGATCAAGTTATAAAATCACA
GAGGGTGATGGTGGGTGACCTTGAGGATATCAACGAGATGATCATCAAGCAGAAGGCAACAATGCAGGATTTGGAAC
AGAGGCGTCCCCAGTTGGAAGAACTCATTACCGCTGCCCAAAATTTGAAAAACAAGACCAGCAATCAAGAGGCTAGA
ACAATCATTACGGATCGAATTGAAAGAATTCAGAATCAGTGGGATGAAGTACAAGAACACCTTCAGAACCGGAGGCA
ACAGTTGAATGAA SEQ ID NO: 34: Repeat 21
ATGTTAAAGGATTCAACACAATGGCTGGAAGCTAAGGAAGAAGCTGAGCAGGTCTTAGGACAGGCCAGAGCCAAGCT
TGAGTCATGGAAGGAGGGTCCCTATACAGTAGATGCAATCCAAAAGAAAATCACAGAAACCAAGCAGTTGGCCAAAG
ACCTCCGCCAGTGGCAGACAAATGTAGATGTGGCAAATGACTTGGCCCTGAAACTTCTCCGGGATTATTCTGCAGAT
GATACCAGAAAAGTCCACATGATAACAGAGAATATCAATGCCTCTTGGAGAAGCATTCATAAAAGGGTGAGTGAGCG
AGAGGCTGCTTTGGAAGAA SEQ ID NO: 35: Repeat 22
ACTCATAGATTACTGCAACAGTTCCCCCTGGACCTGGAAAAGTTTCTTGCCTGGCTTACAGAAGCTGAAACAACTGC
CAATGTCCTACAGGATGCTACCCGTAAGGAAAGGCTCCTAGAAGACTCCAAGGGAGTAAAAGAGCTGATGAAACAAT
GGCAAGACCTCCAAGGTGAAATTGAAGCTCACACAGATGTTTATCACAACCTGGATGAAAACAGCCAAAAAATCCTG
AGATCCCTGGAAGGTTCCGATGATGCAGTCCTGTTACAAAGACGTTTGGATAACATGAACTTCAAGTGGAGTGAACT
TCGGAAAAAGTCTCTCAACATTAGGTCCCATTTGGAAGCC SEQ ID NO: 36: Repeat 23
AGTTCTGACCAGTGGAAGCGTCTGCACCTTTCTCTGCAGGAACTTCTGGTGTGGCTACAGCTGAAAGATGATGAATT
AAGCCGGCAGGCACCTATTGGAGGCGACTTTCCAGCAGTTCAGAAGCAGAACGATGTACATAGGGCCTTCAAGAGGG
AATTGAAAACTAAAGAACCTGTAATCATGAGTACTCTTGAGACTGTACGAATATTTCTGACAGAGCAGCCTTTGGAA
GGACTAGAGAAACTCTACCAGGAGCCCAGAGAGCTGCCTCCTGAGGAGAGAGCCCAGAATGTCACTCGGCTTCTACG
AAAGCAGGCTGAGGAGGTCAATACTGAGTGGGAAAAATTGAACCTGCACTCCGCTGACTGGCAGAGAAAAATAGATG
AG SEQ ID NO: 37: Repeat 24
ACCCTTGAAAGACTCCAGGAACTTCAAGAGGCCACGGATGAGCTGGACCTCAAGCTGCGCCAAGCTGAGGTGATCAA
GGGATCCTGGCAGCCCGTGGGCGATCTCCTCATTGACTCTCTCCAAGATCACCTCGAGAAAGTCAAGGCACTTCGAG
GAGAAATTGCGCCTCTGAAAGAGAACGTGAGCCACGTCAATGACCTTGCTCGCCAGCTTACCACTTTGGGCATTCAG
CTCTCACCGTATAACCTCAGCACTCTGGAAGACCTGAACACCAGATGGAAGCTTCTGCAGGTGGCCGTCGAGGACCG
AGTCAGGCAGCTGCATGAA SEQ ID NO: 38: Hinge 4
GCCCACAGGGACTTTGGTCCAGCATCTCAGCACTTTCTTTCCACGTCTGTCCAGGGTCCCTGGGAGAGAGCCATCTC
GCCAAACAAAGTGCCCTACTATATCAACCACGAGACTCAAACAACTTGCTGGGACCATCCCAAAATGACAGAGCTCT
ACCAGTCTTTAGCTGACCTGAATAATGTCAGATTCTCAGCTTATAGGACTGCCATGAAACTC SEQ ID NO: 39: Cysteine-rich domain
CGAAGACTGCAGAAGGCCCTTTGCTTGGATCTCTTGAGCCTGTCAGCTGCATGTGATGCCTTGGACCAGCACAACCT
CAAGCAAAATGACCAGCCCATGGATATCCTGCAGATTATTAATTGTTTGACCACTATTTATGACCGCCTGGAGCAAG
AGCACAACAATTTGGTCAACGTCCCTCTCTGCGTGGATATGTGTCTGAACTGGCTGCTGAATGTTTATGATACGGGA
CGAACAGGGAGGATCCGTGTCCTGTCTTTTAAAACTGGCATCATTTCCCTGTGTAAAGCACATTTGGAAGACAAGTA
CAGATACCTTTTCAAGCAAGTGGCAAGTTCAACAGGATTTTGTGACCAGCGCAGGCTGGGCCTCCTTCTGCATGATT
CTATCCAAATTCCAAGACAGTTGGGTGAAGTTGCATCCTTTGGGGGCAGTAACATTGAGCCAAGTGTCCGGAGCTGC
TTCCAATTTGCTAATAATAAGCCAGAGATCGAAGCGGCCCTCTTCCTAGACTGGATGAGACTGGAACCCCAGTCCAT
GGTGTGGCTGCCCGTCCTGCACAGAGTGGCTGCTGCAGAAACTGCCAAGCATCAGGCCAAATGTAACATCTGCAAAG

FIG. 29 (cont'd)

AGTGTCCAATCATTGGATTCAGGTACAGGAGTCTAAAGCACTTTAATTATGACATCTGCCAAAGCTGCTTTTTTTCT
GGTCGAGTTGCAAAAGGCCATAAAATGCACTATCCCATGGTGGAATATTGCACTCCGACTACATCAGGAGAAGATGT
TCGAGACTTTGCCAAGGTACTAAAAAACAAATTTCGAACCAAAAGGTATTTTGCGAAGCATCCCCGAATGGGCTACC
TGCCAGTGCAGACTGTCTTAGAGGGGGACAACATGGAAACT

SEQ ID NO: 40: C-terminal domain
CCCGTTACTCTGATCAACTTCTGGCCAGTAGATTCTGCGCCTGCCTCGTCCCCTCAGCTTTCACACGATGATACTCA
TTCACGCATTGAACATTATGCTAGCAGGCTAGCAGAAATGGAAAACAGCAATGGATCTTATCTAAATGATAGCATCT
CTCCTAATGAGAGCATAGATGATGAACATTTGTTAATCCAGCATTACTGCCAAAGTTTGAACCAGGACTCCCCCCTG
AGCCAGCCTCGTAGTCCTGCCCAGATCTTGATTTCCTTAGAGAGTGAGGAAAGAGGGGAGCTAGAGAGAATCCTAGC
AGATCTTGAGGAAGAAAACAGGAATCTGCAAGCAGAATATGACCGTCTAAAGCAGCAGCACGAACATAAAGGCCTGT
CCCCACTGCCGTCCCCTCCTGAAATGATGCCCACCTCTCCCCAGAGTCCCCGGGATGCTGAGCTCATTGCTGAGGCC
AAGCTACTGCGTCAACACAAAGGCCGCCTGGAAGCCAGGATGCAAATCCTGGAAGACCACAATAAACAGCTGGAGTC
ACAGTTACACAGGCTAAGGCAGCTGCTGGAGCAACCCGAGGCAGAGGCCAAAGTGAATGGCACAACGGTGTCCTCTC
CTTCTACCTCTCTACAGAGGTCCGACAGCAGTCAGCCTATGCTGCTCCGAGTGGTTGGCAGTCAAACTTCGGACTCC
ATGGGTGAGGAAGATCTTCTCAGTCCTCCCCAGGACACAAGCACAGGGTTAGAGGAGGTGATGGAGCAACTCAACAA
CTCCTTCCCTAGTTCAAGAGGAAGAAATACCCCTGGAAAGCCAATGAGAGAGGACACAATGTAG

FIG. 30 ngth human dystrophin protein domain structure (total 3685 aa)

SEQ ID NO: 41: N-terminal domain (from 1 aa to 252 aa; total 252 aa)
MLWWEEVEDCYEREDVQKKTFTKWVNAQFSKFGKQHIENLFSDLQDGRRLLDLLEGLTGQKLPKEKGSTRVHALNNV
NKALRVLQNNNVDLVNIGSTDIVDGNHKLTLGLIWNIILHWQVKVMKNIMAGLQQTNSEKILLSWVRQSTRNYPQVN
VINFTTSWSDGLALNALIHSHRPDLFDWNSVVCQQSATQRLEHAFNIARYQLGIEKLLDPEDVDTTYPDKKSILMYI
TSLFQVLPQQVSIEAIQEVE SEQ ID NO: 42: Mid-rod domain (from 253 aa to 3112 aa; total 2860 aa)
MLPRPPKVTKEEHFQLHHQMHYSQQITVSLAQGYERTSSPKPRFKSYAYTQAAYVTTSDPTRSPFPSQHLEAPEDKS
FGSSLMESEVNLDRYQTALEEVLSWLLSAEDTLQAQGEISNDVEVVKDQFHTHEGYMMDLTAHQGRVGNILQLGSKL
IGTGKLSEDEETEVQEQMNLLNSRWECLRVASMEKQSNLHRVLMDLQNQKLKELNDWLTKTEERTRKMEEEPLGPDL
EDLKRQVQQHKVLQEDLEQEQVRVNSLTHMVVVVDESSGDHATAALEEQLKVLGDRWANICRWTEDRWVLLQDILLK
WQRLTEEQCLFSAWLSEKEDAVNKIHTTGFKDQNEMLSSLQKLAVLKADLEKKKQSMGKLYSLKQDLLSTLKNKSVT
QKTEAWLDNFARCWDNLVQKLEKSTAQISQAVTTTQPSLTQTTVMETVTTVTTREQILVKHAQEELPPPPPQKKRQI
TVDSEIRKRLDVDITELHSWITRSEAVLQSPEFAIFRKEGNFSDLKEKVNAIEREKAEKFRKLQDASRSAQALVEQM
VNEGVNADSIKQASEQLNSRWIEFCQLLSERLNWLEYQNNIIAFYNQLQQLEQMTTTAENWLKIQPTTPSEPTAIKS
QLKICKDEVNRLSGLQPQIERLKIQSIALKEKGQGPMFLDADFVAFTNHFKQVFSDVQAREKELQTIFDTLPPMRYQ
ETMSAIRTWVQQSETKLSIPQLSVTDYEIMEQRLGELQALQSSLQEQQSGLYYLSTTVKEMSKKAPSEISRKYQSEF
EEIEGRWKKLSSQLVEHCQKLEEQMNKLRKIQNHIQTLKKWMAEVDVFLKEEWPALGDSEILKKQLKQCRLLVSDIQ
TIQPSLNSVNEGGQKIKNEAEPEFASRLETELKELNTQWDHMCQQVYARKEALKGGLEKTVSLQKDLSEMHEWMTQA
EEEYLERDFEYKTPDELQKAVEEMKRAKEEAQQKEAKVKLLTESVNSVIAQAPPVAQEALKKELETLTTNYQWLCTR
LNGKCKTLEEVWACWHELLSYLEKANKWLNEVEFKLKTTENIPGGAEEISEVLDSLENLMRHSEDNPNQIRILAQTL
TDGGVMDELINEELETFNSRWRELHEEAVRRQKLLEQSIQSAQETEKSLHLIQESLTFIDKQLAAYIADKVDAAQMP
QEAQKIQSDLTSHEISLEEMKKHNQGKEAAQRVLSQIDVAQKKLQDVSMKFRLFQKPANFELRLQESKMILDEVKMH
LPALETKSVEQEVVQSQLNHCVNLYKSLSEVKSEVEMVIKTGRQIVQKKQTENPKELDERVTALKLHYNELGAKVTE
RKQQLEKCLKLSRKMRKEMNVLTEWLAATDMELTKRSAVEGMPSNLDSEVAWGKATQKEIEKQKVHLKSITEVGEAL
KTVLGKKETLVEDKLSLLNSNWIAVTSRAEEWLNLLLEYQKHMETFDQNVDHITKWIIQADTLLDESEKKKPQQKED
VLKRLKAELNDIRPKVDSTRDQAANLMANRGDHCRKLVEPQISELNHRFAAISHRIKTGKASIPLKELEQFNSDIQK
LLEPLEAEIQQGVNLKEEDFNKDMNEDNEGTVKELLQRGDNLQQRITDERKREEIKIKQQLLQTKHNALKDLRSQRR
KKALEISHQWYQYKRQADDLLKCLDDIEKKLASLPEPRDERKIKEIDRELQKKKEELNAVRRQAEGLSEDGAAMAVE
PTQIQLSKRWREIESKFAQFRRLNFAQIHTVREETMMVMTEDMPLEISYVPSTYLTEITHVSQALLEVEQLLNAPDL
CAKDFEDLFKQEESLKNIKDSLQQSSGRIDIIHSKKTAALQSATPVERVKLQEALSQLDFQWEKVNKMYKDRQGRFD
RSVEKWRRFHYDIKIFNQWLTEAEQFLRKTQIPENWEHAKYKWYLKELQDGIGQRQTVVRTLNATGEEIIQQSSKTD
ASILQEKLGSLNLRWQEVCKQLSDRKKRLEEQKNILSEFQRDLNEFVLWLEEADNIASIPLEPGKEQQLKEKLEQVK
LLVEELPLRQGILKQLNETGGPVLVSAPISPEEQDKLENKLKQTNLQWIKVSRALPEKQGEIEAQIKDLGQLEKKLE
DLEEQLNHLLLWLSPIRNQLEIYNQPNQEGPFDVQETEIAVQAKQPDVEEILSKGQHLYKEKPATQPVKRKLEDLSS
EWKAVNRLLQELRAKQPDLAPGLTTIGASPTQTVTLVTQPVVTKETAISKLEMPSSLMLEVPALADFNRAWTELTDW
LSLLDQVIKSQRVMVGDLEDINEMIIKQKATMQDLEQRRPQLEELITAAQNLKNKTSNQEARTIITDRIERIQNQWD
EVQEHLQNRRQQLNEMLKDSTQWLEAKEEAEQVLGQARAKLESWKEGPYTVDAIQKKITETKQLAKDLRQWQTNVDV
ANDLALKLLRDYSADDTRKVHMITENINASWRSIHKRVSEREAALEETHRLLQQFPLDLEKFLAWLTEAETTANVLQ
DATRKERLLEDSKGVKELMKQWQDLQGEIEAHTDVYHNLDENSQKILRSLEGSDDAVLLQRRLDNMNFKWSELRKKS
LNIRSHLEASSDQWKRLHLSLQELLVWLQLKDDELSRQAPIGGDFPAVQKQNDVHRAFKRELKTKEPVIMSTLETVR
IFLTEQPLEGLEKLYQEPRELPPEERAQNVTRLLRKQAEEVNTEWEKLNLHSADWQRKIDETLERLQELQEATDELD
LKLRQAEVIKGSWQPVGDLLIDSLQDHLEKVKALRGEIAPLKENVSHVNDLARQLTTLGIQLSPYNLSTLEDLNTRW
KLLQVAVEDRVRQLHEAHRDFGPASQHFLSTSVQGPWERAISPNKVPYYINHETQTTCWDHPKMTELYQSLADLNNV
RFSAYRTAMKL SEQ ID NO: 43: Cysteine-rich domain (from 3113 aa to 3408 aa; total 296 aa, cysteine residues are bolded)
RRLQKALCLDLLSLSAACDALDQHNLKQNDQPMDILQIINCLTTIYDRLEQEHNNLVNVPLCVDMCLNWLLNVYDTG
RTGRIRVLSFKTGIISLCKAHLEDKYRYLFKQVASSTGFCDQRRLGLLLHDSIQIPRQLGEVASFGGSNIEPSVRSC
FQFANNKPEIEAALFLDWMRLEPQSMVWLPVLHRVAAAETAKHQAKCNICKECPIIGFRYRSLKHFNYDICQSCFFS
GRVAKGHKMHYPMVEYCTPTTSGEDVRDFAKVLKNKFRTKRYFAKHPRMGYLPVQTVLEGDNMET

FIG. 30 (cont'd)

SEQ ID NO: 44: C-terminal domain (from 3409 aa to 3695 aa; total 277 aa)
FVTLINFWPVDSAPASSFQLSHDDTHSRIEHYASRLAEMENSNGSYLNDSISPNESIDDEHLLIQHYCQSLNQDSPL
SQPRSPAQILISLESEERGELERILADLEEENRNLQAEYDRLKQQHEHKGLSPLPSPPEMMPTSPQSPRDAELIAEA
KLLRQHKGRLEARMQILEDHNKQLESQLHRLRQLLEQPQAEAKVNGTTVSSPSTSLQRSDSSQPMLLRVVGSQTSDS
MGEEDLLSPPQDTSTGLEEVMEQLNNSFPSSRGRNTPGKPMREDTM

FIG. 31

SEQ ID NO: 45: Δexon17-48 (mini-dystrophin with 8.5 repeats and 3 hinges)
(This minigene does not carry R16 or R17. It cannot restore nNOS)

ATGCTTTGGTGGGAAGAAGTAGAGGACTGTTATGAAAGAGAAGATGTTCAAAAGAAAACATTCACAAAATGGGTAAA
TGCACAATTTTCTAAGTTTGGGAAGCAGCATATTGAGAACCTCTTCAGTGACCTACAGGATGGGAGGCGCCTCCTAG
ACCTCCTCGAAGGCCTGACAGGGCAAAAACTGCCAAAAGAAAAAGGATCCACAAGAGTTCATGCCCTGAACAATGTC
AACAAGGCACTGCGGGTTTTGCAGAACAATAATGTTGATTTAGTGAATATTGGAAGTACTGACATCGTAGATGGAAA
TCATAAACTGACTCTTGGTTTGATTTGGAATATAATCCTCCACTGGCAGGTCAAAAATGTAATGAAAAATATCATGG
CTGGATTGCAACAAACCAACAGTGAAAAGATTCTCCTGAGCTGGGTCCGACAATCAACTCGTAATTATCCACAGGTT
AATGTAATCAACTTCACCACCAGCTGGTCTGATGGCCTGGCTTTGAATGCTCTCATCCATAGTCATAGGCCAGACCT
ATTTGACTGGAATAGTGTGGTTTGGCAGCAGTCAGCCACACAACGACTGGAACATGCATTCAACATCGCCAGATATC
AATTAGGCATAGAGAAAGTACTCGATCCTGAAGATGTTGATACCACCTATCCAGATAAGAAGTCCATCTTAATGTAC
ATCACATCACTCTTCCAAGTTTTGCCTCAACAAGTGAGCATTGAAGCCATCCAGGAAGTGGAAATGTTGCCAAGGCC
ACCTAAAGTGACTAAAGAAGAACATTTTCAGTACATCATCAAATGCACTATTCTCAACAGATCACGGTCAGTCTAGC
ACAGGGATATGAGAGAACTTCTTCCCCTAAGCCTCGATTCAAGAGCTATGCCTACACACAGGCTGCTTATGTCACCA
CCTCTGACCCTACACGGAGCCCATTTCCTTCACAGCATTTGGAAGCTCCTGAAGACAAGTCATTTGGCAGTTCATTG
ATGGAGAGTGAAGTAAACCTGGACCGTTATCAAACAGCTTTAGAAGAAGTATTATCGTGGCTTCTTTCTGCTGAGGA
CACATTGCAAGCACAAGGAGAGATTTCTAATGATGTGGAAGTGGTGAAAGACCAGTTTCATACTCATGAGGGGTACA
TGATGGATTTGACAGCCCATCAGGGCCGGGTTGGTAATATTCTACAATTGGGAAGTAAGCTGATTGGAACAGGAAAA
TTATCAGAAGATGAAGAAACTGAAGTACAAGAGCAGATGAATCTCCTAAATTCAAGATGGGAATGCCTCAGGGTAGC
TAGCATGGAAAAACAAAGCAATTTACATAGAGTTTTAATGGATCTCCAGAATCAGAAACTGAAAGAGTTGAATGACT
GGCTAACAAAAACAGAAGAAAGAACAAGGAAAATGGAGGAAGAGCCTCTTGGACCTGATCTTGAAGACCTAAAACGC
CAAGTACAACAACATAAGGTGCTTCAAGAAGATCTAGAACAAGAACAAGTCAGGGTCAATTCTCTCACTCACATGGT
GGTGGTAGTTGATGAATCTAGTGGAGATCACGCAACTGCTGCTTTGGAAGAACAAGTTTAAGGTATTGGGAGATCGA
TGGGCAAACATCTGTAGATGGACAGAAGACCGCTGGGTTCTTTTACAAGACATCCTTCTCAAATGGCAACGTCTTAC
TGAAGAACAGTGCCTTTTTAGTGCATGGCTTTCAGAAAAAGAAGATGCAGTGAACAAGATTCACACAACTGGCTTTA
AAGATCAAAATGAAATGTTATCAAGTCTTCAAAAACTGGCCGTTTTAAAAGCGGATCTAGAAAAGAAAAAGCAATCC
ATGGGCAAACTGTATTCACTCAAACAAGATCTTCTTTCAACACTGAAGAATAAGTCAGTGACCCAGAAGACGGAAGC
ATGGCTGGATAACTTTGCCCGGTGTTGGGATAATTTAGTCCAAAAACTTGAAAAGAGTACAGCACAGGAAACTGAAA
TAGCAGTTCAAGCTAAACAACCGGATGTGGAAGAGATTTTGTCTAAAGGGCAGCATTTGTACAAGGAAAAACCAGCC
ACTCAGCCAGTGAAGAGGAAGTTAGAAGATCTGAGCTCTGAGTGGAAGGCGGTAAACCGTTTACTTCAAGAGCTGAG
GGCAAAGCAGCCTGACCTAGCTCCTGGACTGACCACTATTGGAGCCTCTCCTACTCAGACTGTTACTCTGGTGACAC
AACCTGTGGTTAGTAAGGAAACTGCCATCTCCAAACTAGAAATGCCATCTTCCTTGATGTTGGAGGTACCTGCTCTG
GCAGATTTCAACGGGGCTTGGACAGAACTTACCGAGTGGCTTTCTCTGCTTGATCAAGTTATAAAATCACAGAGGGT
GATGGTGGGTGACCTTGAGGATATCAACGAGATGATCATCAAGCAGAAGGCAACAATGCAGGATTTGGAACAGAGGC
GTCCCCAGTTGGAAGAACTCATTACCGCTGCCCAAAATTTGAAAAACAAGACCAGCAATCAAGAGGCTAGAACAATC
ATTACGGATCGAATTGAAAGAATTCAGAATCAGTGGGATGAAGTACAAGAACACCTTCAGAACCGGAGGCAACAGTT
GAATGAAATGTTAAAGGATTCAACACAATGGCTGGAAGCTAAGGAAGAAGCTGAGCAGGTCTTAGGACAGGCCAGAG
CCAAGCTTGAGTCATGGAAGGAGGGTCCCTATACAGTAGATGCAATCCAAAAGAAAATCACAGAAACCAAGCAGTTG
GCCAAAGACCTCCGCCAGTGGCAGACAAATGTAGATGTGGCAAATGACTTGGCCCTGAAACTTCTCCGGGATTATTC
TGCAGATGATACCAGAAAAGTCCACATGATAACAGAGAATATCAATGCCTCTTGGAGAAGCATTCATAAAAGGGTGA
GTGAGCGAGAGGCTGCTTTGGAAGAAACTCATAGATTACTGCAACAGTTCCCCCTGGACCTGGAAAAGTTTCTTGCC
TGGCTTACAGAAGCTGAAACAACTGCCAATGTCCTACAGGATGCTACCCGTAAGGAAAGGCTCCTAGAAGACTCCAA
GGGAGTAAAAGAGCTGATGAAACAATGGCAAGACCTCCAAGGTGAAATTGAAGCTCACACAGATGTTTATCACAACC
TGGATGAAAACAGCCAAAAAATCCTGAGATCCCTGGAAGGTTCCGATGATGCAGTCCTGTTACAAAGACGTTTGGAT
AACATGAACTTCAAGTGGAGTGAACTTCGGAAAAAGTCTCTCAACATTAGGTCCCATTTGGAAGCCAGTTCTGACCA
GTGGAAGCGTCTGCACCTTTCTCTGCAGGAACTTCTGGTGTGGCTACAGCTGAAAGATGATGAATTAAGCCGGCAGG
CACCTATTGGAGGCGACTTTCCAGCAGTTCAGAAGCAGAACGATGTACATAGGGCCTTCAAGAGGGAATTGAAAACT
AAAGAACCTGTAATCATGAGTACTCTTGAGACTGTACGAATATTTCTGACAGAGCAGCCTTTGGAAGGACTAGAGAA
ACTCTACCAGGAGCCCAGAGAGCTGCCTCCTGAGGAGAGAGCCCAGAATGTCACTCGGCTTCTACGAAAGCAGGCTG
AGGAGGTCAATACTGAGTGGGAAAAATTGAACCTGCACTCCGCTGACTGGCAGAGAAAAATAGATGAGACCCTTGAA
AGACTCCAGGAACTTCAAGAGGCCACGGATGAGCTGGACCTCAAGCTGCGCCAAGCTGAGGTGATCAAGGGATCCTG
GCAGCCCGTGGGCGATCTCCTCATTGACTCTCTCCAAGATCACCTCGAGAAAGTCAAGGCACTTCGAGGAGAAATTG

FIG. 31 (cont'd)

CGCCTCTGAAAGAGAACGTGAGCCACGTCAATGACCTTGCTCGCCAGCTTACCACTTTGGGCATTCAGCTCTCACCG
TATAACCTCAGCACTCTGGAAGACCTGAACACCAGATGGAAGCTTCTGCAGGTGGCCGTCGAGGACCGAGTCAGGCA
GCTGCATGAAGCCCACAGGGACTTTGGTCCAGCATCTCAGCACTTTCTTTCCACGTCTGTCCAGGGTCGGTGGGAGA
GAGCCATCTCGCCAAACAAAGTGCCCTACTATATCAACCACGAGACTCAAACAACTTGCTGGGACCATCCCAAAATG
ACAGAGCTCTACCAGTCTTTAGCTGACCTGAATAATGTCAGATTCTCAGCTTATAGGACTGCCATGAAACTCCGAAG
ACTGCAGAAGGCCCTTTGCTTGGATCTCTTGAGCCTGTCAGCTGCATGTGATGCCTTGGACCAGCACAACCTCAAGC
AAAATGACCAGCCCATGGATATCCTGCAGATTATTAATTGTTTGACCACTATTTATGACCGCCTGGAGCAAGAGCAC
AACAATTTGGTCAACGTCCCTCTCTGCGTGGATATGTGTCTGAACTGGCTGCTGAATGTTTATGATACGGGACGAAC
AGGGAGGATCCGTGTCCTGTCTTTTAAAACTGGCATCATTTCCCTGTGTAAAGCACATTTGGAAGACAAGTACAGAT
ACCTTTTCAAGCAAGTGGCAAGTTCAACAGGATTTTGTGACCAGCGCAGGCTGGGCCTCCTTCTGCATGATTCTATC
CAAATTCCAAGACAGTTGGGTGAAGTTGCATCCTTTGGGGGCAGTAACATTGAGCCAAGTGTCCGGAGCTGCTTCCA
ATTTGCTAATAATAAGCCAGAGATCGAAGCGGCCCTCTTCCTAGACTGGATGAGACTGGAACCCCAGTCCATGGTGT
GGCTGCCCGTCCTGCACAGAGTGGCTGCTGCAGAAACTGCCAAGCATCAGGCCAAATGTAACATCTGCAAAGAGTGT
CCAATCATTGGATTCAGGTACAGGAGTCTAAAGCACTTTAATTATGACATCTGCCAAAGCTGCTTTTTTTCTGGTCG
AGTTGCAAAAGGCCATAAAATGCACTATCCCATGGTGGAATATTGCACTCCGACTACATCAGGAGAAGATGTTCGAG
ACTTTGCCAAGGTACTAAAAAACAAATTTCGAACCAAAAGGTATTTTGCGAAGCATCCCCGAATGGGCTACCTGCCA
GTGCAGACTGTCTTAGAGGGGGACAACATGGAAACTCCCGTTACTCTGATCAACTTCTGGCCAGTAGATTCTGCGCC
TGCCTCGTCCCCTCAGCTTTCACACGATGATACTCATTCACGCATTGAACATTATGCTAGCAGGCTAGCAGAAATGG
AAAACAGCAATGGATCTTATCTAAATGATAGCATCTCTCCTAATGAGAGCATAGATGATGAACATTTGTTAATCCAG
CATTACTGCCAAAGTTTGAACCAGGACTCCCCCCTGAGCCAGCCTCGTAGTCCTGCCCAGATCTTGATTTCCTTAGA
GAGTGAGGAAAGAGGGGAGCTAGAGAGAATCCTAGCAGATCTTGAGGAAGAAAACAGGAATCTGCAAGCAGAATATG
ACCGTCTAAAGCAGCAGCACGAACATAAAGGCCTGTCCCCACTGCCGTCCCCTCCTGAAATGATGCCCACCTCTCCC
CAGAGTCCCCGGGATGCTGAGCTCATTGCTGAGGCCAAGCTACTGCGTCAACACAAAGGCCGCCTGGAAGCCAGGAT
GCAAATCCTGGAAGACCACAATAAACAGCTGGAGTCACAGTTACACAGGCTAAGGCAGGTGCTGGAGCAACCCCAGG
CAGAGGCCAAAGTGAATGGCACAACGGTGTCCTCTCCTTCTACCTCTCTACAGAGGTCCGACAGCAGTCAGCCTATG
CTGCTCCGAGTGGTTGGCAGTCAAACTTCGGACTCCATGGGTGAGGAAGATCTTCTCAGTCGTCCCCAGGACACAAG
CACAGGGTTAGAGGAGGTGATGGAGCAACTCAACAACTCCTTTCCCTAGTTCAAGAGGAAGAAATACCCCTGGAAAG
CCAATGAGAGAGGACACAATGTAG

SEQUENCE LISTING

```
<160> NUMBER OF SEQ ID NOS: 76

<210> SEQ ID NO 1
<211> LENGTH: 5749
<212> TYPE: DNA
<213> ORGANISM: Artificial Sequence
<220> FEATURE:
<223> OTHER INFORMATION: Synthetic construct: Nucleotide sequence of
      delta-H2-R19 (mini-dystrophin with 8 repeats and 3 hinges; does
      not carry R16 or R17, cannot restore nNOS)

<400> SEQUENCE: 1

atgcttggtg ggaagaagta gaggactgtt atgaaagaga agatgttcaa aagaaaacat      60

tcacaaaatg ggtaaatgca caattttcta agtttgggaa gcagcatatt gagaacctct     120

tcagtgacct acaggatggg aggcgcctcc tagacctcct cgaaggcctg acagggcaaa     180
```

-continued

```
aactgccaaa agaaaaagga tccacaagag ttcatgccct gaacaatgtc aacaaggcac    240
tgcgggtttt gcagaacaat aatgttgatt tagtgaatat tggaagtact gacatcgtag    300
atggaaatca taaactgact cttggtttga tttggaatat aatcctccac tggcaggtca    360
aaaatgtaat gaaaaatatc atggctggat tgcaacaaac caacagtgaa aagattctcc    420
tgagctgggt gcgacaatca actcgtaatt atccacaggt taatgtaatc aacttcacca    480
ccagctggtc tgatggcctg gctttgaatg ctctcatcca tagtcatagg ccagacctat    540
ttgactggaa tagtgtggtt tgccagcagt cagccacaca acgactggaa catgcattca    600
acatcgccag atatcaatta ggcatagaga aactactcga tcctgaagat gttgatacca    660
cctatccaga taagaagtcc atctttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tgggaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca gcagcctgac ctagctcctg gactgaccac tattggagcc   2040
tctcctactc agactgttac tctggtgaca caacctgtgg ttactaagga aactgccatc   2100
tccaaactag aaatgccatc ttccttgatg ttggaggtac ctgctctggc agatttcaac   2160
cgggcttgga cagaacttac cgactggctt tctctgcttg atcaagttat aaaatcacag   2220
agggtgatgg tgggtgacct tgaggatatc aacgagatga tcatcaagca gaaggcaaca   2280
atgcaggatt tggaacagag gcgtccccag ttggaagaac tcattaccgc tgcccaaaat   2340
ttgaaaaaca agaccagcaa tcaagaggct agaacaatca ttacggatcg aattgaaaga   2400
attcagaatc agtgggatga agtacaagaa caccttcaga accggaggca acagttgaat   2460
gaaatgttaa aggattcaac acaatggctg gaagctaagg aagaagctga gcaggtctta   2520
```

-continued

```
ggacaggcca gagccaagct tgagtcatgg aaggagggtc cctatacagt agatgcaatc   2580
caaaagaaaa tcacagaaac caagcagttg gccaaagacc tccgcgagtg gcagacaaat   2640
gtagatgtgg caaatgactt ggccctgaaa cttctgcggg attattctgc agatgatacc   2700
agaaaagtcc acatgataac agagaatatc aatgcctctt ggagaagcat tcataaaagg   2760
gtgagtgagc gagaggctgc tttggaagaa actcatagat tactgcaaca gttccccctg   2820
gacctggaaa agtttcttgc ctggcttaca gaagctgaaa caactgccaa tgtcctacag   2880
gatgctaccc gtaaggaaag gctcctagaa gactccaagg gagtaaaaga gctgatgaaa   2940
caatggcaag acctccaagg tgaaattgaa gctcacacag atgtttatga caacctggat   3000
gaaaacagcc aaaaaatcct gagatccctg gaaggttccg atgatgcagt cctgttacaa   3060
agacgtttgg ataacatgaa cttcaagtgg agtgaacttc ggaaaaagtc tctcaacatt   3120
aggtcccatt tggaagccag ttctgaccag tggaagcgtc tgcacctttc tctgcaggaa   3180
cttctggtgt ggctacagct gaaagatgat gaattaagcc ggcaggcacc tattggaggc   3240
gactttccag cagttcagaa gcagaacgat gtacataggg ccttcaagag ggaattgaaa   3300
actaaagaac ctgtaatcat gagtactctt gagactgtac gaatatttct gacagagcag   3360
cctttggaag gactagagaa actctaccag gagcccagag agctgcctcc tgaggagaga   3420
gcccagaatg tcactcggct tctacgaaag caggctgagg aggtcaatac tgagtgggaa   3480
aaattgaacc tgcactccgc tgactggcag agaaaaatag atgagaccct tgaaagactc   3540
caggaacttc aagaggccac ggatgagctg gacctcaagc tgcgccaagc tgaggtgatc   3600
aagggatcct ggcagcccgt gggcgatctc ctgattgact ctctccaaga tcacctcgag   3660
aaagtcaagg cacttcgagg agaaattgcg cctctgaaag agaacgtgag cgacgtcaat   3720
gaccttgctc gccagcttac cactttgggc attcagctct caccgtataa cctcagcact   3780
ctggaagacc tgaacaccag atggaagctt ctgcaggtgg ccgtcgagga ccgagtcagg   3840
cagctgcatg aagcccacag ggactttggt ccagcatctc agcactttct ttccacgtct   3900
gtccagggtc cctgggagag agccatctcg ccaaacaaag tgccctacta tatcaaccac   3960
gagactcaaa caacttgctg ggaccatccc aaaatgacag agctctacca gtctttagct   4020
gacctgaata atgtcagatt ctcagcttat aggactgcca tgaaactccg aagactgcag   4080
aaggcccttt gcttggatct cttgagcctg tcagctgcat gtgatgcctt ggaccagcac   4140
aacctcaagc aaaatgacca gcccatggat atcctgcaga ttattaattg tttgaccact   4200
atttatgacc gcctggagca agagcacaac aatttggtca acgtccctct ctgcgtggat   4260
atgtgtctga actggctgct gaatgtttat gatacgggac gaacagggag gatccgtgtc   4320
ctgtctttaa aagtggcatc atttccctgt gtaaagcaca tttggaagac aagtacagat   4380
accttttcaa gcaagtggca agttcaacag gattttgtga ccagcgcagg ctgggcctcc   4440
ttctgcatga ttctatccaa atccaagaca gttgggtgaa gttgcatcct ttgggggcag   4500
taacattgag ccaagtgtcc ggagctgctt ccaatttgct aataataagc cagagatcga   4560
agcggccctc ttcctagact ggatgagact ggaaccccag tccatggtgt ggctgcccgt   4620
cctgcacaga gtggctgctg gagaaactgc caagcatcag gccaaatgta acatctgcaa   4680
agagtgtcca atcattggat tcaggtacag gagtctaaag cactttaatt atgacatctg   4740
ccaaagctgc tttttttctg gtcgagttgc aaaaggccat aaaatgcact atcccatggt   4800
ggaatattgc actccgacta catcaggaga agatgttcga gactttgcca aggtactaaa   4860
aaacaaattt cgaaccaaaa ggtattttgc gaagcatccc cgaatgggct acctgccagt   4920
```

gcagactgtc ttagaggggg acaacatgga aacgcctgcc tcgtcccctc agctttcaca 4980
cgatgatact cattcacgca ttgaacatta tgctagcagg ctagcagaaa tggaaaacag 5040
caatggatct tatctaaatg atagcatctc tcctaatgag agcatagatg atgaacattt 5100
gttaatccag cattactgcc aaagtttgaa ccaggactcc cccctgagcc agcctcgtag 5160
tcctgcccag atcttgattt ccttagagag tgaggaaaga ggggagctag agagaatcct 5220
agcagatctt gaggaagaaa acaggaatct gcaagcagaa tatgaccgtc taaagcagca 5280
gcacgaacat aaaggcctgt ccccactgcc gtcccctcct gaaatgatgc ccacctctcc 5340
ccagagtccc cgggatgctg agctcattgc tgaggccaag ctactgcgtc aacacaaagg 5400
ccgcctggaa gccaggatgc aaatcctgga agaccacaat aaacagctgg agtcacagtt 5460
acacaggcta aggcagctgc tggagcaacc ccaggcagag gccaaagtga atggcacaac 5520
ggtgtcctct ccttctacct ctctacagag gtccgacagc agtcagccta tgctgctccg 5580
agtggttggc agtcaaactt cggactccat gggtgaggaa gatcttctca gtcctcccca 5640
ggacacaagc acagggttag aggaggtgat ggagcaactc aacaactcct tccctagttg 5700
aagaggaaga aataccccctg gaaagccaat gagagaggac acaatgtag 5749

<210> SEQ ID NO 2
<211> LENGTH: 7049
<212> TYPE: DNA
<213> ORGANISM: Artificial Sequence
<220> FEATURE:
<223> OTHER INFORMATION: Synthetic construct: Nucleotide sequence of delta-H2-R15 (mini-dystrophin with 12 repeats and 3 hinges; carries both R16 and R17, can restore nNOS)

<400> SEQUENCE: 2
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatgccc tgaacaatgt caacaaggca 240
ctgcgggttt tgcagaacaa taatgttgat ttagtgaata ttggaagtac tgacatcgta 300
gatggaaatc ataaactgac tgttggtttg atttggaata taatcctcca ctggcaggtc 360
aaaaatgtaa tgaaaaatat catggctgga ttgcaacaaa ccaacagtga aaagattctc 420
ctgagctggg tccgacaatc aactcgtaat tatccacagg ttaatgtaat caacttcacc 480
accagctggt ctgatggcct ggctttgaat gctctcatcc atagtcatag gccagaccta 540
tttgactgga atagtgtggt ttgccagcag tcagccacac aacgactgga acatgcattc 600
aacatcgcca gatatcaatt aggcatagag aaactactcg atcctgaaga tgttgatacc 660
acctatccag ataagaagtc catcttaatg tacatcacat cactcttcca agttttgcct 720
caacaagtga gcattgaagc catccaggaa gtggaaatgt tgccaaggcc acctaaagtg 780
actaaagaag aacattttca gttacatcat caaatgcact attctcaaca gatcacggtc 840
agtctagcac agggatatga gagaacttct tcccctaagc ctcgattcaa gagctatgcc 900
tacacacagg ctgcttatgt caccacctct gaccctacac ggagcccatt tccttcacag 960
catttggaag ctcctgaaga caagtcattt ggcagttcat tgatggagag tgaagtaaac 1020
ctggaccgtt atcaaacagc tttagaagaa gtattatcgt ggcttctttc tgctgaggac 1080
acattgcaag cacaaggaga gatttctaat gatgtggaag tggtgaaaga ccagtttcat 1140

-continued

```
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtatttgg gagatcgatg   1620
ggcaaacatc tgtagatgga cagaagaccg ctgggttctt ttacaagaca tccttctcaa   1680
atggcaacgt cttactgaag aacagtgcct tttagtgca tggctttcag aaaaagaaga   1740
tgcagtgaac aagattcaca caactggctt taaagatcaa aatgkaatgt tatcaagtct   1800
tcaaaaagtg gccgttttaa aagcggatct agaaaagaaa aagcaatcca tgggcaaact   1860
gtattcactc aaacaagatc ttctttcaac actgaagaat aagtcagtga cccagaagac   1920
ggaagcatgg ctggataact ttgcccggtg ttgggataat ttagtccaaa aacttgaaaa   1980
gagtacagca cagatttcac aggaaatttc ttatgtgcct tctacttatt tgactgaaat   2040
cactcatgtc tcacaagccc tattagaagt ggaacaactt ctcaatgctc ctgacctctg   2100
tgctaaggac tttgaagatc tctttaagca agaggagtct ctgaagaata taaaagatag   2160
tctacaacaa agctcaggtc ggattgacat tattcatagc aagaagacag cagcattgca   2220
aagtgcaacg cctgtggaaa gggtgaagct acaggaagct ctctcccagc ttgatttcca   2280
atgggaaaaa gttaacaaaa tgtacaagga ccgacaaggg cgatttgaca gatctgttga   2340
gaaatggcgg cgttttcatt atgatataaa gatatttaat cagtggctaa cagaagctga   2400
acagtttctc agaaagacac aaattcctga gaattgggaa catgctaaat acaaatggta   2460
tcttaaggaa ctccaggatg gcattgggca gcggcaaact gttgtcagaa cattgaatgc   2520
aactggggaa gaaataattc agcaatcctc aaaaacagat gccagtattc tacaggaaaa   2580
attgggaagc ctgaatctgc ggtggcagga ggtctgcaaa cagctgtcag acagaaaaaa   2640
gaggctagaa gaacaaaaga atatcttgtc agaatttcaa agagatttaa atgaatttgt   2700
tttatggttg gaggaagcag ataacattgc tagtatccca cttgaacctg gaaaagagca   2760
gcaactaaaa gaaaagcttg agcaagtcaa gttactggtg gaagagttgc ccctgcgcca   2820
gggaattctc aaacaattaa atgaaactgg aggacccgtg cttgtaagtg ctcccataag   2880
cccagaagag caagataaac ttgaaaataa gctcaagcag acaaatctcc agtggataaa   2940
ggtttccaga gctttacctg agaaacaagg agaaattgaa gctcaaataa aagaccttgg   3000
gcagcttgaa aaaaagcttg aagaccttga agagcagtta aatcatctgc tgctgtggtt   3060
atctcctatt aggaatcagt tggaaattta taaccaacca aaccaagaag gaccatttga   3120
cgttcaggaa actgaaatag cagttcaagc taaacaaccg gatgtggaag agattttgtc   3180
taaagggcag catttgtaca aggaaaaacc agccactcag ccagtgaaga ggaagttaga   3240
agatctgagc tctgagtgga aggcggtaaa ccgtttactt caagagctga gggcaaagca   3300
gcctgaccta gctcctggac tgaccactat tggagcctct cctactcaga ctgttactct   3360
ggtgacacaa cctgtggtta ctaaggaaac tgccatctcc aaactagaaa tgccatcttc   3420
cttgatgttg gaggtacctg ctctggcaga tttcaaccgg gcttggacag aacttaccga   3480
ctggctttct ctgcttgatc aagttataaa atcacagagg gtgatggtgg gtgaccttga   3540
```

-continued

```
ggatatcaac gagatgatca tcaagcagaa ggcaacaatg caggatttgg aacagaggcg   3600
tccccagttg gaagaactca ttaccgctgg ccaaaatttg aaaaacaaga ccagcaatca   3660
agaggctaga acaatcatta cggatcgaat tgaaagaatt cagaatcagt gggatgaagt   3720
acaagaacac cttcagaacc ggaggcaaca gttgaatgaa atgttaaagg attcaacaca   3780
atggctggaa gctaaggaag aagctgagca ggtcttagga caggccagag ccaagcttga   3840
gtcatggaag gagggtccct atacagtaga tgcaatccaa aagaaaatca cagaaaccaa   3900
gcagttggcc aaagacctcc gccagtggca gacaaatgta gatgtggcaa atgacttggc   3960
cctgaaactt ctccgggatt attctgcaga tgataccaga aaagtccaca tgataacaga   4020
gaatatcaat gcctcttgga gaagcattca taaaagggtg agtgagcgag aggctgcttt   4080
ggaagaaact catagattac tgcaacagtt cccccctggac ctggaaaagt ttcttgcctg   4140
gcttacagaa gctgaaacaa ctgccaatgt cctacaggat gctacccgta aggaaaggct   4200
cctagaagac tccaagggag taaaagagct gatgaaacaa tggcaagacc tccaaggtga   4260
aattgaagct cacacagatg tttatcacaa cctggatgaa aacagccaaa aaatcctgag   4320
atccctggaa ggttccgatg atgcagtcct gttacaaaga cgtttggata acatgaactt   4380
caagtggagt gaacttcgga aaaagtctct caacattagg tcccatttgg aagccagttc   4440
tgaccagtgg aagcgtctgc acctttctct gcaggaactt ctggtgtggc tacagctgaa   4500
agatgatgaa ttaagccggc aggcacctat tggaggcgac tttccagcag ttcagaagca   4560
gaacgatgta catagggcct tcaagaggga attgaaaact aaagaacctg taatcatgag   4620
tactcttgag actgtacgaa tatttctgac agagcagcct ttggaaggac tagagaaact   4680
ctaccaggag cccagagagc tgcctcctga ggagagagcc cagaatgtca ctcggcttct   4740
acgaaagcag gctgaggagg tcaatactga gtgggaaaaa ttgaacctgc actccgctga   4800
ctggcagaga aaaatagatg agacccttga aagactccag gaacttcaag aggccacgga   4860
tgagctggac ctcaagctgc gcgaagctga ggtgatcaag ggatcctggc agcccgtggg   4920
cgatctcctc attgactctc tccaagatca cctcgagaaa gtcaaggcac ttcgaggaga   4980
aattgcgcct ctgaaagaga acgtgagcca cgtcaatgac cttgctcgcc agcttaccac   5040
tttgggcatt cagctctcac cgtataacct cagcactctg gaagacctga acaccagatg   5100
gaagcttctg caggtggccg tcgaggaccg agtcaggcag ctgcatgaag cccacaggga   5160
ctttggtcca gcatctcagc actttctttc cacgtctgtc cagggtccct gggagagagc   5220
catctcgcca aacaaagtgc cctactatat caaccacgag actcaaacaa cttgctggga   5280
ccatcccaaa atgacagagc tctaccagtc tttagctgac ctgaataatg tcagattctc   5340
agcttatagg actgccatga aactccgaag actgcagaag gccctttgct tggatctctt   5400
gagcctgtca gctgcatgtg atgccttgga ccagcacaac ctcaagcaaa atgaccagcc   5460
catggatatc ctgcagatta ttaattgttt gaccactatt tatgaccgcc tggagcaaga   5520
gcacaacaat ttggtgaacg tgcctctctg cgtggatatg tgtctgaact ggctggtgaa   5580
tgtttatgat acgggacgaa cagggaggat ccgtgtcctg tcttttaaaa ctggcatcat   5640
ttccctgtgt aaagcacatt tggaagacaa gtacagatac cttttcaagc aagtgggaag   5700
ttcaacagga ttttgtgacc agcgcaggct gggcctcctt ctgcatgatt ctatccaaat   5760
tccaagacag ttgggtgaag ttgcatcctt tgggggcagt aacattgagc caagtgtccg   5820
gagctgcttc caatttgcta ataataagcc agagatcgaa gcggccctct tcctagactg   5880
```

-continued

```
gatgagactg gaaccccagt ccatggtgtg gctgcccgtc ctgcacagag tggctgctgc   5940

agaaactgcc aagcatcagg ccaaatgtaa catctgcaaa gagtgtccaa tcattggatt   6000

caggtacagg agtctaaagc actttaatta tgacatctgc caaagctgct ttttttctgg   6060

tcgagttgca aaaggccata aaatgcacta tcccatggtg gaatattgca ctccgactac   6120

atcaggagaa gatgttcgag actttgccaa ggtactaaaa aacaaatttc gaaccaaaag   6180

gtattttgcg aagcatcccc gaatgggcta cctgccagtg cagactgtct tagaggggga   6240

caacatggaa acgcctgcct cgtcccctca gctttcacag gatgatactc attcacgcat   6300

tgaacattat gctagcaggc tagcagaaat ggaaaacagc aatggatctt tatctaaatg   6360

atagcatctc tcctaatgag agcatagatg atgaacattt gttaatccag cattactgcc   6420

aaagtttgaa ccaggactcc cccctgagcc agcctcgtag tcctgcccag atcttgattt   6480

ccttagagag tgaggaaaga ggggagctag agagaatcct agcagatctt gaggaagaaa   6540

acaggaatct gcaagcagaa tatgaccgtc taaagcagca gcacgaacat aaaggcctgt   6600

ccccactgcc gtcccctcct gaaatgatgc ccacctctcc ccagagtccc cgggatgctg   6660

agctcattgc tgaggccaag ctactgcgtc aacacaaagg ccgcctggaa gccaggatgc   6720

aaatcctgga agaccacaat aaacagctgg agtcacagtt acacaggcta aggcagctgg   6780

tggagcaacc ccaggcagag gccaaagtga atggcacaac ggtgtcctct ccttctacct   6840

ctctacagag gtccgacagc agtcagccta tgctgctccg agtggttggc agtcaaactt   6900

cggactccat gggtgaggaa gatcttctca gtcctcccca ggacacaagc acagggttag   6960

aggaggtgat ggagcaactc aacaactcct tccctagttc aagaggaaga aatacccctg   7020

gaaagccaat gagagaggac acaatgtag                                     7049
```

<210> SEQ ID NO 3
<211> LENGTH: 3434
<212> TYPE: DNA
<213> ORGANISM: Artificial Sequence
<220> FEATURE:
<223> OTHER INFORMATION: Synthetic construct: Nucleotide sequence of delta-R2-R15/delta-R18-23/delta-C (micro-dystrophin with 4 repeats and 2 hinges, no C-terminal domain; carries both R16 and R17; can restore nNOS)

<400> SEQUENCE: 3

```
atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaaatgt tgccaaggcc acctaaagtg    780
```

-continued actaaagaag aacattttca gttacatcat caaatgcact attctcaaca gatcacggtc 840
agtctagcac agggatatga gagaacttct tcccctaagc ctcgattcaa gagctatgcc 900
tacacacagg ctgcttatgt caccacctct gaccctacac ggagcccatt tccttcacag 960
catttggaag ctcctgaaga caagtcattt ggcagttcat tgatggagag tgaagtaaac 1020
ctggaccgtt atcaaacagc tttagaagaa gtattatcgt ggcttctttc tgctgaggac 1080
acattgcaag cacaaggaga gatttctaat gatgtggaag tggtgaaaga ccagtttcat 1140
actcatgagg ggtacatgat ggatttgaca gcccatcagg gccgggttgg taatattcta 1200
caattgggaa gtaagctgat tggaacagga aaattatcag aagatgaaga aactgaagta 1260
caagagcaga tgaatctcct aaattcaaga tgggaatgcc tcagggtagc tagcatggaa 1320
aaacaaagca attacataga gaaatttctt atgtgccttc tacttatttg actgaaatca 1380
ctcatgtctc acaagcccta ttagaagtgg aacaacttct caatgctcct gacctctgtg 1440
ctaaggactt tgaagatctc tttaagcaag aggagtctct gaagaatata aaagatagtc 1500
tacaacaaag ctcaggtcgg attgacatta ttcatagcaa gaagacagca gcattgcaaa 1560
gtgcaacgcc tgtggaaagg gtgaagctac aggaagctct ctcccagctt gatttccaat 1620
gggaaaaagt taacaaaatg tacaaggacc gacaagggcg atttgacaga tctgttgaga 1680
aatggcggcg ttttcattat gatataaaga tatttaatca gtggctaaca gaagctgaac 1740
agtttctcag aaagacacaa attcctgaga attgggaaca tgctaaatac aaatggtatc 1800
ttaaggaact ccaggatggc attgggcagc ggcaaactgt tgtcagaaca ttgaatgcaa 1860
ctggggaaga aataattcag caatcctcaa aaacagatgc cagtattcta caggaaaaat 1920
tgggaagcct gaatctgcgg tggcaggagg tctgcaaaca gctgtcagac agaaaaaaga 1980
ggctagaaga aacccttgaa agactccagg aacttcaaga ggccacggat gagctggacc 2040
tcaagctgcg ccaagctgag gtgatcaagg gatcctggca gcccgtgggc gatctcctca 2100
ttgactctct ccaagatcac ctcgagaaag tcaaggcact tcgaggagaa attgcgcctc 2160
tgaaagagaa cgtgagccac gtcaatgacc ttgctcgcca gcttaccact ttgggcattc 2220
agctctcacc gtataacctc agcactctgg aagacctgaa caccagatgg aagcttctgc 2280
aggtggccgt cgaggaccga gtcaggcagc tgcatgaagc ccacagggac tttggtccag 2340
catctcagca ctttctttcc acgtctgtcc agggtccctg ggagagagcc atctcgccaa 2400
acaaagtgcc ctactatatc aaccacgaga ctcaaacaac ttgctgggac gatcccaaaa 2460
tgacagagct ctaccagtct ttagctgacc tgaataatgt cagattctca gcttatagga 2520
ctgccatgaa actccgaaga ctgcagaagg ccctttgctt ggatctcttg agcctgtcag 2580
ctgcatgtga tgccttggac cagcacaacc tcaagcaaaa tgaccagccc atggatatcc 2640
tgcagattat taattgtttg accactattt atgaccgcct ggagcaagag cacaacaatt 2700
tggtcaacgt ccctctctgc gtggatatgt gtctgaactg gctgctgaat gtttatgata 2760
cgggacgaac agggaggatc cgtgtcctgt cttttaaaac tggcatcatt tccctgtgta 2820
aagcacattt ggaagacaag tacagatacc ttttcaagca agtggcaagt tcaacaggat 2880
tttgtgacca gcgcaggctg ggcctccttc tgcatgattc tatccaaatt ccaagacagt 2940
tgggtgaagt tgcatccttt gggggcagta acattgagcc aagtgtccgg agctgcttcc 3000
aatttgctaa taataagcca gagatcgaag cggccctctt cctagactgg atgagactgg 3060
aaccccagtc catggtgtgg ctgcccgtcc tgcacagagt ggctgctgca gaaactgcca 3120
agcatcaggc caaatgtaac atctgcaaag agtgtccaat cattggattc aggtacagga 3180

```
gtctaaagca ctttaattat gacatctgcc aaagctgctt tttttctggt cgagttgcaa   3240

aaggccataa aatgcactat cccatggtgg aatattgcac tccgactaca tcaggagaag   3300

atgttcgaga ctttgccaag gtactaaaaa acaaatttcg aaccaaaagg tattttgcga   3360

agcatccccg aatgggctac ctgccagtgc agactgtctt agagggggac aacatggaaa   3420

ctgacacaat gtag                                                     3434
```

<210> SEQ ID NO 4
<211> LENGTH: 3594
<212> TYPE: DNA
<213> ORGANISM: Artificial Sequence
<220> FEATURE:
<223> OTHER INFORMATION: Synthetic construct: Nucleotide sequence of delta-R4-R23/delta-C (micro-dystrophin with 4 repeats and 3 hinges, no C-terminal domain; does not include R16 or R17, cannot restore nNOS)

<400> SEQUENCE: 4

```
atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaaatgt tgccaaggcc acctaaagtg    780

actaaagaag aacattttca gttacatcat caaatgcact attctcaaca gatcacggtc    840

agtctagcac agggatatga gagaacttct tcccctaagc ctcgattcaa gagctatgcc    900

tacacacagg ctgcttatgt caccacctct gaccctacac ggagcccatt tccttcacag    960

catttggaag ctcctgaaga caagtcattt ggcagttcat tgatggagag tgaagtaaac   1020

ctggaccgtt atcaaacagc tttagaagaa gtattatcgt ggcttctttc tgctgaggac   1080

acattgcaag cacaaggaga gatttctaat gatgtggaag tggtgaaaga ccagtttcat   1140

actcatgagg ggtacatgat ggatttgaca gcccatcagg gccgggttgg taatattcta   1200

caattgggaa gtaagctgat tggaacagga aaattatcag aagatgaaga aactgaagta   1260

caagagcaga tgaatctcct aaattcaaga tgggaatgcc tcagggtagc tagcatggaa   1320

aaacaaagca atttacatag agttttaatg gatctccaga atcagaaact gaaagagttg   1380

aatgactggc taacaaaaac agaagaaaga acaaggaaaa tggaggaaga gcctcttgga   1440

cctgatcttg aagacctaaa acgccaagta caacaacata aggtgcttca agaagatcta   1500

gaacaagaac aagtcagggt caattctctc actcacatgg tggtggtagt tgatgaatct   1560

agtggagatc acgcaactgc tgctttggaa gaacaactta aggtattggg agatcgatgg   1620

gcaaacatct gtagatggac agaagaccgc tgggttcttt tacaagacat ccttctcaaa   1680
```

tggcaacgtc ttactgaaga acagtgcctt tttagtgcat ggctttcaga aaaagaagat 1740
gcagtgaaca agattcacac aactggcttt aaagatcaaa atgaaatgtt atcaagtctt 1800
caaaaactgg ccgttttaaa agcggatcta gaaaagaaaa agcaatccat gggcaaactg 1860
tattcactca aacaagatct tctttcaaca ctgaagaata agtcagtgac ccagaagacg 1920
gaagcatggc tggataactt tgcccggtgt tgggataatt tagtccaaaa acttgaaaag 1980
agtacagcac agatttcaca ggctgtcacc accactcagc catcactaac acagacaact 2040
gtaatggaaa cagtaactac ggtgaccaca agggaacaga tcctggtaaa gcatgctcaa 2100
gaggaacttc caccaccacc tccccaaaag aagaggcaga ttactgtgga tacccttgaa 2160
agactccagg aacttcaaga ggccacggat gagctggacc tcaagctgcg ccaagctgag 2220
gtgatcaagg gatcctggca gcccgtgggc gatctcctca ttgactctct ccaagatcac 2280
ctcgagaaag tcaaggcact tcgaggagaa attgcgcctc tgaaagagaa cgtgagccac 2340
gtcaatgacc ttgctcgcca gcttaccact ttgggcattc agctctcacc gtataacctc 2400
agcactctgg aagacctgaa caccagatgg aagcttctgc aggtggccgt cgaggaccga 2460
gtcaggcagc tgcatgaagc ccacagggac tttggtccag catctcagca ctttctttcc 2520
acgtctgtcc agggtccctg ggagagagcc atctcgccaa acaaagtgcc ctactatatc 2580
aaccacgaga ctcaaacaac ttgctgggac gatcccaaaa tgacagagct ctaccagtct 2640
ttagctgacc tgaataatgt cagattctca gcttatagga ctgccatgaa actccgaaga 2700
ctgcagaagg ccctttgctt ggatctcttg agcctgtcag ctgcatgtga tgccttggac 2760
cagcacaacc tcaagcaaaa tgaccagccc atggatatcc tgcagattat taattgtttg 2820
accactattt atgaccgcct ggagcaagag cacaacaatt tggtcaacgt ccctctctgc 2880
gtggatatgt gtctgaactg gctgctgaat gtttatgata cgggacgaac agggaggatc 2940
cgtgtcctgt cttttaaaac tggcatcatt tccctgtgta aagcacattt ggaagacaag 3000
tacagatacc ttttcaagca agtggcaagt tcaacaggat tttgtgacca gcgcaggctg 3060
ggcctccttc tgcatgattc tatccaaatt ccaagacagt tgggtgaagt tgcatccttt 3120
gggggcagta acattgagcc aagtgtccgg agctgcttcc aatttgctaa taataagcca 3180
gagatcgaag cggccctctt cctagactgg atgagactgg aaccccagtc catggtgtgg 3240
ctgcccgtcc tgcacagagt ggctgctgca gaaactgcca agcatcaggc caaatgtaac 3300
atctgcaaag agtgtccaat cattggattc aggtacagga gtctaaagca ctttaattat 3360
gacatctgcc aaagctgctt tttttctggt cgagttgcaa aaggccataa aatgcactat 3420
cccatggtgg aatattgcac tccgactaca tcaggagaag atgttcgaga ctttgccaag 3480
gtactaaaaa acaaatttcg aaccaaaagg tattttgcga agcatccccg aatgggctac 3540
ctgccagtgc agactgtctt agagggggac aacatggaaa ctgacacaat gtag 3594

<210> SEQ ID NO 5
<211> LENGTH: 8312
<212> TYPE: DNA
<213> ORGANISM: Artificial Sequence
<220> FEATURE:
<223> OTHER INFORMATION: Synthetic construct: AAV vector containing four repeats and two hinges; carries both R16 and R17 and it can restore nNOS

<400> SEQUENCE: 5
cattaatgaa tcggccaacg cgcggggaga ggcggtttgc gtattgggcg ctcttccgct 60

-continued

```
tcctcgctca ctgactcgct gcgctcggtc gttcggctgc ggcgagcggt atcagctcac    120
tcaaaggcgg taatacggtt atccacagaa tcaggggata acgcaggaaa gaacatgtga    180
gcaaaaggcc agcaaaaggc caggaaccgt aaaaaggccg cgttgctggc gtttttccata   240
ggctccgccc ccctgacgag catcacaaaa atcgacgctc aagtcagagg tggcgaaacc    300
cgacaggact ataaagatac caggcgtttc cccctggaag ctccctcgtg cgctctcctg    360
ttccgaccct gccgcttacc ggatacctgt ccgcctttct cccttcggga agcgtggcgc    420
tttctcatag ctcacgctgt aggtatctca gttcggtgta ggtcgttcgc tccaagctgg    480
gctgtgtgca cgaacccccc gttcagcccg accgctgcgc cttatccggt aactatcgtc    540
ttgagtccaa cccggtaaga cacgacttat cgccactggc agcagccact ggtaacagga    600
ttagcagagc gaggtatgta ggcggtgcta cagagttctt gaagtggtgg cctaactacg    660
gctacactag aaggacagta tttggtatct gcgctctgct gaagccagtt accttcggaa    720
aaagagttgg tagctcttga tccggcaaac aaaccaccgc tggtagcggt ggtttttttg    780
tttgcaagca gcagattacg cgcagaaaaa aaggatctca agaagatcct ttgatctttt    840
ctacggggtc tgacgctcag tggaacgaaa actcacgtta agggattttg gtcatgagat    900
tatcaaaaag gatcttcacc tagatccttt taaattaaaa atgaagtttt aaatcaatct    960
aaagtatata tgagtaaact tggtctgaca gttaccaatg cttaatcagt gaggcaccta   1020
tctcagcgat ctgtctattt cgttcatcca tagttgcctg actccccgtc gtgtagataa   1080
ctacgatacg ggagggctta ccatctggcc ccagtgctgc aatgataccg cgagacccac   1140
gctgaccggc tccagattta tcagcaataa accagccagc cggaagggcc gagcgcagaa   1200
gtggtcctgc aagtttatcc gcctccatcc agtgtattaa ttgttgccgg gaagctagag   1260
taagtagttc gccagttaat agtttgcgca acgttgttgc cattgctaca ggcatcgtgg   1320
tgtcaggctc gtcgtttggt atggcttcat tcagctccgg ttcccaacga tcaaggcgag   1380
ttacatgatc ccccatgttg tgcaaaaaag cggttagctc cttcggtcct ccgatcgttg   1440
tcagaagtaa gttggccgca gtgttatcac tcatggttat ggcagcactg cataattctc   1500
ttactgtcat gccatccgta agatgctttt ctgtgactgg tgagtactca accaagtcat   1560
tctgagaata gtgtatgcgg cgaccgagtt gctcttgccc ggcgtcaata cgggataata   1620
ccgcgccaca tagcagaact ttaaaagtgc tcatcattgg aaaacgttct tcggggcgaa   1680
aactctcaag gatcttaccg ctgttgagat ccagtcgatg taacccactc gtgcacccaa   1740
ctgatcttca gcatctttta ctttcaccag cgtttctggg tgagcaaaaa caggaaggca   1800
aaatgccgca aaaaagggaa taagggcgac acggaaatgt tgatactcat actcttcctt   1860
tttcaatatt attgaagcat ttatcagggt tattgtctca tgagcggata catatttgaa   1920
tgtatttaga aaaataaaca aataggggtt ccgcgcacat ttccccgaaa agtgccacct   1980
gacgtctaag aaaccattat tatcatgaca ttaacctata aaaataggcg tatcacgagg   2040
ccctttcgtc tcgcgcgttt cggtgatgac ggtgaaaagc tctgacacat gcagctcccg   2100
gagacggtca cagcttgtct gtaagcggat gccgggagca gacaagcccg tcagggcgcg   2160
tcagcgggtg ttggcgggtg tcggggctgg cttaactatg cggcatcaga gcagattgta   2220
ctgagagtgc accatatgcg gtgtgaaata ccgcacagat gcgtaaggag aaaataccgc   2280
atcaggaatt ccaacatcca ataaatcata caggcaaggc aaagaattag caaaattaag   2340
caataaagcc tcagagcata aagctaaatc ggttgtacca aaaacattat gaccctgtaa   2400
tacttttgcg ggagaagcct ttatttcaac gcaaggataa aaatttttag aaccctcata   2460
```

-continued

```
tattttaaat gcaatgcctg agtaatgtgt aggtaaagat tcaaacgggt gagaaaggcc   2520
ggagacagtc aaatcaccat caatatgata ttcaaccgtt ctagctgata aattcatgcc   2580
ggagagggta gctatttttg agaggtctct acaaaggcta tcaggtcatt gcctgagagt   2640
ctggagcaaa caagagaatc gatgaacggt aatcgtaaaa ctagcatgtc aatcatatgt   2700
accccggttg ataatcagaa aagccccaaa aacaggaaga ttgtataagc aaatatttaa   2760
attgtaaacg ttaatatttt gttaaaattc gcgttaaatt tttgtaaatc agctcatttt   2820
ttaaccaata ggccgaaatc ggcaaaatcc cttataaatc aaaagaatag accgagatag   2880
ggttgagtgt tgttccagtt tggaacaaga gtccactatt aaagaacgtg gactccaacg   2940
tcaaagggcg aaaaaccgtc tatcagggcg atggcccact acgtgaacca tcaccctaat   3000
caagtttttt ggggtcgagg tgccgtaaag cactaaatcg gaaccctaaa gggagccccc   3060
gatttagagc ttgacgggga aagccggcga acgtggcgag aaaggaaggg aagaaagcga   3120
aaggagcggg cgctagggcg ctggcaagtg tagcggtcac gctgcgcgta accaccacac   3180
ccgccgcgct taatgcgccg ctacagggcg cgtactatgg ttgctttgac gagcaggtat   3240
aacgtgcttt cctcgttaga atcagagcgg gagctaaaca ggaggccgat taaagggatt   3300
ttagacagga acggtacgcc agaatcctga gaagtgtttt tataatcagt gaggccaccg   3360
agtaaaagag tctgtcgatc acgcaaatta accgttgtcg caatacttct ttgattagta   3420
ataacatcac ttgcctgagt agaagaactc aaactatcgg ccttgctggt aatatccaga   3480
acaatattac cgccagccat tgcaagagga aaaacgctca tggaaatacc tacattttga   3540
cgctcaatcg tctggaattc cattcgccat tcaggctgcg caactgttgg gaagggcgat   3600
cggtgcgggc ctcttcgcta ttacgccagc tggcgcgctc gctcgctcac tgaggccgcc   3660
cgggcaaagc ccgggcgtcg ggcgaccttt ggtcgcccgg cctcagtgag cgagcgagcg   3720
cgcagagagg gagtggccaa ctccatcact aggggttcct tgtagttaat gattaacccg   3780
ccatgctact tatctacggc cgcggtaccg cgttacataa cttacggtaa atggcccgcc   3840
tggctgaccg cccaacgacc cccgcccatt gacgtcaata atgacgtatg ttcgcatagt   3900
aacgccaata gggactttcc attgacgtca atgggtggag tatttacggt aaactgccca   3960
cttggcagta catcaagtgt atcatatgcc aagtacgccc cctattgacg tcaatgacgg   4020
taaatggccc gcctggcatt atgcccagta catgacctta tgggactttc ctacttggca   4080
gtacatctac gtattagtca tcgctattac catggtgatg cggttttggc agtacatcaa   4140
tgggcgtgga tagcggtttg actcacgggg atttccaagt ctccacccca ttgacgtcaa   4200
tgggagtttg ttttggcacc aaaatcaacg ggactttcca aaatgtcgta acaactccgc   4260
cccattgacg caaatgggcg gtaggcgtgt acggtgggag gtctatataa gcagagctcg   4320
tttagtgaac cgtctagacg gccgcggttt tttttatcgc tgccttgata tacactttcc   4380
accatgcttt ggtgggaaga agtagaggac tgttatgaaa gagaagatgt tcaaaagaaa   4440
acattcacaa aatgggtaaa tgcacaattt tctaagtttg ggaagcagca tattgagaac   4500
ctcttcagtg acctacagga tgggaggggc ctcctagacc tcctcgaagg cctgacaggg   4560
caaaaactgc caaaagaaaa aggatccaca agagttcatg ccctgaacaa tgtcaacaag   4620
gcactgcggg ttttgcagaa caataatgtt gatttagtga atattggaag tactgacatc   4680
gtagatggaa atcataaact gactcttggt ttgatttgga atataatcct ccactggcag   4740
gtcaaaaatg taatgaaaaa tatcatggct ggattgcaac aaaccaacag tgaaaagatt   4800
```

-continued

```
ctcctgagct gggtccgaca atcaactcgt aattatccac aggttaatgt aatcaacttc   4860
accaccagct ggtctgatgg cctggctttg aatgctctca tccatagtca taggccagac   4920
ctatttgact ggaatagtgt ggtttgccag cagtcagcca cacaacgact ggaacatgca   4980
ttcaacatcg ccagatatca attaggcata gagaaactac tcgatcctga agatgttgat   5040
accacctatc cagataagaa gtccatctta atgtacatca catcactctt ccaagttttg   5100
cctcaacaag tgagcattga agccatccag gaagtggaaa tgttgccaag gccacctaaa   5160
gtgactaaag aagaacattt tcagttacat catcaaatgc actattctca acagatcacg   5220
gtcagtctag cacagggata tgagagaact tcttccccta agcctcgatt caagagctat   5280
gcctacacac aggctgctta tgtcaccacc tctgacccta cacggagccc atttccttca   5340
cagcatttgg aagctcctga agacaagtca tttggcagtt cattgatgga gagtgaagta   5400
aacctggacc gttatcaaac agctttagaa gaagtattat cgtggcttct ttctgctgag   5460
gacacattgc aagcacaagg agagatttct aatgatgtgg aagtggtgaa agaccagttt   5520
catactcatg aggggtacat gatggatttg acagcgcatc agggccgggt tggtaatatt   5580
ctacaattgg gaagtaagct gattggaaca ggaaaattat cagaagatga agaaactgaa   5640
gtacaagagc agatgaatct cctaaattca agatgggaat gcctcagggt agctagcatg   5700
gaaaaacaaa gcaatttaca tagagaaatt tcttatgtgc cttctactta tttgactgaa   5760
atcactcatg tctcacaagc cctattagaa gtggaacaac ttctcaatgc tcctgacctc   5820
tgtgctaagg actttgaaga tctctttaag caagaggagt ctctgaagaa tataaaagat   5880
agtctacaac aaagctcagg tcggattgac attattcata gcaagaagac agcagcattg   5940
caaagtgcaa cgcctgtgga aagggtgaag ctacaggaag ctctctccga gcttgatttc   6000
caatgggaaa aagttaacaa aatgtacaag gaccgacaag ggcgatttga cagatctgtt   6060
gagaaatggc ggcgttttca ttatgatata aagatattta atcagtggct aacagaagct   6120
gaacagtttc tcagaaagag acaaattcct gagaattggg aacatgctaa atacaaatgg   6180
tatcttaagg aactccagga tggcattggg cagcggcaaa ctgttgtcag aacattgaat   6240
gcaactgggg aagaaataat tcagcaatcc tcaaaaacag atgccagtat tctacaggaa   6300
aaattgggaa gcctgaatct gcggtggcag gaggtctgca aacagctgtc agacagaaaa   6360
aagaggctag aagaaaccct tgaaagactc caggaacttc aagaggccac ggatgaggtg   6420
gacctcaagc tgcgccaagc tgaggtgatc aagggatcct ggcagcccgt gggcgatctc   6480
ctcattgact ctctccaaga tcacctcgag aaagtcaagg cacttcgagg agaaattgcg   6540
cctctgaaag agaacgtgag ccacgtcaat gaccttgctc gccagcttac cactttgggc   6600
attcagctct caccgtataa cctcagcact ctggaagacc tgaacaccag atggaagctt   6660
ctgcaggtgg ccgtcgagga ccgagtcagg cagctgcatg aagcccacag ggactttggt   6720
ccagcatctc agcactttct ttccacgtct gtccagggtc cctgggagag agccatctcg   6780
ccaaacaaag tgccctacta tatcaaccac gagactcaaa caacttgctg ggaccatccc   6840
aaaatgacag agctctacca gtctttagct gacctgaata atgtcagatt ctcagcttat   6900
aggactgcca tgaaactccg aagactgcag aaggcccttt gcttggatct cttgagcctg   6960
tcagctgcat gtgatgcctt ggaccagcac aacctcaagc aaaatgacca gcccatggat   7020
atcctgcaga ttattaattg tttgaccact atttatgacc gcctggagca agagcacaac   7080
aatttggtca acgtccctct ctgcgtggat atgtgtctga actggctgct gaatgtttat   7140
gatacgggac gaacagggag gatccgtgtc ctgtctttta aaactggcat catttccctg   7200
```

-continued tgtaaagcac atttggaaga caagtacaga taccttttca agcaagtggc aagttcaaca 7260
ggattttgtg accagcgcag gctgggcctc cttctgcatg attctatcca aattccaaga 7320
cagttgggtg aagttgcatc ctttgggggc agtaacattg agccaagtgt ccggagctgc 7380
ttccaatttg ctaataataa gccagagatc gaagcggccc tcttcctaga ctggatgaga 7440
ctggaacccc agtccatggt gtggctgccc gtcctgcaca gagtggctgc tgcagaaact 7500
gccaagcatc aggccaaatg taacatctgc aaagagtgtc caatcattgg attcaggtac 7560
aggagtctaa agcactttaa ttatgacatc tgccaaagct gcttttttc tggtcgagtt 7620 gcaaaaggcc ataaaatgca ctatcccatg gtggaatatt gcactccgac tacatcagga 7680
gaagatgttc gagactttgc caaggtacta aaaaacaaat ttcgaaccaa aaggtatttt 7740
gcgaagcatc cccgaatggg ctacctgcca gtgcagactg tcttagaggg ggacaacatg 7800
gaaactgaca caatgtagga agtcttttcc acatggcaga tgatttgggc agagcgatgg 7860
agtccttagt atcagtcatg acagatgaag aaggagcaga ataaatgttt tacaactcct 7920
gattcccgca tgcggccgat ccagacatga taagatacat tgatgagttt ggacaaacca 7980
caactagaat gcagtgaaaa aaatgcttta tttgtgaaat ttgtgatgct attgctttat 8040
ttgtaaccat tataagctgc aataaacaag ttaacaacaa caattgcatt cattttatgt 8100
ttcaggttca gggggaggtg tgggaggttt tttgcggccg tagataagta gcatggcggg 8160
ttaatcatta actacaagga acccctagtg atggagttgg ccactccctc tctgcgcgct 8220
cgctcgctca ctgaggccgg gcgaccaaag gtcgcccgac gcccgggctt tgcccgggcg 8280
gcctcagtga gcgagcgagc gcgcagctgc tg 8312

<210> SEQ ID NO 6
<211> LENGTH: 705
<212> TYPE: DNA
<213> ORGANISM: Artificial Sequence
<220> FEATURE:
<223> OTHER INFORMATION: Synthetic construct: Nucleotide sequence of human dystrophin spectrin-like repeats 16 and 17 (R16/R17)

<400> SEQUENCE: 6
attcacactg tccgtgaaga aacgatgatg gtgatgactg aagacatgcc tttggaaatt 60
tcttatgtgc cttctactta tttgactgaa atcactcatg tctcacaagc cctattagaa 120
gtggaacaac ttctcaatgc tcctgacctc tgtgctaagg actttgaaga tctctttaag 180
caagaggagt ctctgaagaa tataaaagat agtctacaac aaagctcagg tcggattgac 240
attattcata gcaagaagac agcagcattg caaagtgcaa cgcctgtgga aagggtgaag 300
ctacaggaag ctctctccca gcttgatttc caatgggaaa aagttaacaa aatgtacaag 360
gaccgacaag ggcgatttga cagatctgtt gagaaatggc ggcgttttca ttatgatata 420
aagatattta atcagtggct aacagaagct gaacagtttc tcagaaagac acaaattcct 480
gagaattggg aacatgctaa atacaaatgg tatcttaagg aactccagga tggcattggg 540
cagcggcaaa ctgttgtcag aacattgaat gcaactgggg aagaaataat tcagcaatcc 600
tcaaaaacag atgccagtat tctacaggaa aaattgggaa gcctgaatct gcggtggcag 660
gaggtctgca aacagctgtc agacagaaaa aagaggctag aagaa 705

<210> SEQ ID NO 7
<211> LENGTH: 217
<212> TYPE: PRT
<213> ORGANISM: Artificial Sequence -continued
<220> FEATURE:
<223> OTHER INFORMATION: Synthetic construct: Amino acid sequence of human dystrophin spectrin-like repeats 16 and 17 (R16/R17)

<400> SEQUENCE: 7

```
Glu Ile Ser Tyr Val Pro Ser Thr Tyr Leu Thr Glu Ile Thr His Val
1               5                   10                  15

Ser Gln Ala Leu Leu Glu Val Glu Gln Leu Leu Asn Ala Pro Asp Leu
            20                  25                  30

Cys Ala Lys Asp Phe Glu Asp Leu Phe Lys Gln Glu Glu Ser Leu Lys
        35                  40                  45

Asn Ile Lys Asp Ser Leu Gln Gln Ser Ser Gly Arg Ile Asp Ile Ile
    50                  55                  60

His Ser Lys Lys Thr Ala Ala Leu Gln Ser Ala Thr Pro Val Glu Arg
65                  70                  75                  80

Val Lys Leu Gln Glu Ala Leu Ser Gln Leu Asp Glu Gln Trp Glu Lys
                85                  90                  95

Val Asn Lys Met Tyr Lys Asp Arg Gln Gly Arg Phe Asp Arg Ser Val
            100                 105                 110

Glu Lys Trp Arg Arg Phe His Tyr Asp Ile Lys Ile Phe Asn Gln Trp
        115                 120                 125

Leu Thr Glu Ala Glu Gln Phe Leu Arg Lys Thr Gln Ile Pro Glu Asn
    130                 135                 140

Trp Glu His Ala Lys Tyr Lys Trp Tyr Leu Lys Glu Leu Gln Asp Gly
145                 150                 155                 160

Ile Gly Gln Arg Gln Thr Val Val Arg Thr Leu Asn Ala Thr Gly Glu
                165                 170                 175

Glu Ile Ile Gln Gln Ser Ser Lys Thr Asp Ala Ser Ile Leu Gln Glu
            180                 185                 190

Lys Leu Gly Ser Leu Asn Leu Arg Trp Gln Glu Val Cys Lys Gln Leu
        195                 200                 205

Ser Asp Arg Lys Lys Arg Leu Glu Glu
    210                 215
```

<210> SEQ ID NO 8
<211> LENGTH: 11057
<212> TYPE: DNA
<213> ORGANISM: Homo sapiens
<220> FEATURE:
<221> NAME/KEY: misc_feature
<222> LOCATION: (1)..(11055)
<223> OTHER INFORMATION: Full-length dystrophin nucleotide sequence (The full-length gene carries R16 and R17. It can restore nNOS)
<220> FEATURE:
<221> NAME/KEY: misc_feature
<222> LOCATION: (1085)..(1086)
<223> OTHER INFORMATION: n is a, c, g, t, unknown or other

<400> SEQUENCE: 8

```
atgctttggt gggaagaagt agaggactgt tatgaaagag aagatgttca aaagaaaaca      60

ttcacaaaat gggtaaatgc acaattttct aagtttggga agcagcatat tgagaacctc     120

ttcagtgacc tacaggatgg gaggcgcctc ctagacctcc tcgaaggcct gacagggcaa     180

aaactgccaa aagaaaaagg atccacaaga gttcatgccc tgaacaatgt caacaaggca     240

ctgcgggttt tgcagaacaa taatgttgat ttagtgaata ttggaagtac tgacatcgta     300

gatggaaatc ataaactgac tcttggtttg atttggaata taatcctcca ctggcaggtc     360

aaaaatgtaa tgaaaaatat catggctgga ttgcaacaaa ccaacagtga aaagattctc     420
```

-continued

```
ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaaatgt tgccaaggcc acctaaagtg    780

actaaagaag aacattttca gttacatcat caaatgcact attctcaaca gatcacggtc    840

agtctagcac agggatatga gagaacttct tcccctaagc ctcgattcaa gagctatgcc    900

tacacacagg ctgcttatgt caccacctct gaccctacac ggagcccatt tccttcacag    960

catttggaag ctcctgaaga caagtcattt ggcagttcat tgatggagag tgaagtaaac   1020

ctggaccgtt atcaaacagc tttagaagaa gtattatcgt ggcttctttc tgctgaggac   1080

acatnngcaa gcacaaggag agattctaat gatgtggaag tggtgaaaga ccagtttcat   1140

actcatgagg ggtacatgat ggatttgaca gcccatcagg gccgggttgg taatattcta   1200

caattgggaa gtaagctgat tggaacagga aaattatcag aagatgaaga aactgaagta   1260

caagagcaga tgaatctcct aaattcaaga tgggaatgcc tcagggtagc tagcatggaa   1320

aaacaaagca atttacatag agttttaatg gatctccaga atcagaaact gaaagagttg   1380

aatgactggc taacaaaaac agaagaaaga acaaggaaaa tggaggaaga gcctcttgga   1440

cctgatcttg aagacctaaa acgccaagta caacaacata aggtgcttca agaagatcta   1500

gaacaagaac aagtcagggt caatttctct cactcacatg gtggtggtag ttgatgaatg   1560

tagtggagat cacgcaactg ctgctttgga agaacaactt aaggtattgg gagatcgatg   1620

ggcaaacatc tgtagatgga cagaagaccg ctgggttctt ttacaagaca tccttctcaa   1680

atggcaacgt cttactgaag aacagtgcct tttagtgca tggctttcag aaaaagaaga   1740

tgcagtgaac aagattcaca caactggctt taaagatcaa aatgaaatgt tatcaagtct   1800

tcaaaaactg gccgttttaa aagcggatct agaaaagaaa aagcaatcca tgggcaaact   1860

gtattcactc aaacaagatc ttctttcaac actgaagaat aagtcagtga cccagaagac   1920

ggaagcatgg ctggataact ttgcccggtg ttgggataat ttagtccaaa aacttgaaaa   1980

gagtacagca cagatttcac aggctgtcac caccactcag ccatcactaa cacagacaac   2040

tgtaatggaa acagtaacta cggtgaccac aagggaacag atcctggtaa agcatgctca   2100

agaggaactt ccaccaccac ctccccaaaa gaagaggcag attactgtgg attctgaaat   2160

ttaggaaaag gttggatgtt gatataactg aacttcacag ctggattact cgctcagaag   2220

ctgtgttgca gagtcctgaa tttgcaatct ttcggaagga aggcaacttc tcagacttaa   2280

aagaaaaagt caatgccata gagcgagaaa aagctgagaa gttcagaaaa ctgcaagatg   2340

ccagcagatc agctcaggcc ctggtggaac agatggtgaa tgagggtgtt aatgcagata   2400

gcatcaaaca agcctcagaa caactgaaca gccggtggat cgaattctgc cagttgctaa   2460

gtgagagact taactggctg gagtatcaga acaacatcat cgctttctat aatcagctac   2520

aacaattgga gcagatgaca actactgctg aaaactggtt gaaaatccaa cccaccaccc   2580

catcagagcc aacagcaatt aaaagtcagt taaaaatttg taaggatgaa gtcaaccggc   2640

tatcaggtct tcaacctcaa attgaacgat taaaaattca aagcatagcc ctgaaagaga   2700

aaggacaagg acccatgttc ctggatgcag actttgtggc ctttacaaat cattttaagc   2760

aagtcttttc tgatgtgcag gccagagaga aagagctaca gacaattttt gacactttgc   2820
```

-continued

```
caccaatgcg ctatcaggag accatgagtg ccatcaggac atgggtccag cagtcagaaa   2880
ccaaactctc catagctcaa cttagtgtca ccgactatga aatcatggag cagagactcg   2940
gggaattgca ggctttacaa agttctctgc aagagcaaca aagtggccta tactatctca   3000
gcaccactgt gaaagagatg tcgaagaaag cgccctctga aattagccgg aaatatcaat   3060
cagaatttga agaaattgag ggacgctgga agaagctctc ctcccagctg gttgagcatt   3120
tgtcaaaagc tagaggagca aatgaataaa ctccgaaaaa ttcagaatca catacaaacc   3180
ctgaagaaat ggatggctga agttgatgtt tttctgaagg aggaatggcc tgcccttggg   3240
gattcagaaa ttctaaaaaa gcagctgaaa cagtgcagac ttttagtcag tgatattcag   3300
acaattcagc ccagtctaaa cagtgtcaat gaaggtgggc agaagataaa gaatgaagca   3360
gagccagagt ttgcttcgag acttgagaca gaactcaaag aacttaacac tcagtgggat   3420
cacatgtggc aacaggtcta tgccagaaag gaggccttga agggaggttt ggagaaaact   3480
gtaagcctcc agaaagatct atcagagatg cacgaatgga tgacacaagc tgaagaagag   3540
tatcttgaga gagattttga atataaaact ccagatgaat tacagaaagc agttgaagag   3600
atgaagagag ctaaagaaga ggcccaacaa aaagaagcga aagtgaaact ccttactgag   3660
tctgtaaata gtgtcatagc tcaagctcca cctgtagcac aagaggcctt aaaaaaggaa   3720
cttgaaactc taaccaccaa ctaccagtgg ctctgcacta ggctgaatgg gaaatgcaag   3780
actttggaag aagtttgggc atgttggcat gagttattgt catacttgga gaaagcaaac   3840
aagtggctaa atgaagtaga atttaaactt aaaaccactg aaaacattcc tggcggagct   3900
gaggaaatct ctgaggtgct agattcactt gaaaatttga tgcgacattc agaggataac   3960
ccaaatcaga ttcgcatatt ggcacagacc ctaacagatg gcggagtcat ggatgagcta   4020
atcaatgagg aacttgagac atttaattct cgttggaggg aactacatga agaggctgta   4080
aggaggcaaa agttgcttga acagagcatc cagtctgccc aggagactga aaaatcctta   4140
cacttaatcc aggagtccct cacattcatt gacaagcagt tggcagctta tattgcagac   4200
aaggtggacg cagctcaaat gcctcaggaa gcccagaaaa tccaatctga tttgacaagt   4260
catgagatca gtttagaaga aatgaagaaa cataatcagg ggaaggaggc tgcccaaaga   4320
gtcctgtctc agattgatgt tgcacagaaa aaattacaag atgtctccat gaagtttcga   4380
ttattccaga aaccagccaa tttgagctgc gtctagaaga aagtaagatg attttagatg   4440
aagtgaagat gcacttgcct gcattggaaa caaagagtgt ggaacaggaa gtagtacagt   4500
cacagctaaa tcattgtgtg aacttgtata aaagtctgag tgaagtgaag tctgaagtgg   4560
aaatggtgat aaagactgga cgtcagattg tacagaaaaa gcagacggaa aatcccaaag   4620
aacttgatga aagagtaaca gctttgaaat tgcattataa tgagctggga gcaaaggtaa   4680
cagaaagaaa gcaacagttg gagaaatgct tgaaattgtc ccgtaagatg cgaaaggaaa   4740
tgaatgtctt gacagaatgg ctggcagcta cagatatgga attgacaaag agatcagcag   4800
ttgaaggaat gcctagtaat ttggattctg aagttgcctg ggaaaaggct actcaaaaag   4860
agattgagaa acagaaggtg cacctgaaga gtatcacaga ggtaggagag gccttgaaaa   4920
cagttttggg caagaaggag acgttggtgg aagataaact cagtcttctg aatagtaact   4980
ggatagctgt cacctcccga gcagaagagt ggttaaatct tttgttggaa taccagaaac   5040
acatggaaac ttttgaccag aatgtggacc acatcacaaa gtggatcatt caggctgaca   5100
cacttttgga tgaatcagag aaaaagaaac cccagcaaaa agaagacgtg cttaagcgtt   5160
```

```
taaaggcaga actgaatgac atacgcccaa aggtggactc tacacgtgac caagcagcaa   5220
acttgatggc aaaccgcggt gaccactgca ggaaattagt agagccccaa atctcagagc   5280
tcaaccatcg atttgcagcc atttcacaca gaattaagac tggaaaggcc tccattcctt   5340
tgaaggaatg gagcagttta actcagatat acaaaaattg cttgaaccac tggaggctga   5400
aattcagcag ggggtgaatc tgaaagagga agagttcaat aaagatatga atgaagacaa   5460
tgagggtact gtaaaagaat tgtgcaaaga ggagacaact tacaacaaag aatcacagat   5520
gagagaaaga gagaggaaat aaagataaaa cagcagctgt tacagacaaa acataatgct   5580
ctcaaggatt tgaggtctca aagaagaaaa aaggctctag aaatttctca tcagtggtat   5640
cagtacaaga ggcaggctga tgatctcctg aaatgcttgg atgacattga aaaaaaatta   5700
gccagcctac ctgagcccag agatgaaagg aaaataaagg aaattgatcg ggaattgcag   5760
aagaagaaag aggagctgaa tgcagtgcgt aggcaagctg agggcttgtc tgaggatggg   5820
gccgcaatgg cagtggagcc aactcagatc cagctcagca agcgctggcg ggaaattgag   5880
agcaaatttg ctcagtttcg aagactcaac tttgcacaaa ttcacactgt ccgtgaagaa   5940
acgatgatgg tgatgactga agacatgcct ttggaaattt cttatgtgcc ttctacttat   6000
ttgactgaaa tcactcatgt ctcacaagcc ctattagaag tggaacaact tctcaatgct   6060
cctgacctct gtgctaagga ctttgaagat ctctttaagc aagaggagtc tctgaagaat   6120
ataaaagata gtctacaaca aagctcaggt cggattgaca ttattcatag caagaagaca   6180
gcagcattgc aaagtgcaac gcctgtggaa agggtgaagc tacaggaagc tctctcccag   6240
cttgatttcc aatgggaaaa agttaacaaa atgtacaagg accgacaagg gcgatttgac   6300
agatctgttg agaaatggcg gcgttttcat tatgatataa agatatttaa tcagtggcta   6360
acagaagctg aacagtttct cagaaagaca caaattcctg agaattggga acatgctaaa   6420
tacaaatggt atcttaagga actccaggat gggatgggca gcggcaaact gttgtcagaa   6480
cattgaatgc aactggggaa gaaataattc agcaatcctc aaaaacagat ggcagtattc   6540
tacaggaaaa attgggaagc ctgaatctgc ggtggcagga ggtctgcaaa cagctgtcag   6600
acagaaaaaa gaggctagaa gaacaaaaga atatcttgtc agaatttcaa agagatttaa   6660
atgaatttgt tttatggttg gaggaagcag ataacattgc tagtatccca cttgaacctg   6720
gaaaagagca gcaactaaaa gaaaagcttg agcaagtcaa gttactggtg gaagagttgc   6780
ccctgcgcca gggaattctc aaacaattaa atgaaactgg aggacccgtg cttgtaagtg   6840
ctcccataag cccagaagag caagataaac ttgaaaataa gctcaagcag acaaatctcc   6900
agtggataaa ggtttccaga gctttacctg agaaacaagg agaaatttga agctcaaata   6960
aaagaccttg ggcagcttga aaaaaagctt gaagaccttg aagagcagtt aaatcatctg   7020
ctgctgtggt atctcctatt aggaatcagt tggaaattta taaccaacca aaccaagaag   7080
gaccatttga cgttcaggaa actgaaatag cagttcaagc taaacaaccg gatgtggaag   7140
agattttgtc taaagggcag catttgtaca aggaaaaacc agccactcag ccagtgaaga   7200
ggaagttaga agatctgagc tctgagtgga aggcggtaaa ccgtttactt caagagctga   7260
gggcaaagca gcctgaccta gctcctggac tgaccactat tggagcctct cctactcaga   7320
ctgttactct ggtgacacaa cctgtggtta ctaaggaaac tgccatctcc aaactagaaa   7380
tgccatcttc cttgatgttg gaggtacctg ctctggcaga tttcaaccgg gcttggacag   7440
aacttaccga ctggctttct ctgcttgatc aagttataaa atcacagagg gtgatggtgg   7500
gtgaccttga ggatatcaac gagatgatca tcaagcagaa ggcaacaatg caggatttgg   7560
```

-continued

```
aacagaggcg tccccagttg gaagaactca ttaccgctgc ccaaaatttg aaaaacaaga   7620
ccagcaatca agaggctaga acaatcatta cggatcgaat tgaaagaatt cagaatcagt   7680
gggatgaagt acaagaacac cttcagaacc ggaggcaaca gttgaatgaa atgttaaagg   7740
attcaacaca atggctggaa gctaaggaag aagctgagca ggtcttagga caggccagag   7800
ccaagcttga gtcatggaag gagggtccct atacagtaga tgcaatccaa aagaaaatca   7860
cagaaaccaa gcagttggcc aaagacctcc gccagtggca gacaaatgta gatgtggcaa   7920
atgacttggc cctgaaactt ctccgggatt attctgcaga tgataccaga aaagtccaca   7980
tgataacaga gaatatcaat gcctcttgga gaagcattca taaaagggtg agtgagcgag   8040
aggctgcttt ggaagaaact catagattac tgcaacagtt ccccctggac ctggaaaagt   8100
ttctgcctgg cttacagaag ctgaaacaac tgccaatgtc ctacaggatg ctacccgtaa   8160
ggaaaggctc ctagaagact ccaagggagt aaaagagctg atgaaacaat ggcaagacct   8220
ccaaggtgaa attgaagctc acacagatgt ttatcacaac ctggatgaaa acagccaaaa   8280
aatcctgaga tccctggaag gttccgatga tgcagtcctg ttacaaagac gtttggataa   8340
catgaacttc aagtggagtg aacttcggaa aaagtctctc aacattaggt cccatttgga   8400
agccagttct gaccagtgga agcgtctgca cctttctctg caggaacttc tggtgtggct   8460
acagctgaaa gatgatgaat taagccggca ggcacctatt tggaggcgac tttccagcag   8520
ttcagaagca gaacgatgta catagggcct tcaagaggga attgaaaact aaagaacctg   8580
taatcatgag tactcttgag actgtacgaa tatttctgac agagcagcct ttggaaggac   8640
tagagaaact ctaccaggag cccagagagc tgcctcctga ggagagagcc cagaatgtca   8700
ctcggcttct acgaaagcag gctgaggagg tcaatactga gtgggaaaaa ttgaacctgc   8760
actccgctga ctggcagaga aaaatagatg agacccttga aagactccag gaacttcaag   8820
aggccacgga tgagctggac ctcaagctgc gccaagctga ggtgatcaag ggatcctggc   8880
agcccgtggg cgatctcctc attgactctc tccaagatca cctcgagaaa gtcaaggcac   8940
ttcgaggaga aattgcgcct ctgaaagaga acgtgagcca cgtcaatgac cttgctcgcc   9000
agcttaccac tttgggcatt cagctctcac cgtataacct cagcactctg gaagacctga   9060
acaccagatg gaagcttctg caggtggccg tcgaggaccg agtcaggcag ctgcatgaag   9120
cccacaggga ctttggtcca gcatctcagc actttctttc cacgtctgtc cagggtccct   9180
gggagagagc catctcgcca aacaaagtgc cctactatat caaccacgag actgaaacaa   9240
cttgctggga ccatcccaaa atgacagagc tctaccagtc tttagctgac ctgaataatg   9300
tcagattctc agcttatagg actgccatga aactccgaag actgcagaag gccctttgct   9360
tggatctctt gagcctgtca gctgcatgtg atgccttgga cgagcacaac ctcaagcaaa   9420
atgaccagcc catggatatc ctgcagatta ttaattgttt gaccactatt tatgaccgcc   9480
tggagcaaga gcacaacaat ttggtcaacg tccctctctg cgtggatatg tgtctgaact   9540
ggctgctgaa tgtttatgat acgggacgaa cagggaggat ccgtgtcctg tcttttaaaa   9600
ctggcatcat ttccctgtgt aaagcacatt tggaagacaa gtacagatac cttttcaagc   9660
aagtggcaag ttcaacagga ttttgtgacc agcgcaggct gggcctcctt ctgcatgatt   9720
ctatccaaat tccaagacag ttgggtgaag ttgcatcctt tgggggcagt aacattgagc   9780
caagtgtccg gagctgcttc caatttgcta ataataagcc agagatcgaa gcggccctct   9840
tcctagactg gatgagactg gaaccccagt ccatggtgtg gctgcccgtc ctgcacagag   9900
```

-continued

```
tggctgctgc agaaactgcc aagcatcagg ccaaatgtaa catctgcaaa gagtgtccaa   9960

tcatttggat tcaggtacag gagtctaaag cactttaatt atgacatctg ccaaagctgc  10020

ttttttctg gtcgagttgc aaaaggccat aaaatgcact atcccatggt ggaatattgc  10080

actccgacta catcaggaga agatgttcga gactttgcca aggtactaaa aaacaaattt  10140

cgaaccaaaa ggtattttgc gaagcatccc cgaatgggct acctgccagt gcagactgtc  10200

ttagaggggg acaacatgga aactcccgtt actctgatca acttctggcc agtagattct  10260

gcgcctgcct cgtcccctca gctttcacac gatgatactc attcacgcat tgaacattat  10320

gctagcaggc tagcagaaat ggaaaacagc aatggatctt atctaaatga tagcatctct  10380

cctaatgaga gcatagatga tgaacatttg ttaatccagc attactgcca aagtttgaac  10440

caggactccc ccctgagcca gcctcgtagt cctgcccaga tcttgattcc ttagagagtg  10500

aggaaagagg ggagctagag agaatcctag cagatcttga ggaagaaaac aggaatctgc  10560

aaggagaata tgaccgtcta aagcagcagc acgaacataa aggcctgtcc ccactgccgt  10620

cccctcctga aatgatgccc acctgtcccc agagtccccg ggatgctgag ctcattgctg  10680

aggccaagct actgcgtcaa cacaaaggcc gcctggaagc caggatgcaa atcctggaag  10740

accacaataa acagctggag tcacagttac acaggctaag gcagctgctg gagcaacccc  10800

aggcagaggc caaagtgaat ggcacaacgg tgtcctctcc ttctacctct ctacagaggt  10860

ccgacagcag tcagcctatg ctgctccgag tggttggcag tcaaacttcg gactccatgg  10920

gtgaggaaga tcttctcagt cctccccagg acacaagcac agggttagag gaggtgatgg  10980

agcaactcaa caactccttc cctagttcaa gaggaagaaa taccccctgga aagccaatga  11040

gagaggacac aatgtag                                                 11057
```

<210> SEQ ID NO 9
<211> LENGTH: 3685
<212> TYPE: PRT
<213> ORGANISM: Homo sapiens
<220> FEATURE:
<221> NAME/KEY: misc_feature
<222> LOCATION: (1)..(3684)
<223> OTHER INFORMATION: Full-length human dystrophin amino acid sequence
<220> FEATURE:
<221> NAME/KEY: misc_feature
<222> LOCATION: (2294)..(2294)
<223> OTHER INFORMATION: Xaa can be any naturally occurring amino acid
<220> FEATURE:
<221> NAME/KEY: misc_feature
<222> LOCATION: (2479)..(2479)
<223> OTHER INFORMATION: Xaa can be any naturally occurring amino acid

<400> SEQUENCE: 9

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95
```

-continued

```
Thr Asp Thr Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Thr Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
```

-continued

```
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
    850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940
```

-continued

Gln Glu Thr Met Ser Ala Ile Arg Thr Trp Val Gln Gln Ser Glu Thr
945 950 955 960

Lys Leu Ser Ile Pro Gln Leu Ser Val Thr Asp Tyr Glu Ile Met Glu
965 970 975

Gln Arg Leu Gly Glu Leu Gln Ala Leu Gln Ser Ser Leu Gln Glu Gln
980 985 990

Gln Ser Gly Leu Tyr Tyr Leu Ser Thr Thr Val Lys Glu Met Ser Lys
995 1000 1005

Lys Ala Pro Ser Glu Ile Ser Arg Lys Tyr Gln Ser Glu Phe Glu
1010 1015 1020

Glu Ile Glu Gly Arg Trp Lys Lys Leu Ser Ser Gln Leu Val Glu
1025 1030 1035

His Cys Gln Lys Leu Glu Glu Gln Met Asn Lys Leu Arg Lys Ile
1040 1045 1050

Gln Asn His Ile Gln Thr Leu Lys Lys Trp Met Ala Glu Val Asp
1055 1060 1065

Val Phe Leu Lys Glu Glu Trp Pro Ala Leu Gly Asp Ser Glu Ile
1070 1075 1080

Leu Lys Lys Gln Leu Lys Gln Cys Arg Leu Leu Val Ser Asp Ile
1085 1090 1095

Gln Thr Ile Gln Pro Ser Leu Asn Ser Val Asn Glu Gly Gly Gln
1100 1105 1110

Lys Ile Lys Asn Glu Ala Glu Pro Glu Phe Ala Ser Arg Leu Glu
1115 1120 1125

Thr Glu Leu Lys Glu Leu Asn Thr Gln Trp Asp His Met Cys Gln
1130 1135 1140

Gln Val Tyr Ala Arg Lys Glu Ala Leu Lys Gly Gly Leu Glu Lys
1145 1150 1155

Thr Val Ser Leu Gln Lys Asp Leu Ser Glu Met His Glu Trp Met
1160 1165 1170

Thr Gln Ala Glu Glu Glu Tyr Leu Glu Arg Asp Phe Glu Tyr Lys
1175 1180 1185

Thr Pro Asp Glu Leu Gln Lys Ala Val Glu Glu Met Lys Arg Ala
1190 1195 1200

Lys Glu Glu Ala Gln Gln Lys Glu Ala Lys Val Lys Leu Leu Thr
1205 1210 1215

Glu Ser Val Asn Ser Val Ile Ala Gln Ala Pro Pro Val Ala Gln
1220 1225 1230

Glu Ala Leu Lys Lys Glu Leu Glu Thr Leu Thr Thr Asn Tyr Gln
1235 1240 1245

Trp Leu Cys Thr Arg Leu Asn Gly Lys Cys Lys Thr Leu Glu Glu
1250 1255 1260

Val Trp Ala Cys Trp His Glu Leu Leu Ser Tyr Leu Glu Lys Ala
1265 1270 1275

Asn Lys Trp Leu Asn Glu Val Glu Phe Lys Leu Lys Thr Thr Glu
1280 1285 1290

Asn Thr Pro Gly Gly Ala Glu Glu Ile Ser Glu Val Leu Asp Ser
1295 1300 1305

Leu Glu Asn Leu Met Arg His Ser Glu Asp Asn Pro Asn Gln Ile
1310 1315 1320

Arg Ile Leu Ala Gln Thr Leu Thr Asp Gly Gly Val Met Asp Glu
1325 1330 1335

-continued

```
Leu Ile  Asn Glu Glu Leu Glu  Thr Phe Asn Ser Arg  Trp Arg Glu
    1340                 1345                 1350

Leu His  Glu Glu Ala Val Arg  Arg Gln Lys Leu Leu  Glu Gln Ser
    1355                 1360                 1365

Ile Gln  Ser Ala Gln Glu Thr  Glu Lys Ser Leu His  Leu Ile Gln
    1370                 1375                 1380

Glu Ser  Leu Thr Phe Ile Asp  Lys Gln Leu Ala Ala  Tyr Ile Ala
    1385                 1390                 1395

Asp Lys  Val Asp Ala Ala Gln  Met Pro Gln Glu Ala  Gln Lys Ile
    1400                 1405                 1410

Gln Ser  Asp Leu Thr Ser His  Glu Ile Ser Leu Glu  Glu Met Lys
    1415                 1420                 1425

Lys His  Asn Gln Gly Lys Glu  Ala Ala Gln Arg Val  Leu Ser Gln
    1430                 1435                 1440

Ile Asp  Val Ala Gln Lys Lys  Leu Gln Asp Val Ser  Met Lys Phe
    1445                 1450                 1455

Arg Leu  Phe Gln Lys Pro Ala  Asn Phe Glu Leu Arg  Leu Gln Glu
    1460                 1465                 1470

Ser Lys  Met Ile Leu Asp Glu  Val Lys Met His Leu  Pro Ala Leu
    1475                 1480                 1485

Glu Thr  Lys Ser Val Glu Gln  Glu Val Val Gln Ser  Gln Leu Asn
    1490                 1495                 1500

His Cys  Val Asn Leu Tyr Lys  Ser Leu Ser Glu Val  Lys Ser Glu
    1505                 1510                 1515

Val Glu  Met Val Ile Lys Thr  Gly Arg Gln Ile Val  Gln Lys Lys
    1520                 1525                 1530

Gln Thr  Glu Asn Pro Lys Glu  Leu Asp Glu Arg Val  Thr Ala Leu
    1535                 1540                 1545

Lys Leu  His Tyr Asn Glu Leu  Gly Ala Lys Val Thr  Glu Arg Lys
    1550                 1555                 1560

Gln Gln  Leu Glu Lys Cys Leu  Lys Leu Ser Arg Lys  Met Arg Lys
    1565                 1570                 1575

Glu Met  Asn Val Leu Thr Glu  Trp Leu Ala Ala Thr  Asp Met Glu
    1580                 1585                 1590

Leu Thr  Lys Arg Ser Ala Val  Glu Gly Met Pro Ser  Asn Leu Asp
    1595                 1600                 1605

Ser Glu  Val Ala Trp Gly Lys  Ala Thr Gln Lys Glu  Ile Glu Lys
    1610                 1615                 1620

Gln Lys  Val His Leu Lys Ser  Ile Thr Glu Val Gly  Glu Ala Leu
    1625                 1630                 1635

Lys Thr  Val Leu Gly Lys Lys  Glu Thr Leu Val Glu  Asp Lys Leu
    1640                 1645                 1650

Ser Leu  Leu Asn Ser Asn Trp  Ile Ala Val Thr Ser  Arg Ala Glu
    1655                 1660                 1665

Glu Trp  Leu Asn Leu Leu Leu  Glu Tyr Gln Lys His  Met Glu Thr
    1670                 1675                 1680

Phe Asp  Gln Asn Val Asp His  Ile Thr Lys Trp Ile  Ile Gln Ala
    1685                 1690                 1695

Asp Thr  Leu Leu Asp Glu Ser  Glu Lys Lys Lys Pro  Gln Gln Lys
    1700                 1705                 1710

Glu Asp  Val Leu Lys Arg Leu  Lys Ala Glu Leu Asn  Asp Ile Arg
    1715                 1720                 1725

Pro Lys  Val Asp Ser Thr Arg  Asp Gln Ala Ala Asn  Leu Met Ala
```

-continued

```
    1730                1735                1740

Asn Arg Gly Asp His Cys Arg Lys Leu Val Glu Pro Gln Ile Ser
    1745                1750                1755

Glu Leu Asn His Arg Phe Ala Ala Ile Ser His Arg Ile Lys Thr
    1760                1765                1770

Gly Lys Ala Ser Ile Pro Leu Lys Glu Leu Glu Gln Phe Asn Ser
    1775                1780                1785

Asp Ile Gln Lys Leu Leu Glu Pro Leu Glu Ala Glu Ile Gln Gln
    1790                1795                1800

Gly Val Asn Leu Lys Glu Glu Asp Phe Asn Lys Asp Met Asn Glu
    1805                1810                1815

Asp Asn Glu Gly Thr Val Lys Glu Leu Leu Gln Arg Gly Asp Asn
    1820                1825                1830

Leu Gln Gln Arg Ile Thr Asp Glu Arg Lys Arg Glu Glu Ile Lys
    1835                1840                1845

Ile Lys Gln Gln Leu Leu Gln Thr Lys His Asn Ala Leu Lys Asp
    1850                1855                1860

Leu Arg Ser Gln Arg Arg Lys Lys Ala Leu Glu Ile Ser His Gln
    1865                1870                1875

Trp Tyr Gln Tyr Lys Arg Gln Ala Asp Asp Leu Leu Lys Cys Leu
    1880                1885                1890

Asp Asp Ile Glu Lys Lys Leu Ala Ser Leu Pro Glu Pro Arg Asp
    1895                1900                1905

Glu Arg Lys Ile Lys Glu Ile Asp Arg Glu Leu Gln Lys Lys Lys
    1910                1915                1920

Glu Glu Leu Asn Ala Val Arg Arg Gln Ala Glu Gly Leu Ser Glu
    1925                1930                1935

Asp Gly Ala Ala Met Ala Val Glu Pro Thr Gln Ile Gln Leu Ser
    1940                1945                1950

Lys Arg Trp Arg Glu Ile Glu Ser Lys Phe Ala Gln Phe Arg Arg
    1955                1960                1965

Leu Asn Phe Ala Gln Ile His Thr Val Arg Glu Glu Thr Met Met
    1970                1975                1980

Val Met Thr Glu Asp Met Pro Leu Glu Ile Ser Tyr Val Pro Ser
    1985                1990                1995

Thr Tyr Leu Thr Glu Ile Thr His Val Ser Gln Ala Leu Leu Glu
    2000                2005                2010

Val Glu Gln Leu Leu Asn Ala Pro Asp Leu Cys Ala Lys Asp Phe
    2015                2020                2025

Glu Asp Leu Phe Lys Gln Glu Glu Ser Leu Lys Asn Ile Lys Asp
    2030                2035                2040

Ser Leu Gln Gln Ser Ser Gly Arg Ile Asp Ile Ile His Ser Lys
    2045                2050                2055

Lys Thr Ala Ala Leu Gln Ser Ala Thr Pro Val Glu Arg Val Lys
    2060                2065                2070

Leu Gln Glu Ala Leu Ser Gln Leu Asp Phe Gln Trp Glu Lys Val
    2075                2080                2085

Asn Lys Met Tyr Lys Asp Arg Gln Gly Arg Phe Asp Arg Ser Val
    2090                2095                2100

Glu Lys Trp Arg Arg Phe His Tyr Asp Ile Lys Ile Phe Asn Gln
    2105                2110                2115

Trp Leu Thr Glu Ala Glu Gln Phe Leu Arg Lys Thr Gln Ile Pro
    2120                2125                2130
```

```
Glu Asn  Trp Glu His Ala Lys  Tyr Lys Trp Tyr Leu  Lys Glu Leu
    2135                 2140                 2145

Gln Asp  Gly Ile Gly Gln Arg  Gln Thr Val Val Arg  Thr Leu Asn
    2150                 2155                 2160

Ala Thr  Gly Glu Glu Ile Ile  Gln Gln Ser Ser Lys  Thr Asp Ala
    2165                 2170                 2175

Ser Ile  Leu Gln Glu Lys Leu  Gly Ser Leu Asn Leu  Arg Trp Gln
    2180                 2185                 2190

Glu Val  Cys Lys Gln Leu Ser  Asp Arg Lys Lys Arg  Leu Glu Glu
    2195                 2200                 2205

Gln Lys  Asn Ile Leu Ser Glu  Phe Gln Arg Asp Leu  Asn Glu Phe
    2210                 2215                 2220

Val Leu  Trp Leu Glu Glu Ala  Asp Asn Ile Ala Ser  Ile Pro Leu
    2225                 2230                 2235

Glu Pro  Gly Lys Glu Gln Gln  Leu Lys Glu Lys Leu  Glu Gln Val
    2240                 2245                 2250

Lys Leu  Leu Val Glu Glu Leu  Pro Leu Arg Gln Gly  Ile Leu Lys
    2255                 2260                 2265

Gln Leu  Asn Glu Thr Gly Gly  Pro Val Leu Val Ser  Ala Pro Ile
    2270                 2275                 2280

Ser Pro  Glu Glu Gln Asp Lys  Leu Glu Asn Xaa Leu  Lys Gln Thr
    2285                 2290                 2295

Asn Leu  Gln Trp Ile Lys Val  Ser Arg Ala Leu Pro  Glu Lys Gln
    2300                 2305                 2310

Gly Glu  Ile Glu Ala Gln Ile  Lys Asp Leu Gly Gln  Leu Glu Lys
    2315                 2320                 2325

Lys Leu  Glu Asp Leu Glu Glu  Gln Leu Asn His Leu  Leu Leu Trp
    2330                 2335                 2340

Leu Ser  Pro Ile Arg Asn Gln  Leu Glu Ile Tyr Asn  Gln Pro Asn
    2345                 2350                 2355

Gln Glu  Gly Pro Phe Asp Val  Gln Glu Thr Glu Ile  Ala Val Gln
    2360                 2365                 2370

Ala Lys  Gln Pro Asp Val Glu  Glu Ile Leu Ser Lys  Gly Gln His
    2375                 2380                 2385

Leu Tyr  Lys Glu Lys Pro Ala  Thr Gln Pro Val Lys  Arg Lys Leu
    2390                 2395                 2400

Glu Asp  Leu Ser Ser Glu Trp  Lys Ala Val Asn Arg  Leu Leu Gln
    2405                 2410                 2415

Glu Leu  Arg Ala Lys Gln Pro  Asp Leu Ala Pro Gly  Leu Thr Thr
    2420                 2425                 2430

Ile Gly  Ala Ser Pro Thr Gln  Thr Val Thr Leu Val  Thr Gln Pro
    2435                 2440                 2445

Val Val  Thr Lys Glu Thr Ala  Ile Ser Lys Leu Glu  Met Pro Ser
    2450                 2455                 2460

Ser Leu  Asn Leu Glu Val Pro  Ala Leu Ala Asp Phe  Asn Arg Ala
    2465                 2470                 2475

Xaa Thr  Glu Leu Thr Asp Trp  Leu Ser Leu Leu Asp  Gln Val Ile
    2480                 2485                 2490

Lys Ser  Gln Arg Val Met Val  Gly Asp Leu Glu Asp  Ile Asn Glu
    2495                 2500                 2505

Met Ile  Ile Lys Gln Lys Ala  Thr Met Gln Asp Leu  Glu Gln Arg
    2510                 2515                 2520
```

-continued

```
Arg Pro  Gln Leu Glu Glu Leu  Ile Thr Ala Ala Gln  Asn Leu Lys
    2525                 2530                 2535

Asn Lys  Thr Ser Asn Gln Glu  Ala Arg Thr Ile Ile  Thr Asp Arg
    2540                 2545                 2550

Ile Glu  Arg Ile Gln Asn Gln  Trp Asp Glu Val Gln  Glu His Leu
    2555                 2560                 2565

Gln Asn  Arg Arg Gln Gln Leu  Asn Glu Met Leu Lys  Asp Ser Thr
    2570                 2575                 2580

Gln Trp  Leu Glu Ala Lys Glu  Glu Ala Glu Gln Val  Leu Gly Gln
    2585                 2590                 2595

Ala Arg  Ala Lys Leu Glu Ser  Trp Lys Glu Gly Pro  Tyr Thr Val
    2600                 2605                 2610

Asp Ala  Ile Gln Lys Lys Ile  Thr Glu Thr Lys Gln  Leu Ala Lys
    2615                 2620                 2625

Asp Leu  Arg Gln Trp Gln Thr  Asn Val Asp Val Ala  Asn Asp Leu
    2630                 2635                 2640

Ala Leu  Lys Leu Leu Arg Asp  Tyr Ser Ala Asp Asp  Thr Arg Lys
    2645                 2650                 2655

Val His  Met Ile Thr Glu Asn  Ile Asn Ala Ser Trp  Arg Ser Ile
    2660                 2665                 2670

His Lys  Arg Val Ser Glu Arg  Glu Ala Ala Leu Glu  Glu Thr His
    2675                 2680                 2685

Arg Leu  Leu Gln Gln Phe Pro  Leu Asp Leu Glu Lys  Phe Leu Ala
    2690                 2695                 2700

Trp Leu  Thr Glu Ala Glu Thr  Thr Ala Asn Val Leu  Gln Asp Ala
    2705                 2710                 2715

Thr Arg  Lys Glu Arg Leu Leu  Glu Asp Ser Lys Gly  Val Lys Glu
    2720                 2725                 2730

Leu Met  Lys Gln Trp Gln Asp  Leu Gln Gly Glu Ile  Glu Ala His
    2735                 2740                 2745

Thr Asp  Val Tyr His Asn Leu  Asp Glu Asn Ser Gln  Lys Ile Leu
    2750                 2755                 2760

Arg Ser  Leu Glu Gly Ser Asp  Asp Ala Val Leu Leu  Gln Arg Arg
    2765                 2770                 2775

Leu Asp  Asn Met Met Phe Lys  Trp Ser Glu Leu Arg  Lys Lys Ser
    2780                 2785                 2790

Leu Asn  Ile Arg Ser His Leu  Glu Ala Ser Ser Asp  Gln Trp Lys
    2795                 2800                 2805

Arg Leu  His Leu Ser Leu Gln  Glu Leu Leu Val Trp  Leu Gln Leu
    2810                 2815                 2820

Lys Asp  Asp Glu Leu Ser Arg  Gln Ala Pro Ile Gly  Gly Asp Phe
    2825                 2830                 2835

Pro Ala  Val Gln Lys Gln Asn  Asp Val His Arg Ala  Phe Lys Arg
    2840                 2845                 2850

Glu Leu  Lys Thr Lys Glu Pro  Val Ile Met Ser Thr  Leu Glu Thr
    2855                 2860                 2865

Val Arg  Ile Phe Leu Thr Glu  Gln Pro Leu Glu Gly  Leu Glu Lys
    2870                 2875                 2880

Leu Tyr  Gln Glu Pro Arg Glu  Leu Pro Pro Glu Glu  Arg Ala Gln
    2885                 2890                 2895

Asn Val  Thr Arg Leu Leu Arg  Lys Gln Ala Glu Glu  Val Asn Thr
    2900                 2905                 2910

Glu Trp  Glu Lys Leu Asn Leu  His Ser Ala Asp Trp  Gln Arg Lys
```

```
    2915                2920                2925

Ile Asp  Glu Thr Leu Glu Arg  Leu Gln Glu Leu Gln  Glu Ala Thr
    2930                2935                2940

Asp Glu  Leu Asp Leu Lys Leu  Arg Gln Ala Glu Val  Ile Lys Gly
    2945                2950                2955

Ser Trp  Gln Pro Val Gly Asp  Leu Leu Ile Asp Ser  Leu Gln Asp
    2960                2965                2970

His Leu  Glu Lys Val Lys Ala  Leu Arg Gly Glu Ile  Ala Pro Leu
    2975                2980                2985

Lys Glu  Asn Val Ser His Val  Asn Asp Leu Ala Arg  Gln Leu Thr
    2990                2995                3000

Thr Leu  Gly Ile Gln Leu Ser  Pro Tyr Asn Leu Ser  Thr Leu Glu
    3005                3010                3015

Asp Leu  Asn Thr Arg Trp Lys  Leu Leu Gln Val Ala  Val Glu Asp
    3020                3025                3030

Arg Val  Arg Gln Leu His Glu  Ala His Arg Asp Phe  Gly Pro Ala
    3035                3040                3045

Ser Gln  His Phe Leu Ser Thr  Ser Val Gln Gly Pro  Trp Glu Arg
    3050                3055                3060

Ala Ile  Ser Pro Asn Lys Val  Pro Tyr Tyr Ile Asn  His Glu Thr
    3065                3070                3075

Gln Thr  Thr Cys Trp Asp His  Pro Lys Met Thr Glu  Leu Tyr Gln
    3080                3085                3090

Ser Leu  Ala Asp Leu Asn Asn  Val Arg Phe Ser Ala  Tyr Arg Thr
    3095                3100                3105

Ala Met  Lys Leu Arg Arg Leu  Gln Lys Ala Leu Cys  Leu Asp Leu
    3110                3115                3120

Leu Ser  Leu Ser Ala Ala Cys  Asp Ala Leu Asp Gln  His Asn Leu
    3125                3130                3135

Lys Gln  Asn Asp Gln Pro Met  Asp Ile Leu Gln Ile  Ile Asn Cys
    3140                3145                3150

Leu Thr  Thr Ile Tyr Asp Arg  Leu Glu Gln Glu His  Asn Asn Leu
    3155                3160                3165

Val Asn  Val Pro Leu Cys Val  Asp Met Cys Leu Asn  Trp Leu Leu
    3170                3175                3180

Asn Val  Tyr Asp Thr Gly Arg  Thr Gly Arg Ile Arg  Val Leu Ser
    3185                3190                3195

Phe Lys  Thr Gly Ile Ile Ser  Leu Cys Lys Ala His  Leu Glu Asp
    3200                3205                3210

Lys Tyr  Arg Tyr Leu Phe Lys  Gln Val Ala Ser Ser  Thr Gly Phe
    3215                3220                3225

Cys Asp  Gln Arg Arg Leu Gly  Leu Leu Leu His Asp  Ser Ile Gln
    3230                3235                3240

Ile Pro  Arg Gln Leu Gly Glu  Val Ala Ser Phe Gly  Gly Ser Asn
    3245                3250                3255

Ile Glu  Pro Ser Val Arg Ser  Cys Phe Gln Phe Ala  Asn Asn Lys
    3260                3265                3270

Pro Glu  Ile Glu Ala Ala Leu  Phe Leu Asp Trp Met  Arg Leu Glu
    3275                3280                3285

Pro Gln  Ser Met Val Trp Leu  Pro Val Leu His Arg  Val Ala Ala
    3290                3295                3300

Ala Glu  Thr Ala Lys His Gln  Ala Lys Cys Asn Ile  Cys Lys Glu
    3305                3310                3315
```

```
Cys Pro  Ile Ile Gly Phe Arg  Tyr Arg Ser Leu Lys  His Phe Asn
    3320                 3325                 3330

Tyr Asp  Ile Cys Gln Ser Cys  Phe Phe Ser Gly Arg  Val Ala Lys
    3335                 3340                 3345

Gly His  Lys Met His Tyr Pro  Met Val Glu Tyr Cys  Thr Pro Thr
    3350                 3355                 3360

Thr Ser  Gly Glu Asp Val Arg  Asp Phe Ala Lys Val  Leu Lys Asn
    3365                 3370                 3375

Lys Phe  Arg Thr Lys Arg Tyr  Phe Ala Lys His Pro  Arg Met Gly
    3380                 3385                 3390

Tyr Leu  Pro Val Gln Thr Val  Leu Glu Gly Asp Asn  Met Glu Thr
    3395                 3400                 3405

Pro Val  Thr Leu Ile Asn Phe  Trp Pro Val Asp Ser  Ala Pro Ala
    3410                 3415                 3420

Ser Ser  Pro Gln Leu Ser His  Asp Asp Thr His Ser  Arg Ile Glu
    3425                 3430                 3435

His Tyr  Ala Ser Arg Leu Ala  Glu Met Glu Asn Ser  Asn Gly Ser
    3440                 3445                 3450

Tyr Leu  Asn Asp Ser Ile Ser  Pro Asn Glu Ser Ile  Asp Asp Glu
    3455                 3460                 3465

His Leu  Leu Ile Gln His Tyr  Cys Gln Ser Leu Asn  Gln Asp Ser
    3470                 3475                 3480

Pro Leu  Ser Gln Pro Arg Ser  Pro Ala Gln Ile Leu  Ile Ser Leu
    3485                 3490                 3495

Glu Ser  Glu Glu Arg Gly Glu  Leu Glu Arg Ile Leu  Ala Asp Leu
    3500                 3505                 3510

Glu Glu  Glu Asn Arg Asn Leu  Gln Ala Glu Tyr Asp  Arg Leu Lys
    3515                 3520                 3525

Gln Gln  His Glu His Lys Gly  Leu Ser Pro Leu Pro  Ser Pro Pro
    3530                 3535                 3540

Glu Asn  Met Pro Thr Ser Pro  Gln Ser Pro Arg Asp  Ala Glu Leu
    3545                 3550                 3555

Ile Ala  Glu Ala Lys Leu Leu  Arg Gln His Lys Gly  Arg Leu Glu
    3560                 3565                 3570

Ala Arg  Met Gln Ile Leu Glu  Asp His Asn Lys Gln  Leu Glu Ser
    3575                 3580                 3585

Gln Leu  His Arg Leu Arg Gln  Leu Leu Glu Gln Pro  Gln Ala Glu
    3590                 3595                 3600

Ala Lys  Val Asn Gly Thr Thr  Val Ser Ser Pro Ser  Thr Ser Leu
    3605                 3610                 3615

Gln Arg  Ser Asp Ser Ser Gln  Pro Met Leu Leu Arg  Val Val Gly
    3620                 3625                 3630

Ser Gln  Thr Ser Asp Ser Met  Gly Glu Glu Asp Leu  Leu Ser Pro
    3635                 3640                 3645

Pro Gln  Asp Thr Ser Thr Gly  Leu Glu Glu Val Met  Glu Gln Leu
    3650                 3655                 3660

Asn Asn  Ser Phe Pro Ser Ser  Arg Gly Arg Asn Thr  Pro Gly Lys
    3665                 3670                 3675

Pro Met  Arg Glu Asp Thr Met
    3680                 3685
```

<210> SEQ ID NO 10
<211> LENGTH: 756

<212> TYPE: DNA
<213> ORGANISM: Homo sapiens
<220> FEATURE:
<221> NAME/KEY: misc_feature
<222> LOCATION: (1)..(756)
<223> OTHER INFORMATION: N-terminal domain

<400> SEQUENCE: 10
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatggcc tgaacaatgt caacaaggca 240
ctgcgggttt tgcagaacaa taatgttgat ttagtgaata ttggaagtac tgacatcgta 300
gatggaaatc ataaactgac tcttggtttg atttggaata taatcctcca ctggcaggtc 360
aaaaatgtaa tgaaaaatat catggctgga ttgcaacaaa ccaacagtga aaagattctc 420
ctgagctggg tccgacaatc aactcgtaat tatccacagg ttaatgtaat caacttcacc 480
accagctggt ctgatggcct ggctttgaat gctctcatcc atagtcatag gccagaccta 540
tttgactgga atagtgtggt ttgccagcag tcagccacac aacgactgga acatgcattc 600
aacatcgcca gatatcaatt aggcatagag aaactactcg atcctgaaga tgttgatacc 660
acctatccag ataagaagtc catcttaatg tacatcacat cactcttcca agttttgcct 720
caacaagtga gcattgaagc catccaggaa gtggaa 756

<210> SEQ ID NO 11
<211> LENGTH: 252
<212> TYPE: DNA
<213> ORGANISM: Homo sapiens
<220> FEATURE:
<221> NAME/KEY: misc_feature
<222> LOCATION: (1)..(252)
<223> OTHER INFORMATION: Hinge 1

<400> SEQUENCE: 11
atgttgccaa ggccacctaa agtgactaaa gaagaacatt ttcagttaca tcatcaaatg 60
cactattctc aacagatcac ggtcagtcta gcacagggat atgagagaac ttcttcccct 120
aagcctcgat tcaagagcta tgcctacaca caggctgctt atgtcaccac ctctgaccct 180
acacggagcc catttccttc acagcatttg gaagctcctg aagacaagtc atttggcagt 240
tcattgatgg ag 252

<210> SEQ ID NO 12
<211> LENGTH: 333
<212> TYPE: DNA
<213> ORGANISM: Homo sapiens
<220> FEATURE:
<221> NAME/KEY: misc_feature
<222> LOCATION: (1)..(333)
<223> OTHER INFORMATION: Repeat 1

<400> SEQUENCE: 12
agtgaagtaa acctggaccg ttatcaaaca gctttagaag aagtattatc gtggcttctt 60
tctgctgagg acacattgca agcacaagga gagatttcta atgatgtgga agtggtgaaa 120
gaccagtttc atactcatga ggggtacatg atggatttga cagcccatca gggccgggtt 180
ggtaatattc tacaattggg aagtaagctg attggaacag gaaaattatc agaagatgaa 240
gaaactgaag tacaagagca gatgaatctc ctaaattcaa gatgggaatg cctcagggta 300
gctagcatgg aaaaacaaag caatttacat aga 333

<210> SEQ ID NO 13
<211> LENGTH: 327
<212> TYPE: DNA
<213> ORGANISM: Homo sapiens
<220> FEATURE:
<221> NAME/KEY: misc_feature
<222> LOCATION: (1)..(327)
<223> OTHER INFORMATION: Repeat 2

<400> SEQUENCE: 13
gttttaatgg atctccagaa tcagaaactg aaagagttga atgactggct aacaaaaaca 60
gaagaaagaa caaggaaaat ggaggaagag cctcttggac ctgatcttga agacctaaaa 120
cgccaagtac aacaacataa ggtgcttcaa gaagatctag aacaagaaca agtcagggtc 180
aattctctca ctcacatggt ggtggtagtt gatgaatcta gtggagatca cgcaactgct 240
gctttggaag aacaacttaa ggtattggga gatcgatggg caaacatctg tagatggaca 300
gaagaccgct gggttctttt acaagac 327

<210> SEQ ID NO 14
<211> LENGTH: 333
<212> TYPE: DNA
<213> ORGANISM: Homo sapiens
<220> FEATURE:
<221> NAME/KEY: misc_feature
<222> LOCATION: (1)..(333)
<223> OTHER INFORMATION: Repeat 3

<400> SEQUENCE: 14
atccttctca aatggcaacg tcttactgaa gaacagtgcc tttttagtgc atggctttca 60
gaaaaagaag atgcagtgaa caagattcac acaactggct ttaaagatca aaatgaaatg 120
ttatcaagtc ttcaaaaact ggccgtttta aaagcggatc tagaaaagaa aaagcaatcc 180
atgggcaaac tgtattcact caaacaagat cttctttcaa cactgaagaa taagtcagtg 240
acccagaaga cggaagcatg gctggataac tttgcccggt gttgggataa tttagtccaa 300
aaacttgaaa agagtacagc acagatttca cag 333

<210> SEQ ID NO 15
<211> LENGTH: 150
<212> TYPE: DNA
<213> ORGANISM: Homo sapiens
<220> FEATURE:
<221> NAME/KEY: misc_feature
<222> LOCATION: (1)..(150)
<223> OTHER INFORMATION: Hinge 1

<400> SEQUENCE: 15
gctgtcacca ccactcagcc atcactaaca cagacaactg taatggaaac agtaactacg 60
gtgaccacaa gggaacagat cctggtaaag catgctcaag aggaacttcc accaccacct 120
ccccaaaaga agaggcagat tactgtggat 150

<210> SEQ ID NO 16
<211> LENGTH: 262
<212> TYPE: DNA
<213> ORGANISM: Homo sapiens
<220> FEATURE:
<221> NAME/KEY: misc_feature
<222> LOCATION: (1)..(262)
<223> OTHER INFORMATION: Repeat 4

<400> SEQUENCE: 16

```
tctgaaatta ggaaaaggtt ggatgttgat ataactgaac ttcacagctg gattactcgc     60

tcagaagctg tgttgcagag tcctgaattt gcaatctttc ggaaggaagg caacttctca    120

gacttaaaag aaaaagtcaa tgccatagag cgagaaaaag ctgagaagtt cagaaaactg    180

caagatgcca gcagatcagc tcaggccctg gtggaacaga tggtgaatga gggtgttaat    240

gcagatagca tcaaacaagc ct                                             262
```

```
<210> SEQ ID NO 17
<211> LENGTH: 389
<212> TYPE: DNA
<213> ORGANISM: Homo sapiens
<220> FEATURE:
<221> NAME/KEY: misc_feature
<222> LOCATION: (1)..(389)
<223> OTHER INFORMATION: Repeat 5

<400> SEQUENCE: 17

cagaacaact gaacagccgg tggatcgaat tctgccagtt gctaagtgag agacttaact     60

ggctggagta tcagaacaac atcatcgctt tctataatca gctacaacaa ttggagcaga    120

tgacaactac tgctgaaaac tggttgaaaa tccaacccac caccccatca gagccaacag    180

caattaaaag tcagttaaaa atttgtaagg atgaagtcaa ccggctatca ggtcttcaac    240

ctcaaattga acgattaaaa attcaaagca tagccctgaa agagaaagga caaggaccca    300

tgttcctgga tgcagacttt gtggccttta caaatcattt taagcaagtc ttttctgatg    360

tgcaggccag agagaaagag ctacagaca                                      389
```

```
<210> SEQ ID NO 18
<211> LENGTH: 333
<212> TYPE: DNA
<213> ORGANISM: Homo sapiens
<220> FEATURE:
<221> NAME/KEY: misc_feature
<222> LOCATION: (1)..(333)
<223> OTHER INFORMATION: Repeat 6

<400> SEQUENCE: 18

atttttgaca ctttgccacc aatgcgctat caggagacca tgagtgccat caggacatgg     60

gtccagcagt cagaaaccaa actctccata cctcaactta gtgtcaccga ctatgaaatc    120

atggagcaga gactcgggga attgcaggct ttacaaagtt ctctgcaaga gcaacaaagt    180

ggcctatact atctcagcac cactgtgaaa gagatgtcga agaaagcgcc ctctgaaatt    240

agccggaaat atcaatcaga atttgaagaa attgagggac gctggaagaa gctctcctcc    300

cagctggttg agcattgtca aaagctagag gag                                 333
```

```
<210> SEQ ID NO 19
<211> LENGTH: 327
<212> TYPE: DNA
<213> ORGANISM: Homo sapiens
<220> FEATURE:
<221> NAME/KEY: misc_feature
<222> LOCATION: (1)..(327)
<223> OTHER INFORMATION: Repeat 7

<400> SEQUENCE: 19

caaatgaata aactccgaaa aattcagaat cacatacaaa ccctgaagaa atggatggct     60

gaagttgatg tttttctgaa ggaggaatgg cctgcccttg gggattcaga aattctaaaa    120

aagcagctga aacagtgcag acttttagtc agtgatattc agacaattca gcccagtcta    180
```

```
aacagtgtca atgaaggtgg gcagaagata aagaatgaag cagagccaga gtttgcttcg    240

agacttgaga cagaactcaa agaacttaac actcagtggg atcacatgtg ccaacaggtc    300

tatgccagaa aggaggcctt gaaggga                                        327


<210> SEQ ID NO 20
<211> LENGTH: 327
<212> TYPE: DNA
<213> ORGANISM: Homo sapiens
<220> FEATURE:
<221> NAME/KEY: misc_feature
<222> LOCATION: (1)..(327)
<223> OTHER INFORMATION: Repeat 8

<400> SEQUENCE: 20

ggtttggaga aaactgtaag cctccagaaa gatctatcag agatgcacga atggatgaca     60

caagctgaag aagagtatct tgagagagat tttgaatata aaactccaga tgaattacag    120

aaagcagttg aagagatgaa gagagctaaa gaagaggccc aacaaaaaga agcgaaagtg    180

aaactcctta ctgagtctgt aaatagtgtc atagctcaag ctccacctgt agcacaagag    240

gccttaaaaa aggaacttga aactctaacc accaactacc agtggctctg cactaggctg    300

aatgggaaat gcaagacttt ggaagaa                                        327


<210> SEQ ID NO 21
<211> LENGTH: 312
<212> TYPE: DNA
<213> ORGANISM: Homo sapiens
<220> FEATURE:
<221> NAME/KEY: misc_feature
<222> LOCATION: (1)..(312)
<223> OTHER INFORMATION: Repeat 9

<400> SEQUENCE: 21

gtttgggcat gttggcatga gttattgtca tacttggaga aagcaaacaa gtggctaaat     60

gaagtagaat ttaaacttaa aaccactgaa aacattcctg gcggagctga ggaaatctct    120

gaggtgctag attcacttga aaatttgatg cgacattcag aggataaccc aaatcagatt    180

cgcatattgg cacagaccct aacagatggc ggagtcatgg atgagctaat caatgaggaa    240

cttgagacat ttaattctcg ttggagggaa ctacatgaag aggctgtaag gaggcaaaag    300

ttgcttgaac ag                                                        312


<210> SEQ ID NO 22
<211> LENGTH: 288
<212> TYPE: DNA
<213> ORGANISM: Homo sapiens
<220> FEATURE:
<221> NAME/KEY: misc_feature
<222> LOCATION: (1)..(288)
<223> OTHER INFORMATION: Repeat 10

<400> SEQUENCE: 22

agcatccagt ctgcccagga gactgaaaaa tccttacact taatccagga gtccctcaca     60

ttcattgaca agcagttggc agcttatatt gcagacaagg tggacgcagc tcaaatgcct    120

caggaagccc agaaaatcca atctgatttg acaagtcatg agatcagttt agaagaaatg    180

aagaaacata atcaggggaa ggaggctgcc caaagagtcc tgtctcagat tgatgttgca    240

cagaaaaaat tacaagatgt ctccatgaag tttcgattat tccagaaa                 288


<210> SEQ ID NO 23
<211> LENGTH: 315
```

<212> TYPE: DNA
<213> ORGANISM: Homo sapiens
<220> FEATURE:
<221> NAME/KEY: misc_feature
<222> LOCATION: (1)..(315)
<223> OTHER INFORMATION: Repeat 11

<400> SEQUENCE: 23
ccagccaatt ttgagctgcg tctacaagaa agtaagatga ttttagatga agtgaagatg 60
cacttgcctg cattggaaac aaagagtgtg gaacaggaag tagtacagtc acagctaaat 120
cattgtgtga acttgtataa aagtctgagt gaagtgaagt ctgaagtgga aatggtgata 180
aagactggac gtcagattgt acagaaaaag cagacggaaa atcccaaaga acttgatgaa 240
agagtaacag ctttgaaatt gcattataat gagctgggag caaaggtaac agaaagaaag 300
caacagttgg agaaa 315

<210> SEQ ID NO 24
<211> LENGTH: 324
<212> TYPE: DNA
<213> ORGANISM: Homo sapiens
<220> FEATURE:
<221> NAME/KEY: misc_feature
<222> LOCATION: (1)..(324)
<223> OTHER INFORMATION: Repeat 12

<400> SEQUENCE: 24
tgcttgaaat tgtcccgtaa gatgcgaaag gaaatgaatg tcttgacaga atggctggca 60
gctacagata tggaattgac aaagagatca gcagttgaag gaatgcctag taatttggat 120
tctgaagttg cctggggaaa ggctactcaa aaagagattg agaaacagaa ggtgcacctg 180
aagagtatca cagaggtagg agaggccttg aaaacagttt tgggcaagaa ggagacgttg 240
gtggaagata aactcagtct tctgaatagt aactggatag ctgtcacctc ccgagcagaa 300
gagtggttaa atcttttgtt ggaa 324

<210> SEQ ID NO 25
<211> LENGTH: 306
<212> TYPE: DNA
<213> ORGANISM: Homo sapiens
<220> FEATURE:
<221> NAME/KEY: misc_feature
<222> LOCATION: (1)..(306)
<223> OTHER INFORMATION: Repeat 13

<400> SEQUENCE: 25
taccagaaac acatggaaac ttttgaccag aatgtggacc acatcacaaa gtggatcatt 60
caggctgaca cacttttgga tgaatcagag aaaaagaaac cccagcaaaa agaagacgtg 120
cttaagcgtt taaaggcaga actgaatgac atacgcccaa aggtggactc tacacgtgac 180
caagcagcaa acttgatggc aaaccgcggt gaccactgca ggaaattagt agagccccaa 240
atctcagagc tcaaccatcg atttgcagcc atttcacaca gaattaagac tggaaaggcc 300
tccatt 306

<210> SEQ ID NO 26
<211> LENGTH: 288
<212> TYPE: DNA
<213> ORGANISM: Homo sapiens
<220> FEATURE:
<221> NAME/KEY: misc_feature
<222> LOCATION: (1)..(288)
<223> OTHER INFORMATION: Repeat 14

<400> SEQUENCE: 26
cctttgaagg aattggagca gtttaactca gatatacaaa aattgcttga accactggag 60
gctgaaattc agcagggggt gaatctgaaa gaggaagact tcaataaaga tatgaatgaa 120
gacaatgagg gtactgtaaa agaattgttg caaagaggag acaacttaca acaaagaatc 180
acagatgaga gaaagagaga ggaaataaag ataaaacagc agctgttaca gacaaaacat 240
aatgctctca aggatttgag gtctcaaaga agaaaaaagg ctctagaa 288

<210> SEQ ID NO 27
<211> LENGTH: 297
<212> TYPE: DNA
<213> ORGANISM: Homo sapiens
<220> FEATURE:
<221> NAME/KEY: misc_feature
<222> LOCATION: (1)..(297)
<223> OTHER INFORMATION: Repeat 15

<400> SEQUENCE: 27
atttctcatc agtggtatca gtacaagagg caggctgatg atctcctgaa atgcttggat 60
gacattgaaa aaaaattagc cagcctacct gagcccagag atgaaaggaa aataaaggaa 120
attgatcggg aattgcagaa gaagaaagag gagctgaatg cagtgcgtag gcaagctgag 180
ggcttgtctg aggatggggc cgcaatggca gtggagccaa ctcagatcca gctcagcaag 240
cgctggcggg aaattgagag caaatttgct cagtttcgaa gactcaactt tgcacaa 297

<210> SEQ ID NO 28
<211> LENGTH: 384
<212> TYPE: DNA
<213> ORGANISM: Homo sapiens
<220> FEATURE:
<221> NAME/KEY: misc_feature
<222> LOCATION: (1)..(384)
<223> OTHER INFORMATION: Repeat 16

<400> SEQUENCE: 28
attcacactg tccgtgaaga aacgatgatg gtgatgactg aagacatgcc tttggaaatt 60
tcttatgtgc cttctactta tttgactgaa atcactcatg tctcacaagc cctattagaa 120
gtggaacaac ttctcaatgc tcctgacctc tgtgctaagg actttgaaga tctctttaag 180
caagaggagt ctctgaagaa tataaaagat agtctacaac aaagctcagg tcggattgac 240
attattcata gcaagaagac agcagcattg caaagtgcaa cgcctgtgga aagggtgaag 300
ctacaggaag ctctctccca gcttgatttc caatgggaaa aagttaacaa aatgtacaag 360
gaccgacaag ggcgatttga caga 384

<210> SEQ ID NO 29
<211> LENGTH: 321
<212> TYPE: DNA
<213> ORGANISM: Homo sapiens
<220> FEATURE:
<221> NAME/KEY: misc_feature
<222> LOCATION: (1)..(321)
<223> OTHER INFORMATION: Repeat 17

<400> SEQUENCE: 29
tctgttgaga aatggcggcg ttttcattat gatataaaga tatttaatca gtggctaaca 60
gaagctgaac agtttctcag aaagacacaa attcctgaga attgggaaca tgctaaatac 120
aaatggtatc ttaaggaact ccaggatggc attgggcagc ggcaaactgt tgtcagaaca 180
ttgaatgcaa ctggggaaga aataattcag caatcctcaa aaacagatgc cagtattcta 240
caggaaaaat tgggaagcct gaatctgcgg tggcaggagg tctgcaaaca gctgtcagac 300
agaaaaaaga ggctagaaga a 321

<210> SEQ ID NO 30
<211> LENGTH: 330
<212> TYPE: DNA
<213> ORGANISM: Homo sapiens
<220> FEATURE:
<221> NAME/KEY: misc_feature
<222> LOCATION: (1)..(330)
<223> OTHER INFORMATION: Repeat 18

<400> SEQUENCE: 30
caaaagaata tcttgtcaga atttcaaaga gatttaaatg aatttgtttt atggttggag 60
gaagcagata acattgctag tatcccactt gaacctggaa aagagcagca actaaaagaa 120
aagcttgagc aagtcaagtt actggtggaa gagttgcccc tgcgccaggg aattctcaaa 180
caattaaatg aaactggagg acccgtgctt gtaagtgctc ccataagccc agaagagcaa 240
gataaacttg aaaataagct caagcagaca aatctccagt ggataaaggt ttccagagct 300
ttacctgaga aacaaggaga aattgaagct 330

<210> SEQ ID NO 31
<211> LENGTH: 315
<212> TYPE: DNA
<213> ORGANISM: Homo sapiens
<220> FEATURE:
<221> NAME/KEY: misc_feature
<222> LOCATION: (1)..(315)
<223> OTHER INFORMATION: Repeat 19

<400> SEQUENCE: 31
caaataaaag accttgggca gcttgaaaaa aagcttgaag accttgaaga gcagttaaat 60
catctgctgc tgtggttatc tcctattagg aatcagttgg aaatttataa ccaaccaaac 120
caagaaggac catttgacgt tcaggaaact gaaatagcag ttcaagctaa acaaccggat 180
gtggaagaga ttttgtctaa agggcagcat ttgtacaagg aaaaaccagc cactcagcca 240
gtgaagagga agttagaaga tctgagctct gagtggaagg cggtaaaccg tttacttcaa 300
gagctgaggg caaag 315

<210> SEQ ID NO 32
<211> LENGTH: 141
<212> TYPE: DNA
<213> ORGANISM: Homo sapiens
<220> FEATURE:
<221> NAME/KEY: misc_feature
<222> LOCATION: (1)..(141)
<223> OTHER INFORMATION: Hinge 3

<400> SEQUENCE: 32
cagcctgacc tagctcctgg actgaccact attggagcct ctcctactca gactgttact 60
ctggtgacac aacctgtggt tactaaggaa actgccatct ccaaactaga aatgccatct 120
tccttgatgt tggaggtacc t 141

<210> SEQ ID NO 33
<211> LENGTH: 321
<212> TYPE: DNA
<213> ORGANISM: Homo sapiens
<220> FEATURE:
<221> NAME/KEY: misc_feature
<222> LOCATION: (1)..(321)

<223> OTHER INFORMATION: Repeat 20

<400> SEQUENCE: 33
gctctggcag atttcaaccg ggcttggaca gaacttaccg actggctttc tctgcttgat 60
caagttataa aatcacagag ggtgatggtg ggtgaccttg aggatatcaa cgagatgatc 120
atcaagcaga aggcaacaat gcaggatttg gaacagaggc gtccccagtt ggaagaactc 180
attaccgctg cccaaaattt gaaaaacaag accagcaatc aagaggctag aacaatcatt 240
acggatcgaa ttgaaagaat tcagaatcag tgggatgaag tacaagaaca ccttcagaac 300
cggaggcaac agttgaatga a 321

<210> SEQ ID NO 34
<211> LENGTH: 327
<212> TYPE: DNA
<213> ORGANISM: Homo sapiens
<220> FEATURE:
<221> NAME/KEY: misc_feature
<222> LOCATION: (1)..(327)
<223> OTHER INFORMATION: Repeat 21

<400> SEQUENCE: 34
atgttaaagg attcaacaca atggctggaa gctaaggaag aagctgagca ggtcttagga 60
caggccagag ccaagcttga gtcatggaag gagggtccct atacagtaga tgcaatccaa 120
aagaaaatca cagaaaccaa gcagttggcc aaagacctcc gccagtggca gacaaatgta 180
gatgtggcaa atgacttggc cctgaaactt ctccgggatt attctgcaga tgataccaga 240
aaagtccaca tgataacaga gaatatcaat gcctcttgga gaagcattca taaaagggtg 300
agtgagcgag aggctgcttt ggaagaa 327

<210> SEQ ID NO 35
<211> LENGTH: 348
<212> TYPE: DNA
<213> ORGANISM: Homo sapiens
<220> FEATURE:
<221> NAME/KEY: misc_feature
<222> LOCATION: (1)..(348)
<223> OTHER INFORMATION: Repeat 22

<400> SEQUENCE: 35
actcatagat tactgcaaca gttccccctg gacctggaaa agtttcttgc ctggcttaca 60
gaagctgaaa caactgccaa tgtcctacag gatgctaccc gtaaggaaag gctcctagaa 120
gactccaagg gagtaaaaga gctgatgaaa caatggcaag acctccaagg tgaaattgaa 180
gctcacacag atgtttatca caacctggat gaaaacagcc aaaaaatcct gagatccctg 240
gaaggttccg atgatgcagt cctgttacaa agacgtttgg ataacatgaa cttcaagtgg 300
agtgaacttc ggaaaaagtc tctcaacatt aggtcccatt tggaagcc 348

<210> SEQ ID NO 36
<211> LENGTH: 387
<212> TYPE: DNA
<213> ORGANISM: Homo sapiens
<220> FEATURE:
<221> NAME/KEY: misc_feature
<222> LOCATION: (1)..(387)
<223> OTHER INFORMATION: Repeat 23

<400> SEQUENCE: 36
agttctgacc agtggaagcg tctgcacctt tctctgcagg aacttctggt gtggctacag 60
ctgaaagatg atgaattaag ccggcaggca cctattggag gcgactttcc agcagttcag 120
aagcagaacg atgtacatag ggccttcaag agggaattga aaactaaaga acctgtaatc 180
atgagtactc ttgagactgt acgaatattt ctgacagagc agcctttgga aggactagag 240
aaactctacc aggagcccag agagctgcct cctgaggaga gagcccagaa tgtcactcgg 300
cttctacgaa agcaggctga ggaggtcaat actgagtggg aaaaattgaa cctgcactcc 360
gctgactggc agagaaaaat agatgag 387

<210> SEQ ID NO 37
<211> LENGTH: 327
<212> TYPE: DNA
<213> ORGANISM: Homo sapiens
<220> FEATURE:
<221> NAME/KEY: misc_feature
<222> LOCATION: (1)..(327)
<223> OTHER INFORMATION: Repeat 24

<400> SEQUENCE: 37
acccttgaaa gactccagga acttcaagag gccacggatg agctggacct caagctgcgc 60
caagctgagg tgatcaaggg atcctggcag cccgtgggcg atctcctcat tgactctctc 120
caagatcacc tcgagaaagt caaggcactt cgaggagaaa ttgcgcctct gaaagagaac 180
gtgagccacg tcaatgacct tgctcgccag cttaccactt tgggcattca gctctcaccg 240
tataacctca gcactctgga agacctgaac accagatgga agcttctgca ggtggccgtc 300
gaggaccgag tcaggcagct gcatgaa 327

<210> SEQ ID NO 38
<211> LENGTH: 216
<212> TYPE: DNA
<213> ORGANISM: Homo sapiens
<220> FEATURE:
<221> NAME/KEY: misc_feature
<222> LOCATION: (1)..(216)
<223> OTHER INFORMATION: Hinge 4

<400> SEQUENCE: 38
gcccacaggg actttggtcc agcatctcag cactttcttt ccacgtctgt ccagggtccc 60
tgggagagag ccatctcgcc aaacaaagtg ccctactata tcaaccacga gactcaaaca 120
acttgctggg accatcccaa aatgacagag ctctaccagt ctttagctga cctgaataat 180
gtcagattct cagcttatag gactgccatg aaactc 216

<210> SEQ ID NO 39
<211> LENGTH: 888
<212> TYPE: DNA
<213> ORGANISM: Homo sapiens
<220> FEATURE:
<221> NAME/KEY: misc_feature
<222> LOCATION: (1)..(888)
<223> OTHER INFORMATION: Cysteine-rich domain

<400> SEQUENCE: 39
cgaagactgc agaaggccct ttgcttggat ctcttgagcc tgtcagctgc atgtgatgcc 60
ttggaccagc acaacctcaa gcaaaatgac cagcccatgg atatcctgca gattattaat 120
tgtttgacca ctatttatga ccgcctggag caagagcaca acaatttggt caacgtccct 180
ctctgcgtgg atatgtgtct gaactggctg ctgaatgttt atgatacggg acgaacaggg 240
aggatccgtg tcctgtcttt taaaactggc atcatttccc tgtgtaaagc acatttggaa 300
gacaagtaca gatacctttt caagcaagtg gcaagttcaa caggattttg tgaccagcgc 360

```
aggctgggcc tccttctgca tgattctatc caaattccaa gacagttggg tgaagttgca    420

tcctttgggg gcagtaacat tgagccaagt gtccggagct gcttccaatt tgctaataat    480

aagccagaga tcgaagcggc cctcttccta gactggatga gactggaacc ccagtccatg    540

gtgtggctgc ccgtcctgca cagagtggct gctgcagaaa ctgccaagca tcaggccaaa    600

tgtaacatct gcaaagagtg tccaatcatt ggattcaggt acaggagtct aaagcacttt    660

aattatgaca tctgccaaag ctgctttttt tctggtcgag ttgcaaaagg ccataaaatg    720

cactatccca tggtggaata ttgcactccg actacatcag gagaagatgt tcgagacttt    780

gccaaggtac taaaaaacaa atttcgaacc aaaaggtatt ttgcgaagca tccccgaatg    840

ggctacctgc cagtgcagac tgtcttagag gggacaacaa tggaaact                 888
```

<210> SEQ ID NO 40
<211> LENGTH: 834
<212> TYPE: DNA
<213> ORGANISM: Homo sapiens
<220> FEATURE:
<221> NAME/KEY: misc_feature
<222> LOCATION: (1)..(834)
<223> OTHER INFORMATION: C-terminal domain

<400> SEQUENCE: 40

```
cccgttactc tgatcaactt ctggccagta gattctgcgc ctgcctcgtc ccctcagctt     60

tcacacgatg atactcattc acgcattgaa cattatgcta gcaggctagc agaaatggaa    120

aacagcaatg gatcttatct aaatgatagc atctctccta atgagagcat agatgatgaa    180

catttgttaa tccagcatta ctgccaaagt ttgaaccagg actccccccct gagccagcct    240

cgtagtcctg cccagatctt gatttcctta gagagtgagg aaagagggga gctagagaga    300

atcctagcag atcttgagga agaaaacagg aatctgcaag cagaatatga ccgtctaaag    360

cagcagcacg aacataaagg cctgtcccca ctgccgtccc ctcctgaaat gatgcccacc    420

tctccccaga gtccccggga tgctgagctc attgctgagg ccaagctact gcgtcaacac    480

aaaggccgcc tggaagccag gatgcaaatc ctggaagacc acaataaaca gctggagtca    540

cagttacaca ggctaaggca gctgctggag caacccgagg cagaggccaa agtgaatggc    600

acaacggtgt cctctccttc tacctctcta cagaggtccg acagcagtca gcctatgctg    660

ctccgagtgg ttggcagtca aacttcggac tccatgggtg aggaagatct tctcagtcct    720

ccccaggaca caagcacagg gttagaggag gtgatggagc aactcaacaa ctccttccct    780

agttcaagag gaagaaatac ccctggaaag ccaatgagag aggacacaat gtag          834
```

<210> SEQ ID NO 41
<211> LENGTH: 251
<212> TYPE: PRT
<213> ORGANISM: Homo sapiens
<220> FEATURE:
<221> NAME/KEY: misc_feature
<222> LOCATION: (1)..(251)
<223> OTHER INFORMATION: N-terminal domain

<400> SEQUENCE: 41

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45
```

```
Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Val Met Lys Asn Ile Met Ala
        115                 120                 125

Gly Leu Gln Gln Thr Asn Ser Glu Lys Ile Leu Leu Ser Trp Val Arg
    130                 135                 140

Gln Ser Thr Arg Asn Tyr Pro Gln Val Asn Val Ile Asn Phe Thr Thr
145                 150                 155                 160

Ser Trp Ser Asp Gly Leu Ala Leu Asn Ala Leu Ile His Ser His Arg
                165                 170                 175

Pro Asp Leu Phe Asp Trp Asn Ser Val Val Cys Gln Gln Ser Ala Thr
            180                 185                 190

Gln Arg Leu Glu His Ala Phe Asn Ile Ala Arg Tyr Gln Leu Gly Ile
        195                 200                 205

Glu Lys Leu Leu Asp Pro Glu Asp Val Asp Thr Thr Tyr Pro Asp Lys
    210                 215                 220

Lys Ser Ile Leu Met Tyr Ile Thr Ser Leu Phe Gln Val Leu Pro Gln
225                 230                 235                 240

Gln Val Ser Ile Glu Ala Ile Gln Glu Val Glu
                245                 250


<210> SEQ ID NO 42
<211> LENGTH: 2860
<212> TYPE: PRT
<213> ORGANISM: Homo sapiens
<220> FEATURE:
<221> NAME/KEY: misc_feature
<222> LOCATION: (1)..(2860)
<223> OTHER INFORMATION: Mid-rod domain

<400> SEQUENCE: 42

Met Leu Pro Arg Pro Pro Lys Val Thr Lys Glu Glu His Phe Gln Leu
1               5                   10                  15

His His Gln Met His Tyr Ser Gln Gln Ile Thr Val Ser Leu Ala Gln
            20                  25                  30

Gly Tyr Glu Arg Thr Ser Ser Pro Lys Pro Arg Phe Lys Ser Tyr Ala
        35                  40                  45

Tyr Thr Gln Ala Ala Tyr Val Thr Thr Ser Asp Pro Thr Arg Ser Pro
    50                  55                  60

Phe Pro Ser Gln His Leu Glu Ala Pro Glu Asp Lys Ser Phe Gly Ser
65                  70                  75                  80

Ser Leu Met Glu Ser Glu Val Asn Leu Asp Arg Tyr Gln Thr Ala Leu
                85                  90                  95

Glu Glu Val Leu Ser Trp Leu Leu Ser Ala Glu Asp Thr Leu Gln Ala
            100                 105                 110

Gln Gly Glu Ile Ser Asn Asp Val Glu Val Val Lys Asp Gln Phe His
        115                 120                 125

Thr His Glu Gly Tyr Met Met Asp Leu Thr Ala His Gln Gly Arg Val
    130                 135                 140

Gly Asn Ile Leu Gln Leu Gly Ser Lys Leu Ile Gly Thr Gly Lys Leu
```

```
145                 150                 155                 160

Ser Glu Asp Glu Glu Thr Glu Val Gln Glu Gln Met Asn Leu Leu Asn
                165                 170                 175

Ser Arg Trp Glu Cys Leu Arg Val Ala Ser Met Glu Lys Gln Ser Asn
            180                 185                 190

Leu His Arg Val Leu Met Asp Leu Gln Asn Gln Lys Leu Lys Glu Leu
        195                 200                 205

Asn Asp Trp Leu Thr Lys Thr Glu Glu Arg Thr Arg Lys Met Glu Glu
    210                 215                 220

Glu Pro Leu Gly Pro Asp Leu Glu Asp Leu Lys Arg Gln Val Gln Gln
225                 230                 235                 240

His Lys Val Leu Gln Glu Asp Leu Glu Gln Glu Gln Val Arg Val Asn
                245                 250                 255

Ser Leu Thr His Met Val Val Val Val Asp Glu Ser Ser Gly Asp His
            260                 265                 270

Ala Thr Ala Ala Leu Glu Glu Gln Leu Lys Val Leu Gly Asp Arg Trp
        275                 280                 285

Ala Asn Ile Cys Arg Trp Thr Glu Asp Arg Trp Val Leu Leu Gln Asp
    290                 295                 300

Ile Leu Leu Lys Trp Gln Arg Leu Thr Glu Glu Gln Cys Leu Phe Ser
305                 310                 315                 320

Ala Trp Leu Ser Glu Lys Glu Asp Ala Val Asn Lys Ile His Thr Thr
                325                 330                 335

Gly Phe Lys Asp Gln Asn Glu Met Leu Ser Ser Leu Gln Lys Leu Ala
            340                 345                 350

Val Leu Lys Ala Asp Leu Glu Lys Lys Lys Gln Ser Met Gly Lys Leu
        355                 360                 365

Tyr Ser Leu Lys Gln Asp Leu Leu Ser Thr Leu Lys Asn Lys Ser Val
    370                 375                 380

Thr Gln Lys Thr Glu Ala Trp Leu Asp Asn Phe Ala Arg Cys Trp Asp
385                 390                 395                 400

Asn Leu Val Gln Lys Leu Glu Lys Ser Thr Ala Gln Ile Ser Gln Ala
                405                 410                 415

Val Thr Thr Thr Gln Pro Ser Leu Thr Gln Thr Thr Val Met Glu Thr
            420                 425                 430

Val Thr Thr Val Thr Thr Arg Glu Gln Ile Leu Val Lys His Ala Gln
        435                 440                 445

Glu Glu Leu Pro Pro Pro Pro Pro Gln Lys Lys Arg Gln Ile Thr Val
    450                 455                 460

Asp Ser Glu Ile Arg Lys Arg Leu Asp Val Asp Ile Thr Glu Leu His
465                 470                 475                 480

Ser Trp Ile Thr Arg Ser Glu Ala Val Leu Gln Ser Pro Glu Phe Ala
                485                 490                 495

Ile Phe Arg Lys Glu Gly Asn Phe Ser Asp Leu Lys Glu Lys Val Asn
            500                 505                 510

Ala Ile Glu Arg Glu Lys Ala Glu Lys Phe Arg Lys Leu Gln Asp Ala
        515                 520                 525

Ser Arg Ser Ala Gln Ala Leu Val Glu Gln Met Val Asn Glu Gly Val
    530                 535                 540

Asn Ala Asp Ser Ile Lys Gln Ala Ser Glu Gln Leu Asn Ser Arg Trp
545                 550                 555                 560

Ile Glu Phe Cys Gln Leu Leu Ser Glu Arg Leu Asn Trp Leu Glu Tyr
                565                 570                 575
```

-continued

```
Gln Asn Asn Ile Ile Ala Phe Tyr Asn Gln Leu Gln Gln Leu Glu Gln
            580                 585                 590

Met Thr Thr Thr Ala Glu Asn Trp Leu Lys Ile Gln Pro Thr Thr Pro
        595                 600                 605

Ser Glu Pro Thr Ala Ile Lys Ser Gln Leu Lys Ile Cys Lys Asp Glu
    610                 615                 620

Val Asn Arg Leu Ser Gly Leu Gln Pro Gln Ile Glu Arg Leu Lys Ile
625                 630                 635                 640

Gln Ser Ile Ala Leu Lys Glu Lys Gly Gln Gly Pro Met Phe Leu Asp
                645                 650                 655

Ala Asp Phe Val Ala Phe Thr Asn His Phe Lys Gln Val Phe Ser Asp
            660                 665                 670

Val Gln Ala Arg Glu Lys Glu Leu Gln Thr Ile Phe Asp Thr Leu Pro
        675                 680                 685

Pro Met Arg Tyr Gln Glu Thr Met Ser Ala Ile Arg Thr Trp Val Gln
    690                 695                 700

Gln Ser Glu Thr Lys Leu Ser Ile Pro Gln Leu Ser Val Thr Asp Tyr
705                 710                 715                 720

Glu Ile Met Glu Gln Arg Leu Gly Glu Leu Gln Ala Leu Gln Ser Ser
                725                 730                 735

Leu Gln Glu Gln Gln Ser Gly Leu Tyr Tyr Leu Ser Thr Thr Val Lys
            740                 745                 750

Glu Met Ser Lys Lys Ala Pro Ser Glu Ile Ser Arg Lys Tyr Gln Ser
        755                 760                 765

Glu Phe Glu Glu Ile Glu Gly Arg Trp Lys Lys Leu Ser Ser Gln Leu
    770                 775                 780

Val Glu His Cys Gln Lys Leu Glu Glu Gln Met Asn Lys Leu Arg Lys
785                 790                 795                 800

Ile Gln Asn His Ile Gln Thr Leu Lys Lys Trp Met Ala Glu Val Asp
                805                 810                 815

Val Phe Leu Lys Glu Glu Trp Pro Ala Leu Gly Asp Ser Glu Ile Leu
            820                 825                 830

Lys Lys Gln Leu Lys Gln Cys Arg Leu Leu Val Ser Asp Ile Gln Thr
        835                 840                 845

Ile Gln Pro Ser Leu Asn Ser Val Asn Glu Gly Gly Gln Lys Ile Lys
    850                 855                 860

Asn Glu Ala Glu Pro Glu Phe Ala Ser Arg Leu Glu Thr Glu Leu Lys
865                 870                 875                 880

Glu Leu Asn Thr Gln Trp Asp His Met Cys Gln Gln Val Tyr Ala Arg
                885                 890                 895

Lys Glu Ala Leu Lys Gly Gly Leu Glu Lys Thr Val Ser Leu Gln Lys
            900                 905                 910

Asp Leu Ser Glu Met His Glu Trp Met Thr Gln Ala Glu Glu Glu Tyr
        915                 920                 925

Leu Glu Arg Asp Phe Glu Tyr Lys Thr Pro Asp Glu Leu Gln Lys Ala
    930                 935                 940

Val Glu Glu Met Lys Arg Ala Lys Glu Glu Ala Gln Gln Lys Glu Ala
945                 950                 955                 960

Lys Val Lys Leu Leu Thr Glu Ser Val Asn Ser Val Ile Ala Gln Ala
                965                 970                 975

Pro Pro Val Ala Gln Glu Ala Leu Lys Lys Glu Leu Glu Thr Leu Thr
            980                 985                 990
```

```
Thr Asn Tyr Gln Trp Leu Cys Thr  Arg Leu Asn Gly Lys  Cys Lys Thr
        995                 1000                 1005

Leu Glu  Glu Val Trp Ala Cys  Trp His Glu Leu Leu  Ser Tyr Leu
    1010                 1015                 1020

Glu Lys  Ala Asn Lys Trp Leu  Asn Glu Val Glu Phe  Lys Leu Lys
    1025                 1030                 1035

Thr Thr  Glu Asn Ile Pro Gly  Gly Ala Glu Glu Ile  Ser Glu Val
    1040                 1045                 1050

Leu Asp  Ser Leu Glu Asn Leu  Met Arg His Ser Glu  Asp Asn Pro
    1055                 1060                 1065

Asn Gln  Ile Arg Ile Leu Ala  Gln Thr Leu Thr Asp  Gly Gly Val
    1070                 1075                 1080

Met Asp  Glu Leu Ile Asn Glu  Glu Leu Glu Thr Phe  Asn Ser Arg
    1085                 1090                 1095

Trp Arg  Glu Leu His Glu Glu  Ala Val Arg Arg Gln  Lys Leu Leu
    1100                 1105                 1110

Glu Gln  Ser Ile Gln Ser Ala  Gln Glu Thr Glu Lys  Ser Leu His
    1115                 1120                 1125

Leu Ile  Gln Glu Ser Leu Thr  Phe Ile Asp Lys Gln  Leu Ala Ala
    1130                 1135                 1140

Tyr Ile  Ala Asp Lys Val Asp  Ala Ala Gln Met Pro  Gln Glu Ala
    1145                 1150                 1155

Gln Lys  Ile Gln Ser Asp Leu  Thr Ser His Glu Ile  Ser Leu Glu
    1160                 1165                 1170

Glu Met  Lys Lys His Asn Gln  Gly Lys Glu Ala Ala  Gln Arg Val
    1175                 1180                 1185

Leu Ser  Gln Ile Asp Val Ala  Gln Lys Lys Leu Gln  Asp Val Ser
    1190                 1195                 1200

Met Lys  Phe Arg Leu Phe Gln  Lys Pro Ala Asn Phe  Glu Leu Arg
    1205                 1210                 1215

Leu Gln  Glu Ser Lys Met Ile  Leu Asp Glu Val Lys  Met His Leu
    1220                 1225                 1230

Pro Ala  Leu Glu Thr Lys Ser  Val Glu Gln Glu Val  Val Gln Ser
    1235                 1240                 1245

Gln Leu  Asn His Cys Val Asn  Leu Tyr Lys Ser Leu  Ser Glu Val
    1250                 1255                 1260

Lys Ser  Glu Val Glu Met Val  Ile Lys Thr Gly Arg  Gln Ile Val
    1265                 1270                 1275

Gln Lys  Lys Gln Thr Glu Asn  Pro Lys Glu Leu Asp  Glu Arg Val
    1280                 1285                 1290

Thr Ala  Leu Lys Leu His Tyr  Asn Glu Leu Gly Ala  Lys Val Thr
    1295                 1300                 1305

Glu Arg  Lys Gln Gln Leu Glu  Lys Cys Leu Lys Leu  Ser Arg Lys
    1310                 1315                 1320

Met Arg  Lys Glu Met Asn Val  Leu Thr Glu Trp Leu  Ala Ala Thr
    1325                 1330                 1335

Asp Met  Glu Leu Thr Lys Arg  Ser Ala Val Glu Gly  Met Pro Ser
    1340                 1345                 1350

Asn Leu  Asp Ser Glu Val Ala  Trp Gly Lys Ala Thr  Gln Lys Glu
    1355                 1360                 1365

Ile Glu  Lys Gln Lys Val His  Leu Lys Ser Ile Thr  Glu Val Gly
    1370                 1375                 1380

Glu Ala  Leu Lys Thr Val Leu  Gly Lys Lys Glu Thr  Leu Val Glu
```

```
    1385                1390                1395

Asp Lys  Leu Ser Leu Leu Asn  Ser Asn Trp Ile Ala  Val Thr Ser
    1400                1405                1410

Arg Ala  Glu Glu Trp Leu Asn  Leu Leu Leu Glu Tyr  Gln Lys His
    1415                1420                1425

Met Glu  Thr Phe Asp Gln Asn  Val Asp His Ile Thr  Lys Trp Ile
    1430                1435                1440

Ile Gln  Ala Asp Thr Leu Leu  Asp Glu Ser Glu Lys  Lys Lys Pro
    1445                1450                1455

Gln Gln  Lys Glu Asp Val Leu  Lys Arg Leu Lys Ala  Glu Leu Asn
    1460                1465                1470

Asp Ile  Arg Pro Lys Val Asp  Ser Thr Arg Asp Gln  Ala Ala Asn
    1475                1480                1485

Leu Met  Ala Asn Arg Gly Asp  His Cys Arg Lys Leu  Val Glu Pro
    1490                1495                1500

Gln Ile  Ser Glu Leu Asn His  Arg Phe Ala Ala Ile  Ser His Arg
    1505                1510                1515

Ile Lys  Thr Gly Lys Ala Ser  Ile Pro Leu Lys Glu  Leu Glu Gln
    1520                1525                1530

Phe Asn  Ser Asp Ile Gln Lys  Leu Leu Glu Pro Leu  Glu Ala Glu
    1535                1540                1545

Ile Gln  Gln Gly Val Asn Leu  Lys Glu Glu Asp Phe  Asn Lys Asp
    1550                1555                1560

Met Asn  Glu Asp Asn Glu Gly  Thr Val Lys Glu Leu  Leu Gln Arg
    1565                1570                1575

Gly Asp  Asn Leu Gln Gln Arg  Ile Thr Asp Glu Arg  Lys Arg Glu
    1580                1585                1590

Glu Ile  Lys Ile Lys Gln Gln  Leu Leu Gln Thr Lys  His Asn Ala
    1595                1600                1605

Leu Lys  Asp Leu Arg Ser Gln  Arg Arg Lys Lys Ala  Leu Glu Ile
    1610                1615                1620

Ser His  Gln Trp Tyr Gln Tyr  Lys Arg Gln Ala Asp  Asp Leu Leu
    1625                1630                1635

Lys Cys  Leu Asp Asp Ile Glu  Lys Lys Leu Ala Ser  Leu Pro Glu
    1640                1645                1650

Pro Arg  Asp Glu Arg Lys Ile  Lys Glu Ile Asp Arg  Glu Leu Gln
    1655                1660                1665

Lys Lys  Lys Glu Glu Leu Asn  Ala Val Arg Arg Gln  Ala Glu Gly
    1670                1675                1680

Leu Ser  Glu Asp Gly Ala Ala  Met Ala Val Glu Pro  Thr Gln Ile
    1685                1690                1695

Gln Leu  Ser Lys Arg Trp Arg  Glu Ile Glu Ser Lys  Phe Ala Gln
    1700                1705                1710

Phe Arg  Arg Leu Asn Phe Ala  Gln Ile His Thr Val  Arg Glu Glu
    1715                1720                1725

Thr Met  Met Val Met Thr Glu  Asp Met Pro Leu Glu  Ile Ser Tyr
    1730                1735                1740

Val Pro  Ser Thr Tyr Leu Thr  Glu Ile Thr His Val  Ser Gln Ala
    1745                1750                1755

Leu Leu  Glu Val Glu Gln Leu  Leu Asn Ala Pro Asp  Leu Cys Ala
    1760                1765                1770

Lys Asp  Phe Glu Asp Leu Phe  Lys Gln Glu Glu Ser  Leu Lys Asn
    1775                1780                1785
```

```
Ile Lys Asp Ser Leu Gln Gln Ser Ser Gly Arg Ile Asp Ile Ile
    1790                1795                1800

His Ser Lys Lys Thr Ala Ala Leu Gln Ser Ala Thr Pro Val Glu
    1805                1810                1815

Arg Val Lys Leu Gln Glu Ala Leu Ser Gln Leu Asp Phe Gln Trp
    1820                1825                1830

Glu Lys Val Asn Lys Met Tyr Lys Asp Arg Gln Gly Arg Phe Asp
    1835                1840                1845

Arg Ser Val Glu Lys Trp Arg Arg Phe His Tyr Asp Ile Lys Ile
    1850                1855                1860

Phe Asn Gln Trp Leu Thr Glu Ala Glu Gln Phe Leu Arg Lys Thr
    1865                1870                1875

Gln Ile Pro Glu Asn Trp Glu His Ala Lys Tyr Lys Trp Tyr Leu
    1880                1885                1890

Lys Glu Leu Gln Asp Gly Ile Gly Gln Arg Gln Thr Val Val Arg
    1895                1900                1905

Thr Leu Asn Ala Thr Gly Glu Glu Ile Ile Gln Gln Ser Ser Lys
    1910                1915                1920

Thr Asp Ala Ser Ile Leu Gln Glu Lys Leu Gly Ser Leu Asn Leu
    1925                1930                1935

Arg Trp Gln Glu Val Cys Lys Gln Leu Ser Asp Arg Lys Lys Arg
    1940                1945                1950

Leu Glu Glu Gln Lys Asn Ile Leu Ser Glu Phe Gln Arg Asp Leu
    1955                1960                1965

Asn Glu Phe Val Leu Trp Leu Glu Glu Ala Asp Asn Ile Ala Ser
    1970                1975                1980

Ile Pro Leu Glu Pro Gly Lys Glu Gln Gln Leu Lys Glu Lys Leu
    1985                1990                1995

Glu Gln Val Lys Leu Leu Val Glu Glu Leu Pro Leu Arg Gln Gly
    2000                2005                2010

Ile Leu Lys Gln Leu Asn Glu Thr Gly Gly Pro Val Leu Val Ser
    2015                2020                2025

Ala Pro Ile Ser Pro Glu Glu Gln Asp Lys Leu Glu Asn Lys Leu
    2030                2035                2040

Lys Gln Thr Asn Leu Gln Trp Ile Lys Val Ser Arg Ala Leu Pro
    2045                2050                2055

Glu Lys Gln Gly Glu Ile Glu Ala Gln Ile Lys Asp Leu Gly Gln
    2060                2065                2070

Leu Glu Lys Lys Leu Glu Asp Leu Glu Glu Gln Leu Asn His Leu
    2075                2080                2085

Leu Leu Trp Leu Ser Pro Ile Arg Asn Gln Leu Glu Ile Tyr Asn
    2090                2095                2100

Gln Pro Asn Gln Glu Gly Pro Phe Asp Val Gln Glu Thr Glu Ile
    2105                2110                2115

Ala Val Gln Ala Lys Gln Pro Asp Val Glu Glu Ile Leu Ser Lys
    2120                2125                2130

Gly Gln His Leu Tyr Lys Glu Lys Pro Ala Thr Gln Pro Val Lys
    2135                2140                2145

Arg Lys Leu Glu Asp Leu Ser Ser Glu Trp Lys Ala Val Asn Arg
    2150                2155                2160

Leu Leu Gln Glu Leu Arg Ala Lys Gln Pro Asp Leu Ala Pro Gly
    2165                2170                2175
```

-continued

```
Leu Thr  Thr Ile Gly Ala Ser  Pro Thr Gln Thr Val  Thr Leu Val
    2180                 2185                 2190

Thr Gln  Pro Val Val Thr Lys  Glu Thr Ala Ile Ser  Lys Leu Glu
    2195                 2200                 2205

Met Pro  Ser Ser Leu Met Leu  Glu Val Pro Ala Leu  Ala Asp Phe
    2210                 2215                 2220

Asn Arg  Ala Trp Thr Glu Leu  Thr Asp Trp Leu Ser  Leu Leu Asp
    2225                 2230                 2235

Gln Val  Ile Lys Ser Gln Arg  Val Met Val Gly Asp  Leu Glu Asp
    2240                 2245                 2250

Ile Asn  Glu Met Ile Ile Lys  Gln Lys Ala Thr Met  Gln Asp Leu
    2255                 2260                 2265

Glu Gln  Arg Arg Pro Gln Leu  Glu Glu Leu Ile Thr  Ala Ala Gln
    2270                 2275                 2280

Asn Leu  Lys Asn Lys Thr Ser  Asn Gln Glu Ala Arg  Thr Ile Ile
    2285                 2290                 2295

Thr Asp  Arg Ile Glu Arg Ile  Gln Asn Gln Trp Asp  Glu Val Gln
    2300                 2305                 2310

Glu His  Leu Gln Asn Arg Arg  Gln Gln Leu Asn Glu  Met Leu Lys
    2315                 2320                 2325

Asp Ser  Thr Gln Trp Leu Glu  Ala Lys Glu Glu Ala  Glu Gln Val
    2330                 2335                 2340

Leu Gly  Gln Ala Arg Ala Lys  Leu Glu Ser Trp Lys  Glu Gly Pro
    2345                 2350                 2355

Tyr Thr  Val Asp Ala Ile Gln  Lys Lys Ile Thr Glu  Thr Lys Gln
    2360                 2365                 2370

Leu Ala  Lys Asp Leu Arg Gln  Trp Gln Thr Asn Val  Asp Val Ala
    2375                 2380                 2385

Asn Asp  Leu Ala Leu Lys Leu  Leu Arg Asp Tyr Ser  Ala Asp Asp
    2390                 2395                 2400

Thr Arg  Lys Val His Met Ile  Thr Glu Asn Ile Asn  Ala Ser Trp
    2405                 2410                 2415

Arg Ser  Ile His Lys Arg Val  Ser Glu Arg Glu Ala  Ala Leu Glu
    2420                 2425                 2430

Glu Thr  His Arg Leu Leu Gln  Gln Phe Pro Leu Asp  Leu Glu Lys
    2435                 2440                 2445

Phe Leu  Ala Trp Leu Thr Glu  Ala Glu Thr Thr Ala  Asn Val Leu
    2450                 2455                 2460

Gln Asp  Ala Thr Arg Lys Glu  Arg Leu Leu Glu Asp  Ser Lys Gly
    2465                 2470                 2475

Val Lys  Glu Leu Met Lys Gln  Trp Gln Asp Leu Gln  Gly Glu Ile
    2480                 2485                 2490

Glu Ala  His Thr Asp Val Tyr  His Asn Leu Asp Glu  Asn Ser Gln
    2495                 2500                 2505

Lys Ile  Leu Arg Ser Leu Glu  Gly Ser Asp Asp Ala  Val Leu Leu
    2510                 2515                 2520

Gln Arg  Arg Leu Asp Asn Met  Asn Phe Lys Trp Ser  Glu Leu Arg
    2525                 2530                 2535

Lys Lys  Ser Leu Asn Ile Arg  Ser His Leu Glu Ala  Ser Ser Asp
    2540                 2545                 2550

Gln Trp  Lys Arg Leu His Leu  Ser Leu Gln Glu Leu  Leu Val Trp
    2555                 2560                 2565

Leu Gln  Leu Lys Asp Asp Glu  Leu Ser Arg Gln Ala  Pro Ile Gly
```

-continued

```
    2570                2575                2580

Gly Asp  Phe Pro Ala Val Gln  Lys Gln Asn Asp Val  His Arg Ala
    2585                2590                2595

Phe Lys  Arg Glu Leu Lys Thr  Lys Glu Pro Val Ile  Met Ser Thr
    2600                2605                2610

Leu Glu  Thr Val Arg Ile Phe  Leu Thr Glu Gln Pro  Leu Glu Gly
    2615                2620                2625

Leu Glu  Lys Leu Tyr Gln Glu  Pro Arg Glu Leu Pro  Pro Glu Glu
    2630                2635                2640

Arg Ala  Gln Asn Val Thr Arg  Leu Leu Arg Lys Gln  Ala Glu Glu
    2645                2650                2655

Val Asn  Thr Glu Trp Glu Lys  Leu Asn Leu His Ser  Ala Asp Trp
    2660                2665                2670

Gln Arg  Lys Ile Asp Glu Thr  Leu Glu Arg Leu Gln  Glu Leu Gln
    2675                2680                2685

Glu Ala  Thr Asp Glu Leu Asp  Leu Lys Leu Arg Gln  Ala Glu Val
    2690                2695                2700

Ile Lys  Gly Ser Trp Gln Pro  Val Gly Asp Leu Leu  Ile Asp Ser
    2705                2710                2715

Leu Gln  Asp His Leu Glu Lys  Val Lys Ala Leu Arg  Gly Glu Ile
    2720                2725                2730

Ala Pro  Leu Lys Glu Asn Val  Ser His Val Asn Asp  Leu Ala Arg
    2735                2740                2745

Gln Leu  Thr Thr Leu Gly Ile  Gln Leu Ser Pro Tyr  Asn Leu Ser
    2750                2755                2760

Thr Leu  Glu Asp Leu Asn Thr  Arg Trp Lys Leu Leu  Gln Val Ala
    2765                2770                2775

Val Glu  Asp Arg Val Arg Gln  Leu His Glu Ala His  Arg Asp Phe
    2780                2785                2790

Gly Pro  Ala Ser Gln His Phe  Leu Ser Thr Ser Val  Gln Gly Pro
    2795                2800                2805

Trp Glu  Arg Ala Ile Ser Pro  Asn Lys Val Pro Tyr  Tyr Ile Asn
    2810                2815                2820

His Glu  Thr Gln Thr Thr Cys  Trp Asp His Pro Lys  Met Thr Glu
    2825                2830                2835

Leu Tyr  Gln Ser Leu Ala Asp  Leu Asn Asn Val Arg  Phe Ser Ala
    2840                2845                2850

Tyr Arg  Thr Ala Met Lys Leu
    2855                2860
```

```
<210> SEQ ID NO 43
<211> LENGTH: 296
<212> TYPE: PRT
<213> ORGANISM: Homo sapiens
<220> FEATURE:
<221> NAME/KEY: misc_feature
<222> LOCATION: (1)..(296)
<223> OTHER INFORMATION: Cysteine-rich domain

<400> SEQUENCE: 43

Arg Arg Leu Gln Lys Ala Leu Cys Leu Asp Leu Leu Ser Leu Ser Ala
1               5                   10                  15

Ala Cys Asp Ala Leu Asp Gln His Asn Leu Lys Gln Asn Asp Gln Pro
            20                  25                  30

Met Asp Ile Leu Gln Ile Ile Asn Cys Leu Thr Thr Ile Tyr Asp Arg
        35                  40                  45
```

-continued

```
Leu Glu Gln Glu His Asn Asn Leu Val Asn Val Pro Leu Cys Val Asp
    50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
        115                 120                 125

Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr
    290                 295


<210> SEQ ID NO 44
<211> LENGTH: 277
<212> TYPE: PRT
<213> ORGANISM: Homo sapiens
<220> FEATURE:
<221> NAME/KEY: misc_feature
<222> LOCATION: (1)..(277)
<223> OTHER INFORMATION: C-terminal domain

<400> SEQUENCE: 44

Pro Val Thr Leu Ile Asn Phe Trp Pro Val Asp Ser Ala Pro Ala Ser
1               5                   10                  15

Ser Pro Gln Leu Ser His Asp Asp Thr His Ser Arg Ile Glu His Tyr
            20                  25                  30

Ala Ser Arg Leu Ala Glu Met Glu Asn Ser Asn Gly Ser Tyr Leu Asn
        35                  40                  45

Asp Ser Ile Ser Pro Asn Glu Ser Ile Asp Asp Glu His Leu Leu Ile
    50                  55                  60

Gln His Tyr Cys Gln Ser Leu Asn Gln Asp Ser Pro Leu Ser Gln Pro
65                  70                  75                  80

Arg Ser Pro Ala Gln Ile Leu Ile Ser Leu Glu Ser Glu Glu Arg Gly
                85                  90                  95
```

-continued

```
Glu Leu Glu Arg Ile Leu Ala Asp Leu Glu Glu Glu Asn Arg Asn Leu
            100                 105                 110

Gln Ala Glu Tyr Asp Arg Leu Lys Gln Gln His Glu His Lys Gly Leu
        115                 120                 125

Ser Pro Leu Pro Ser Pro Pro Glu Met Met Pro Thr Ser Pro Gln Ser
    130                 135                 140

Pro Arg Asp Ala Glu Leu Ile Ala Glu Ala Lys Leu Leu Arg Gln His
145                 150                 155                 160

Lys Gly Arg Leu Glu Ala Arg Met Gln Ile Leu Glu Asp His Asn Lys
                165                 170                 175

Gln Leu Glu Ser Gln Leu His Arg Leu Arg Gln Leu Leu Glu Gln Pro
            180                 185                 190

Gln Ala Glu Ala Lys Val Asn Gly Thr Thr Val Ser Ser Pro Ser Thr
        195                 200                 205

Ser Leu Gln Arg Ser Asp Ser Ser Gln Pro Met Leu Leu Arg Val Val
    210                 215                 220

Gly Ser Gln Thr Ser Asp Ser Met Gly Glu Glu Asp Leu Leu Ser Pro
225                 230                 235                 240

Pro Gln Asp Thr Ser Thr Gly Leu Glu Glu Val Met Glu Gln Leu Asn
                245                 250                 255

Asn Ser Phe Pro Ser Ser Arg Gly Arg Asn Thr Pro Gly Lys Pro Met
            260                 265                 270

Arg Glu Asp Thr Met
        275


<210> SEQ ID NO 45
<211> LENGTH: 5953
<212> TYPE: DNA
<213> ORGANISM: Homo sapiens
<220> FEATURE:
<221> NAME/KEY: misc_feature
<222> LOCATION: (1)..(5953)
<223> OTHER INFORMATION: delta-exon17-48 (mini-dystrophin with 8.5
      repeats and 3 hinges; minigene does not carry R16 or R17; cannot
      restore nNOS)

<400> SEQUENCE: 45

atgctttggt gggaagaagt agaggactgt tatgaaagag aagatgttca aaagaaaaca      60

ttcacaaaat gggtaaatgc acaattttct aagtttggga agcagcatat tgagaacctc     120

ttcagtgacc tacaggatgg gaggcgcctc ctagacctcc tcgaaggcct gacagggcaa     180

aaactgccaa aagaaaaagg atccacaaga gttcatgccc tgaacaatgt caacaaggca     240

ctgcgggttt tgcagaacaa taatgttgat ttagtgaata ttggaagtac tgacatcgta     300

gatggaaatc ataaactgac tcttggtttg atttggaata taatcctcca ctggcaggtc     360

aaaaatgtaa tgaaaaatat catggctgga ttgcaacaaa ccaacagtga aaagattctc     420

ctgagctggg tccgacaatc aactcgtaat tatccacagg ttaatgtaat caacttcacc     480

accagctggt ctgatggcct ggctttgaat gctctcatcc atagtcatag gccagaccta     540

tttgactgga atagtgtggt ttggcagcag tcagccacac aacgactgga acatgcattc     600

aacatcgcca gatatcaatt aggcatagag aaagtactcg atcctgaaga tgttgatacc     660

acctatccag ataagaagtc catcttaatg tacatcacat cactcttcca agttttgcct     720

caacaagtga gcattgaagc catccaggaa gtggaaatgt tgccaaggcc acctaaagtg     780

actaaagaag aacattttca gtacatcatc aaatgcacta ttctcaacag atcacggtca     840

gtctagcaca gggatatgag agaacttctt cccctaagcc tcgattcaag agctatgcct     900
```

```
acacacaggc tgcttatgtc accacctctg accctacacg gagcccattt ccttcacagc    960

atttggaagc tcctgaagac aagtcatttg gcagttcatt gatggagagt gaagtaaacc   1020

tggaccgtta tcaaacagct ttagaagaag tattatcgtg gcttctttct gctgaggaca   1080

cattgcaagc acaaggagag atttctaatg atgtggaagt ggtgaaagac cagtttcata   1140

ctcatgaggg gtacatgatg gatttgacag cccatcaggg ccgggttggt aatattctac   1200

aattgggaag taagctgatt ggaacaggaa aattatcaga agatgaagaa actgaagtac   1260

aagagcagat gaatctccta aattcaagat gggaatgcct cagggtagct agcatggaaa   1320

aacaaagcaa tttacataga gttttaatgg atctccagaa tcagaaactg aaagagttga   1380

atgactggct aacaaaaaca gaagaaagaa caaggaaaat ggaggaagag cctcttggac   1440

ctgatcttga agacctaaaa cgccaagtac aacaacataa ggtgcttcaa gaagatctag   1500

aacaagaaca agtcagggtc aattctctca ctcacatggt ggtggtagtt gatgaatcta   1560

gtggagatca cgcaactgct gctttggaag aacaagttta aggtattggg agatcgatgg   1620

gcaaacatct gtagatggac agaagaccgc tgggttcttt tacaagacat ccttctcaaa   1680

tggcaacgtc ttactgaaga acagtgcctt tttagtgcat ggctttcaga aaaagaagat   1740

gcagtgaaca agattcacac aactggcttt aaagatcaaa atgaaatgtt atcaagtctt   1800

caaaaactgg ccgttttaaa agcggatcta gaaaagaaaa agcaatccat gggcaaactg   1860

tattcactca aacaagatct tctttcaaca ctgaagaata agtcagtgac ccagaagacg   1920

gaagcatggc tggataactt tgcccggtgt tgggataatt tagtccaaaa acttgaaaag   1980

agtacagcac aggaaactga aatagcagtt caagctaaac aaccggatgt ggaagagatt   2040

ttgtctaaag ggcagcattt gtacaaggaa aaaccagcca ctcagccagt gaagaggaag   2100

ttagaagatc tgagctctga gtggaaggcg gtaaaccgtt tacttcaaga gctgagggca   2160

aagcagcctg acctagctcc tggactgacc actattggag cctctcctac tcagactgtt   2220

actctggtga cacaacctgt ggttagtaag gaaactgcca tctccaaact agaaatgcca   2280

tcttccttga tgttggaggt acctgctctg gcagatttca acggggcttg gacagaactt   2340

accgagtggc tttctctgct tgatcaagtt ataaaatcac agagggtgat ggtgggtgac   2400

cttgaggata tcaacgagat gatcatcaag cagaaggcaa caatgcagga tttggaacag   2460

aggcgtcccc agttggaaga actcattacc gctgcccaaa atttgaaaaa caagaccagc   2520

aatcaagagg ctagaacaat cattacggat cgaattgaaa gaattcagaa tcagtgggat   2580

gaagtacaag aacaccttca gaaccggagg caacagttga atgaaatgtt aaaggattca   2640

acacaatggc tggaagctaa ggaagaagct gagcaggtct taggacaggg cagagccaag   2700

cttgagtcat ggaaggaggg tccctataca gtagatgcaa tccaaaagaa aatcacagaa   2760

accaagcagt tggccaaaga cctccgccag tggcagacaa atgtagatgt ggcaaatgac   2820

ttggccctga aacttctccg ggattattct gcagatgata ccagaaaagt ccacatgata   2880

acagagaata tcaatgcctc ttggagaagc attcataaaa gggtgagtga gcgagaggct   2940

gctttggaag aaactcatag attactgcaa cagttccccc tggacctgga aaagtttctt   3000

gcctggctta cagaagctga aacaactgcc aatgtcctac aggatgctac ccgtaaggaa   3060

aggctcctag aagactccaa gggagtaaaa gagctgatga aacaatggca agacctccaa   3120

ggtgaaattg aagctcacac agatgtttat cacaacctgg atgaaaacag ccaaaaaatc   3180

ctgagatccc tggaaggttc cgatgatgca gtcctgttac aaagacgttt ggataacatg   3240
```

-continued

```
aacttcaagt ggagtgaact tcggaaaaag tctctcaaca ttaggtccca tttggaagcc   3300
agttctgacc agtggaagcg tctgcacctt tctctgcagg aacttctggt gtggctacag   3360
ctgaaagatg atgaattaag ccggcaggca cctattggag gcgactttcc agcagttcag   3420
aagcagaacg atgtacatag ggccttcaag agggaattga aactaaaga acctgtaatc    3480
atgagtactc ttgagactgt acgaatattt ctgacagagc agcctttgga aggactagag   3540
aaactctacc aggagcccag agagctgcct cctgaggaga gagcccagaa tgtcactcgg   3600
cttctacgaa agcaggctga ggaggtcaat actgagtggg aaaaattgaa cctgcactcc   3660
gctgactggc agagaaaaat agatgagacc cttgaaagac tccaggaact tcaagaggcc   3720
acggatgagc tggacctcaa gctgcgccaa gctgaggtga tcaagggatc ctggcagccc   3780
gtgggcgatc tcctcattga ctctctccaa gatcacctcg agaaagtcaa ggcacttcga   3840
ggagaaattg cgcctctgaa agagaacgtg agccacgtca atgaccttgc tcgccagctt   3900
accactttgg gcattcagct ctcaccgtat aacctcagca ctctggaaga cctgaacacc   3960
agatggaagc ttctgcaggt ggccgtcgag gaccgagtca ggcagctgca tgaagcccac   4020
agggactttg gtccagcatc tcagcacttt ctttccacgt ctgtccaggg tcggtgggag   4080
agagccatct cgccaaacaa agtgccctac tatatcaacc acgagactca aacaacttgc   4140
tgggaccatc ccaaaatgac agagctctac cagtctttag ctgacctgaa taatgtcaga   4200
ttctcagctt ataggactgc catgaaactc cgaagactgc agaaggccct ttgcttggat   4260
ctcttgagcc tgtcagctgc atgtgatgcc ttggaccagc acaacctcaa gcaaaatgac   4320
cagcccatgg atatcctgca gattattaat tgtttgacca ctatttatga ccgcctggag   4380
caagagcaca acaatttggt caacgtccct ctctgcgtgg atatgtgtct gaactggctg   4440
ctgaatgttt atgatacggg acgaacaggg aggatccgtg tcctgtcttt taaaactggc   4500
atcatttccc tgtgtaaagc acatttggaa gacaagtaca gatacctttt caagcaagtg   4560
gcaagttcaa caggattttg tgaccagcgc aggctgggcc tccttctgca tgattctatc   4620
caaattccaa gacagttggg tgaagttgca tcctttgggg gcagtaacat tgagccaagt   4680
gtccggagct gcttccaatt tgctaataat aagccagaga tcgaagcggc cctcttccta   4740
gactggatga gactggaacc ccagtccatg gtgtggctgc ccgtcctgca cagagtggct   4800
gctgcagaaa ctgccaagca tcaggccaaa tgtaacatct gcaaagagtg tccaatcatt   4860
ggattcaggt acaggagtct aaagcacttt aattatgaca tctgccaaag ctgctttttt   4920
tctggtcgag ttgcaaaagg ccataaaatg cactatccca tggtggaata ttgcactccg   4980
actacatcag gagaagatgt tcgagacttt gccaaggtac taaaaaacaa atttcgaacc   5040
aaaaggtatt ttgcgaagca tccccgaatg ggctacctgc cagtgcagac tgtcttagag   5100
ggggacaaca tggaaactcc cgttactctg atcaacttct ggccagtaga ttctgcgcct   5160
gcctcgtccc ctcagctttc acacgatgat actcattcac gcattgaaca ttatgctagc   5220
aggctagcag aaatggaaaa cagcaatgga tcttatctaa atgatagcat ctctcctaat   5280
gagagcatag atgatgaaca tttgttaatc cagcattact gccaaagttt gaaccaggac   5340
tccccccctga gccagcctcg tagtcctgcc cagatcttga tttccttaga gagtgaggaa  5400
agaggggagc tagagagaat cctagcagat cttgaggaag aaaacaggaa tctgcaagca   5460
gaatatgacc gtctaaagca gcagcacgaa cataaaggcc tgtccccact gccgtcccct   5520
cctgaaatga tgcccacctc tccccagagt ccccgggatg ctgagctcat tgctgaggcc   5580
aagctactgc gtcaacacaa aggccgcctg gaagccagga tgcaaatcct ggaagaccac   5640
```

```
aataaacagc tggagtcaca gttacacagg ctaaggcagg tgctggagca accccaggca   5700

gaggccaaag tgaatggcac aacggtgtcc tctccttcta cctctctaca gaggtccgac   5760

agcagtcagc ctatgctgct ccgagtggtt ggcagtcaaa cttcggactc catgggtgag   5820

gaagatcttc tcagtcgtcc ccaggacaca agcacagggt tagaggaggt gatggagcaa   5880

ctcaacaact cctttcccta gttcaagagg aagaaatacc cctggaaagc caatgagaga   5940

ggacacaatg tag                                                      5953


<210> SEQ ID NO 46
<211> LENGTH: 10
<212> TYPE: PRT
<213> ORGANISM: Artificial Sequence
<220> FEATURE:
<223> OTHER INFORMATION: Synthetic peptide

<400> SEQUENCE: 46

Arg Phe His Tyr Asp Ile Lys Ile Phe Asn
1               5                   10


<210> SEQ ID NO 47
<211> LENGTH: 15
<212> TYPE: PRT
<213> ORGANISM: Artificial Sequence
<220> FEATURE:
<223> OTHER INFORMATION: Synthetic peptide

<400> SEQUENCE: 47

Arg Gln Ile Lys Trp Phe Gln Asn Arg Arg Met Lys Trp Lys Lys
1               5                   10                  15


<210> SEQ ID NO 48
<211> LENGTH: 11
<212> TYPE: PRT
<213> ORGANISM: Artificial Sequence
<220> FEATURE:
<223> OTHER INFORMATION: Synthetic peptide: TAT

<400> SEQUENCE: 48

Tyr Gly Arg Lys Lys Arg Arg Gln Arg Arg Arg
1               5                   10


<210> SEQ ID NO 49
<211> LENGTH: 11
<212> TYPE: PRT
<213> ORGANISM: Artificial Sequence
<220> FEATURE:
<223> OTHER INFORMATION: Synthetic peptide: modified TAT having one or
      more mutated residues

<400> SEQUENCE: 49

Tyr Ala Arg Ala Ala Ala Arg Gln Ala Arg Ala
1               5                   10


<210> SEQ ID NO 50
<211> LENGTH: 13
<212> TYPE: PRT
<213> ORGANISM: Artificial Sequence
<220> FEATURE:
<223> OTHER INFORMATION: Synthetic peptide:  R9-Tat

<400> SEQUENCE: 50

Gly Arg Arg Arg Arg Arg Arg Arg Arg Arg Pro Pro Gln
1               5                   10
```

<210> SEQ ID NO 51
<211> LENGTH: 10
<212> TYPE: PRT
<213> ORGANISM: Artificial Sequence
<220> FEATURE:
<223> OTHER INFORMATION: Synthetic peptide: R10

<400> SEQUENCE: 51

Arg Arg Arg Arg Arg Arg Arg Arg Arg Arg
1               5                   10

<210> SEQ ID NO 52
<211> LENGTH: 18
<212> TYPE: PRT
<213> ORGANISM: Artificial Sequence
<220> FEATURE:
<223> OTHER INFORMATION: Synthetic peptide: SynB1

<400> SEQUENCE: 52

Arg Gly Gly Arg Leu Ser Tyr Ser Arg Arg Arg Phe Ser Thr Ser Thr
1               5                   10                  15

Gly Arg

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide: SynB3

<400> SEQUENCE: 53

Arg Arg Leu Ser Tyr Ser Arg Arg Arg Phe
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide: PTD-4

<400> SEQUENCE: 54

Pro Ile Arg Arg Arg Lys Lys Leu Arg Arg Leu Lys
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide: PTD-5

<400> SEQUENCE: 55

Arg Arg Gln Arg Arg Thr Ser Lys Leu Met Lys Arg
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide: FHV Coat-(35-49)

<400> SEQUENCE: 56

Arg Arg Arg Arg Asn Arg Thr Arg Arg Asn Arg Arg Arg Val Arg
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: Synthetic peptide: BMV Gag-(7-25)

<400> SEQUENCE: 57

Lys Met Thr Arg Ala Gln Arg Arg Ala Ala Ala Arg Arg Asn Arg Trp
1 5 10 15

Thr Ala Arg

<210> SEQ ID NO 58
<211> LENGTH: 13
<212> TYPE: PRT
<213> ORGANISM: Artificial Sequence
<220> FEATURE:
<223> OTHER INFORMATION: Synthetic peptide: HTLV-II Rex-(4-16)

<400> SEQUENCE: 58

Thr Arg Arg Gln Arg Thr Arg Arg Ala Arg Arg Asn Arg
1 5 10

<210> SEQ ID NO 59
<211> LENGTH: 13
<212> TYPE: PRT
<213> ORGANISM: Artificial Sequence
<220> FEATURE:
<223> OTHER INFORMATION: Synthetic peptide: D-Tat

<400> SEQUENCE: 59

Gly Arg Lys Lys Arg Arg Gln Arg Arg Arg Pro Pro Gln
1 5 10

<210> SEQ ID NO 60
<211> LENGTH: 27
<212> TYPE: PRT
<213> ORGANISM: Artificial Sequence
<220> FEATURE:
<223> OTHER INFORMATION: Synthetic peptide: Transportan chimera

<400> SEQUENCE: 60

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 61
<211> LENGTH: 17
<212> TYPE: PRT
<213> ORGANISM: Artificial Sequence
<220> FEATURE:
<223> OTHER INFORMATION: Synthetic peptide: MAP

<400> SEQUENCE: 61

Lys Leu Ala Leu Lys Leu Ala Leu Lys Leu Ala Leu Ala Leu Lys Leu
1 5 10 15

Ala

<210> SEQ ID NO 62
<211> LENGTH: 27
<212> TYPE: PRT
<213> ORGANISM: Artificial Sequence
<220> FEATURE:

<223> OTHER INFORMATION: Synthetic peptide: SBP

<400> SEQUENCE: 62

Met Gly Leu Gly Leu His Leu Leu Val Leu Ala Ala Ala Leu Gln Gly
1 5 10 15

Ala Trp Ser Gln Pro Lys Lys Lys Arg Lys Val
20 25

<210> SEQ ID NO 63
<211> LENGTH: 27
<212> TYPE: PRT
<213> ORGANISM: Artificial Sequence
<220> FEATURE:
<223> OTHER INFORMATION: Synthetic peptide: FBP

<400> SEQUENCE: 63

Gly Ala Leu Phe Leu Gly Trp Leu Gly Ala Ala Gly Ser Thr Met Gly
1 5 10 15

Ala Trp Ser Gln Pro Lys Lys Lys Arg Lys Val
20 25

<210> SEQ ID NO 64
<211> LENGTH: 27
<212> TYPE: PRT
<213> ORGANISM: Artificial Sequence
<220> FEATURE:
<223> OTHER INFORMATION: Synthetic peptide: MPG
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (27)..(27)
<223> OTHER INFORMATION: Cysteamide (Cya) tag

<400> SEQUENCE: 64

Gly Ala Leu Phe Leu Gly Phe Leu Gly Ala Ala Gly Ser Thr Met Gly
1 5 10 15

Ala Trp Ser Gln Pro Lys Lys Lys Arg Lys Val
20 25

<210> SEQ ID NO 65
<211> LENGTH: 27
<212> TYPE: PRT
<213> ORGANISM: Artificial Sequence
<220> FEATURE:
<223> OTHER INFORMATION: Synthetic peptide: MPG(delta-NLS)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (27)..(27)
<223> OTHER INFORMATION: Cysteamide (Cya) tag

<400> SEQUENCE: 65

Gly Ala Leu Phe Leu Gly Phe Leu Gly Ala Ala Gly Ser Thr Met Gly
1 5 10 15

Ala Trp Ser Gln Pro Lys Ser Lys Arg Lys Val
20 25

<210> SEQ ID NO 66
<211> LENGTH: 21
<212> TYPE: PRT
<213> ORGANISM: Artificial Sequence -continued

```
<220> FEATURE:
<223> OTHER INFORMATION: Synthetic peptide: Pep-1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: Cysteamide (Cya) tag

<400> SEQUENCE: 66

Lys Glu Thr Trp Trp Glu Thr Trp Trp Thr Glu Trp Ser Gln Pro Lys
1               5                   10                  15

Lys Lys Arg Lys Val
            20


<210> SEQ ID NO 67
<211> LENGTH: 21
<212> TYPE: PRT
<213> ORGANISM: Artificial Sequence
<220> FEATURE:
<223> OTHER INFORMATION: Synthetic peptide: Pep-2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: Cysteamide (Cya) tag

<400> SEQUENCE: 67

Lys Glu Thr Trp Phe Glu Thr Trp Phe Thr Glu Trp Ser Gln Pro Lys
1               5                   10                  15

Lys Lys Arg Lys Val
            20


<210> SEQ ID NO 68
<211> LENGTH: 110
<212> TYPE: PRT
<213> ORGANISM: Artificial Sequence
<220> FEATURE:
<223> OTHER INFORMATION: Synthetic peptide: Dys R16

<400> SEQUENCE: 68

Glu Ile Ser Tyr Val Pro Ser Thr Tyr Leu Thr Glu Ile Thr His Val
1               5                   10                  15

Ser Gln Ala Leu Leu Glu Val Glu Gln Leu Leu Asn Ala Pro Asp Leu
            20                  25                  30

Cys Ala Lys Asp Phe Glu Asp Leu Phe Lys Gln Glu Glu Ser Leu Lys
        35                  40                  45

Asn Ile Lys Asp Ser Leu Gln Gln Ser Ser Gly Arg Ile Asp Ile Ile
    50                  55                  60

His Ser Lys Lys Thr Ala Ala Leu Gln Ser Ala Thr Pro Val Glu Arg
65                  70                  75                  80

Val Lys Leu Gln Glu Ala Leu Ser Gln Leu Asp Phe Gln Trp Glu Lys
                85                  90                  95

Val Asn Lys Met Tyr Lys Asp Arg Gln Gly Arg Phe Asp Arg
            100                 105                 110


<210> SEQ ID NO 69
<211> LENGTH: 109
<212> TYPE: PRT
<213> ORGANISM: Artificial Sequence
```

```
<220> FEATURE:
<223> OTHER INFORMATION: Synthetic peptide: Ultro R15

<400> SEQUENCE: 69

Ser Ala Leu Pro Ala Asp Tyr Leu Val Glu Ile Asn Lys Ile Leu Leu
1               5                   10                  15

Thr Leu Asp Asp Ile Glu Leu Ser Leu Asn Met Pro Glu Leu Asn Thr
            20                  25                  30

Thr Val Tyr Lys Asp Phe Ser Phe Gln Glu Asp Ser Leu Lys Ser Ile
        35                  40                  45

Lys Gly Gln Leu Gln Arg Leu Gly Glu Gln Ile Ala Val Val His Glu
    50                  55                  60

Lys Gln Pro Asp Val Ile Val Glu Ala Ser Gly Pro Glu Ala Ile Gln
65                  70                  75                  80

Ile Arg Asp Met Leu Ala Gln Leu Asn Ala Lys Trp Asp Arg Val Asn
                85                  90                  95

Arg Val Tyr Ser Asp Arg Arg Gly Ser Phe Ala Arg Ala
            100                 105


<210> SEQ ID NO 70
<211> LENGTH: 107
<212> TYPE: PRT
<213> ORGANISM: Artificial Sequence
<220> FEATURE:
<223> OTHER INFORMATION: Synthetic peptide: Dys R17

<400> SEQUENCE: 70

Ser Val Glu Lys Trp Arg Arg Phe His Tyr Asp Ile Lys Ile Phe Asn
1               5                   10                  15

Gln Trp Leu Thr Glu Ala Glu Gln Phe Leu Arg Lys Thr Gln Ile Pro
            20                  25                  30

Glu Asn Trp Glu His Ala Lys Tyr Lys Trp Tyr Leu Lys Glu Leu Gln
        35                  40                  45

Asp Gly Ile Gly Gln Arg Gln Thr Val Val Arg Thr Leu Asn Ala Thr
    50                  55                  60

Gly Glu Glu Ile Ile Gln Gln Ser Ser Lys Thr Asp Ala Ser Ile Leu
65                  70                  75                  80

Gln Glu Lys Leu Gly Ser Leu Asn Leu Arg Trp Gln Glu Val Cys Lys
                85                  90                  95

Gln Leu Ser Asp Arg Lys Lys Arg Leu Glu Glu
            100                 105


<210> SEQ ID NO 71
<211> LENGTH: 108
<212> TYPE: PRT
<213> ORGANISM: Artificial Sequence
<220> FEATURE:
<223> OTHER INFORMATION: Synthetic peptide: Ultro R16

<400> SEQUENCE: 71

Val Glu Glu Trp Arg Gln Phe His His Asp Leu Asp Asp Leu Thr Gln
1               5                   10                  15

Trp Leu Ser Glu Ala Glu Asp Leu Leu Val Asp Thr Cys Ala Pro Asp
            20                  25                  30

Gly Ser Leu Asp Leu Glu Lys Ala Arg Ala Gln Gln Leu Glu Leu Glu
        35                  40                  45

Glu Gly Leu Ser Ser His Gln Pro Ser Leu Ile Lys Val Asn Arg Lys
    50                  55                  60
```

```
Gly Glu Asp Leu Val Gln Arg Leu Arg Pro Ser Glu Ala Ser Phe Leu
65                  70                  75                  80

Lys Glu Lys Leu Ala Gly Phe Asn Gln Arg Trp Ser Thr Leu Val Ala
                85                  90                  95

Glu Val Glu Ala Leu Gln Pro Arg Leu Lys Gly Glu
            100                 105


<210> SEQ ID NO 72
<211> LENGTH: 6
<212> TYPE: PRT
<213> ORGANISM: Artificial Sequence
<220> FEATURE:
<223> OTHER INFORMATION: Synthetic peptide: Original linker sequence
      (R16/R17)
<220> FEATURE:
<221> NAME/KEY: misc_feature
<222> LOCATION: (3)..(3)
<223> OTHER INFORMATION: Xaa is Arg or Ser

<400> SEQUENCE: 72

Phe Asp Xaa Val Glu Lys
1               5


<210> SEQ ID NO 73
<211> LENGTH: 6
<212> TYPE: PRT
<213> ORGANISM: Artificial Sequence
<220> FEATURE:
<223> OTHER INFORMATION: Synthetic peptide: Mutant-1
<220> FEATURE:
<221> NAME/KEY: misc_feature
<222> LOCATION: (3)..(3)
<223> OTHER INFORMATION: Xaa is Arg or Ser

<400> SEQUENCE: 73

Phe Ala Xaa Val Glu Lys
1               5


<210> SEQ ID NO 74
<211> LENGTH: 6
<212> TYPE: PRT
<213> ORGANISM: Artificial Sequence
<220> FEATURE:
<223> OTHER INFORMATION: Synthetic peptide: Mutant-2
<220> FEATURE:
<221> NAME/KEY: misc_feature
<222> LOCATION: (3)..(3)
<223> OTHER INFORMATION: Xaa is Gln or Ser

<400> SEQUENCE: 74

Phe Ala Xaa Val Glu Lys
1               5


<210> SEQ ID NO 75
<211> LENGTH: 6
<212> TYPE: PRT
<213> ORGANISM: Artificial Sequence
<220> FEATURE:
<223> OTHER INFORMATION: Synthetic peptide: Mutant-3
<220> FEATURE:
<221> NAME/KEY: misc_feature
<222> LOCATION: (3)..(3)
<223> OTHER INFORMATION: Xaa is Glu or Ser

<400> SEQUENCE: 75

Leu Glu Xaa Val Glu Lys
1               5
```

-continued

```
<210> SEQ ID NO 76
<211> LENGTH: 6
<212> TYPE: PRT
<213> ORGANISM: Artificial Sequence
<220> FEATURE:
<223> OTHER INFORMATION: Synthetic peptide: Mutant-4
<220> FEATURE:
<221> NAME/KEY: misc_feature
<222> LOCATION: (3)..(3)
<223> OTHER INFORMATION: Xaa is Arg or Ala

<400> SEQUENCE: 76

Phe Asp Xaa Val Glu Glu
1               5
```

MICRODYSTROPHIN PEPTIDES AND METHODS FOR TREATING MUSCULAR DYSTROPHY USING THE SAME

PRIORITY CLAIM

This application is a continuation of U.S. patent application Ser. No. 14/091,326, filed Nov. 26, 2013 and now pending, which claims benefit to U.S. Provisional Patent Application No. 61/797,012, filed Nov. 26, 2012, the subject matter of both of which is hereby incorporated by reference in its entirety, as if fully set forth herein.

STATEMENT OF GOVERNMENT INTEREST

The present invention was made with government support under Grant No. AR49419 awarded by the National Institutes of Health (NIH). The Government has certain rights in the invention.

BACKGROUND

Duchenne Muscular Dystrophy (DMD) is an X-linked inherited muscle disease caused by mutations of the dystrophin gene. While increased membrane fragility has been considered as a primary pathogenic mechanism of DMD, accumulated evidence suggests that the loss of sarcolemmal nNOS also contributes to the dystrophic process. For example, the mild variant of DMD, Becker Muscular Dystrophy (BMD), results from in-frame mutations of dystrophin, thus expressing the truncated dystrophins in muscle. Many of the truncated dystrophins in BMD lose the ability to tether neuronal nitric oxide synthase (nNOS) to the sarcolemma. Clear evidence shows that deficiency of sarcolemmal nNOS causes muscle ischemia and predominantly contributes to the characteristic symptoms of BMD, such as muscle cramp and pain on exercise, muscle fatigue and reduced exercise endurance. However, current therapies are less effective for muscle ischemia and the resultant symptoms.

Since loss of sarcolemmmal nNOS is responsible for BMD symptoms, recovering sarcolemmal nNOS has been suggested as a plausible approach to treat BMD and DMD. It has been known that sarcolemmal localization of nNOS is sustained by dystrophin, and the inventors' previous studies, through systemic structure-function analysis, have found that dystrophin spectrin-like repeats 16 and 17 (R16/17) are required for sarcolemmal distribution of nNOS. Basically, dystrophins that contain R16/17 show membrane expression of nNOS while those without R16/17 do not. However, the current mini-genes or micro-genes with repeats R16/17 still require the retention of other dystrophin domains. For example, even the smallest nNOS binding dystrophin (ΔR2-R15/ΔR18-R23/ΔC) engineered in previous studies still carries the NT and CR domains, H1, H4, R1 and R24. Furthermore, though the mini-genes or micro-genes previously identified are reduced in size as compared to existing gene therapy, more significant size reduction is desired to increase efficacy of delivery of the therapy.

Therefore, there is a need to provide a series of new biological materials containing certain domains/sections of the dystrophin repeats R16 and R17 for anchoring nNOS to the sarcolemma as a new therapy/treatment for DMD and BMD.

SUMMARY

According to some embodiments, a therapeutic composition is provided herein. In one aspect the therapeutic composition may include an amino acid sequence which comprises dystrophin spectrin-like repeats 16 and 17 (R16/R17) or a functional fragment, component, or domain thereof. In one embodiment, the R16/R17 or a functional fragment, component, or domain thereof is an amino acid sequence motif which comprises RFHYDIKIFN (SEQ ID NO:46). In a further embodiment, the therapeutic composition may further include at least one α helix of dystrophin spectrin-like repeat 16 (R16) and at least one α helix of dystrophin spectrin-like repeat 17 (R17).

In another aspect, the therapeutic composition may include a delivery vehicle. The delivery vehicle may be any suitable moiety that facilitates delivery of the R16/R17 or a functional fragment, component, or domain thereof to a target cell. In some embodiments, the delivery vehicle is a cell-penetrating peptide. In other embodiments, the delivery vehicle is a recombinant adeno-associated viral vector (AAV) that is able to express the R16/R17 or a functional fragment, component, or domain thereof.

According to another embodiment, a method of treating Duchenne Muscular Dystrophy (DMD) Becker Muscular Dystrophy (BMD) is provided. Such a method may include a step of administering a therapeutic amount of a therapeutic composition described above to a subject having DMD or BMD.

BRIEF DESCRIPTION OF THE DRAWINGS

FIG. 4(A) lists the amino acid sequence alignment of dystrophin R16/17 and utrophin R15/16, with micro-domains boxed and numbered from I to XIV. FIG. 4(B) includes the representative photomicrographs of dystrophin and nNOS immunostaining, and nNOS activity staining.

FIG. 8(A) is a schematic outline of the μ-Dys+Utro R15 and μ-Dys+Utro R16 chimerical microdystrophin constructs. In the μ-Dys+Utro R15 construct, dystrophin R16 is replaced by utrophin R15. In the μ-Dys+Utro R16 construct, dystrophin R17 is replaced by utrophin R16. FIG. 8(B) is a representative images of dystrophin H1, R16, R17, and nNOS immunofluorescence staining and nNOS activity staining on the serial sections of chimerical microdystrophin AAV vector infected mdx muscle. Asterisks indicate the same myofiber in the serial sections. (Scale bar, 50 μm.) FIG. 8(C) is a representative Western blot results from whole muscle lysate and microsomal preparation. ΔR4-R23/ΔC and ΔR2-R15/ΔR18-R23/ΔC are two transgenic mouse lines that specifically express microgenes in skeletal muscle. The ΔR4-23/ΔC microdystrophin gene does not contain dystrophin R16/17 (negative control). The ΔR2-R15/ΔR18-R23/ΔC microdystrophin gene contains dystrophin R16/17 (positive control). α-Tubulin was used as the loading control for whole muscle lysate. α1-Na+/K+ ATPase was used as the loading control for microsomal preparation.

FIG. 9 is a table showing a summary of microdystrophin and microutrophin constructs used in the studies described herein.

FIG. 10 is a table showing the impact of indicated mutations on nNOS binding in vivo.

FIG. 13 is a table summarizing the expression of dystrophin and sarcolemmal nNOS in different settings.

FIG. 14 is a table illustrating the comparison of two minidystrophin genes, ΔH2-R19 and ΔH2-R15.

FIG. 19 is a table showing the experimental design of the studies described.

FIG. 21 shows the nucleic acid sequence of ΔH2-R19 dystrophin minigene construct (SEQ ID NO:1).

FIG. 22 shows the nucleic acid sequence of ΔH2-R15 dystrophin minigene construct (SEQ ID NO:2).

FIG. 23 shows the nucleic acid sequence of ΔR2-R15/ΔR18-23/ΔC dystrophin microgene construct (SEQ ID NO:3).

FIG. 24 shows the nucleic acid sequence of ΔR4-R23/ΔC dystrophin microgene construct (SEQ ID NO:4).

FIG. 25 shows the nucleic acid sequence of an AV.CMV.ΔR2-15/ΔR18-23/ΔC AAV vector construct (SEQ ID NO:5).

FIG. 26 shows the nucleic acid sequence (SEQ ID NO:6) and the amino acid sequence (SEQ ID NO:7) of human dystrophin spectrin-like repeats 16 and 17 (R16/R17).

FIG. 27 shows the nucleic acid sequence (SEQ ID NO:8) of full-length human dystrophin.

FIG. 28 shows the amino acid sequence (SEQ ID NO:9) of full-length human dystrophin.

FIG. 29 shows the nucleic acid sequences corresponding to the N-terminal (NT), the 24 spectrin like repeats (STRs), the 4 hinge regions, the cysteine-rich (CR), and the C-terminal (SEQ ID NOS: 10-40) of human dystrophin.

FIG. 30 shows the amino acid sequences corresponding to each of the functional domains (NT domain, mid rod domain, CR domain and the C-terminal domain) of human dystrophin (SEQ ID NOS:41-44).

FIG. 31 shows the nucleic acid sequence of Δexon 17-48 mini-dystrophin (SEQ ID NO: 45), which is a truncated dystrophin found in BMD.

DETAILED DESCRIPTION

Figure 1A:
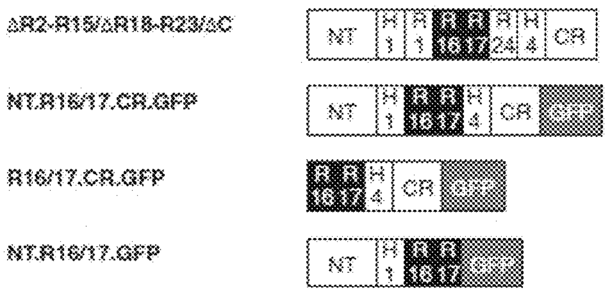
FIG. 1(A) lists the schematic outlines of the microdystrophin constructs of the ΔR2-R15/ΔR18-R23/ΔC and its various deletions.

The embodiments described herein provide a series of biological materials that may be used in treatment and/or therapy of DMD and BMD through the recovery of sarcolemmal nNOS. According to some embodiments, the biological materials include a microdystrophin gene, protein, peptide, or functional fragment thereof.

A "dystrophin microgene" or "micro-dystrophin gene" or "microgene" as referred to herein means a nucleic acid molecule that is 5 kb or less in length and encodes a modified or non-full-length dystrophin polypeptide (also referred to as micro-dystrophin protein or polypeptide in the present application). A "micro-dystrophin" as referred to herein means a modified or non-full-length dystrophin protein or peptide molecule that retains biological function of a full-length dystrophin protein and the coding sequence of which is 5 kb or less. A micro-dystrophin may also include a "micro-domain" which refers to a portion or functional fragment of a micro-dystrophin protein or peptide that has biological activity, such as a peptide or protein that includes a relevant binding site (e.g., an nNOS binding site for recruitment of nNOS) or structural units that improve or are required for the biological activity. Examples of microgenes which encode micro-dystrophin proteins that are used in the studies described herein include, but are not limited to, those sequences in FIGS. 23 and 24.

A "dystrophin minigene," "mini-dystrophin gene," or "minigene" as referred to herein means a nucleic acid molecule that is more than 5 kb in length but less than the full-length of dystrophin coding sequence, preferably, between 5 kb to about 10 kb in length, more preferably about 5 kb to about 8 kb in length, even more preferably, about 7 kb in length, and encodes a modified or non-full-length dystrophin polypeptide (also referred to as mini-dystrophin protein or peptide in the present application). A "mini-dystrophin" protein or peptide is meant a modified or non-full-length dystrophin protein molecule that retains the biological functions of a full-length dystrophin protein and the coding sequence of which is more than 5 kb in length but less than the full-length of dystrophin coding sequence. Examples of microgenes which encode micro-dystrophin proteins that are used in the studies described herein include, but are not limited to, those sequences in FIGS. 21 and 22.

Dystrophin and its Spectrin-Type Repeats (STRs)

Spectrin-type repeats (STR) are common structural elements found in a variety of proteins, especially cytoskeletal proteins. STRs are composed of 106-122 amino acids folded in a triple α-helical unit. STRs exist either as a single-copy or in tandem repeats. STR-containing proteins play a fundamental role in maintaining the cytoskeletal architecture and organizing protein complexes (Djinovic-Carugo et al. 2002; Le Rumeur et al. 2012). Dystrophin is a vital STR-containing protein in striated muscles that links the cytoskeleton with the extracellular matrix and, hence, preserves sarcolemmal integrity during muscle contraction. Besides mechanical support, dystrophin also scaffolds neuronal nitric oxide synthase (nNOS) and several other signaling proteins to the sarcolemma. The nucleotide and amino acid sequences of human dystrophin are shown in FIGS. 27 and 28, respectively.

Absence of dystrophin results in Duchenne muscular dystrophy (DMD), an X-linked lethal muscle disease (Kunkel 2005). Although increased membrane fragility has been considered as a primary pathogenic mechanism of DMD, accumulated evidence suggests that the loss of sarcolemmal nNOS also contributes to the dystrophic process (Lai et al. 2009; Sander et al 2000; Thomas et al 1998; Li et al. 2011a). A clear understanding of how nNOS is localized to the membrane may thus offer insight to the understanding of the disease and open new therapeutic avenues.

Dystrophin has four functional domains including the N-terminal (NT), middle rod, cysteine-rich (CR), and C-terminal domains (FIG. 30; SEQ ID NOs:41-44). The middle rod domain contains 24 STRs and four interspersed hinges. The nucleic acid sequences of the functional domains and STRs are shown in FIG. 29 (SEQ ID NOs:10-40). It was initially thought that nNOS indirectly binds to the dystrophin C-terminal domain via syntrophin (Hillier et al. 1999; Tochio et al. 1999). However, later studies show that merely restoring syntrophin to the membrane cannot anchor nNOS (Lai et al. 2005; Yue et al. 2006; Judge et al. 2006). Through systemic structure-function analysis, it has been determined that dystrophins that contain STRs 16 and 17 (R16/17) show membrane expression of nNOS but those without R16/17 do not. These findings raise an important question as to why and how R16/17 interacts with nNOS. Therefore, as described in the Examples below, the molecular attributes of dystrophin R16/17 that are responsible for nNOS binding were investigated. In these studies, membrane localized R16/17 was determined the minimal unit for dystrophin-nNOS interaction. It was also found that a 10-residue microdomain in the α1 helix of dystrophin R17 (RFHYDIKIFN; SEQ ID NO:46) contains the nNOS binding site. Further, it was demonstrated that the last two α-helices (α2 and α3 helices) of both R16 and R17 were required to anchor nNOS to the sarcolemma although they are dispensable for nNOS binding in vitro.

Therapeutic Compositions

According to the embodiments described herein, therapeutic compositions for treating DMD and BMD are provided. The therapeutic compositions may include a micro-dystrophin protein, peptide, microdomain, or a functional fragment thereof that is able to restore nNOS to the sarcolemma. In some embodiments, the microdystrophin protein may be encoded by a corresponding microdystrophin gene. In one embodiment, the microdystrophin protein includes the complete dystrophin repeats R16 and R17 or functional domains, sections, or fragments thereof. In some aspects, functional domains, sections or fragments of dystrophin repeats R16 and R17 that may be used in accordance with the embodiments described herein may include, but are not limited to, the following sequence motifs: a 10-residue microdomain in the α1 helix of dystrophin R17 (RFHYDIKIFN; SEQ ID NO:46), a dystrophin R17 α1 helix, a dystrophin R17 α2 helix, a dystrophin R17 α3 helix, a dystrophin R16 α2 helix, a dystrophin R16 α3 helix, or a combination thereof. In one embodiment, the microdystrophin peptide that is part of the therapeutic composition has an amino acid sequence which comprises dystrophin spectrin-type repeats 16 and 17 (R16/R17) (FIG. 26, SEQ ID NOS:6-7).

According to another embodiment, the microdystrophin peptide that is part of the therapeutic composition includes a dystrophin R17 α1 helix. In such an embodiment, the therapeutic composition may also include a dystrophin R17 α2 helix, a dystrophin R17 α3 helix, a dystrophin R16 α2 helix, a dystrophin R16 α3 helix, or a combination thereof.

According to another embodiment, the microdystrophin peptide that is part of the therapeutic composition includes a sequence motif of RFHYDIKIFN (a ten-residue microdomain in the dystrophin R17 α1 helix; SEQ ID NO:46). In such an embodiment, the therapeutic composition may also include a dystrophin R17 α2 helix, a dystrophin R17 α3 helix, a dystrophin R16 α2 helix, a dystrophin R16 α3 helix, or a combination thereof.

Figure 1B:
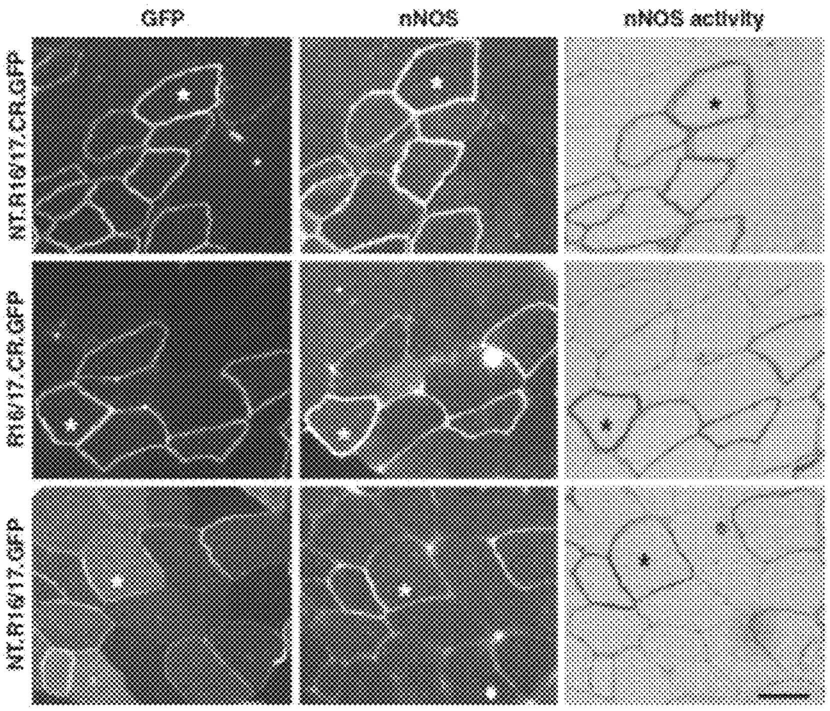
FIG. 1(B) illustrates the microdystrophin genes' representative photomicrographs of GFP, nNOS immunostaining and nNOS activity staining.

As described in the Examples below, restoration of sarcolemmal nNOS by dystrophin repeats R16/17 is independent of other domains of dystrophin, such as the dystrophin NT and CR domains, H1, H4, R1 and R24, retained in the mini- or micro-genes in previous studies. To determine whether the regions other than R16/17 contribute to dystrophin-nNOS interaction, in vivo nNOS binding was examined in constructs carrying various deletions based on the smallest nNOS binding dystrophin retaining the NT and CR domains, H1, H4, R1 and R24 (ΔR2-R15/ΔR18-R23/ΔC; SEQ ID NO:3). FIGS. 1(A) and (B). FIG. 1(A) lists the schematic outlines of the microdystrophin constructs of ΔR2-R15/ΔR18-R23/ΔC and its various deletions: deletion of R1/R24, further deletion of NT terminal and H1, or further deletion of CR terminal and H4. FIG. 1(B) illustrates the representative photomicrographs of GFP, nNOS immunostaining and nNOS activity staining from mdx mice infected with the indicated micro-dystrophin AAV virus. As indicated in FIG. 1(B), the removal of R1 and R24 does not compromise sarcolemmal nNOS expression in dystrophin-null mdx muscle; and further deletion of the NT domain and H1 or H4 and the CR domain does not alter nNOS membrane localization either. These results suggest that dystrophin R16/17 can recruit nNOS to the sarcolemma independent of other dystrophin domains.

Figure 2A:
FIG. 2(A) lists the schematic outlines of the ΔR2-14/ΔR17-21/ΔC micro-utrophin gene and the chimeric ΔR2-R21/ΔC+Dys R16/17 micro-utrophin gene.
Figure 2B:
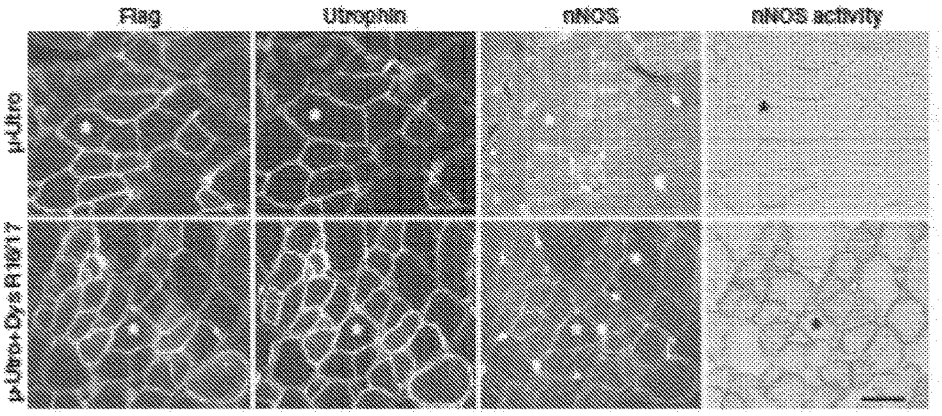
FIG. 2(B) are the representative images of flag, utrophin and nNOS immunofluorescence staining and nNOS activity staining.

To further provide that dystrophin R16/17 binds nNOS in a context independent manner, the studies below provide evidence that the dystrophin R16/17 can restore sarcolemmal nNOS in a foreign context. Refer to FIGS. 2(A) and 2(B), which illustrates that dystrophin R16/17 restores sarcolemmal nNOS expression in the context of microutrophin. As shown in FIG. 2(A), a chimeric micro-utrophin gene, in which utrophin R15/16 is replaced by dystrophin R16/17, is engineered with a flag tag at the N-terminal end to facilitate detection. FIG. 2(B) shows that the AAV viruses expressing the parental or the chimeric micro-utrophin genes are delivered to the tibialis anterior muscle of utrophin/dystrophin double knout mice, and the modified micro-utrophin (with R16/17) effectively restored sarcolemmal nNOS expression in utrophin/dystrophin double knockout (u-dko) mouse muscle.

Figure 3A:
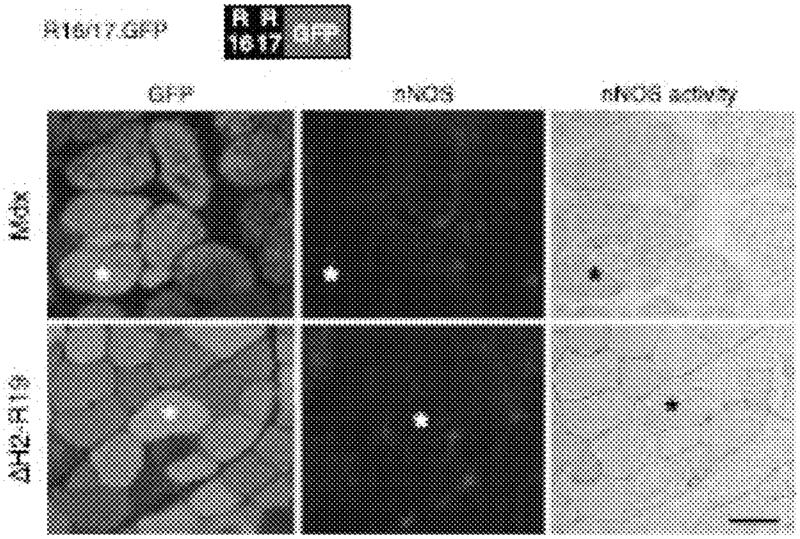
FIG. 3(A) illustrates the morphological evaluation of nNOS expressions following the infection with R16/17.GFP AAV virus in both ΔH2-R19 transgenic and parental mdx mice.
Figure 3B:
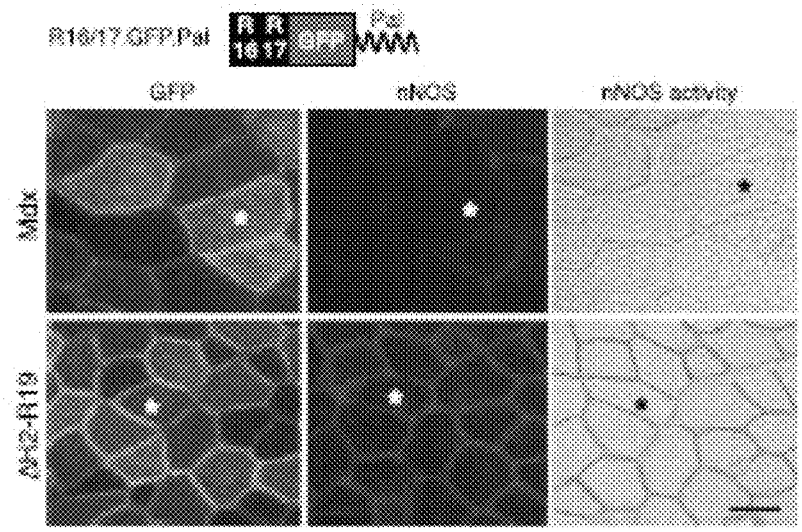
FIG. 3(B) illustrates the morphological evaluation of nNOS expressions following the infection with R16/17.GFP.Pal AAV virus in both ΔH2-R19 transgenic and parental mdx mice.

Further, although R16/17 is the only dystrophin component required for sarcolemmal nNOS restoration, attaching a membrane targeting sequence motif assists in localizing nNOS. Refer to FIG. 3A and FIG. 3B, which illustrate the morphological evaluation of nNOS expressions following the infections with R16/17.GFP AAV virus and R16/17.GFP.Pal AAV virus in both ΔH2-R19 transgenic and parental mdx mice. As shown in FIG. 2(A), robust expression of R16/17.GFP is observed in mdx muscle but nNOS is not detected at the sarcolemma; however as indicated in FIG. 2(B), the R16/17 attached with palmitoylation membrane targeting sequence at the C-terminus, R16/17.GFP.Pal, is transduced into mdx muscle, and most importantly sarcolemmal nNOS is detected in both ΔH2-R19 transgenic and parental mdx mice. Thus, attaching membrane targeting sequence motif to R16/17 may further assist the restoration of sarcolemmal nNOS.

The studies described below also identifies the nNOS-binding domain, a ten-residue sequence motif, RFHYDIKIFN (SEQ ID NO:46), located in the dystrophin R17 α1 helix. FIGS. 4(A) and 4(B), illustrates a panel of micro-domain substitution studies revealing the nNOS binding site in dystrophin R17 α1 helix. FIG. 4(A) lists the amino acid sequence alignment of dystrophin R16/17 and utrophin R15/16, with micro-domains boxed and numbered from I to XIV. 14 chimerical micro-dystrophin constructs have been generated, where the individual micro-domain in dystrophin R16/17 has been replaced by the corresponding micro-domain of utrophin R15/16 in the ΔR2-R15/ΔR18-R23/ΔC micro-dystrophin gene. FIG. 4(B) illustrates the representative photomicrographs of dystrophin and nNOS immunostaining, and nNOS activity staining, after the modified microgenes being transferred to the mdx muscle. As shown in FIG. 4(B), the photmicrographic patterns are not altered in 13 out the 14 constructs, while the construct IX, in which the ten-residue micro-domain in the first half of dystrophin R17 α1 helix is replaced, is the only exception. With replacement of the ten-residue, RFHYDIKIFN (SEQ ID NO:46), membrane-associated nNOS expression is completely abolished in muscles treated with this construct. This suggests that the ten-reside (RFHYDIKIFN; SEQ ID NO:46) micro-domain in construct IX contains the nNOS-binging site.

Figure 5:
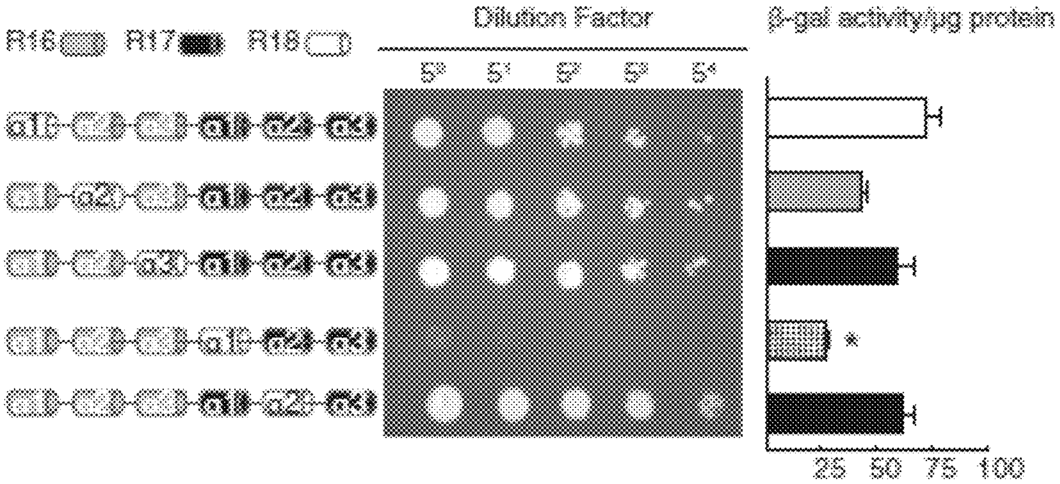
FIG. 5 illustrates the yeast-two-hybrid assay measured by β-galactosidase activity by a series of construct with replaced a helices.

The Examples provide additional evidence that dystrophin R17 α1 helix contains the nNOS-binding site via an in vitro yeast two-hybird assay. As shown in FIG. 5, a series of α helix substitution constructs was generated by replacing one of the α helices of dystrophin R16/17 with the corresponding α helix from dystrophin R18. Interaction with nNOS is not disrupted in most cases except when R17 α1 helix is replaced (FIG. 5).

Figure 6A:
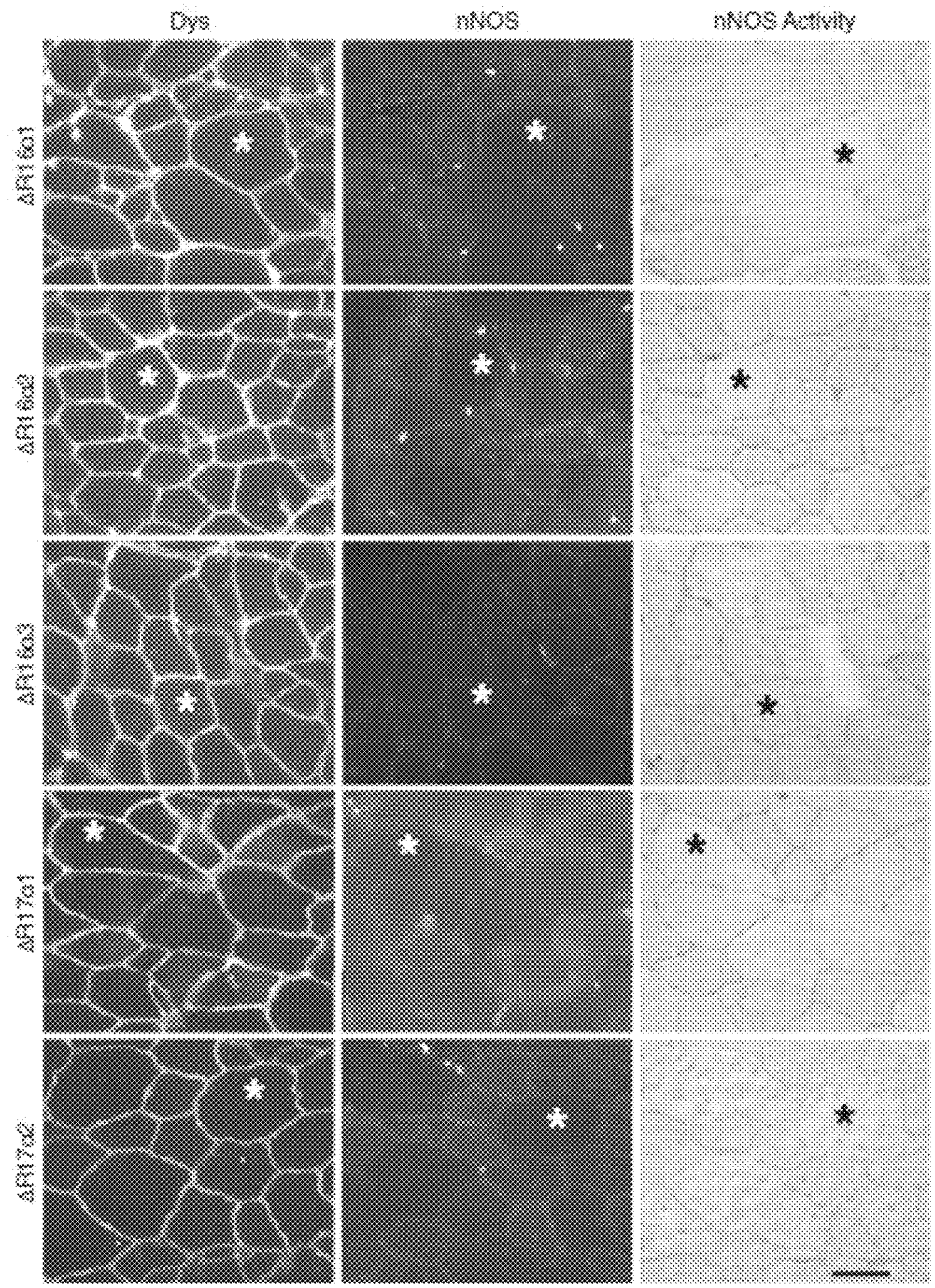
FIG. 6(A) includes the representative photomicrographs of dystrophin and nNOS immunostaining and nNOS activity staining in mdx muscle infected by AAV viruses carrying single α helix deletion of R16/17.

In addition to dystrophin R17 micro-domain IX in α1 helix, other structural features of dystrophin R16/17, such as the α2 and α3 helices of both R16 and R17, may also be needed for sarcolemmal nNOS localization. FIG. 6(A) illustrates an in vivo binding assay using AAV gene transfer with mini-genes carrying single α helix deletion. As shown in FIG. 6(A), nNOS binding is abolished in all the deletion constructs, which suggests that either every α helix is required, or more likely, single α helix deletion has shifted the normal phasing of the entire STR and hence disrupted three-dimensional structure of the binding motif.

Figure 6B:
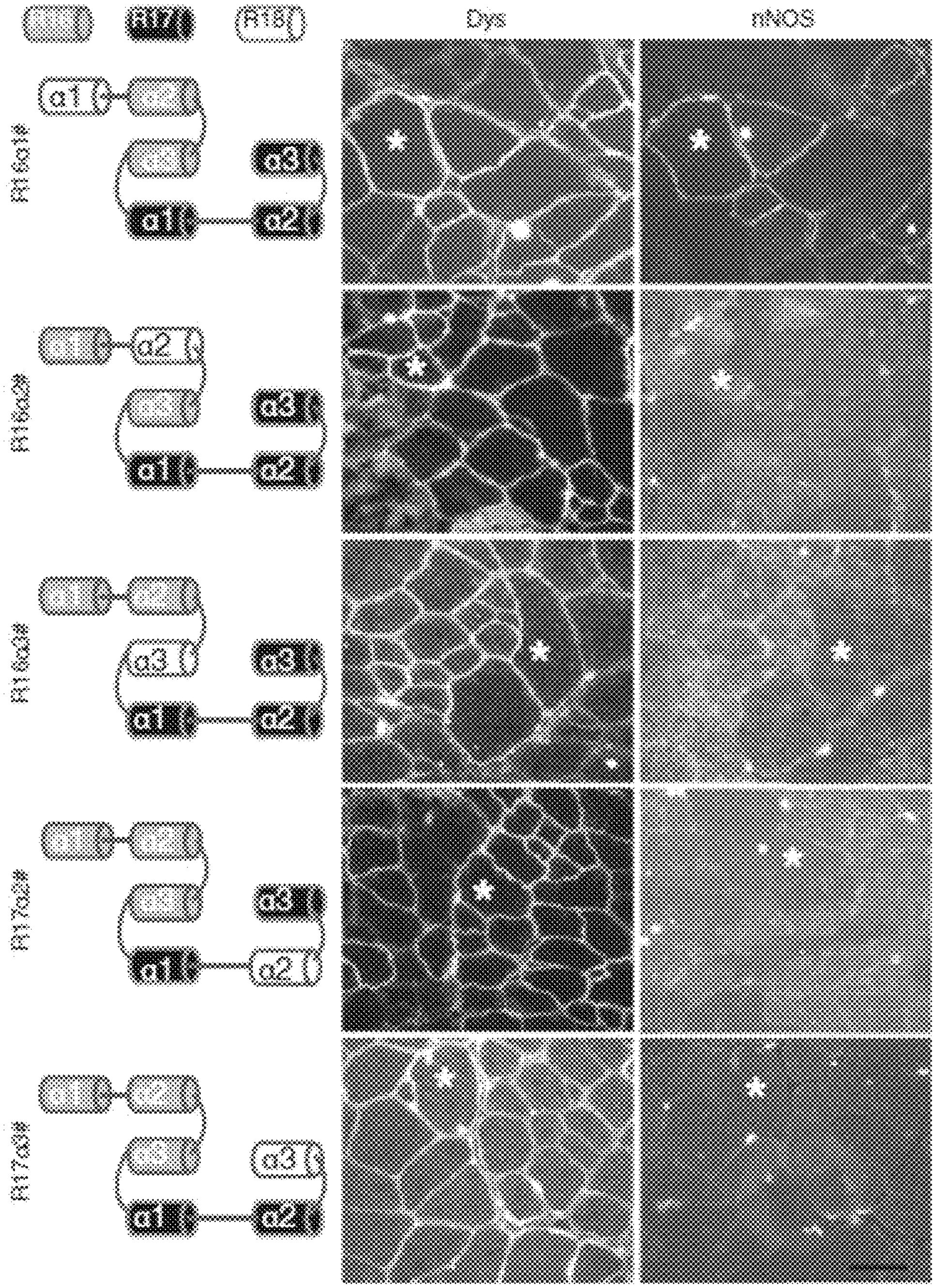
FIG. 6(B) includes the representative photomicrographs of dystrophin and nNOS immunostaining in mdx muscle infected by AAV viruses carrying single α helix substitution.

To further determine the importance of each α helix, a series of α helix substitution micro-dystrophin constructs was generated, where one α helix (or multiple α helices) in dystrophin R16/17 is replaced by the corresponding α helix (or helices) from another dystrophin STR to maintain normal α helix phasing. FIG. 6(B) includes a schematic illustration of the constructs and the representative photomicrographs of dystrophin and corresponding nNOS immunostaining. Substitution of R17 α1 helix destroyed nNOS binding (as aforementioned). Replacement of two or four other α helices also abolished nNOS binding. Single helix substitution of the remaining five α helices revealed more striking results. While R16 α1 helix replacement does not affect nNOS binding, swapping α2 or α3 helix of either R16 or R17 eliminates dystrophin-nNOS interaction. Collectively, the in vivo data (of FIGS. 6(A) and 6(B)) suggest that α2 and α3 helices of both R16 and R17, in addition to α1 helix of R17, may also be important for membrane localization of nNOS in muscle.

In summary, the Examples described below provide a series of biological materials for treatment/therapy of DMD and/or BMD through the recovery of sarcolemmal nNOS. The inventive biological material comprises the complete dystrophin repeats R16 and R17, or alternatively, certain domains/sections of the dystrophin repeats R16 and R17. The aforementioned domains/sections of the dystrophin R16/17 may include a ten-residue carrying the sequence motif of RFHYDIKIFN (SEQ ID NO:46), dystrophin R17 α1 helix, α2 and α3 helices of both R16 and R17 (complete or certain domains or functional fragments thereof), or a combination thereof.

The studies below further provide a series of novel treatment/therapeutic methods for DMD and BMD through restoring the sarcolemmal-nNOS-recruiting function of the truncated dystrophins found in DMD and BMD patients. The restoration of sarcolemmal nNOS may be achieved by delivering a biological material comprising the complete dystrophin repeats R16 and R17, or alternatively certain domains/sections of the dystrophin repeats R16 and R17, to a DMD or BMD patient. The delivery may be achieved by the AAV-mediated gene transfer, the direct delivery of recombinant R16/17 protein or sections thereof via a cell-penetrating peptide, or a direct administration of a certain domain/section of recombinant R16/17 protein.

In certain embodiments, the therapeutic compositions described herein may also include a delivery vehicle to facilitate the delivery of the microdystrophin to target muscle cells. In one embodiment, the delivery vehicle is an adeno-associated viral vector (AAV) or a recombinant adeno-associated AAV (rAAV). In such an embodiment, the AAV vector or rAAV vector includes an expression cassette that includes a microdystrophin gene that expresses the microdystrophin protein.

According to one embodiment, the therapeutic composition for restoring nNOS to sarcolemma comprises an adeno-associated viral vector (AAV) packaged with the dystrophin repeats R16 and R17 without the dystrophin NT and CR domains, H1, H4, R1 or R24. According to another embodiment, the therapeutic composition for restoring nNOS to sarcolemma comprises an AAV packaged with a dystrophin microgene that encodes the complete dystrophin repeats R16 and R17 or functional domains, sections, or fragments thereof. In some aspects, functional domains, sections or fragments of dystrophin repeats R16 and R17 that may be used in accordance with the embodiments described herein may include, but are not limited to, the following sequence motifs: a 10-residue microdomain in the α1 helix of dystrophin R17 (RFHYDIKIFN; SEQ ID NO:46), a dystrophin R17 α1 helix, a dystrophin R17 α2 helix, a dystrophin R17 α3 helix, a dystrophin R16 α2 helix, a dystrophin R16 α3 helix, or a combination thereof. Specific examples of functional domains, sections or fragments of dystrophin repeats R16 and R17 are described above.

In other embodiments, the delivery vehicle is a cell-penetrating peptide. Cell-penetrating peptides (CPPs, also known as protein transduction domains, membrane translocating sequences, and Trojan peptides) short peptides (less than or equal to approximately 40 amino acids), which are able to penetrate a cell membrane to gain access to the interior of a cell. Thus, CPPs may be used to facilitate the transfer of proteins to a muscle cell in vivo. Although expression of R16/17 may be efficiently mediated by AAV gene transfer, safety concerns and immune response to the AAV may potentially arise in clinical applications of AAV gene delivery. Thus, a direct delivery of a microdystrophin protein, peptide or fragment above (such as those described above) via a CPP is an alternative to AAV vector delivery which may make the treatment easier to manipulate and may improve safety profile. CPPs that may be used in accordance with the embodiments described herein include, but are not limited to, Penetratin or Antenapedia PTD (RQIKWFQNRRMKWKK; SEQ ID NO:47), TAT (YGRKKRRQRRR; SEQ ID NO:48) or a modified TAT having one or more mutated residues (e.g., YARAAARQARA, bold indicates mutated residues; SEQ ID NO:49), R9-Tat GRRRRRRRRRPPQ; SEQ ID NO:50), R10 (RRRRRRRRRR; SEQ ID NO:51) SynB1 (RGGRLSYSRRRFSTSTGR; SEQ ID NO:52), SynB3 (RRLSYSRRRF; SEQ ID NO:53), PTD-4 (PIRRRKKLRRLK; SEQ ID NO:54), PTD-5 (RRQRRTSKLMKR SEQ ID NO:55), FHV Coat-(35-49) (RRRRNRTRRNRRRVR; SEQ ID NO:56), BMV Gag-(7-25) (KMTRAQRRAAARRNRWTAR; SEQ ID NO:57), HTLV-II Rex-(4-16) (TRRQRTRRARRNR; SEQ ID NO:58), D-Tat (GRKKRRQRRRPPQ; SEQ ID NO:59), Transportan chimera (GWTLNSAGYLLGKINLKALAALAKKIL; SEQ ID NO:60), MAP (KLALKLALKLALALKLA; SEQ ID NO:61), SBP (MGLGLHLLVLAAALQGAWSQPKKKRKV; SEQ ID NO:62), FBP (GALFLGWLGAAGSTMGAWSQPKKKRKV; SEQ ID NO:63), MPG (ac-GALFLGFLGAAGSTMGAWSQPKKKRKV-cya; SEQ ID NO:64), MPG$^{(\Delta NLS)}$ (ac-GALFLGFLGAAGSTMGAWSQPKSKRKV-cya; SEQ ID NO:65). Pep-1 (ac-KETWWETWWTEWSQPKKKRKV-cya; SEQ ID NO:66), Pep-2 (ac-KETWFETWFTEWSQPKKKRKV-cya; SEQ ID NO:67), or any other suitable CPP.

In one embodiment, the CPP used as a delivery agent is TAT. To facilitate the efficient delivery of recombinant R16/17 protein to the muscle cell, a cell penetrating peptide, such as the TAT protein transduction domain (PTD), may be attached to or conjugated to R16/17 protein via a covalent linkage (e.g., an intra-molecular form of chemical bonding that is characterized by the sharing or one or more pairs of electrons between two components, producing a mutual attraction that holds the resultant molecule together) or a non-covalent linkage (e.g., an interaction—not covalent in nature—that provide force to hold the molecules or parts of molecules together, such as ionic bonds, hydrophobic interactions, hydrogen bonds, van-der-Wals forces, and dipole-dipole bonds). in accordance with methods known in the art. Where the attachment or conjugation involves a covalent linkage, the CPP and the microdystrophin protein, peptide or functional fragment thereof may be directly coupled to each other or may be coupled via a linker molecule. In some embodiments, a covalent linkage may be between nucleotide molecules. In such case, a nucleotide sequence that encodes the CPP may be operably linked to a microdystrophin gene, so that when expressed by a vector (e.g., a plasmid or a viral vector), the CPP-microdystrophin protein is espressed as a single fusion protein.

Cell penetrating peptides have been used in exon skipping to deliver oligonucleotides to the muscle cell (Wu et al. 2008; Ivanova et al. 2008; Jearawiriyapaisarn et al.; Betts et al. 2012; Moulton 2012; Yin et al. 2008; Yin et al. 2010). In addition, the TAT PTD, when attached to recombinant full-length utrophin and micro-utrophin protein, is able to successfully transfer utrophin proteins to the muscle of mdx mice (Sonnemann et al. 2009). Thus, since the expression of R16/17 protein has been successfully induced by AAV transfer, one skilled in the art would understand that because R16/17 protein may be stably expressed in muscle it could be delivered on its own by the TAT PTD in vivo.

According to another embodiment, the therapeutic composition for restoring nNOS to sarcolemma may further include a membrane targeting signal sequence motif attached to the C-terminus of the dystrophin repeats R16/17 or functional domains, sections, or fragments thereof. The membrane targeting sequence may be any suitable targeting or signaling sequence to direct the therapeutic composition to the sarcolemma membrane to increase its efficacy including, but not limited to, a palmitoylation membrane targeting signal (Pal).

Neuronal nitric oxide synthase (nNOS) is mainly localized at the sarcolemma. Its sarcolemmal localization is sustained by dystrophin. However, the truncated dystrophins, expressed in BMD or DMD treated with exon skipping or gene therapy, lose the nNOS-recruiting ability. Hence, absence of sarcolemmal nNOS is a common manifestation in those patients. Since sarcolemmal nNOS is normally present in muscle and is essential for muscle function, recovering sarcolemmal nNOS in those patients would further ameliorate therapeutic outcome.

Loss of sarcolemmal nNOS is responsible for pathogenesis of muscular dystrophy. Neuronal nitric oxide synthase (nNOS) is predominantly confined to the sarcolemma (FIG. 12), and plays an important role in muscle function. Loss of sarcolemmal nNOS is a common manifestation in both Becker muscular dystrophy (BMD) (Chao et al. 1996; Torelli et al. 2004) and Duchenne muscular dystrophy (DMD) (Brenman et al. 1995), and contributes to pathogenesis of BMD and DMD. In DMD, absence of sarcolemmal nNOS accounts for inability to counteract α-adrenergic-mediated vasoconstriction during muscle contraction, thus resulting in muscle ischemia (Thomas et al. 1998; Sander et al. 2000; Thomas et al. 2003). Additionally, loss of sarcolemmal nNOS leads to muscle fatigue (Kobayashi et al. 2008). In BMD, muscle cramp and fatigue on exercise are mostly attributed to deficiency of sarcolemmal nNOS (Kobayashi et al. 2008).

Absence of dystrophin spectrin-like repeats R16 and R17 (R16/17) causes the deficiency of sarcolemmal nNOS in BMD or DMD receiving exon skipping or gene therapy. Both BMD and DMD are caused by gene mutations in dystrophin, which serves as a scaffold to maintain sarcolemmal localization of nNOS (Brenman et al. 1995; Brenman et al. 1996; Lai et al. 2009).

Figure 12:
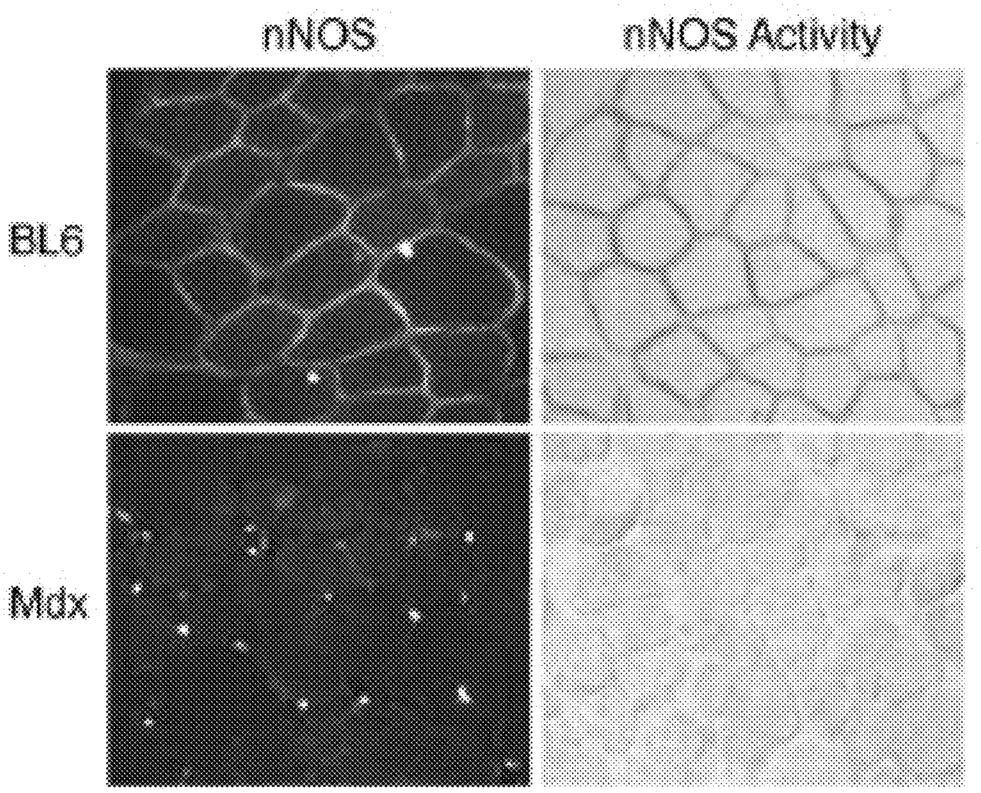
FIG. 12 illustrates that nNOS is predominantly localized at the sarcolemma. Sarcolemmal nNOS is detected by nNOS immunostaining and activity staining. In BL6 mice, nNOS is mainly localized at the sarcolemma while in mdx mice, with the loss of dystrophin, sarcolemmal nNOS is also lost.

In DMD, accompanied by dystrophin deficiency, sarcolemmal nNOS is also lost (FIG. 12). In BMD, although there exists truncated dystrophins due to inframe deletion in the middle rod domain, sarcolemmal nNOS is commonly lost, so that deficiency of sarcolemmal nNOS serves as an important criterion for BMD diagnosis (Torelli et al. 2004).

Gene deletion comprises 72% of dystrophin mutations (van Deutekom et al. 2007). The most prominent hotspot of dystrophin deletion is located at the region from exon 45 to 52 (White & den Dunnen 2006). Previously, it was found that dystrophin R16/17 participate in sarcolemmal localization of nNOS (Lai et al. 2009). R16/17 spans the region from exon 42 to 46, which overlaps with this deletion hotspot. Therefore, deletion usually causes partial or complete loss of R16/17, and subsequently leads to absence of sarcolemmal nNOS in both DMD and BMD.

Molecular therapies such as exon skipping or gene therapy can successfully recover dystrophin expression in DMD. Such therapies convert a DMD phenotype to a BMD-like phenotype, thereby prolonging the survival of DMD patients (van Deutekom et al. 2007; Yokota et al. 2009; Yin et al. 2009; Nakamura & Takeda 2011; Cirak et al. 2011; Bhagavati 2012; Goemans et al. 2011; Harper et al. 2002; Gregorevic et al. 2004; Gregorevic et al. 2006; Wand et al. 2000). However, truncated dystrophins induced by these therapies are mostly incapable of restoring sarcolemmal nNOS.

Exon skipping reconstitutes the reading frame of dystrophin by skipping one or more exons that surround the deletion region, thus producing a truncated but functional dystrophin protein. Since deletions often occur in the region encompassing R16/17, the truncated dystrophin proteins recovered by exon skipping are deficient in R16/17, and therefore unable to restore sarcolemmal nNOS. Additionally, efficient gene delivery has been achieved by adeno-associated viral vector (AAV). Due to limited capacity of AAV vectors, truncated dystrophins have to be generated for AAV gene transfer.

Overall, the truncated dystrophins, expressed in BMD or DMD receiving exon skipping or gene therapy, usually lose the ability to restore sarcolemmal nNOS (FIG. 13). Restoration of sarcolemmal nNOS further improves muscle function in the transgenic mice expressing truncated dystrophins. Previously, transgenic mice have been generated to express two different truncated dystrophins (Lai et al. 2009). Similar to BMD, these minidystrophins carry deletions in the middle rod domain. Although the truncated dystrophins improve muscle force and ameliorates dystrophic phenotype, only the minigene with the function to restore sarcolemmal nNOS could further enhance therapeutic efficacy (FIG. 14).

The minigene ΔH2-R19 cannot restore sarcolemmal nNOS. Both blood flow and running performance have been remarkably compromised in ΔH2-R19 transgenic mice. Furthermore, without sarcolemmal nNOS, strenuous exercise gave rise to ischemic lesion in the muscle of ΔH2-R19 transgenic mice (Lai et al. 2009). Consistent with this finding, another study has shown that in the absence of sarcolemmal nNOS, long-term treadmill exercise caused the decline of muscle force and restricted lesion of degeneration and regeneration in utrophin transgenic mice (Li et al. 2010) (FIG. 14).

An R16/17-containing minidystrophin, ΔH2-R15, was also engineered. The minigene ΔH2-R15 restores sarcolemmal nNOS. More importantly, ΔH2-R15 significantly improved blood flow in contracting muscle, boosted exercise performance and prevented muscle ischemic injury following vigorous exercise 9. Hence, restoration of sarcolemmal nNOS further improves therapeutic outcome of truncated dystrophins (FIG. 14).

In BMD or DMD treated with exon skipping or gene therapy, the truncated dystrophins are unable to restore sarcolemmal nNOS. Nitric oxide produced by sarcolemmal nNOS can dilate blood vessel and increase blood flow via activating cGMP-mediated pathway (Kobayashi et al. 2008). Loss of sarcolemmal nNOS compromises this signaling pathway. Those patients are vulnerable to muscle ischemia during exercise.

To date, a clinical trial is testing therapeutic effect of Tadalafil on muscle ischemia of BMD patients. Tadalafil is the inhibitor of 5'-phosphodiesterase (PDE-5) and it can increase the level of cGMP and subsequently improve blood flow (http://clinicaltrials.qov/ct2/show/NCT01070511). But, currently, there is no therapy to restore sarcolemmal nNOS in BMD or DMD receiving exon skipping or gene therapy. Since sarcolemmal nNOS is normally present in muscle and recovery of sarcolemmal nNOS further improves therapeutic efficacy of truncated dystrophins, an adjunct therapy to restore sarcolemmal nNOS would provide therapeutic improvement for those patients.

Figure 15A:
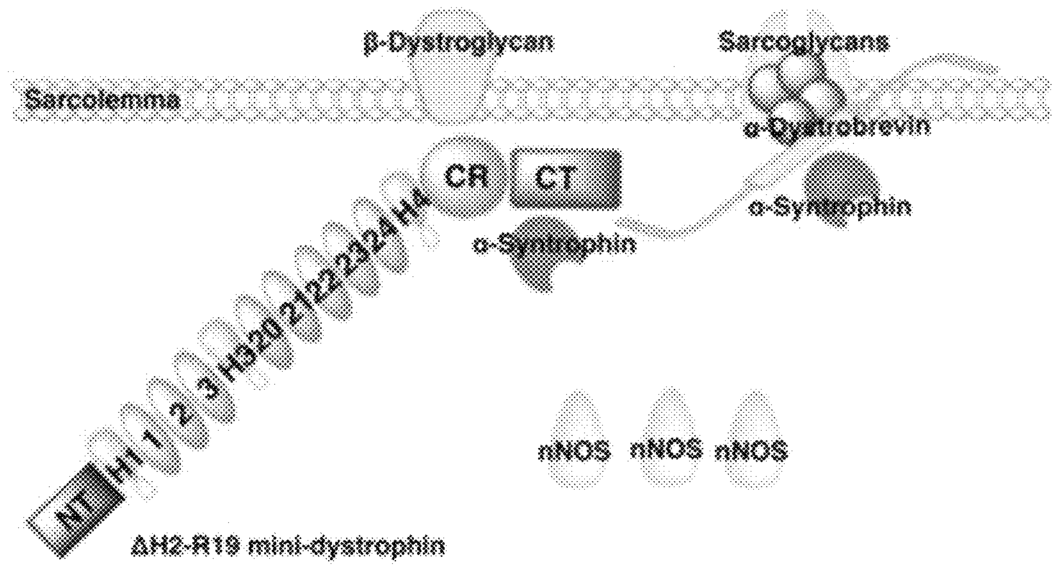
FIG. 15(A) is a schematic showing that sarcolemmal nNOS is absent in ΔH2-R19 transgenic mice. The expression of ΔH2-R19 minidystrophin gene recovers dystroglycan, syntrophin, sarcoglycans and dystobrevin to the sarcolemma. But it cannot restore nNOS to the sarcolemma so nNOS is still in the cytosol
Figure 15B:
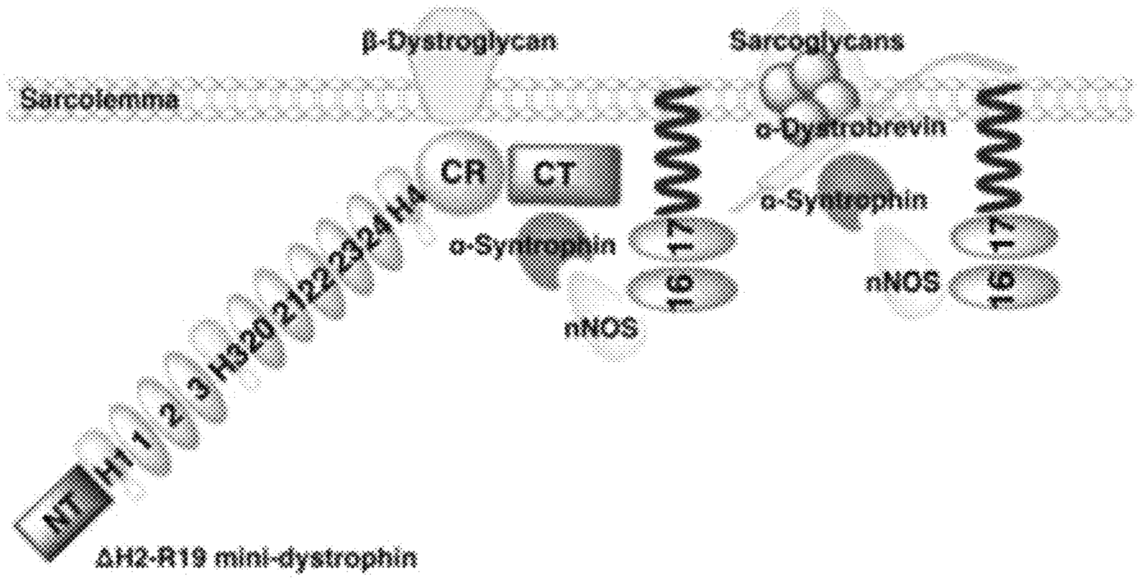
FIG. 15(B) is a schematic showing that sarcolemmal nNOS is restored in ΔH2-R19 transgenic mice by membrane-associated R16/17. Dystrophin R16/R17 are attached with a membrane-targeting motif so R16/17 are associated with the sarcolemma. The expression of membrane-associated R16/17 in ΔH2-R19 transgenic mice restores sarcolemmal nNOS. Therefore, R16/17 recovers the missing nNOS-recruiting function of the ΔH2-R19 minigene. (NT: N-terminus of dystrophin; H: hinge region; CR: cysteine-rich domain; CT: c-terminus of dystrophin).

The missing nNOS-recruiting functionality is transcomplemented by membrane-associated R16/17 in ΔH2-R19 transgenic mice. Previously, it was shown that a ΔH2-R19 minigene loses the ability to restore sarcolemmal nNOS (Lai et al. 2009). In the studies described in the Examples above, it was found that the lost nNOS-recruiting ability of ΔH2-R19 minigene can be recovered by membrane-associated R16/17. An AAV was used to induce the expression of membrane-associated R16/17 in ΔH2-R19 transgenic mice, and which successfully restored sarcolemmal nNOS, indicating that the missing nNOS-recruiting functionality of ΔH2-R19 can be transcomplemented by membrane-targeting R16/17 (FIGS. 15A and 15B).

Since ΔH2-R19 is a truncated dystrophin, similar to the dystrophins in BMD (England et al. 1990), these results have significant potential for restoring sarcolemmal nNOS in the patients with truncated dystrophins but without sarcolemmal nNOS.

Thus, there is an underappreciated gap in treating BMD or DMD receiving exon skipping or gene therapy. They are characterized by the presence of truncated dystrophins but the absence of sarcolemmal nNOS. These patients suffer from muscle ischemia and fatigue during exercise. Sarcolemmal nNOS is normally present in muscle and is critical for muscle function. Furthermore, restoration of sarcolemmal nNOS by an R16/17-inclusive minidystrophin gene (ΔH2-R15) improved blood flow in contracting muscle, boosted running performance, and prevented ischemic injury. So it would be therapeutically significant to restore sarcolemmal nNOS in such patients.

In the studies described below, the expression of dystrophin R16/17 was induced by AAV gene transfer and restore sarcolemmal nNOS in ΔH2-R19 mice. Further, recombinant R16/17 protein may be delivered directly to the muscle cells to restore sarcolemmal nNOS in ΔH2-R19 mice. This direct delivery of the recombinant R16/17 protein may be accomplished using a cell-penetrating peptide, the TAT PTD, which is attached to R16/17 to facilitate the delivery of R16/17 protein to the muscle cell of ΔH2-R19 mice.

Further, blood flow, running performance and ischemic injury may be evaluated in ΔH2-R19 transgenic mice receiving direct delivery of recombinant R16/17 protein. Restoration of sarcolemmal nNOS by transcomplementation of R16/17 would improve therapeutic efficacy, resulting in effects such as improving blood flow and running performance, and preventing ischemic injury. The results gained from this study assist in developing a clinically applicable treatment and shed new light on therapeutic outcome of this novel therapy.

Methods of Treatment

Based on the studies below and in accordance with the embodiments described herein, the microdystrophin proteins, peptides, or fragments thereof or therapeutic compositions which include the same (such as those described herein) may be used in methods for treating Duchenne Muscular Dystrophy (DMD) or Becker Muscular Dystrophy (BMD). Although the studies described herein focus on forms of muscular dystrophy, the methods described herein may be used to treat any disease or condition that is associated with a deficiency, absence or malformation of dystrophin including, but not limited to, muscular dystrophies (e.g., DMD and BMD) and X-linked dilated cardiomyopathy (XLDC).

According to some embodiments, the methods described herein include a step of administering a therapeutically effective amount of the microdystrophin protein, peptide, or fragments thereof to a subject having DMD, BMD, or XLDC. The subject may be a human, mouse, rat, dog, cat, pig, or any other mammal in need of treatment. The microdystrophin protein, peptide, or fragments thereof may be administered alone or as part of a therapeutic composition, which may include a delivery vehicle such as a CPP or an AAV vector as described above.

The microdystrophin protein, peptide, or fragments thereof, may be administered by any suitable route of administration, alone or as part of a therapeutic composition. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the route of the administration accordance with the methods described herein includes local or regional muscle injection to improve local muscle function in patients, systemic delivery (such as intravenous, intra-artery, intraperitoneal) to all muscles in a region or in the whole body in patients, or in vitro infection of myogenic stem cells with an AAV or lentiviral vector followed by local and/or systemic delivery.

The term "effective amount" as used herein refers to an amount of a microdystrophin protein, peptide, or fragment thereof that produces a desired effect. For example, a population of cells may be contacted with an effective amount of a microdystrophin protein, peptide, or fragment thereof to study its effect in vitro (e.g., cell culture) or to produce a desired therapeutic effect ex vivo or in vitro. An effective amount of a microdystrophin protein, peptide, or fragment thereof may be used to produce a therapeutic effect in a subject, such as preventing or treating a target condition, alleviating symptoms associated with the condition, or producing a desired physiological effect. In such a case, the effective amount of an arginine depleting agent is a "therapeutically effective amount," "therapeutically effective concentration" or "therapeutically effective dose." The precise effective amount or therapeutically effective amount is an amount of the microdystrophin protein, peptide, or fragment thereof that will yield the most effective results in terms of efficacy of treatment in a given subject or population of cells. This amount will vary depending upon a variety of factors, including but not limited to the characteristics of the microdystrophin protein, peptide, or fragment thereof (including activity, pharmacokinetics, pharmacodynamics, and bioavailability), the physiological condition of the subject (including age, sex, disease type and stage, general physical condition, responsiveness to a given dosage, and type of medication) or cells, the nature of a pharmaceutically acceptable carrier or carriers in the formulation, and the route of administration. Further, an effective or therapeutically effective amount may vary depending on whether the a microdystrophin protein, peptide, or fragment thereof is administered alone or in combination with a compound, drug, therapy or other therapeutic method or modality. One skilled in the clinical and pharmacological arts will be able to determine an effective amount or therapeutically effective amount through routine experimentation, namely by monitoring a cell's or subject's response to administration of a microdystrophin protein, peptide, or fragment thereof and adjusting the dosage accordingly. For additional guidance, see Remington: The Science and Practice of Pharmacy, $21^{st}$ Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

In some embodiments, the method of treatment may be a stand-alone treatment, or may be used as an adjunct treatment which may complement the nNOS-recruiting function of treatment with truncated dystrophins, and may provide therapeutic benefits for both BMD and DMD. Hence, this therapy holds great promise to become an adjunct therapy for patients receiving currently available treatments.

While the invention has been described in connection with specific embodiments thereof, it will be understood that the inventive materials are capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: α2 and α3 Helices of Dystrophin R16 and R17 Frame a Microdomain in the α1 Helix of Dystrophin R17 for nNOS Binding Materials and Methods Animals.

Figure 8A:
FIGS. 8(A)-8(C) show that substitution of dystrophin R16 or 17 with respective utrophin R15 or R16 compromises nNOS membrane targeting by ΔR2-R15/ΔR18-R23/ΔC microdystrophin.
Figure 8B:
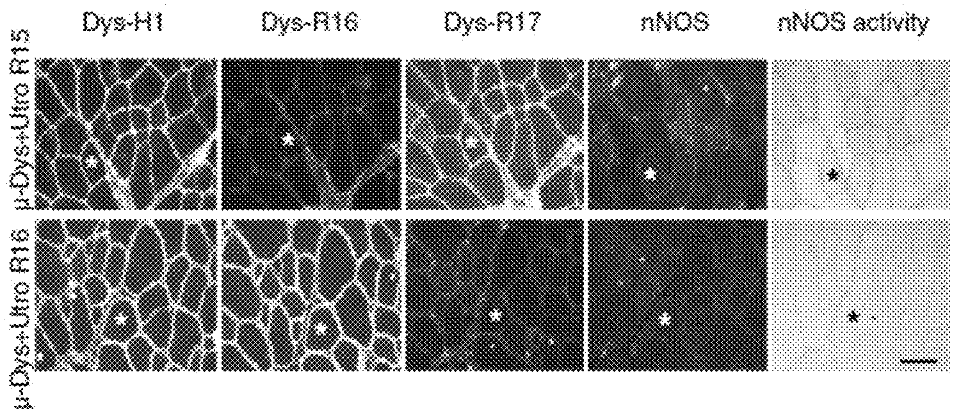
Figure 8C:
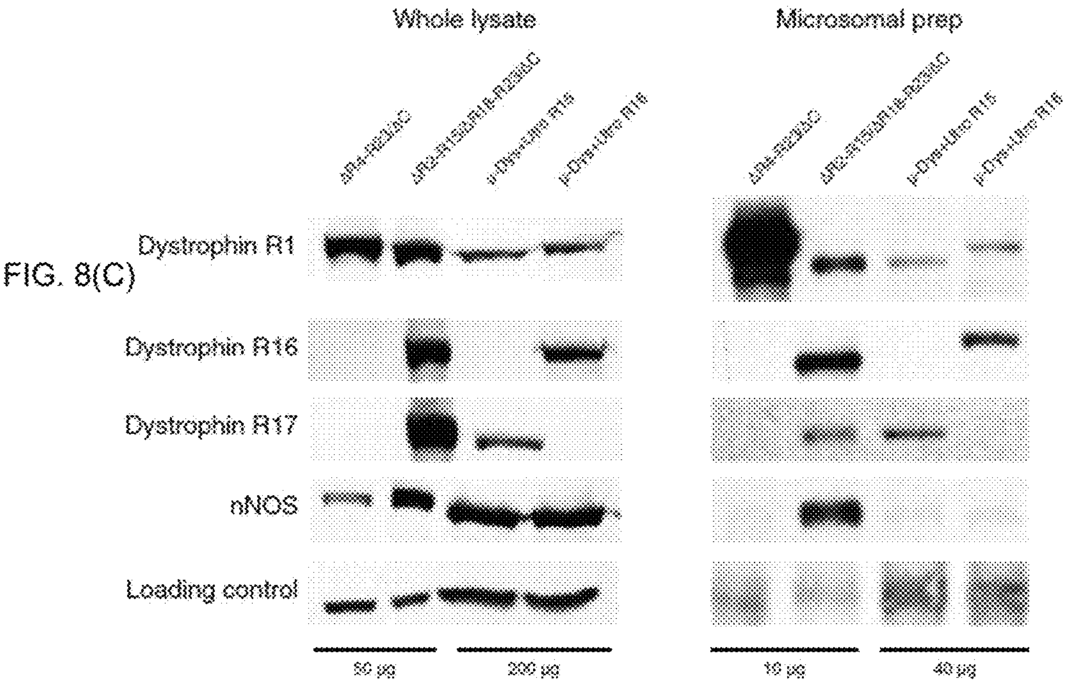

Dystrophin-deficient mdx mice were purchased from The Jackson Laboratory. Utrophin heterozygous mdx mice (mdx/utro+/−) were originally provided by Mark Grady (Washington University, St. Louis, Mo.) (Grady et al. 1997). Experimental utrophin/dystrophin double knockout (u-dko) mice were generated by crossing mdx/utro+/− mice, as previously described (Yue et al. 2006). The skeletal muscle specific mini- and microdystrophin transgenic mdx mice were published previously (Lai et al. 2009; Li et al. 2011a). In these transgenic mice, the mini- or microdystrophin genes were expressed under the transcriptional regulation of the human skeletal α-actin promoter. Three transgenic strains were used in the study. The ΔH2-R19 minidystrophin transgenic mdx mice were used to determine in vivo neuronal NOS (nNOS) binding by the stripped-down R16/17 construct (FIG. 3). This minigene carries the C-terminal domain but does not contain dystrophin R16/17. The ΔR4-23/ΔC and the ΔR2-R15/ΔR18-R23/ΔC microgene transgenic mdx mice were used as negative and positive controls, respectively, for nNOS binding in muscle (FIG. 8B). Dystrophin R16/17 is present in the ΔR2-R15/ΔR18-R23/ΔC microgene but not in the ΔR4-23/ΔC microgene. Experimental mice were housed in a specific pathogen-free animal facility.

Microdystrophins and Microutrophins.

A total of 48 different microdystrophin and microutrophin constructs were used for in vivo nNOS binding assay (FIG. 9). A total of five different microdystrophin constructs were evaluated in vitro for their nNOS binding activity by yeast two-hybrid assay. These microgenes were generated using PCR-based cloning method and all were confirmed by DNA sequencing (FIG. 9). Microgene expression was regulated by the CMV promoter and SV40 polyadenylation signal. For microdystrophin cloning, a human ΔR2-R15/ΔR18-R23/ΔC microgene was used as the backbone (Lai et al. 2009). All dystrophin-related modifications were made according to the human dystrophin sequence. The microutrophin genes were cloned using the full-length mouse utrophin cDNA as the template (a gift of James Ervasti, University of Minnesota, Minneapolis, Minn.) (Rybakova et al. 2002). All utrophin-related modifications were made according to the mouse utrophin sequence.

Recombinant Adeno-Associated Virus Vector and In Vivo Gene Transfer.

The microgene expression cassette was cloned between two inverted terminal repeats in a cis AAV packaging plasmid (Shin et al. 2012). All experimental adeno-associated virus (AAV) vectors were pseudotyped using the Y445F AAV-6 tyrosine mutant capsid (a gift of Arun Srivastava, University of Florida, Gainesville, Fla.) (Zhong et al. 2008; Qiao et al. 2010). AAV vectors were purified through two rounds of CsCl gradient ultracentrifugation and the viral titer was determined by quantitative PCR according a published protocol (6). To test in vivo nNOS binding activity, $1\times10^{10}$ vector genome (vg) particles of AAV vectors were directly injected into the tibialis anterior (TA) muscle of 2- to 6-mo-old mdx or transgenic mdx mice, or 3-wk-old u-dko mice (Lai et al. 2005).

AAV-Mediated In Vivo nNOS Binding.

All animal experiments were approved by the University of Missouri Institutional Animal Care and Use Committee. Modified microdystrophins/utrophins were packaged in Y445F AAV-6 vector. The 1010 viral particles were injected to the tibialis anterior muscle to young adult mice. Microgene expression and nNOS expression were examined 5 wk later by immunofluorescence staining, in situ nNOS activity assay, and Western blot (whole-muscle lysate and microsomal preparation) (Lai et al. 2009). Details of each assay are provided below.

Immunofluorescence Staining and nNOS Activity Staining.

Freshly collected muscle samples were embedded in Tissue-Tek OCT (Sakura Finetek) and snap-frozen in 2-methylbutane with liquid nitrogen.GFP was visualized under the FITC channel using aNikon E800 fluorescence microscope. Human dystrophin derived microdystrophin was detected with Dys-3, a human dystrophin-specific monoclonal antibody (1:20; Novocastra). This antibody recognizes an epitope in human dystrophin hinge 1. Dystrophin spectrin-like repeats 16 and 17 were detected with Mandys 102 (1:20) and Manex 44A (1:300) monoclonal antibodies, respectively (gifts from Glenn Morris, The Robert Jones and Agnes Hunt Orthopedic Hospital, Oswestry, Shropshire, United Kingdom) (Lai et al. 2009; Morris et al. 2011). Utrophin was revealed with a mouse monoclonal antibody against the utrophin N-terminal domain (1:20; Vector Laboratories). nNOS was detected with a rabbit polyclonal antibody against an epitope near the C-terminal end of nNOS (1:2,000; Santa Cruz). Histochemical evaluation of nNOS activity was performed according to a published protocol (Lai et al. 2009; Li et al. 2011a; Li et al. 2010; Li et al. 2011b). This staining revealed the NADPH diaphorase activity of nNOS. The Flag tag was revealed with the monoclonal anti-FLAG M2 antibody (1:1,00; Sigma). Photomicrographs were taken with a Qimage Retiga 1300 camera using a Nikon E800 fluorescence microscope.

Western Blot.

Whole-muscle lysate and membrane-enriched microsomal preparations were obtained from snap-frozen TA muscles according to previously published protocols (Lai et al. 2009; Li et al. 2011a; Li et al. 2010; Li et al. 2011b; Li et al. 2009). ΔH2-R19 minidystrophin was detected with an antibody against the C-terminal domain of dystrophin (Dys-2, 1:100; Novocastra). Microdystrophins (including ΔR4-R23/ΔC, ΔR2-R15/ΔR18-R23/ΔC, μ-Dys+Utro R15 and μ-Dys+Utro R16) were probed with the Dys-B antibody that reacts with dystrophin R1 (1:100; Novocastra, Leica Microsystems). Mandys 102 (1:20) and Manex 44A (1:500) monoclonal antibodies were used to detect dystrophin R16 and R17, respectively. nNOS was detected with a rabbit polyclonal antibody against the N-terminal end of nNOS (1:4,000; Upstate, Millipore). α-Tubulin (1:3,000; Sigma) was used as the loading control for whole-muscle lysate Western blot. α1-Na+/K+ATPase (1:400; Upstate, Millipore) was used as the loading control for microsomal preparation Western blot.

In Vitro nNOS Binding Assay with Yeast Two-Hybrid.

The assay was performed as elaborated in SI Methods. The binding construct carried the nNOS PDZ domain. The activation constructs express various α-helix substituted dystrophin R16/17.

Yeast Two-Hybrid.

A Yeast two-hybrid assay was performed with the Matchmaker GAL4 Two-Hybrid System3 (Clontech) as described previously (Lai et al. 2009). The nNOS PDZ domain [a gift of David Bredt (University of California, San Francisco, Calif.) and Samie R. Jaffrey (Cornell University Weill Medical College, New York, N.Y.)] was cloned into the binding construct (Lai et al. 2009; Brenman et al. 1995). The activation constructs contain the α-helix-modified dystrophin R16/17 in which individual helix within R16/17 was replaced by the corresponding helix from dystrophin R18. A total of five different activation constructs were generated. In each construct, one of the following dystrophin helices including R16α1, R16α2, R16α3, R17α1, or R17α2 was replaced. All constructs were sequenced before use. The positive control for the yeast two-hybrid assay was performed using the syntrophin PDZ domain as the activation construct according to a previous publication (Lai et al. 2009). To detect positive interaction, the binding construct and one of the referred activation construct were cotransfected to yeast cells. The qualitative plate assay and the semiquantitative dot assay were performed on the leucine/tryptophan/histidine triple-deficient medium. The quantitative β-galactosidase activity assay was measured using the Galacto-light system (Applied Biosystems).

Results

Membrane Expression of Dystrophin R16/17 Alone Is Sufficient to Target nNOS to the Sarcolemma. Although previous studies suggest that dystrophin R16/17 is necessary for membrane-associated nNOS expression (Lai et al. 2009; Li et al. 2011a), those skilled in the art at that time would have appreciated that other repeats, hinges or domains would have also been required. This is evidenced by the fact that prior to the studies described herein, the smallest nNOS binding dystrophin (ΔR2-R15/ΔR18-R23/ΔC) also carries the NT and CR domains, H1, H4, R1, and R24 (FIG. 1 and FIG. 9) (Lai et al. 2009). To determine whether these regions contributed to dystrophin-nNOS interaction, in vivo nNOS binding in constructs carrying additional deletions was examined. Removing R1 and R24 did not compromise sarcolemmal nNOS expression in dystrophin-null mdx muscle. Further deletion of the NT domain and H1 or H4 and the CR domain did not alter nNOS membrane localization either (FIG. 1). These results suggest that dystrophin R16/17 can recruit nNOS to the sarcolemma independent of other dystrophin domains.

Figure 3C:
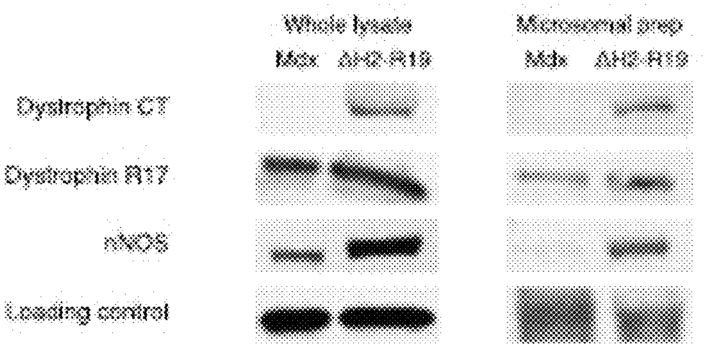
FIG. 3(C) demonstrates that membrane-associated nNOS was detected in R16/17.GFP.Pal-treated_H2-R19 transgenic mdx mice.

Next, a stripped-down construct of only dystrophin R16/17 was used to determine whether it can localize nNOS to the sarcolemma. To facilitate detection, a GFP tag was fused to dystrophin R16/17 (R16/17.GFP) (FIG. 3A and FIG. 9). Robust expression of R16/17. GFP was observed in mdx muscle but nNOS was not detected at the sarcolemma (FIG. 3A). Loss of dystrophin results in the disassociation of syntrophin from the membrane. Syntrophin is also required for sarcolemmal nNOS localization (Adams et al. 2000; Kameya et al. 1999). To more stringently test the R16/17.GFP construct, it was introduced to skeletal muscle specific ΔH2-R19 minidystrophin transgenic mdx mice (FIG. 3A) (Lai et al. 2009). The ΔH2-R19 minidystrophin gene does not restore nNOS to the membrane but it anchors syntrophin to the sarcolemma (Lai et al. 2009; Lai et al. 2005; Harper et al. 2002). The R16/17.GFP AAV virus successfully transduced transgenic mdx muscle. However, the virus still did not restore nNOS to the sarcolemma (FIG. 3A). R16/17.GFP expression was limited to the sarcoplasm only. Failure to localize nNOS to the sarcolemma may be due to the lack of membrane targeting of R16/17.GFP. To address this possibility, a palmitoylation membrane targeting sequence was attached to the C terminus of R16/17.GFP to generate R16/17.GFP.Pal (FIG. 3B and FIG. 9) (Hancock et al. 1990). Compared with R16/17.GFP, palmitoylated dystrophin R16/17 was clearly enriched at the sarcolemma (FIG. 3B). Membrane-associated nNOS was detected in R16/17.GFP.Pal-treated ΔH2-R19 transgenic mdx mice (FIGS. 3B and 3C). Collectively, this data suggest that R16/17 is the only dystrophin component required for sarcolemmal nNOS targeting (Lai et al. 2009).

Figure 11A:
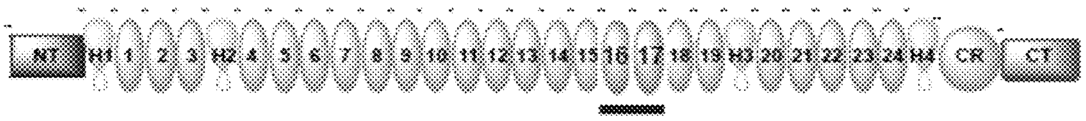
FIG. 11(A) is a schematic diagram of dystrophin.
Figure 11B:
FIG. 11(B) is a schematic diagram of utrophin. Utrophin is a homolog of dystrophin. Dystrophin and utrophin share the similar functional domains. Unlike dystrophin, utrophin is unable to restore sarcolemmal nNOS. Dystrophin R16/17 are involved in sarcolemmal localization of nNOS. In utrophin, R15/16 are highly homological to dystrophin R16/17.

Dystrophin R17 α1 Helix Contains the nNOS-Binding Domain. Utrophin is an autosomal paralog of dystrophin. Utrophin R15/16 is homologous to dystrophin R16/17. (FIG. 11). However, utrophin R15/16 cannot bring nNOS to the sarcolemma (Li et al. 2010). To test whether dystrophin R16/17 can restore sarcolemmal nNOS in a foreign context, a chimeric microutrophin gene was engineered in which utrophin R15/16 was replaced by dystrophin R16/17 (FIG. 2 and FIG. 9). Modified microutrophin effectively restored sarcolemmal nNOS expression in utrophin/dystrophin double knockout (u-dko) mouse muscle (FIG. 2). These results reiterate that dystrophin R16/17 bind nNOS in a context-independent manner.

To identify the nNOS-binding domain in dystrophin R16/17, 14 chimerical microdystrophin constructs were generated. In these constructs, a microdomain of dystrophin R16/17 was substituted by the corresponding sequence from utrophin R15/16 (FIG. 4A and FIG. 9). Each construct was named after the matching microdomain (I to XIV). Following AAV gene transfer to mdx muscle, sarcolemmal nNOS expression was examined. The pattern was not altered in 13 constructs (FIG. 4B). The only exception is construct IX, in which a 10-residue microdomain in the first half of dystrophin R17 α1 helix was replaced. Membrane-associated nNOS expression was completely abolished in muscles treated with this construct (FIG. 4B). These results suggest that the 10-residue microdomain in construct IX contains the nNOS-binding site (FIG. 4B).

Figure 7:
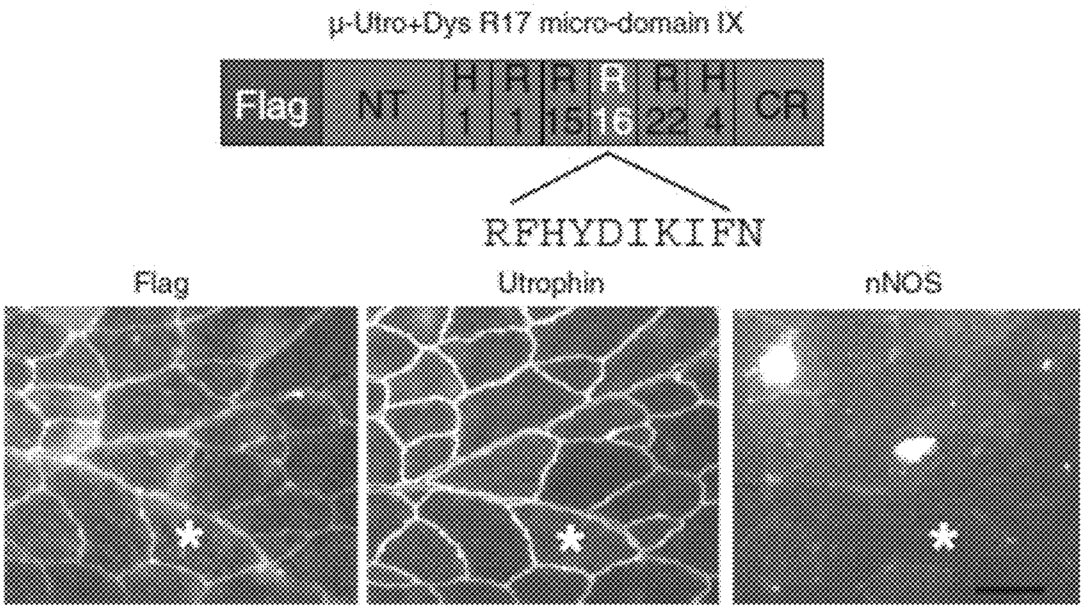
FIG. 7 illustrates that that a dystrophin nNOS binding domain does not recruit nNOS to the sarcolemma in microutrophin. Schematic outline of the chimerical microutrophin construct (μ-Utro+Dys R17 microdomain IX). The microdomain IX of utrophin R16 was replaced by the corresponding microdomain of dystrophin R17 in the ΔR2-14/ΔR17-21/ΔC microutrophin gene. Modified microutrophin was delivered to utrophin/dystrophin double null mouse muscle. Shown are the representative Flag, utrophin, and nNOS immunostaining photomicrographs. Asterisks indicate the same myofiber in the serial sections. (Scale bar, 50 μm.)

To further establish dystrophin R17 α1 helix microdomain IX as the nNOS-binding domain, this microdomain was engineered into the microutrophin gene. Specifically, the corresponding sequence in utrophin R16 was replaced with that of dystrophin R17 (FIG. 9). Despite strong expression, dystrophin R17 microdomain IX did not anchor nNOS to the sarcolemma in the context of utrophin (FIG. 7). This suggests that in addition to dystrophin R17 microdomain IX, other yet undefined structural features of dystrophin R16/17 are also needed for sarcolemmal nNOS localization.

Sarcolemmal nNOS Binding Requires Five Correctly Phased α-Helices, including α2 and α3 Helices of Dystrophin R16 and all Three α-Helices of Dystrophin R17. The linker between adjacent STRs has been implicated in protein-protein interaction (Stabach et al. 2009; Ipsaro & Mondraon 2010). Therefore, to determine whether the junction between dystrophin R16 and R17 was involved in nNOS binding, four linker mutants (mutants 1-4) were generated to test their effect on nNOS membrane localization. However, none of the mutants altered nNOS membrane localization (FIGS. 9 and 10). These results suggest that the linker between R16 and R17 is not required for nNOS binding.

To decipher other regions that may contribute to nNOS binding, the whole STR was re-examined. The nNOS-binding domain is located in dystrophin R17 (FIG. 4); hence, replacing this STR will destroy nNOS interaction. For this reason, on the focus was directed toward dystrophin R16. Individual replacement of eight microdomains of dystrophin R16 with the corresponding microdomains of utrophin R15 had minimal impact on nNOS binding (FIG. 4). This finding seemed to suggest that dystrophin R16 and utrophin R15 may be exchangeable. To determine the contribution of dystrophin R16 in its entirety, another chimeric microdystrophin (μ-Dys+Utro R15) was generated in which dystrophin R16 was replaced by utrophin R15 (FIG. 9). However, modified microdystrophin only yielded very faint sarcolemmal nNOS staining (FIG. 8A). On microsomal preparation Western blot, modified microdystrophin did not localize nNOS to the sarcolemma (FIG. 8B). These results suggest that dystrophin R16 may tolerate single microdomain substitution but not whole STR exchange by homological utrophin R15.

The α-helix is the basic structural unit of STR. Each STR contains three α-helices, α1, α2, and α3. To determine contribution of individual α-helix on nNOS binding, a series of α-helix substitution constructs were screened by a yeast two-hybrid system (FIG. 5). In these constructs, one of the α-helices of dystrophin R16/17 was replaced by the corresponding α-helix from dystrophin R18. Interaction with nNOS was not disrupted in most cases, except when R17 α1 helix was replaced (FIG. 5).

Considering the possibility that in vitro assay may fail to predict protein interaction in vivo, the in vivo binding assay using AAV gene transfer was performed. First, the impact of single α-helix deletion was examined. Interestingly, nNOS binding was abolished in all of the deletion constructs that were examined (FIG. 6A and Table S1). This finding suggests that either every α-helix is required, or that a single α-helix deletion shifts the normal phasing of the entire STR thereby disrupting 3D structure of the binding motif. To further determine the importance of each α-helix, α-helix substitution microdystrophin constructs were generated. In these constructs, one α-helix (or multiple α-helices) in dystrophin R16/17 was replaced by the corresponding α-helix (or helices) from another dystrophin STR (FIGS. 6B, 9 and 10). This design allows the modified constructs to maintain normal α-helix phasing. Substitution of R17 α1 helix destroyed nNOS binding (FIG. 10). Replacement of other α-helices also abolished nNOS binding (FIG. 10). Single helix substitution of the remaining five α-helices revealed more striking results. Although R16 α1 helix replacement did not affect nNOS binding, swapping the α2 or α3 helix of either R16 or R17 eliminated dystrophin-nNOS interaction (FIG. 6B and FIG. 10). Collectively, the in vivo data described herein suggest that the α2 and α3 helices of both R16 and R17 are important for membrane localization of nNOS in muscle.

Discussion

In this study, the molecular mechanisms underlying dystrophin R16/17-mediated nNOS sarcolemmal localization were investigated. Because dystrophin STRs have never been successfully crystallized (Legrand et al. 2011), an in vivo biochemical approach was taken to study how dystrophin recruits nNOS to the sarcolemma. Specifically, more than 48 different dystrophin and utrophin constructs were generated to express various sequence changes that might be involved in dystrophin-nNOS interaction. These constructs were packaged in muscle tropic AAV viruses and delivered to limb muscles of mdx, u-dko, and ΔH2-R19 minidystrophin transgenic mdx mice. nNOS expression was examined by immunofluorescence staining, in situ enzymatic activity assay, and microsomal preparation Western blot. Positive nNOS binding was defined as the detection of nNOS on the sarcolemma. It was found that membrane bound dystrophin R16/17 anchored nNOS to the sarcolemma in the presence of syntrophin. It was further shown that the α1 helix of dystrophin R17 carries the nNOS-binding microdomain. Finally, it was demonstrated that the function of the nNOS binding microdomain not only required correct phasing of all α-helices in R16/17 but also depended on the structural environment formed by four surrounding helices.

STR is a highly conserved structural module consisting of a triple helical bundle. Interestingly, some paired STRs have evolved unique properties to mediate specific protein-protein interaction while still maintaining their tertiary conformation. The molecular basis for functional specialization of STR is poorly understood. The crystal structure of a ligand-bound STR has only been resolved in one case (Ipsaro & Mondraon 2010). Ipsaro and colleagues recently deciphered the atomic structure of spectrin R14/15 in complex with its binding partner ankyrin (Ipsaro & Mondraon 2010). A negatively charged patch in the α3 helix of spectrin R14 interacts with a positively charged patch in ankyrin. They also show that the linker region between spectrin R14 and R15, and the loop between the α2 and α3 helices of spectrin R15, are important for binding (Ipsaro & Mondraon 2010). The authors propose that: (i) a large tilting between spectrin R14 and R15 brings the linker region and spectrin R15 α2/α3 loop close to each other to form the docking interface, and (ii) ankyrin binding occurs through patch electrostatic interaction (Ipsaro & Mondraon 2010). The results herein revealed a different interaction mode. Specifically, it was found that nNOS recognition was likely accomplished via a 10-residue microdomain in dystrophin R17 α1 helix (FIG. 4). This microdomain is highly conserved through evolution, suggesting it may represent an essential structural feature (Legrand et al. 2011). Based on the fact that dystrophin R17 α1 helix alone supported nNOS binding in vitro in yeast two-hybrid assay (FIG. 5), the 10-residue motif likely contains the authentic nNOS binding site. In contrast to the negatively charged patch in spectrin R14 α3 helix reported by Ipsaro et al., the nNOS binding microdomain identified herein includes amino acids of various electrostatic properties. This finding suggests that dystrophin R16/17 may bind to nNOS through a mechanism different from what was shown for spectrin-ankyrin interaction. Future elucidation of this binding mechanism with X-ray crystallography and NMR may shed new light on understanding other STR-mediated protein interactions.

Another aspect of dystrophin R16/17-nNOS interaction is the difference between in vitro and in vivo assay results. Yeast two-hybrid revealed dystrophin R17 α1 helix is the only component needed for nNOS binding. The requirement for other α-helices was appreciated only when the binding assay was performed in vivo. Because the α1 helix of dystrophin R17 independently recruited nNOS in vitro, α2 and α3 helices of dystrophin R16 and R17 may not directly participate in the binding. Rather, these helices may function to stabilize R16/17 in a specific configuration to facilitate in vivo nNOS binding. Because such information can only be obtained from studies performed in muscle, these results highlight the importance of in vivo biochemical approach in studying protein interaction.

The rod domain of dystrophin was initially considered as a flexible spacer that separates more important functional domains at the N and C termini. However, recent studies suggest that some STRs in the rod domain actually play a more active role in a plethora of cellular functions via interaction with membrane phospholipids, cytoskeletal proteins, and signaling proteins (Le Rumeur et al. 2010). Of particular interest is the ability of dystrophin R16/17 to compartmentalize nNOS to the sarcolemma (Lai et al. 2009). Failure to do so causes functional ischemia and muscle fatigue, hence more severe muscle disease (Lai et al. 2009; Kobayashi et al. 2008). Although previous studies explained why nNOS is delocalized from the membrane in patients carrying deletion mutations involving dystrophin R16/17, they cannot justify cases in which R16/17 is intact yet nNOS is lost from the sarcolemma (Chao et al. 1996; Wells et al. 2003; Torelli et al. 2004). The results from the single α-helix deletion/substitution experiments described herein suggest that an in-frame deletion in other regions of dystrophin may disrupt nNOS interaction by altering α-helix phasing.

The studies discussed herein also reveal several new therapeutic opportunities to treat DMD. Utrophin overexpression has been considered as a promising therapy for DMD. Unfortunately, utrophin cannot bind nNOS (Li et al. 2010). The unique dystrophin R16/17-containing microutrophin gene described herein may thus improve utrophin-based gene therapy. Another possibility is to use membrane-targeted R16/17 as a supplementary (or adjunct) therapy to restore sarcolemmal nNOS expression in situations in which nNOS binding activity is lost in muscle because of deletions affecting dystrophin R16/17 coding region (such as in some Becker muscular dystrophy patients or in DMD patients treated with exon 42-45 skipping).

Example 2: Restoration of Sarcolemmal nNOS by an R16/17-Containing Minidystrophin Improves Blood Perfusion in Contracting Muscle and Boosts Exercise Performance A minidystrophin gene ΔH2-R19 (FIG. 21) may be generated by a small adaption to the truncated dystrophin gene Δexon17-48 (FIG. 31) found in BMD patients (Harper et al. 2002; England et al. 1990). Because it does not carry R16/17, the ΔH2-R19 minigene is unable to restore sarcolemmal nNOS. In addition, a minidystrophin gene ΔH2-R15 (FIG. 22) was engineered. The ΔH2-R15 minigene contains R16/17 and restores sarcolemmal nNOS. Both minigenes can recover muscle force to the wild-type level and demonstrate almost identical response to eccentric contraction. But in terms of blood perfusion and running performance following strenuous exercise, ΔH2-R15 minigene displays better therapeutic efficacy, indicating that restoration of sarcolemmal nNOS would exert significant therapeutic effect (FIG. 14) (Lai et al. 2009).

Example 3: R16/17 Protein Alone Restores Sarcolemmal nNOS

Restoration of Sarcolemmal nNOS by Dystrophin R16/17 is Independent of Other Domains of Dystrophin.

Sarcolemmal localization of nNOS was achieved by a microdystrophin gene (ΔR2-R15/ΔR18-R23/ΔC; FIG. 23). In addition to R16/17, this microgene also contains other domains, including N-terminus, hinge 1 and 4, R1 and 24, and cysteine-rich domain (FIG. 1A). Although it is known that R16/17 are involved in sarcolemmal nNOS, it remains elusive whether other domains also participate in sarcolemmal localization of nNOS. Sequential deletion of those domains from this microgene was carried out and it was determined whether sarcolemmal nNOS is affected. It was found that other domains of dystrophin are not involved in sarcolemmal nNOS. Consequently, dystrophin R16/17 independently recruit sarcolemmal nNOS (FIG. 1).

Trans-Complementation of Membrane-Bound Dystrophin R16/17 Alone Restores Sarcolemmal nNOS in ΔH2-R19 Transgenic Mice.

Since R16/17-mediated sarcolemmal nNOS is independent of other domains of dystrophin, it was determined whether dystrophin R16/17 alone can restore sarcolemmal nNOS. First an AAV vector carrying R16/17 alone was made, followed by the GFP tag. The AAV viral vectors were delivered to the TA muscles of mdx mice and ΔH2-R19 mini-dystrophin transgenic mice. Both animal models are deficient in sarcolemmal nNOS. Although R16/17.GFP was successfully expressed in the cytosol of myofibers, R16/17 alone cannot restore sarcolemmal nNOS in both animal models (FIG. 3A). Next a membrane-targeting motif, which is the small motif for palmitoylation (Pal), was attached to the 3'-end of R16/17.GFP to deliver the AAV vectors to the TA muscles of mdx and ΔH2-R19 transgenic mice. The palmitoylation motif successfully localized R16/17.GFP to the membrane of myofibers. In mdx mice, membrane bound R16/17 cannot efficiently restore sarcolemmal nNOS. However, in ΔH2-R19 mice, membrane associated R16/17 successfully restored sarcolemmal nNOS, indicating that membrane-bound R16/17 can trans-complement the missing nNOS-recruiting ability of ΔH2-R19 mindystrophin (FIG. 3B).

Example 4: Direct Infusion of Recombinant R16/17 Protein Restores Sarcolemmal nNOS The study described below, may be performed to determine whether direct delivery of recombinant R16/17 protein can restore sarcolemmal nNOS in ΔH2-R19 transgenic mice when the TAT protein transduction domain (PTD), a cell penetrating peptide, is attached to R16/17.

TAT Protein Transduction Domain (PTD).

In the studies described above, an AAV gene transfer was used to target R16/17 to the muscle membrane. There, membrane associated R16/17 restored sarcolemmal nNOS in ΔH2-R19 transgenic mice. To improve the safety profile and prevent immune response, recombinant R16/17 protein may be delivered directly to muscle to achieve the restoration of sarcolemmal nNOS. To facilitate the transfer of recombinant R16/17 protein to the muscle, the TAT PTD, a cell-penetrating peptide, may be attached to R16/17. The PTD of TAT protein contains a minimum of 11 residues, and is capable of delivering biologically active proteins in vivo (Ho et al. 2001; Morris et al. 2001; Schwarze et al. 1999; Wang et al. 2009). Further, incorporation of the TAT PTD in exon skipping has been shown to increase dystrophin expression in both skeletal and cardiac muscle of mdx mice (Moulton 2012; Sirsi et al. 2008). In addition to transferring oligonucleotides, the TAT PTD has been successfully exploited in delivering the recombinant full-length utrophin and micro-utrophin proteins to the muscle of mdx mice (Sonnemann et al. 2009). Since the molecular size of recombinant R16/17 protein is far less than full-length utrophin and micro-utrophin protein, the cargo capacity of the TAT PTD should be sufficient to transfer recombinant R16/17 protein to the muscle in vivo.

Example 5: Successful Expression of Dystrophin R16/17 Protein in HEK 293 Cells

Figure 16:
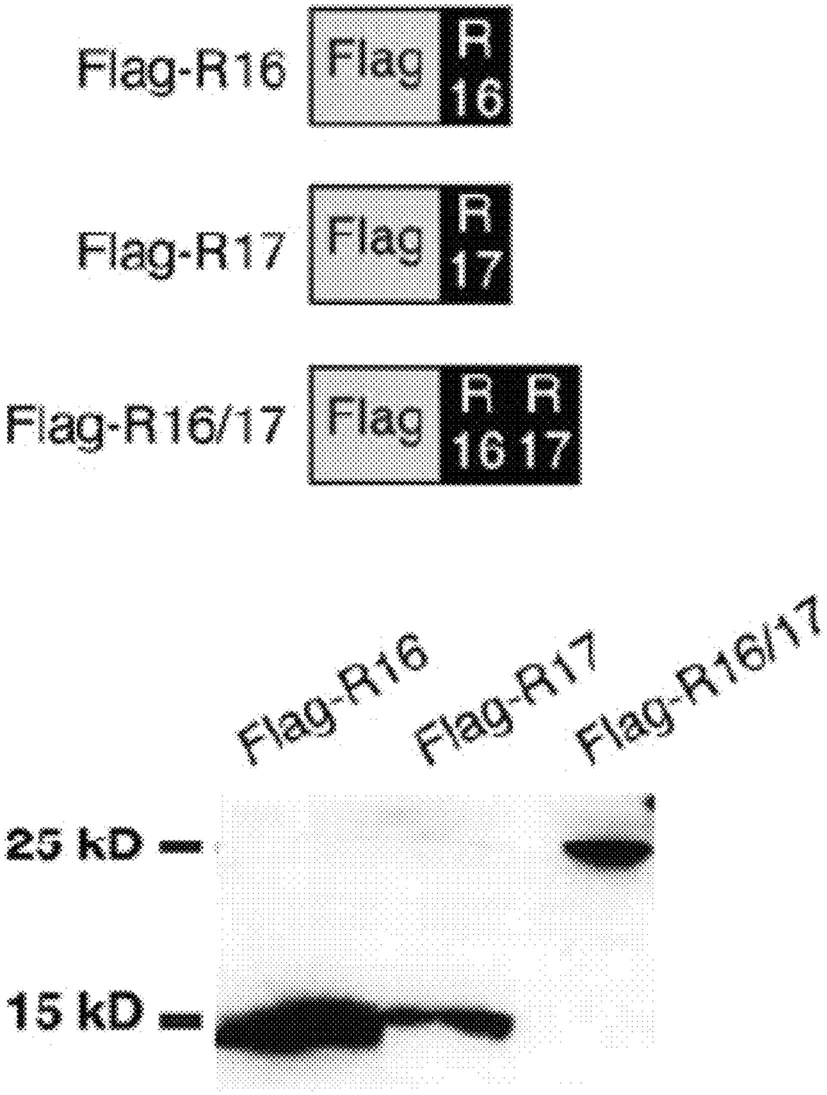
FIG. 16 shows that dystrophin R16/17 protein is stably expressed in HEK 293 cells. Dystrophin R16, R17, and R16/17 are attached with Flag tag and engineered in pFlag-CMV-2 plasmid. After transfection to HEF 293 cells, cell lysates were detected by anti-Flag antibody. The expressed proteins were detected at the expected size, indicating that dystrophin R16, R17, and R16/17 can be stably expressed in vitro.

Dystrophin R16, R17 and R16/17 genes were each cloned into a plasmid pFlag-CMV-2 (Sigma-Aldrich), respectively. In the expression cassette, the Flag tag was fused to the N-terminus of the expressed protein. These three plasmids were transfected into HEK 293 cells and protein expression was detected with anti-Flag antibody. As shown in FIG. 16, the dystrophin R16, R17 and R16/17 proteins were successfully detected, indicating that dystrophin R16/17 can be stably expressed in HEK 293 cells.

R16/17 Protein by Itself is Stable and Eligible to be Delivered by TAT PTD.

It has been reported that individual dystrophin repeats are difficult to express in vitro (Le Rumeur et al. 2010). However, as described above, R16/17 with GFP tag was successfully expressed in muscle by AAV gene transfer (FIG. 3), and R16/17 with Flag tag in HEK 293 cells (FIG. 16), indicating that R16/17 protein is stably present in both in vivo and in vitro systems. Hence, recombinant R16/17 protein may be expressed in in vitro expression systems and then transferred to muscle cells by virtue of an associated TAT PTD in vivo, as described in the Examples below.

Methods

Construction of the Expression Cassette of Recombinant R16/17 Protein.

Figure 17:
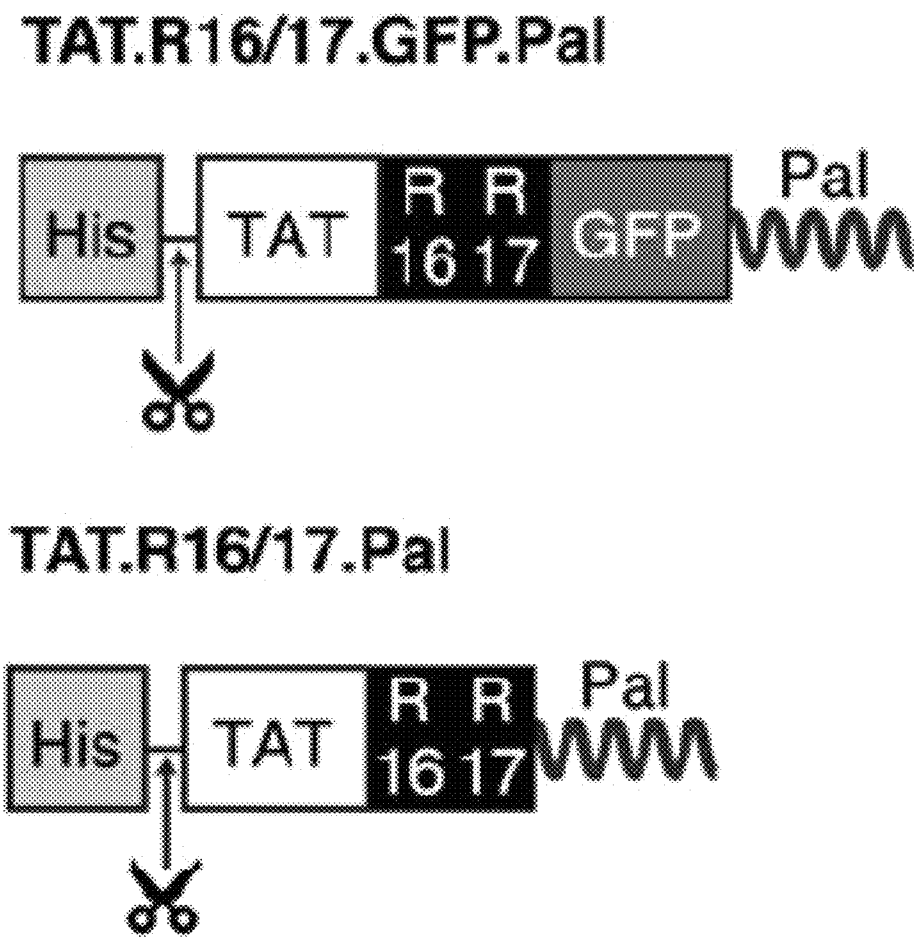
FIG. 17 is a schematic showing the configuration of recombinant R16/17 protein. There are two versions of recombinant R16/17 proteins. For TAT.R16/17.GFP.Pal, TAT PTD is connected with N-terminus of R16. GFP tag is attached with C-terminus of R17, and followed by a Pal signal. A His tag will be removed by digestion of proteinase. For TAT.R16/17.Pal, the GFP tag is removed. (His: polyhistidine tag; TAT: TAT protein transduction domain; Pal: palmitoylation signal for membrane targeting.).

The 11-residue TAT PTD is connected to N-terminus of R16. GFP tag is attached to C-terminus of R17 to help the trace of R16/17 expression in vivo. And GFP is followed by the membrane-targeting motif, the 17-residue palmitoylation signal (Pal). For the clinical application, the GFP tag should be removed so the recombinant R16/17 protein is made without GFP tag (TAT.R16/17.Pal) (FIG. 17). The coding sequence for TAT.R16/17.GFP.Pal and TAT.R16/17.Pal is placed in the baculoviral donor plasmid (pFastBac), and driven by Polyhedrin (polh) promoter. His tag has been engineered at the N-terminus of expression cassettes and may be used for purification. Since a cutting site of proteinase exists between His tag and TAT PTD, it is very convenient to remove His tag after purification of recombinant protein.

Expression of Recombinant R16/17 Protein.

A baculovirus/insect cell protein expression system (Bac-to-Bac system from Invitrogen) may be used to generate recombinant TAT.R16/17.GFP.Pal and TAT.R16/17.Pal protein. The donor plasmid with the expression cassette may be transformed to *E. coli* strain DH10Bac containing bacmid and helper to generate recombinant bacmid through site-specific transposition. Then the recombinant bacmid DNA carrying expression cassettes may be extracted from bacteria cells and used for producing recombinant baculoviruses in insect cells. Recombinant bacmid DNA may then be transfected into insect cells, and the recombinant baculoviruses are then collected to determine viral titer via plaque assay. The recombinant baculoviruses may be used to infect insect cells to express recombinant R16/17 protein. After confirming recombinant protein expression by western blot, the production of recombinant baculovirueses may be scaled up through increasing culture volume and repeated rounds of infection. The baculoviruses with high titer are be used to produce a large amount of protein.

Purification of Recombinant TAT.R16/17.GFP.Pal and TAT.R16/17.Pal Protein.

At the time of maximal expression of recombinant protein, insect cells may be harvested for protein purification. The cells may be pelleted by centrifugation. A ProBond purification system may be used to purify recombinant R16/17 protein. Briefly, pelleted cells are lysed by freeze-thaw cycles in provided buffer. Then cell lysates are passed through purification column. Since the recombinant protein is attached with His tag, the recombinant protein is sequestered on the column. Then the recombinant proteins may be eluted from the column by different concentration of imidazole. An SDS-PAGE gel may then be run to analyze the collections of eluted fractions. The identity of the protein may be confirmed by western blot, and then protein fractions are de-salted and resuspended in PBS buffer for further study.

Determination of Transduction Kinetics and Optimal Dosage of Recombinant R16/17 Protein In Vivo.

Figure 18A:
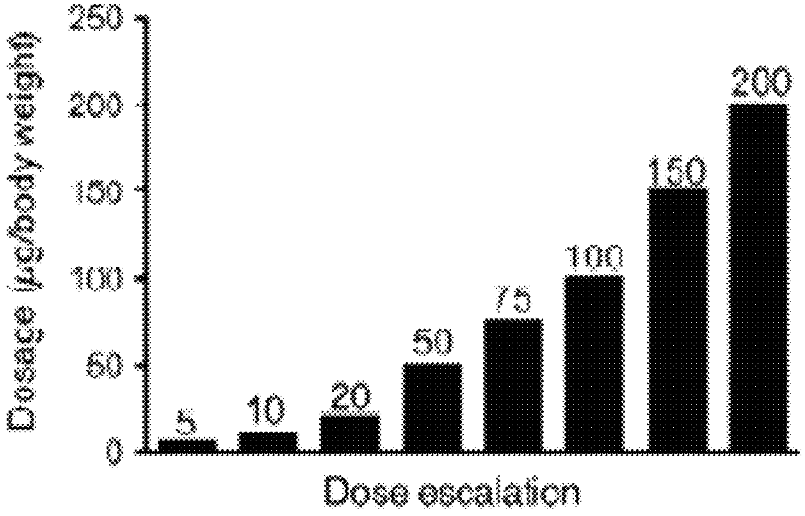
FIG. 18(A) shows a method for determining the optimal dosage to achieve the maximal distribution of R16/17 protein in muscle according to some embodiments. The different dosages will be tested in the studies described herein.
Figure 18B:
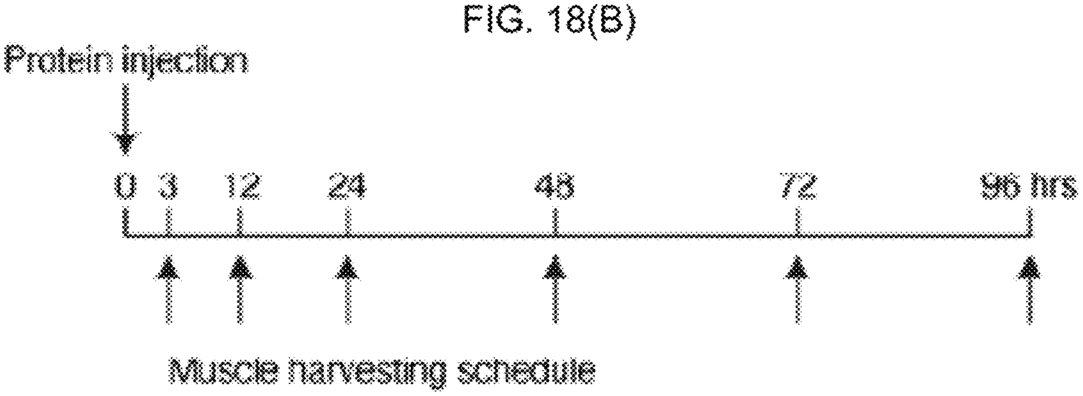
FIG. 18(B) shows a method for determining the optimal time point to achieve the maximal distribution of R16/17 protein in muscle according to some embodiments. The muscle will be harvested according to the above schedule.

The optimal injection scheme may be determined as previously described (Sonnemann et al. 2009). The resuspended proteins may be filtered and intraperitoneally injected into 2 week-old ΔH2-R19 mice. The mice receive a single injection of recombinant R16/17 protein at different dosage, ranging from 5-200 μg/g body weight (n=12 for each dosage). The whole body muscle is harvested at 3 hrs, 12 hrs, 24 hrs, 48 hrs, 72 hrs and 96 hrs post injection. The skeletal muscle group, including muscles in the upper arm, forearm, thigh, lower leg, diaphragm, abdominal wall and tongue, and the heart are sectioned and examined by immunostaining with anti-R17 antibody. Positive myofibers may be counted and used for calculating percentage of positive myofibers. By comparing the percentage of positive myofibers, the specific time point and dosage that lead to the highest expression of recombinant R16/17 protein may be decided (See FIG. 18).

Intraperitoneal Infusion of Recombinant R16/17 Protein into ΔH2-R19 Mice.

The optimal dosage of TAT.R16/17.GFP.Pal or TAT.R16/17.Pal protein may be injected intraperitoneally to the ΔH2-R19 mice and the injections may be repeated at one or more optimal time points over the course of three weeks.

Examination of Membrane-Bound R16/17 and Sarcolemmal nNOS in Muscle.

Three days after the last injection, the whole body muscle is harvested as described above. The membrane-bound R16/17.GFP may be detected by fluorescent microscopy for GFP signal, immunostaining and western blot with R17-specific antibody. The membrane-associated R16/17 may be inspected by immunostaining and western blot with R17-specific antibody. Sarcolemmal nNOS may be examined by immunostaining, nNOS activity staining and western blot as previously described (Lai et al. 2009).

Investigation of Possible Toxicity Reaction Caused by Infusion of Recombinant R16/17 Protein.

The toxicity reaction may be carefully weighed by examining behavior change and blood biochemistry profile. The injected mice are kept separately. The behavior and movement may be monitored daily over three weeks. Blood cell count, liver and kidney functions are inspected weekly during three weeks.

Results

As described above, TAT PTD is able to efficiently deliver various proteins to the muscle (Sonnemann et al. 2009; Ho et al. 2001; Morris et al. 2001; Schwarze et al. 1999; Wang et al. 2009). Those proteins have larger molecular weight than recombinant R16/17 protein, indicating that cargo ability of TAT PTD is sufficient to transfer R16/17 protein. Thus, TAT PTD may be used to effectively transfer recombinant R16/17 protein to the muscle cells. Since a membrane-targeting motif is attached to recombinant R16/17 protein, recombinant R16/17 protein may be localized to the sarcolemma. Based on the results of the studies described above, R16/17 protein is stably present in both in vitro and in vivo expression systems. Hence, membrane-bound recombinant R16/17 protein may be used to restore sarcolemmal nNOS in ΔH2-R19 mice.

The membrane-targeting motif that may be used in this study is the palmitoylation motif from K-ras. Membrane targeting of the palmitoylation motif requires a posttranslational modification that adds a farnesyl isoprenoid lipid to the motif (Karnoub & Weinberg 2008; Choy et al. 1999). This prenylation reaction precedes the association of protein with the cell membrane. Because of a lack of palmitoyl transferase machinery in *E. coli* expression system, the recombinant protein expressed in bacteria is in its non-palmitoylated state (Nishida & Ortiz de Montellano 1998; Navarro-Lerida et al. 2006). Baculovirus/insect cell expression system is a eukaryotic protein expression system and has full posttranslational machinery that can palmitoylate R16/17 protein. Hence, in this study a baculovirus/insect cell expression system may be selected to produce recombinant R16/17 protein.

The yield of recombinant protein may be influenced by multiple factors, such as insect cell lines, virus titer, infection ratio and harvesting time, etc. Thus. this study may be optimized by setting up a series of small-scale experiments to determine optimal cell lines, infection ratio and the best harvesting time to obtain the maximal expression. Further, it is hard to predict the solubility of recombinant R16/17 protein with palmitoylation signal. In a ProBond purification system, the buffer used for purification is decided by solubility of recombinant protein. Therefore, different buffers may be used to determine which buffer can produce high yield of recombinant R16/17 protein.

Example 6: Direct Infusion of Recombinant R16/17 Protein Results in Functional Improvement of Muscle Function The study described below may be performed to evaluate the functional improvement when sarcolemmal nNOS is recovered by trans-complementation of R16/17 in ΔH2-R19 transgenic mice. Restoration of sarcolemmal nNOS by R16/17 in ΔH2-R19 mice should improve blood flow, improve running performance, and prevent ischemic injury on exercise.

Study Design.

In this study, the therapeutic outcome of recovering sarcolemmal nNOS by R16/17 protein in ΔH2-R19 mice. First, sarcolemmal nNOS may be restored by direct administration of recombinant R16/17 protein in ΔH2-R19 mice. Second, functional studies may be carried out. The therapeutic outcome is then compared between ΔH2-R19 mice treated with recombinant R16/17 protein, and ΔH2-R19 mice with saline injection, ΔH2-R19 mice injected with AAV.R16/17.Pal and ΔH2-R15 mice (FIG. 19). ΔH2-R19 mice cannot restore sarcolemmal nNOS so ΔH2-R19 mice with saline injection serve as a negative control. ΔH2-R15 mice restore nNOS to the sarcolemma and may be used as a positive control.

In the studies described above, an AAV gene transfer was expoited to induce sarcolemmal expression of R16/17 and subsequently restore sarcolemmal nNOS in ΔH2-R19 mice. To comprehensively compare therapeutic efficacy, systemic delivery of AAV.SPc5-12.R16/17.Pal serves as a therapeutic control. Since AAV serotype 9-mediated systemic delivery may result in robust expression of transgene in both skeletal and cardiac muscle (Inagaki et al. 2006; Bostick et al. 2007), an AAV9 may be used as a capsid in the systemic delivery of R16/17. The expression of R16/17 may be driven by muscle-specific promoter SPc5-12 (Foster et al. 2008; Li et al. 1999) to prevent untoward expression of R16/17 in the systemic delivery (FIG. 19).

Functional studies to evaluate the effect of sarcolemmal nNOS on muscle function. The goal of this study is to determine the functional improvement caused by restoration of sarcolemmal nNOS in ΔH2-R19 mice. Sarcolemmal nNOS closely relates to the blood flow of muscle. Deficiency of sarcolemmal nNOS causes ischemic injury upon exercise. Thus, evaluation of blood flow and ischemic injury are the focus of the studies described below, and may include a microsphere experiment, treadmill exercise and histological studies. A microsphere experiment is designed to infuse stable isotope labeled microspheres into the blood stream. The capacity of blood flow in active muscle is reflected by distribution of microspheres, which is determined by measuring the intensity of stable isotope (Lai et al. 2009; Li et al. 1999).

Nitric oxide (NO) produced by sarcolemmal nNOS is antagonistic to the α-adrenergic-mediated vasoconstriction during exercise. Without sarcolemmal nNOS, uncontrolled vasoconstriction may cause muscle ischemia, subsequently affecting muscle performance. Previously, it was found that in the absence of sarcolemmal nNOS, strenuous exercise could lead to ischemic injury, which compromises muscle force and running performance (Lai et al. 2009; Li et al. 2010). Hence, in this study, muscle force and running performance may be examined following long term treadmill exercise. Also the evidence of ischemic injury may be sought by histological studies and real-time PCR. These interrelated studies should comprehensively determine the functional improvement caused by restoration of sarcolemmal nNOS.

Methods

Delivery of R16/17.Pal to the Muscle of ΔH2-R19 Mice.

Figure 20:
FIG. 20 is a schematic showing an AAV construct for expressing R16/17.Pal. The construct carries the muscle specific promoter SPc5-12. Pal signal is located at the 3' end of the R17 for membrane targeting. The whole expression cassette is flanked by two AAV inverted terminal repeats (ITR). (Pal: Palmitoylation signal for membrane targeting).

To examine therapeutic effect of recombinant R16/17 protein, the R16/17 protein is first injected into ΔH2-R19 mice to recover sarcolemmal nNOS. The delivery scheme may be the same as described above. Three days after the last injection, the distribution of R16/17.Pal and sarcolemmal nNOS is inspected. As described above, an AAV-mediated gene transfer is used as a therapeutic control. For AAV gene transfer, a muscle-specific promoter (SPc5-12) may be used to drive muscle-specific expression of R16/17.Pal (FIG. 20) and perform systemic delivery of AAV9 viruses to target R16/17.Pal to the whole body muscle. One month following virus injection, the expression of R16/17.Pal and sarcolemmal nNOS is examined as described above. When restoration of sarcolemmal nNOS is confirmed, the remaining injected mice will undergo the following studies.

Determination of Muscle Force Generation and the Response to Eccentric Contraction.

The muscle force and the response to eccentric contraction may be examined on EDL muscle as previously described (Lai et al. 2009). These studies investigate whether the contractility of muscle is affected by restoration of sarcolemmal nNOS.

Measurement of Blood Perfusion in Contracting Muscle.

To evaluate whether restoration of sarcolemmal nNOS improves blood flow in contracting muscle, blood perfusion of contracting muscle is measured by infusing stable isotope labeled microspheres according to an established protocol (Lai et al. 2009; Roseguini et al. 2010). Briefly, mice are given uphill treadmill training (15 degree grade, 10-15 m/min) daily for continuous 4 days. The running time and intensity is recorded. By training, mice become familiar with treadmill exercise. On the experimental day, a carotid artery catheter is inserted and placed in the ascending aorta. Rhenium-labeled microspheres are infused into the anesthetized mice via the catheter at a constant rate. When the mice are recovered from anesthesia (approximately 3 hrs later), the mice will run treadmill for one minute. The same amount of microspheres labeled with Holmium may be infused during running. Then all the tissues may be harvested for detecting the total and specific tissue intensity of stable isotopes. Tissue perfusion at resting and exercise may be calculated according to previously reported methods (Lai et al. 2009; Roseguini et al. 2010). The absolute muscle perfusion and the capacity to increase blood flow (compared with resting flow) may be compared between experimental and control mice.

Running Performance of Treadmill Exercise.

The injected mice will run uphill treadmill exercise until exhaustion daily for consecutive 10 days. The running distance is documented daily. In presence of sarcolemmal nNOS, running distance is elevated gradually until the end of study. At the end of 10-day treadmill exercise, the muscle samples may be harvested for histological studies and real-time PCR.

Measurement of Muscle Force Following Treadmill.

When sarcolemmal nNOS is restored in ΔH2-R19 mice, those mice are divided into two groups. One group will run horizontal treadmill twice a week for 8 weeks. The other group may be the control without exercise. At the end of 8-week treadmill exercise, muscle force of EDL muscle is compared between these two groups. This study examines whether the presence of sarcolemmal nNOS prevents ischemic injury and maintains muscle force following long-term exercise. The muscle samples may be used further for histological studies and real-time PCR.

Evaluation of ischemic injury by histological studies and real-time PCR. The muscle samples following treadmill exercise and muscle force measurement may be inspected by hematoxylin and eosin (H&E) staining, immunostaining and TUNEL assay. The samples may be examined for macrophage, central nucleation, inflammation infiltration and apoptosis. The total RNA may be extracted and used for real-time PCR analysis of three microRNAs level (miR-21, miR-200c and miR-205), which are the markers for focal ischemic injury in muscle (Hsieh et al. 2010).

Results

The results from this study answer an important question about the therapeutic outcome of this novel therapy. Since this therapy is safe and easy to be administered, it has huge potential to be translated into clinical application.

As described above, a ΔH2-R15 minigene restores sarcolemmal nNOS, and in ΔH2-R15 transgenic mice, sarcolemmal nNOS is evenly distributed (Lai et al. 2009). For therapy based on direct delivery of recombinant R16/17 protein, distribution of sarcolmmal nNOS may be mosaic. In other words, direct administration of recombinant R16/17 protein or functional fragments thereof may restore sarcolemmal nNOS in most of muscle cells although it may be difficult to reach 100% of affected muscle cells. However, this should not be a barrier to successful treatment, as it has been found that only 30% dystrophin level can prevent muscular dystrophy in human patients (Neri et al. 2007). So it is possible that a therapeutic effect is exerted when sarcolemmal nNOS reaches the same level. Additionally, ΔH2-R19 mice with saline injection are included as a negative control, ΔH2-R19 mice with AAV.R16/17.Pal gene delivery are included as a therapeutic control and ΔH2-R15 mice are included as a positive control. By comparing with control groups, one skilled in the art would be able to determine a dose and administration that responsible for therapeutic efficacy.

Summary

There is a gap in treating BMD patients or DMD receiving exon skipping or gene therapy since those patients are characterized by the presence of truncated dystrophins but the absence of sarcolemmal nNOS. Results of the studies described herein fill this gap and may be extrapolated to develop therapies in large animal model and human patients.

REFERENCES

The references, patents and published patent applications listed below, and all references cited in the specification above are hereby incorporated by reference in their entirety, as if fully set forth herein.

Adams M E, et al. (2000) Absence of alpha-syntrophin leads to structurally aberrant neuromuscular synapses deficient in utrophin. J Cell Biol 150(6): 1385-1398.

Betts, C. A., Hammond, S. M., Yin, H. F. & Wood, M. J. Optimizing tissue-specific antisense oligonucleotide-Peptide conjugates. Methods Mol Biol 867, 415-435 (2012).

Bhagavati, S. Exon-skipping therapy for Duchenne muscular dystrophy. Lancet 379, e10; author reply el 0-11 (2012).

Bostick, B., Ghosh, A., Yue, Y., Long, C. & Duan, D. Systemic AAV-9 transduction in mice is influenced by animal age but not by the route of administration. Gene Ther 14, 1605-1609 (2007).

Brenman J E, Chao D S, Xia H, Aldape K, Bredt D S (1995) Nitric oxide synthase complexed with dystrophin and absent from skeletal muscle sarcolemma in Duchenne muscular dystrophy. Cell 82(5):743-752.

Brenman, J. E. et al. Interaction of nitric oxide synthase with the postsynaptic density protein PSD-95 and alphal-syntrophin mediated by PDZ domains. Cell 84, 757-767 (1996).

Chao D S, et al. (1996) Selective loss of sarcolemmal nitric oxide synthase in Becker muscular dystrophy. J Exp Med 184(2):609-618.

Choy, E. et al. Endomembrane trafficking of ras: the CAAX motif targets proteins to the E R and Golgi. Cell 98, 69-80 (1999).

Cirak, S. et al. Exon skipping and dystrophin restoration in patients with Duchenne muscular dystrophy after systemic phosphorodiamidate morpholino oligomer treatment: an open-label, phase 2, doseescalation study. Lancet 378, 595-605 (2011).

Djinovic-Carugo K, Gautel M, Ylanne J, Young P (2002) The spectrin repeat: A structural platform for cytoskeletal protein assemblies. FEBS Lett 513(1): 119-123.

England, S. B. et al. Very mild muscular dystrophy associated with the deletion of 46% of dystrophin. Nature 343, 180-182 (1990).

Foster, H. et al. Codon and mRNA sequence optimization of microdystrophin transgenes improves expression and physiological outcome in dystrophic mdx mice following AAV2/8 gene transfer. Mol Ther 16, 1825-1832 (2008).

Goemans, N. M. et al. Systemic administration of PRO051 in Duchenne's muscular dystrophy. N Engl J Med 364, 1513-1522 (2011).

Grady R M, et al. (1997) Skeletal and cardiac myopathies in mice lacking utrophin and dystrophin: A model for Duchenne muscular dystrophy. Cell 90(4):729-738.

Gregorevic, P. et al. rAAV6-microdystrophin preserves muscle function and extends lifespan in severely dystrophic mice. Nat Med 12, 787-789 (2006).

Gregorevic, P. et al. Systemic delivery of genes to striated muscles using adeno-associated viral vectors. Nat Med 10, 828-834 (2004).

Hancock J F, Paterson H, Marshall C J (1990) A polybasic domain or palmitoylation is required in addition to the CAAX motif to localize p21ras to the plasma membrane. Cell 63(1):133-139.

Harper S Q, et al. (2002) Modular flexibility of dystrophin: Implications for gene therapy of Duchenne muscular dystrophy. Nat Med 8(3):253-261.

Hillier B J, Christopherson K S, Prehoda K E, Bredt D S, Lim W A (1999) Unexpected modes of PDZ domain scaffolding revealed by structure of nNOS-syntrophin complex. Science 284(5415):812-815.

Ho, A., Schwarze, S. R., Mermelstein, S. J., Waksman, G. & Dowdy, S. F. Synthetic protein transduction domains: enhanced transduction potential in vitro and in vivo. Cancer Res 61, 474-477 (2001).

Hsieh, C. H. et al. MicroRNA profiling in ischemic injury of the gracilis muscle in rats. BMC Musculoskelet Disord 11, 123 (2010).

Inagaki, K. et al. Robust systemic transduction with AAV9 vectors in mice: efficient global cardiac gene transfer superior to that of AAV8. Mol Ther 14, 45-53 (2006).

Ipsaro J J, Mondragón A (2010) Structural basis for spectrin recognition by ankyrin. Blood 115(20):4093-4101.

Ivanova, G. D. et al. Improved cell-penetrating peptide-PNA conjugates for splicing redirection in HeLa cells and exon skipping in mdx mouse muscle. Nucleic Acids Res 36, 6418-6428 (2008).

Jearawiriyapaisarn, N. et al. Sustained dystrophin expression induced by peptide-conjugated morpholino oligomers in the muscles of mdx mice. Mol Ther 16, 1624-1629 (2008).

Judge L M, Haraguchiln M, Chamberlain J S (2006) Dissecting the signaling and mechanical functions of the dystrophin-glycoprotein complex. J Cell Sci 119 (Pt 8): 1537-1546.

Kameya S, et al. (1999) alphal-syntrophin gene disruption results in the absence of neuronal-type nitric-oxide synthase at the sarcolemma but does not induce muscle degeneration. J Biol Chem 274(4):2193-2200.

Karnoub, A. E. & Weinberg, R. A. Ras oncogenes: split personalities. Nat Rev Mol Cell Biol 9, 517-531 (2008).

Kobayashi Y M, et al. (2008) Sarcolemma-localized nNOS is required to maintain activity after mild exercise. Nature 456(7221):511-515.

Kunkel L M (2005) 2004 William Allan Award address. Cloning of the DMD gene. Am J Hum Genet 76(2):205-214.

Kunkel L M (2005) 2004 William Allan Award address. Cloning of the DMD gene. Am J Hum Genet 76(2):205-214.

Lai Y, et al. (2005) Efficient in vivo gene expression by trans-splicing adeno-associated viral vectors. Nat Biotechnol 23(11):1435-1439.

Lai Y, et al. (2009) Dystrophins carrying spectrin-like repeats 16 and 17 anchor nNOS to the sarcolemma and enhance exercise performance in a mouse model of muscular dystrophy. J Clin Invest 119(3):624-635.

Le Rumeur E, Hubert J F, Winder S J (2012) A new twist to coiled coil. FEBS Lett 586(17): 2717-2722.

Le Rumeur E, Winder S J, Hubert J F (2010) Dystrophin: More than just the sum of its parts. Biochim Biophys Acta 1804(9): 1713-1722.

Legrand B, Giudice E, Nicolas A, Delalande O, Le Rumeur E (2011) Computational study of the human dystrophin repeats: interaction properties and molecular Li D, et al. (2010) Sarcolemmal nNOS anchoring reveals a qualitative difference between dystrophin and utrophin. J Cell Sci 123(Pt 12):2008-2013.

Li D, Long C, Yue Y, Duan D (2009) Sub-physiological sarcoglycan expression contributes to compensatory muscle protection in mdx mice. Hum Mol Genet 18(7): 1209-1220.

Li D, Yue Y, Lai Y, Hakim C H, Duan D (2011a) Nitrosative stress elicited by nNOSp delocalization inhibits muscle force in dystrophin-null mice. J Pathol 223(1):88-98.

Li D, Shin J H, Duan D (2011 b) iNOS ablation does not improve specific force of the extensor digitorum longus muscle in dystrophin-deficient mdx4cv mice. PLoS ONE 6(6):e21618.

Li, X., Eastman, E. M., Schwartz, R. J. & Draghia-Akli, R. Synthetic muscle promoters: activities exceeding naturally occurring regulatory sequences. Nat Biotechnol 17, 241-245 (1999).

Morris G, Man N T, Sewry C A (2011) Monitoring duchenne muscular dystrophy gene therapy with epitope-specific monoclonal antibodies. Methods Mol Biol 709:39-61.

Morris, M. C., Depollier, J., Mery, J., Heitz, F. & Divita, G. A peptide carrier for the delivery of biologically active proteins into mammalian cells. Nat Biotechnol 19, 1173-1176 (2001).

Moulton, H. M. Cell-penetrating peptides enhance systemic delivery of antisense morpholino oligomers. Methods Mol Biol 867, 407-414 (2012).

Nakamura, A. & Takeda, S. Exon-skipping therapy for Duchenne muscular dystrophy. Lancet 378, 546-547 (2011).

Navarro-Lerida, I., Alvarez-Barrientos, A. & Rodriguez-Crespo, I. N-terminal palmitoylation within the appropriate amino acid environment conveys on NOS2 the ability to progress along the intracellular sorting pathways. J Cell Sci 119, 1558-1569 (2006).

Neri, M. et al. Dystrophin levels as low as 30% are sufficient to avoid muscular dystrophy in the human. Neuromuscul Disord 17, 913-918 (2007).

Nishida, C. R. & Ortiz de Montellano, P. R. Electron transfer and catalytic activity of nitric oxide synthases. Chimeric constructs of the neuronal, inducible, and endothelial isoforms. J Biol Chem 273, 5566-5571 (1998).

Qiao C, et al. (2010) AAV6 capsid tyrosine to phenylalanine mutations improve gene transfer to skeletal muscle. Hum Gene Ther 21(10): 1343-1348.

Roseguini, B. T. et al. Intermittent pneumatic leg compressions acutely upregulate VEGF and MCP-1 expression in skeletal muscle. Am J Physiol Heart Circ Physiol 298, H1991-2000 (2010).

Rybakova I N, Patel J R, Davies K E, Yurchenco P D, Ervasti J M (2002) Utrophin binds laterally along actin filaments and can couple costameric actin with sarcolemma when overexpressed in dystrophin-deficient muscle. Mol Biol Cell 13(5):1512-1521.

Sander M, et al. (2000) Functional muscle ischemia in neuronal nitric oxide synthase deficient skeletal muscle of children with Duchenne muscular dystrophy. Proc Natl Acad Sci USA 97(25):13818-13823.

Schwarze, S. R., Ho, A., Vocero-Akbani, A. & Dowdy, S. F. In vivo protein transduction: delivery of a biologically active protein into the mouse. Science 285, 1569-1572 (1999).

Shin J H, Yue Y, Duan D (2012) Recombinant adeno-associated viral vector production and purification. Methods Mol Biol 798:267-284.

Sirsi, S. R. et al. Functionalized PEG-PEI copolymers complexed to exon-skipping oligonucleotides improve dystrophin expression in mdx mice. Hum Gene Ther 19, 795-806 (2008).

Sonnemann, K. J. et al. Functional Substitution by TAT-Utrophin in Dystrophin-Deficient Mice. PLoS Med 6, e1000083 (2009).

Stabach P R, et al. (2009) The structure of the ankyrin-binding site of beta-spectrin reveals how tandem spectrin-repeats generate unique ligand-binding properties.

Blood 113(22):5377-5384.

Thomas G D, et al. (1998) Impaired metabolic modulation of alpha-adrenergic vasoconstriction in dystrophin-deficient skeletal muscle. Proc Natl Acad Sci USA 95(25): 15090-15095.

Thomas, G. D., Shaul, P. W., Yuhanna, I. S., Froehner, S. C. & Adams, M. E. Vasomodulation by skeletal muscle-derived nitric oxide requires alphasyntrophin-mediated sarcolemmal localization of neuronal Nitric oxide synthase. Circ Res 92, 554-560 (2003).

Tochio H, Zhang Q, Mandal P, Li M, Zhang M (1999) Solution structure of the extended neuronal nitric oxide synthase PDZ domain complexed with an associated peptide. Nat Struct Biol 6(5):417-421.

Torelli S, et al. (2004) Absence of neuronal nitric oxide synthase (nNOS) as a pathological marker for the diagnosis of Becker muscular dystrophy with rod domain deletions. Neuropathol Appl Neurobiol 30(5):540-545.

van Deutekom, J. C. et al. Local dystrophin restoration with antisense oligonucleotide PRO051. N Engl J Med 357, 2677-2686 (2007).

Wang, B., Li, J. & Xiao, X. Adeno-associated virus vector carrying human minidystrophin genes effectively ameliorates muscular dystrophy in mdx mouse model. Proc Natl Acad Sci USA 97, 13714-13719 (2000).

Wang, Q. et al. TAT-mediated protein transduction of Nogo extracellular peptide 1-40 and its biological activity. Cell Mol Neurobiol 29, 97-108 (2009).

Wells K E, et al. (2003) Relocalization of neuronal nitric oxide synthase (nNOS) as a marker for complete restoration of the dystrophin associated protein complex in skeletal muscle. Neuromuscul Disord 13(1):21-31.

White, S. J. & den Dunnen, J. T. Copy number variation in the genome; the human DMD gene as an example. Cytogenet Genome Res 115, 240-246 (2006).

Wu, B. et al. Effective rescue of dystrophin improves cardiac function in dystrophin-deficient mice by a modified morpholino oligomer. Proc Natl Acad Sci USA 105, 14814-14819 (2008).

Yin, H. et al. Cell-penetrating peptide-conjugated antisense oligonucleotides restore systemic muscle and cardiac dystrophin expression and function. Hum Mol Genet 17, 3909-3918 (2008).

Yin, H. et al. A fusion peptide directs enhanced systemic dystrophin exon skipping and functional restoration in dystrophin-deficient mdx mice. Hum Mol Genet 18, 4405-4414 (2009).

Yin, H. et al. Optimization of peptide nucleic acid antisense oligonucleotides for local and systemic dystrophin splice correction in the mdx mouse. Mol Ther 18, 819-827 (2010).

Yokota, T. et al. Efficacy of systemic morpholino exon-skipping in Duchenne dystrophy dogs. Ann Neurol 65, 667-676 (2009).

Yue Y, Liu M, Duan D (2006) C-terminal-truncated micro-dystrophin recruits dystrobrevin and syntrophin to the dystrophin-associated glycoprotein complex and reduces muscular dystrophy in symptomatic utrophin/dystrophin double-knockout mice.

Mol Ther 14(1):79-87.

Zhong L, et al. (2008) Next generation of adeno-associated virus 2 vectors: Point mutations in tyrosines lead to high-efficiency transduction at lower doses. Proc Natl Acad Sci USA 105(22):7827-7832.

What is claimed is:

1. A therapeutic composition comprising:

a microdystrophin peptide having an amino acid sequence which comprises dystrophin spectrin-like repeats 16 and 17 (R16/R17) (SEQ ID NO:7) or functional domains comprising at least one α helix of dystrophin spectrin-like repeat 16 (R16) and at least one α helix of dystrophin spectrin-like repeat 17 (R17), but does not include the following dystrophin domains: NT, CR, H1, H4, R1, and R24;

wherein the microdystrophin peptide is expressed by a delivery vehicle, and wherein the delivery vehicle is an adeno-associated virus (AAV) vector or a recombinant adeno-associated AAV (rAAV) vector.

2. The therapeutic composition of claim 1, wherein the therapeutic composition is used to treat Duchenne Muscular Dystrophy (DMD), Becker Muscular Dystrophy (BMD) or X-linked dilated cardiomyopathy (XLDC).

3. A therapeutic composition comprising:

an amino acid sequence motif which comprises RFHYDIKIFN (SEQ ID NO:46) but does not include the following dystrophin domains: NT, CR, H1, H4, R1, and R24; and a delivery vehicle, wherein the delivery vehicle is an adeno-associated virus (AAV) vector or a recombinant adeno-associated AAV (rAAV) vector, and wherein the AAV vector or the rAAV vector expresses the amino acid sequence comprising R16/R17.

4. The therapeutic composition of claim 3, wherein the amino acid sequence comprises:

at least one α helix of dystrophin spectrin-like repeat 16 (R16); and at least one α helix of dystrophin spectrin-like repeat 17 (R17).

5. The therapeutic composition of claim 4, wherein the amino acid sequence comprises:

an α2 helix and an α3 helix of R16; and an α2 helix and an α3 helix of R17.

6. A method of treating DMD, BMD or XLDC comprising administering a therapeutic amount of a therapeutic composition to a subject having DMD or BMD, wherein the therapeutic composition comprises an amino acid sequence comprising R16/R17 or functional domains comprising at least one α helix of dystrophin spectrin-like repeat 16 (R16) and at least one α helix of dystrophin spectrin-like repeat 17 (R17), but does not include the following dystrophin domains: NT, CR, H1, H4, R1, and R24;

wherein the amino acid sequence motif is expressed by a delivery vehicle, and wherein the delivery vehicle is an adeno-associated virus (AAV) vector or a recombinant adeno-associated AAV (rAAV) vector.

7. The method of claim 6, wherein the amino acid sequence comprises:

an α2 helix and an α3 helix of R16; and an α2 helix and an α3 helix of R17.

8. The method of claim 6, wherein the amino acid sequence comprises the 10-residue motif RFHYDIKIFN (SEQ ID NO:46).

* * * * *

UNITED STATES PATENT AND TRADEMARK OFFICE
CERTIFICATE OF CORRECTION

PATENT NO. : 10,351,611 B2  
APPLICATION NO. : 15/487919  
DATED : July 16, 2019  
INVENTOR(S) : Yi Lai et al.

Page 1 of 1

It is certified that error appears in the above-identified patent and that said Letters Patent is hereby corrected as shown below:

In the Specification

Column 1, Lines 15-18, delete the entire paragraph and insert the following paragraph:
-- This invention was made with government support under grant number AR049419 awarded by the National Institutes of Health. The government has certain rights in the invention. --

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*